(12) United States Patent
Viitanen et al.

(10) Patent No.: US 7,998,722 B2
(45) Date of Patent: Aug. 16, 2011

(54) ZYMOMONAS WITH IMPROVED XYLOSE UTILIZATION

(75) Inventors: Paul V. Viitanen, West Chester, PA (US); Luan Tao, Havertown, PA (US); Yuying Zhang, New Hope, PA (US); Perry G. Caimi, Kennett Square, PA (US); Carol M. McCutchen, Wilmington, DE (US); Laura McCole, East Fallowfield, PA (US); Min Zhang, Lakewood, CO (US); Yat-Chen Chou, Lakewood, CO (US); Mary Ann Franden, Centennial, CO (US)

(73) Assignees: E. I. du Pont de Nemours and Company, Wilmington, DE (US); Alliance for Sustainable Energy LLC, Wilmington, DE (US)

( * ) Notice: Subject to any disclaimer, the term of this patent is extended or adjusted under 35 U.S.C. 154(b) by 0 days.

(21) Appl. No.: 12/410,501

(22) Filed: Mar. 25, 2009

(65) Prior Publication Data
US 2009/0246846 A1    Oct. 1, 2009

Related U.S. Application Data

(60) Provisional application No. 61/039,878, filed on Mar. 27, 2008.

(51) Int. Cl.
| | |
|---|---|
| C12N 1/20 | (2006.01) |
| C12N 15/74 | (2006.01) |
| C12N 15/70 | (2006.01) |
| C12N 9/90 | (2006.01) |
| C12P 7/06 | (2006.01) |
| C12P 21/06 | (2006.01) |
| C12Q 1/68 | (2006.01) |
| C07H 21/04 | (2006.01) |

(52) U.S. Cl. ............ 435/252.3; 435/69.1; 435/161; 435/320.1; 435/471; 435/233; 435/6; 536/23.2

(58) Field of Classification Search .............. None
See application file for complete search history.

(56) References Cited

U.S. PATENT DOCUMENTS

| | | |
|---|---|---|
| 4,683,202 A | 7/1987 | Mullis |
| 5,231,020 A | 7/1993 | Jorgensen et al. |
| 5,514,583 A | 5/1996 | Picataggio et al. |
| 5,712,133 A | 1/1998 | Picataggio et al. |
| 6,566,107 B1 | 5/2003 | Zhang |
| 7,223,575 B2 | 5/2007 | Zhang et al. |
| 2003/0162271 A1 | 8/2003 | Zhang et al. |
| 2007/0092957 A1 | 4/2007 | Donaldson et al. |
| 2008/0081358 A1 | 4/2008 | Viitanen et al. |
| 2008/0187973 A1 | 8/2008 | Viitanen et al. |
| 2008/0286870 A1 | 11/2008 | Viitanen et al. |

FOREIGN PATENT DOCUMENTS

| | | |
|---|---|---|
| WO | 9528476 A1 | 10/1995 |
| WO | 2004081185 A2 | 9/2004 |

OTHER PUBLICATIONS

Feldmann et al. Cloning and expression of the genes for xylose isomerase and xylulokinase from *Klebsiella pneumoniae* 1033 in *Escherichia coli* K12, Mol Gen Genet. Aug. 1992;234(2):201-10.*
Schellenberg et al. Xylose isomerase from *Escherichia coli*. Characterization of the protein and the structural gene, J Biol Chem. Jun. 10, 1984;259(11):6826-32.*
Feldmann et al., Pentose Metabolism in *Zymomonas mobilis* Wild-Type and Recombinant Strains, Appl. Microbiol. Biotechnol., 1992, vol. 38:354-361.
Zhang et al., Metabolic Engineering of a Pentose Metabolism Pathway in Ethanologenic *Zymomonas mobillis*, Science, 1995, vol. 267:240-243.
Yanase et al., Genetic Engineering of *Zympbacter palmae* for Production of Ethanol From Xylose, Appl. Environ. Microbiol., 2007, vol. 73:2592-2599.
Sambrook et al., Molecular Cloning: A Laboratory Manual, Second Edition, 1989, Cold Spring Harbor Laboratory: Cold Spring Harbor, New York (Book Not Included).
S. F. Altschul et al., Basic Local Alignment Search Tool. J. Mol. Biol., 1993, vol. 215:403-410.
A. M. Lesk, Computational Molecular Biology, 1988, Oxford University, NY (Book Not Included).
D. W. Smith, Biocomputing: Informatics and Genome Projects, 1993, Academic, NY (Book Not Included).
A. Griffin et al., Computer Analysis of Sequence Data, Part 1, 1994, Humania, NJ (Book Not Included).
G. Von Heinje, Sequence Analysis in Molecular Biology, 1987, Academic (Book Not Included).
M. Gribskov et al., Sequence Analysis Primer, 1991, Stockton, NY (Book Not Included).
Higgins et al., Fast and Sensitive Multiple Sequence Alignment on a Microcomputer, CABIOS, 1989, vol. 5:151-153.
D. G. Higgins et al., Clustal V: Improved Software for Multiple Sequence Alignment, Comput. Appl. Biosci., 1992, vol. 8:189-191.
W. R. Pearson, Comput. Methods Genome Res., [Proc. Int. Symp.], (1994) Meeting Date 1992, p. 111-120.
T. J. Silhavy et al., Experiments With Gene Fusions; 1984, Cold Spring Harbor Laboratory: Cold Spring Harbor, New York (Book Not Included).
F. M. Ausubel et al., Current Protocols in Molecular Biology, 1987, Greene Publishing and Wiley-Interscience (Book Not Included).
S. Tabor et al., A Bacteriophage T7 RNA Polymerase/Promoter System for Controlled Exclusive Expression of Specific Genes, Proc. Acad. Sci., 1985, vol. 82:1074-1078.

(Continued)

*Primary Examiner* — Robert B Mondesi
*Assistant Examiner* — Iqbal H Chowdhury

(57) ABSTRACT

Strains of *Zymomonas* were engineered by introducing a chimeric xylose isomerase gene that contains a mutant promoter of the *Z. mobilis* glyceraldehyde-3-phosphate dehydrogenase gene. The promoter directs increased expression of xylose isomerase, and when the strain is in addition engineered for expression of xylulokinase, transaldolase and transketolase, improved utilization of xylose is obtained.

9 Claims, 16 Drawing Sheets

OTHER PUBLICATIONS

Walker et al., Isothermal In Vitro Amplification of DNA by a Restriction Enzyme/DNA Polymerase System, Proc. Natl. Acad. Sci., 1992, vol. 89:392-396.

K. E. Davis, Diagnosis of Genetic Disorders, Human Genetic Diseases: A Practical Approach, IRL Press, Herndon, VA, 1986, pp. 33-50 (Book Not Included).

W. Rychlik, Selection of Primers for Polymerase Chain Reaction, Methods in Molecular Biology, 1993, vol. 15:31-39.

Ohara et al., One-Sided Polymerase Chain Reaction: The Amplification of CDNA, PNAS, 1989, vol. 86:5673-5677.

Loh et al., Science, 1989, vol. 243:217.

Van Ness et al., The Use of Oligodeoxynucleotide Probes in Chaotrop-Based Hybridization Solutions, Nucl. Acids Res., 1991, vol. 19:5143-5151.

R. D. Finn et al., PFAM: Clans, Web Tools and Services, Nucleic Acids Research, 2006, Database Issue 34:D247-D251.

Durbin et al., Biological Sequenc Analysis: Probabilistic Models of Proteins and Nucleic Acids, 1998 (Book Not Included).

Krogh et al., Hidden Markov Models in Computational Biology, J. Mol. Biol., 1994, vol. 235:1501-1531.

Scott et al., Sequences of Versatile Broad-Host-Range Vectors of the RK2 Family, Plasmid, 2003, vol. 50:74-79.

L. R. Lynd et al., Microbial Cellulose Utilization: Fundamentals and Biotechnology, Microbiol. Mol. Biol. Rev., 2002, vol. 66:506-577.

Crueger et al., Biotechnology: A Textbook of Industiral Microbiology, Second Edition, 1989, Sinauer Associates, Inc. (Book Not Included).

Deshpande et al., Ethanol Production From Cellulose by Coupled Saccharification/Fermentation Using *Saccharomyces cerevisiae* and Cellulase Complex From *Sclerotium rolfsii* UV-8 Mutant, Appl. Biochem. Biotechnol., 1992, vol. 36:227-234.

Cahoon et al., Metabolic Redesign of Vitamin E Biosynthesis in Plants for Tocotrienol Production and Increased Antioxidant Content, Nature Biotechnology, 2003, vol. 21:1082-1087.

National Center for Biotechnology Information General Identifier No. 43692, Oct. 23, 2008, M. E. Fling et al., Nucleotide Sequence of the Transposen TN7 Gene Encoding an Aminoglycoside-Modifying Enzyme, Accession No. X03043.1.

Conway et al., Glyceraldehyde-3-Phosphate Dehydrogenase Gene From *Zymomonas mobilis*: Cloning, Sequencing, and Identification of Promoter Region, J. Bacteriol., 1987, vol. 169:5653-5662.

U.S. Appl. No. 11/862,566, filed Sep. 27, 2007, Applicant: Paul V. Vitanen.

Frohman et al., PNAS USA, 85:8998, 1988.

Eddy, Sean R, HMMER User's Guide, Biological Sequence Analysis Using Profile Hidden Markov Models, (2010), 1-77.

Hulsen, Tim et al., Testing Statistical Significance Scores of Sequence Comparison Methods With Structure Similarity, BMC Bioinformatics (2006), 1471-2105, 7:44.

Office Action mailed Jun. 22, 2010, in co-pending U.S. Appl. No. 12/410,495.

\* cited by examiner

Xylose Isomerase Assay

Xyulokinase Assay

Continue to Fig. 6C

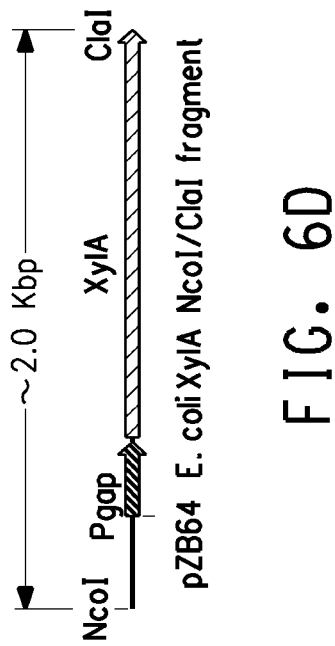
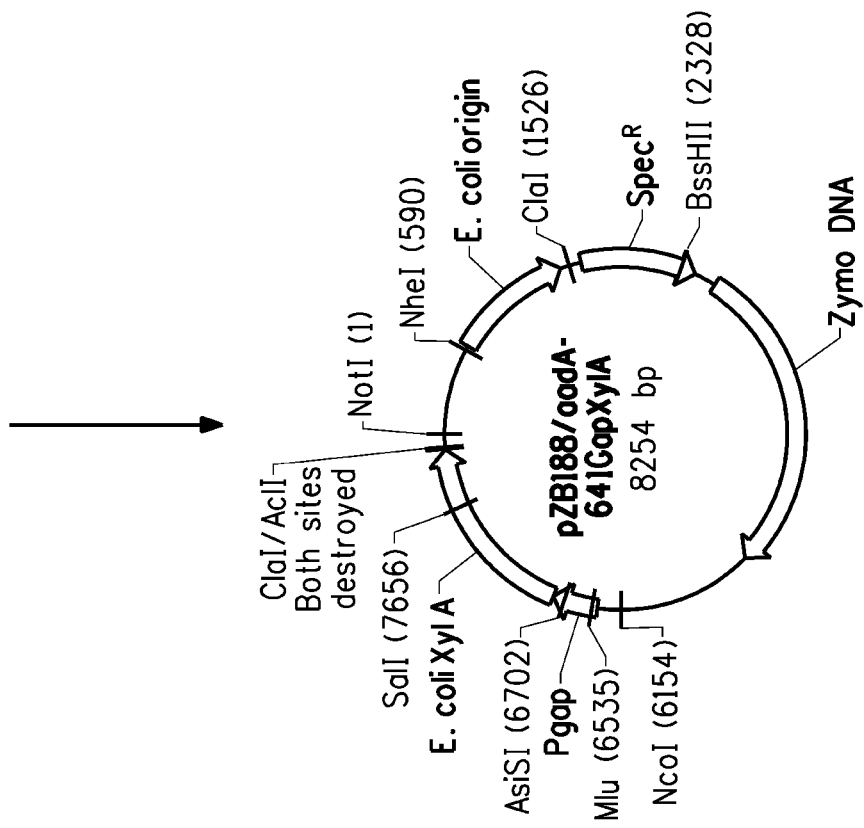
FIG. 6D
FIG. 6C

US 7,998,722 B2

ZYMOMONAS WITH IMPROVED XYLOSE UTILIZATION

CROSS-REFERENCE TO RELATED APPLICATION

This application claims the benefit of U.S. Provisional Application No. 61/039,878 filed on Mar. 27, 2008, which application is incorporated herein by reference.

STATEMENT OF GOVERNMENT RIGHTS

This invention was made with United States government support under Contract Nos. 04-03-CA-70224 and DE-FC36-03GO13146 awarded by the Department of Energy. The United States government has certain rights in this invention. Further, the United States Government has rights in this invention under Contract No. DE-AC36-99GO10337 between the United States Department of Energy and the National Renewable Energy Laboratory, a Division of the Midwest Research Institute.

FIELD OF INVENTION

The invention relates to the fields of microbiology and genetic engineering. More specifically, genetic engineering of Zymomonas strains with improved xylose utilization is described.

BACKGROUND OF INVENTION

Production of ethanol by microorganisms provides an alternative energy source to fossil fuels and is therefore an important area of current research. It is desirable that microorganisms producing ethanol, as well as other useful products, be capable of using xylose as a carbon source since xylose is the major pentose in hydrolyzed lignocellulosic materials, and therefore can provide an abundantly available, low cost carbon substrate. Zymomonas mobilis and other bacterial ethanologens which do not naturally utilize xylose may be genetically engineered for xylose utilization by introduction of genes encoding 1) xylose isomerase, which catalyses the conversion of xylose to xylulose; 2) xylulokinase, which phosphorylates xylulose to form xylulose 5-phosphate; 3) transketolase; and 4) transaldolase.

There has been success in engineering Z. mobilis strains for xylose metabolism (U.S. Pat. No. 5,514,583, U.S. Pat. No. 5,712,133, U.S. Pat. No. 6,566,107, WO 95/28476, Feldmann et al. (1992) Appl Microbiol Biotechnol 38: 354-361, Zhang et al. (1995) Science 267:240-243), as well as a Zymobacter palmae strain (Yanase et al. (2007) Appl. Environ. Mirobiol. 73:2592-2599). However, typically the engineered strains do not grow and produce ethanol as well on xylose as on glucose. Strains engineered for xylose utilization have been adapted by serial passage on xylose medium, resulting in strains with improved xylose utilization as described in U.S. Pat. No. 7,223,575 and commonly owned and co-pending US Patent App. Publication No. US20080286870. However the genetic basis for the improvement had not been determined.

There remains a need for genetically engineered strains of Zymomonas, and other bacterial ethanologens, having improved xylose utilization. Applicants have discovered genetic alterations of Z. mobilis strains engineered for xylose utilization and adapted for improved xylose utilization, and used the discovery to engineer strains for improved xylose utilization.

SUMMARY OF INVENTION

The present invention relates to strains of bacteria that are genetically engineered for xylose utilization by transforming with a chimeric gene encoding xylose isomerase that is expressed from an improved Zymomonas mobilis glyceraldehyde-3-phosphate dehydrogenase gene promoter (Pgap). The strains are also transformed with genes for expression of xylulokinase, transaldolase and transketolase. The improved Pgap directs higher expression than the native Pgap which causes improved xylose utilization as compared to strains not having an improved Pgap for expression of xylose isomerase.

Described herein is a recombinant bacterial strain selected from the group consisting of Zymomonas and Zymobacter comprising a gene introduced by transformation, the gene comprising:
a) an isolated nucleic acid molecule comprising a Z. mobilis glyceraldehyde-3-phosphate dehydrogenase gene promoter that has a base substitution in a position selected from the group consisting of position −190, position −89, or both position −190 and −89; wherein the position numbers are with respect to the natural ATG translation initiation codon for glyceraldehyde-3-phosphate dehydrogenase in the CP4 and ZM4 strains of Z. mobilis; which is an improved Pgap; and
b) an operably linked isolated nucleic acid molecule encoding xylose isomerase. The gene introduced by the transformation steps above may be a chimeric gene comprising the mutations for enhanced expression of Pgap.

Also described herein is a process for engineering a bacterial strain selected from the group consisting of Zymomonas and Zymobacter comprising transforming with a gene, e.g. a chimeric gene comprising;
a) an isolated nucleic acid molecule comprising a Z. mobilis glyceraldehyde-3-phosphate dehydrogenase gene promoter that has a base substitution in a position selected from the group consisting of position −190, position −89, or both position −190 and −89; wherein the position numbers are with respect to the natural ATG translation initiation codon for glyceraldehyde-3-phosphate dehydrogenase in the CP4 and ZM4 strains of Z. mobilis; which is an improved Pgap; and
b) an operably linked isolated nucleic acid molecule encoding a xylose isomerase enzyme.

Another process described herein is for engineering a xylose-utilizing bacterial strain selected from the group consisting of Zymomonas and Zymobacter comprising in any order the steps of:
a) transforming with genes or an operon for expression of transaldolase and transketolase; and
b) transforming with genes or an operon for expression of xylose isomerase and xylulokinase, wherein the xylose isomerase enzyme is expressed from a Z. mobilis glyceraldehyde-3-phosphate dehydrogenase gene promoter that has a base substitution in a position selected from the group consisting of position −190, position −89, or both position −190 and −89; wherein the position numbers are with respect to the natural ATG translation initiation codon for glyceraldehyde-3-phosphate dehydrogenase in the CP4 and ZM4 strains of Z. mobilis; which is an improved Pgap;

Also described herein is a process for production of ethanol from a medium comprising xylose, comprising culturing in the medium a recombinant bacterial strain selected from the group consisting of Zymomonas and Zymobacter comprising a chimeric gene introduced by transformation, the chimeric gene comprising:
a) an isolated nucleic acid molecule comprising a Z. mobilis glyceraldehyde-3-phosphate dehydrogenase gene promoter that has a base substitution in a position selected from the group consisting of position −190, position −89, or both position −190 and −89; wherein the position numbers are with respect to the natural ATG translation initiation codon for glyceraldehyde-3-phosphate dehydrogenase in the CP4 and ZM4 strains of *Z. mobilis*; which is an improved Pgap; and b) an operably linked isolated nucleic acid molecule encoding xylose isomerase.

In addition, a recombinant bacterial strain is describe herein that is selected from the group consisting of *Zymomonas* and *Zymobacter* and which is engineered to express xylose isomerase at a level to produce at least about 0.1 μmoles product/mg protein/minute, as determined by reacting 20 μL of cell free extract in a reaction mix, at 30° C., comprising 0.256 mM NADH, 50 mM xylose, 10 mM MgSO$_4$, 10 mM triethanolamine, and 1 U/ml sorbitol dehydrogenase, wherein D-xylulose is the product.

BRIEF DESCRIPTION OF THE FIGURES AND SEQUENCE DESCRIPTIONS

The various embodiments of the invention can be more fully understood from the following detailed description, the figures, and the accompanying sequence descriptions, which form a part of this application.

Figure 5:
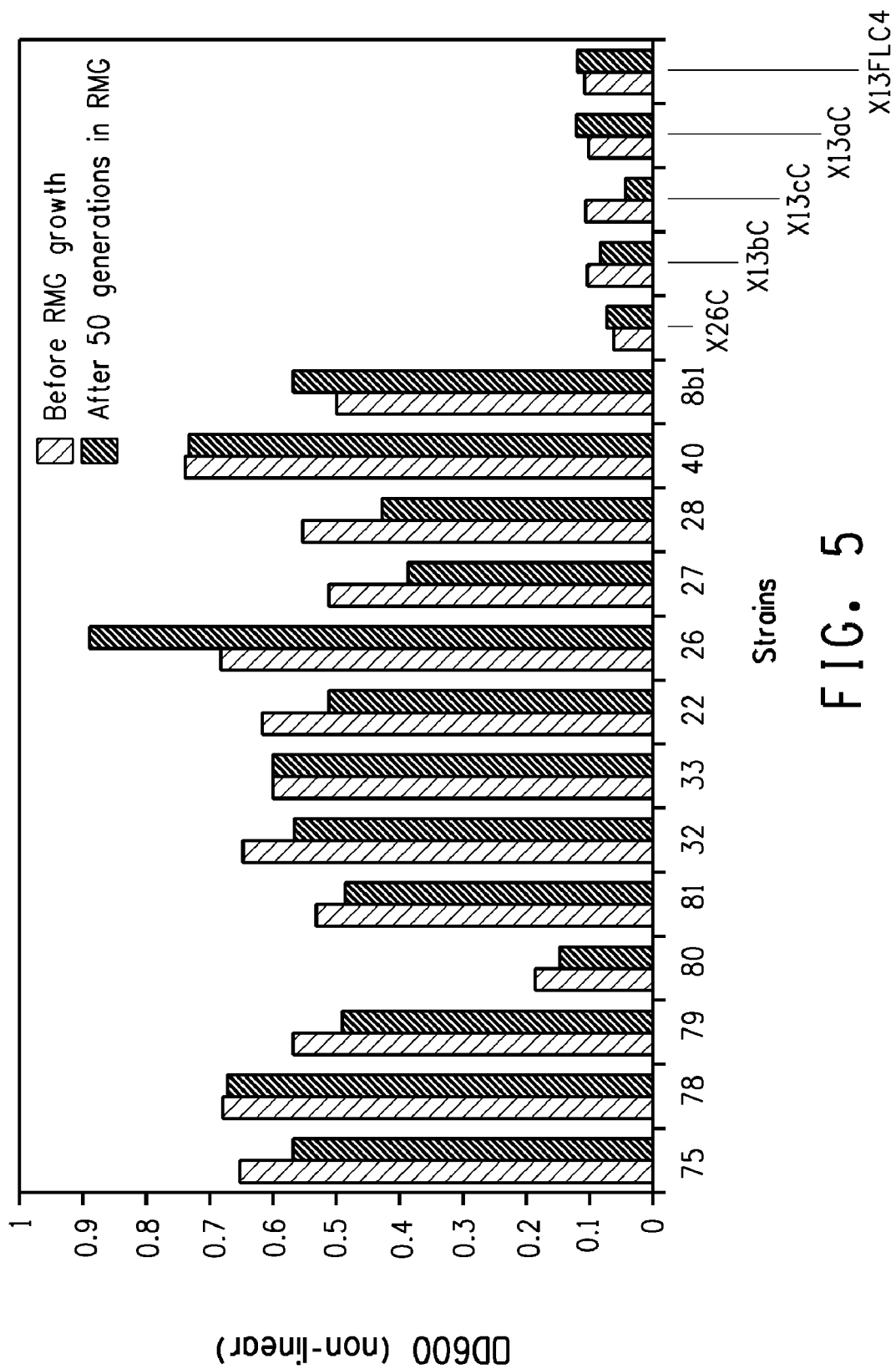

FIG. 5 shows a graph of growth of adapted xylose-utilizing strains at 70 hr on RM (rich medium) with 5% xylose (RMX5%) before and after growing 50 generations in RM with 5% glucose (RMG).

FIG. 6 shows plasmid maps of (A) pZB188; (B) pZB188/aadA; and (C) pZB188/aadA-GapXylA; as well as (D) a schematic representation of the *E. coli* xylose isomerase expression cassette PgapXylA.

FIG. 7 shows plasmid maps of (A) pMOD™-2-<MCS>; (B) pMOD-Linker; and (C) pMOD-Linker-Spec.

Figures 7C, 8:
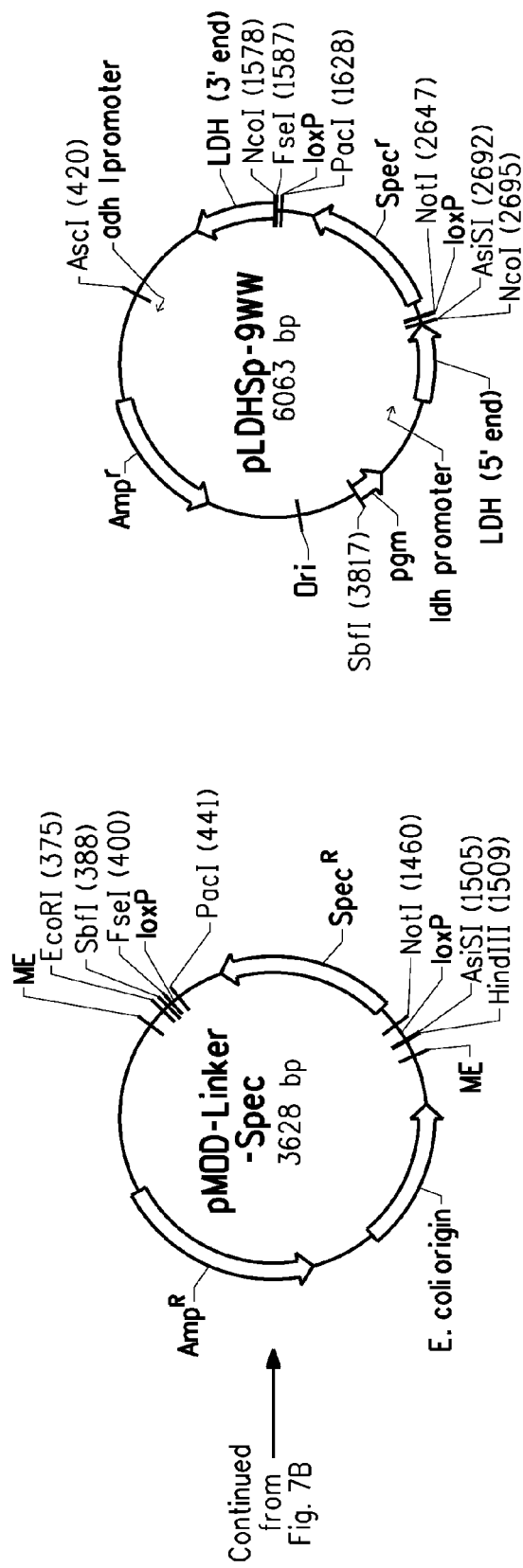

FIG. 8 shows a plasmid map of pLDHSp-9WW.

Figure 9:
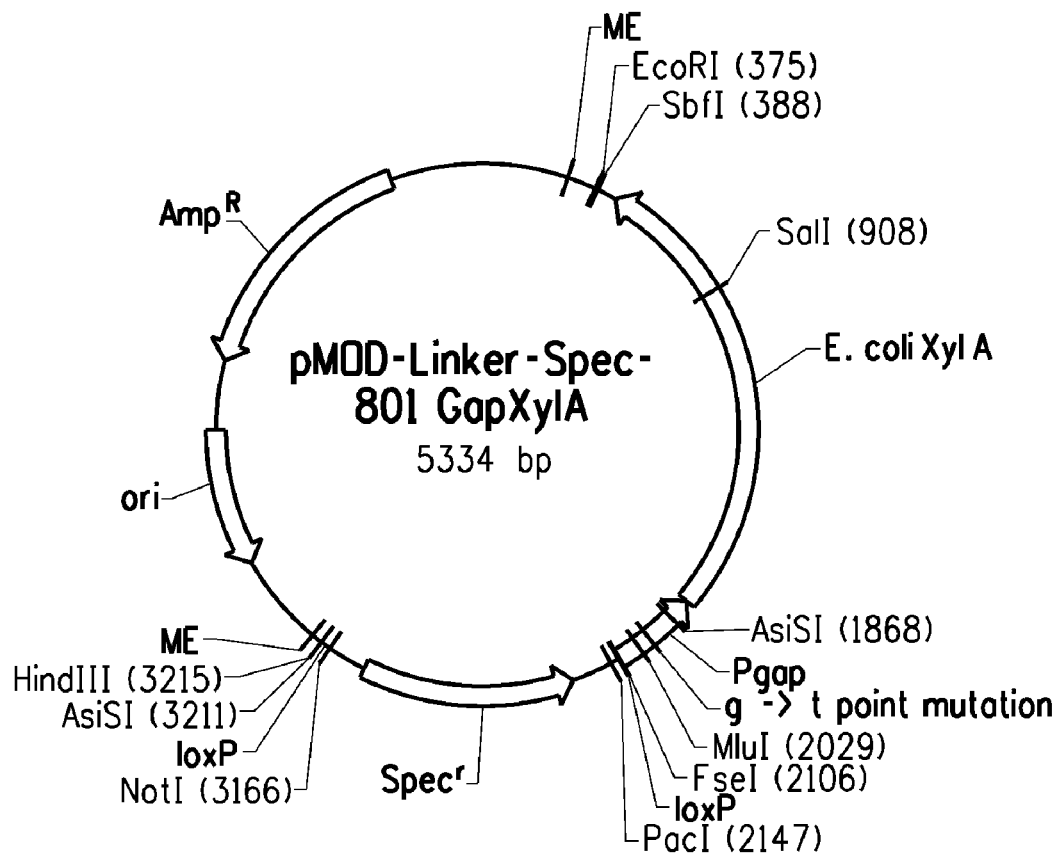

FIG. 9 shows a plasmid map of pMOD-Linker-Spec-801GapXylA.

Figure 10A:
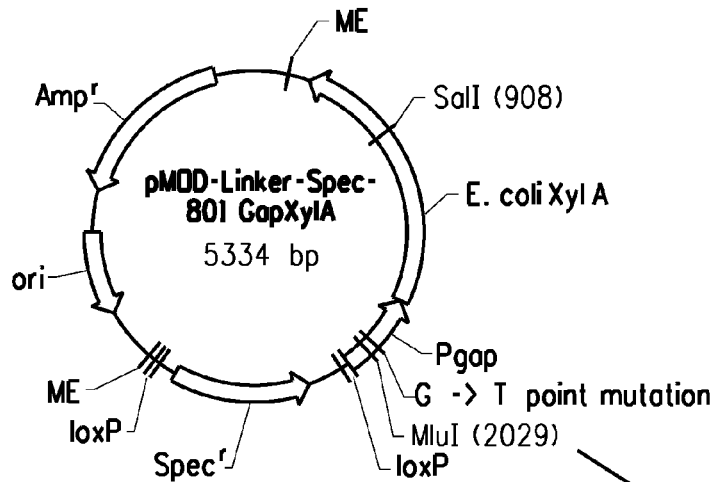
Figure 10B:
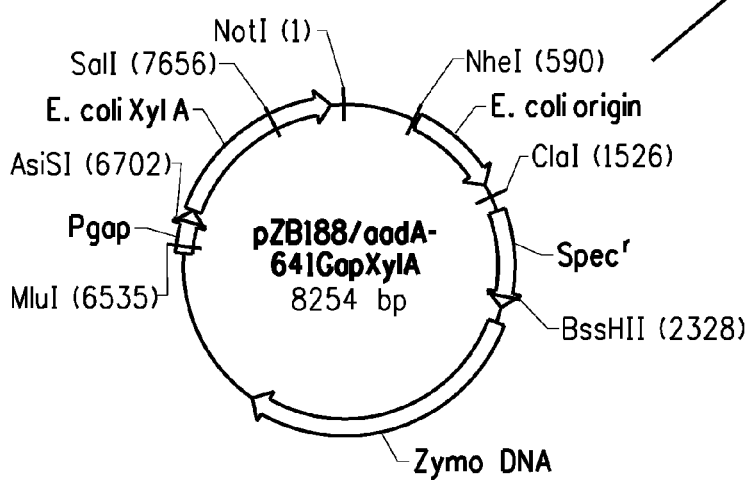

FIG. 10 shows plasmid maps of (A) pMOD-Linker-Spec-801GapXylA; (B) pZB188/aadA-GapXylA; and (C) pZB188/aadA-801GapXylA.

Figure 11:
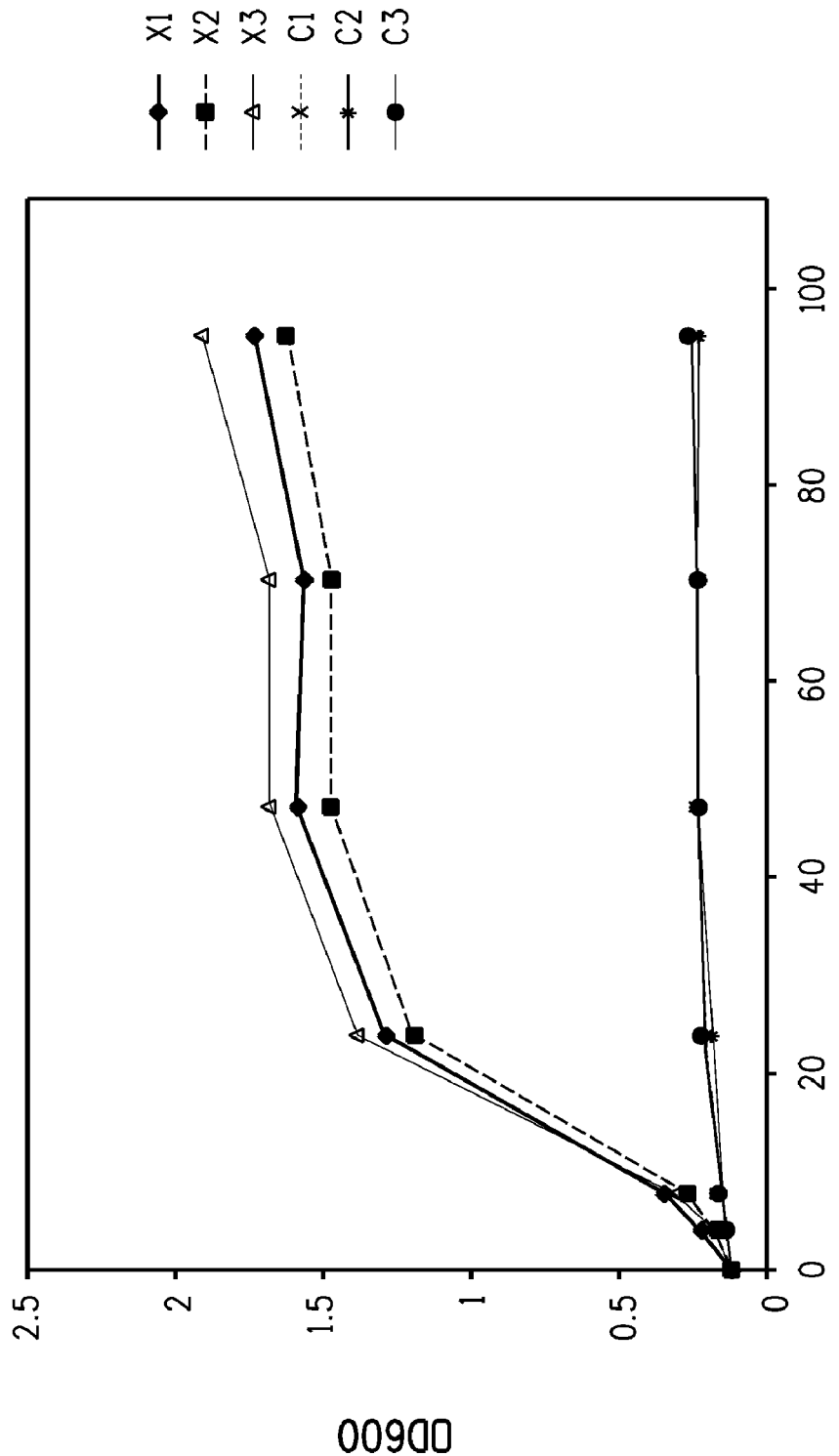

FIG. 11 shows a graph of growth curves (OD600 versus time) in xylose-containing media for the three strains that harbored the Pgap-*E. coli* xylose isomerase expression plasmid (X1, X2 and X2) and the three strains that harbored the control plasmid (C1, C2 and C3).

FIG. 12 shows graphs of growth curves (OD600 versus time) of strains ZW641, ZW658, X1 and C1 in xylose-containing media without spectinomycin plotted in (A) on a linear scale, and in (B) on a logarithmic scale.

FIG. 13 shows graphs of growth curves (OD600 versus time) of three strains with integrated 801 Pgap-XylA (#8-2, #8-4, #8-5) and of three strains with integrated 641 Pgap-XylA (#6-1, #6-3, #6-5) compared to strain ZW658, plotted in (A) on a linear scale, and in (B) on a logarithmic scale.

Table 3 is a table of the Profile HMM for xylose isomerases. Table 3 is submitted herewith electronically and is incorporated herein by reference.

The invention can be more fully understood from the following detailed description and the accompanying sequence descriptions which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the nucleotide sequence of the ZmPgap from the CP4 strain of *Z. mobilis*.

SEQ ID NO:2 is the nucleotide sequence of the ZmPgap from the ZM4 strain of *Z. mobilis*.

SEQ ID NO:3 is the nucleotide sequence of the ZmPgap from pZB4, which is also in the PgapxylAB operon of strains ZW641 and 8XL4.

SEQ ID NO:4 is the nucleotide sequence of the improved Pgap from strain ZW658.

SEQ ID NO:5 is the nucleotide sequence of the improved Pgap from strain 8b.

SEQ ID NO:6 is the nucleotide sequence of an improved Pgap with both −190 (ZW658) and −89 (8b) mutations in the pZB4 variant of Pgap.

SEQ ID NO:7 is the nucleotide sequence of an improved Pgap with the −190 mutation from ZW658 in the CP4 variant of Pgap.

SEQ ID NO:8 is the nucleotide sequence of an improved Pgap with the −89 mutation from 8b in the CP4 variant of Pgap.

SEQ ID NO:9 is the nucleotide sequence of an improved Pgap with both −190 (ZW658) and −89 (8b) mutations in the CP4 variant of Pgap.

SEQ ID NO:10 is the nucleotide sequence of an improved Pgap with the −190 mutation from ZW658 in the ZM4 variant of Pgap.

SEQ ID NO:11 is the nucleotide sequence of an improved Pgap with the −89 mutation from 8b in the ZM4 variant of Pgap.

SEQ ID NO:12 is the nucleotide sequence of an improved Pgap with both −190 (ZW658) and −89 (8b) mutations in the ZM4 variant of Pgap.

SEQ ID NOs:13 and 14 are the nucleotide sequences of primers for amplification of a DNA fragment containing the glyceraldehyde-3-phosphate dehydrogenase gene promoter (Pgap) from pZB4.

SEQ ID NOs:15 and 16 are the nucleotide sequences of primers for amplification of a DNA fragment containing a tal coding region from pZB4.

SEQ ID NOs:17 and 18 are the nucleotide sequences of primers for amplification of a DNA fragment containing Pgaptal from the Pgap and tal fragments.

SEQ ID NOs:19 and 20 are the nucleotide sequences of primers for amplification of a DNA fragment containing loxP::Cm from pZB186.

SEQ ID NO:21 is the complete nucleotide sequence for the pMODPgaptaltktCm plasmid.

SEQ ID NOs:22 and 23 are the nucleotide sequences of primers for amplification of a 3 kb DNA fragment containing tal and tkt coding regions in transformants receiving pMOD-PgaptaltktCm.

SEQ ID NO:24 is the complete nucleotide sequence for the pMODPgapxylABCm plasmid.

SEQ ID NOs:25 and 26 are the nucleotide sequences of primers for amplification of a 1.6 kb PgapxylA DNA fragment from the T2C, T3C, T4C and T5C integrants with pMODPgapxylABCm.

SEQ ID NOs:27 and 28 are the nucleotide sequences of primers for amplification of a DNA fragment containing the Pgap from ZW641 and ZW658.

SEQ ID NOs:29-31 are the nucleotide sequences for primers for sequencing the Pgap from ZW641 and ZW658.

SEQ ID NOs:32 and 33 are the nucleotide sequences of primers for amplification of a DNA fragment containing a Spec$^r$-cassette.

SEQ ID NO:34 is the complete nucleotide sequence of the xylose isomerase expression cassette PgapXylA.

SEQ ID NOs:35 and 36 are the nucleotide sequences of oligonucleotides used to substitute a different multi-cloning site in pMOD2-<MCS>.

SEQ ID NOs:37 and 38 are the nucleotide sequences of primers for amplification of the PgapxylA regions from strains ZW801-4 and ZW641 for insertion into pMOD-Linker-Spec to yield plasmids pMOD-Linker-Spec-801GapXylA and pMOD-Linker-Spec-641GapXylA, respectively.

SEQ ID NOs:39 and 40 are the nucleotide sequences of primers for amplification of a DNA fragment containing the Pgap from 8XL4 and 8b.

SEQ ID NO:41 is the complete nucleotide sequence of a primer for sequencing the Pgap from 8XL4 and 8b.

TABLE 1

Summary of protein and coding region SEQ ID Numbers for xylose isomerases

| Description | SEQ ID NO: Peptide | SEQ ID NO: Coding region |
|---|---|---|
| Xylose isomerase from *Escherichia coli* K12 | 42 | 43 |
| Xylose isomerase from *Lactobacillus brevis* ATCC 367 | 44 | 45 |
| Xylose isomerase from *Thermoanaerobacterium* | 46 | 47 |
| Xylose isomerase from *Clostridium thermosulfurogenes* | 48 | 49 |
| Xylose isomerase from *Actinoplanes Missouriensis* | 50 | 51 |
| Xylose isomerase from *Arthrobacter* Strain B3728 | 52 | 53 |
| Xylose isomerase from *Bacillus licheniformis* ATCC 14580 | 54 | 55 |
| Xylose isomerase from *Geobacillus stearothermophilus* | 56 | 57 |
| Xylose isomerase from *Bacillus coagulans* 36D1 | 58 | 59 |
| Xylose isomerase from *Bacillus subtilis* subsp. *subtilis* str. 168 | 60 | 61 |
| Xylose isomerase from *Bacteroides vulgatus* ATCC 8482 | 62 | 63 |
| Xylose isomerase from *Bifidobacterium adolescentis* ATCC 15703 | 64 | 65 |
| Xylose isomerase from *Erwinia carotovora* subsp. *atroseptica* SCRI1043 | 66 | 67 |
| Xylose isomerase from *Hordeum vulgare* subsp. *Vulgare* | 68 | 69 |
| Xylose isomerase from *Klebsiella pneumoniae* subsp. *pneumoniae* MGH 78578 | 70 | 71 |
| Xylose isomerase from *Lactococcus lactis* subsp. *Lactis* | 72 | 73 |
| Xylose isomerase from *Lactobacillus reuteri* 100-23 | 74 | 75 |
| Xylose isomerase from *Leuconostoc mesenteroides* subsp. *mesenteroides* ATCC 8293 | 76 | 77 |

TABLE 1-continued

Summary of protein and coding region SEQ ID Numbers for xylose isomerases

| Description | SEQ ID NO: Peptide | SEQ ID NO: Coding region |
|---|---|---|
| Xylose isomerase from *Thermoanaerobacterium Thermosulfurigenes* | 78 | 79 |
| Xylose isomerase from *Thermotoga Neapolitana* | 80 | 81 |
| Xylose isomerase from *Streptomyces Rubiginosus* | 82 | 83 |
| Xylose isomerase from *Streptomyces albus* | 84 | 85[1] |
| Xylose isomerase from *Thermus thermophilus* | 86 | 87 |
| Xylose isomerase from *Streptomyces diastaticus* | 88 | 89 |
| Xylose isomerase from *Streptomyces coelicolor* A3(2) | 90 | 91 |
| Xylose isomerase from *Thermus Caldophilus* | 92 | 93[2] |
| Xylose isomerase from *Xanthomonas campestris* pv. *vesicatoria* str. 85-10 | 94 | 95 |
| Xylose isomerase from *Thermus aquaticus* | 96 | 97[3] |
| Xylose isomerase from *Tetragenococcus halophilus* | 98 | 99 |
| Xylose isomerase from *Staphylococcus xylosus* | 100 | 101 |
| Xylose isomerase from *Mycobacterium smegmatis* str. MC2 155 | 102 | 103 |
| Xylose isomerase from *Piromyces* sp. E2 | 104 | 105 |

[1]This coding sequence is designed, based on the *Streptomyces rubiginosus* coding sequence, to encode the *Streptomyces albus* protein (which has three amino acid differences with the *Streptomyces rubiginosus* protein.
[2]This coding sequence is designed, based on a *Thermus thermophilus* coding sequence, to encode the *Thermus Caldophilus* protein (which has 21 amino acid differences with the *Streptomyces rubiginosus* protein.
[3]This coding sequence is from *Thermus thermophilus* and translates to the *Thermus aquaticus* protein, although the *Thermus aquaticus* coding sequence may have differences due to codon degeneracy.

TABLE 2

Summary of Gene and Protein SEQ ID Numbers for xylose utilization

| Description | SEQ ID NO: Peptide | SEQ ID NO: Coding region |
|---|---|---|
| Xylulokinase from *E. coli* | 106 | 107 |
| Xylulokinase from *Pseudomonas putida* W619 | 108 | 109 |
| Xylulokinase from *Rhizobium leguminosarum* bv. *trifolii* WSM2304 | 110 | 111 |
| Xylulokinase from *Klebsiella pneumoniae* | 112 | 113 |
| Xylulokinase from *Salmonella typhimurium* LT2 | 114 | 115 |
| Xylulokinase from *Rhodobacter sphaeroides* ATCC 17025 | 116 | 117 |
| transaldolase from *E. coli* | 118 | 119 |
| transaldolase from *Pseudomonas putida* W619 | 120 | 121 |
| transaldolase from *Rhizobium leguminosarum* bv. *trifolii* WSM2304 | 122 | 123 |
| transaldolase from *Klebsiella pneumoniae* | 124 | 125 |
| transaldolase from *Salmonella typhimurium* LT2 | 126 | 127 |
| transaldolase from *Rhodobacter sphaeroides* ATCC 17025 | 128 | 129 |
| transketolase from *E. coli* | 130 | 131 |
| transketolase from *Pseudomonas putida* W619 | 132 | 133 |
| transketolase from *Rhizobium leguminosarum* bv. *trifolii* WSM2304 | 134 | 135 |
| transketolase from *Klebsiella pneumoniae* | 136 | 137 |
| transketolase from *Salmonella typhimurium* LT2 | 138 | 139 |
| transketolase from *Rhodobacter sphaeroides* ATCC 17025 | 140 | 141 |

DETAILED DESCRIPTION OF THE INVENTION

Described herein are xylose-utilizing recombinant bacterial strains that are genetically engineered to have high expression of xylose isomerase, and a process for engineering bacteria for increased xylose isomerase expression. Expression of xylose isomerase is directed by an improved *Zymomonas mobilis* glyceraldehyde-3-phosphate dehydrogenase gene promoter (ZmPgap) that has at least one mutation which makes it a stronger promoter. The ZmPgap has a mutation at the −190 position, the −89 position, or both positions, with respect to the natural ATG translation initiation codon for glyceraldehyde-3-phosphate dehydrogenase in the CP4 and ZM4 strains of *Z. mobilis* (CP4 strain ZmPgap: SEQ ID NO:1 and ZM4 strain ZmPgap: SEQ ID NO:2). Xylose-utilizing recombinant bacterial strains described herein have improved fermentation on xylose-containing media. Bacteria producing ethanol or other products that are engineered as described herein may be used for increased production when grown in xylose-containing medium. For example, increased amounts of ethanol may be obtained from an ethanolagen such as *Zymomonas* that is engineered as described herein, which may be used as an alternative energy source to fossil fuels.

The following abbreviations and definitions will be used for the interpretation of the specification and the claims.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

"Gene" refers to a nucleic acid fragment that expresses a specific protein or functional RNA molecule, which may include regulatory sequences preceding (5' non-coding sequences) and following (3' non-coding sequences) the coding sequence. "Native gene" or "wild type gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes.

The term "genetic construct" refers to a nucleic acid fragment that encodes for expression of one or more specific proteins or functional RNA molecules. In the gene construct the gene may be native, chimeric, or foreign in nature. Typically a genetic construct will comprise a "coding sequence". A "coding sequence" refers to a DNA sequence that encodes a specific amino acid sequence.

"Promoter" or "Initiation control regions" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters".

The term "expression", as used herein, refers to the transcription and stable accumulation of coding (mRNA) or functional RNA derived from a gene. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts or fragments capable of suppressing the expression of identical or substantially similar foreign or endogenous genes (U.S. Pat. No. 5,231,020).

The term "messenger RNA (mRNA)" as used herein, refers to the RNA that is without introns and that can be translated into protein by the cell.

The term "transformation" as used herein, refers to the transfer of a nucleic acid fragment into a host organism, resulting in genetically stable inheritance. The transferred nucleic acid may be in the form of a plasmid maintained in the host cell, or some transferred nucleic acid may be integrated into the genome of the host cell. Host organisms containing the transformed nucleic acid fragments are referred to as "transgenic" or "recombinant" or "transformed" organisms.

The terms "plasmid" and "vector" as used herein, refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "selectable marker" means an identifying factor, usually an antibiotic or chemical resistance gene, that is able to be selected for based upon the marker gene's effect, i.e., resistance to an antibiotic, wherein the effect is used to track the inheritance of a nucleic acid of interest and/or to identify a cell or organism that has inherited the nucleic acid of interest.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

The term "Z. mobilis glyceraldehyde-3-phosphate dehydrogenase gene promoter" and "ZmPgap" refer to a nucleic acid molecule with promoter activity that has a base sequence that naturally occurs upstream of the glyceraldehyde-3-phosphate dehydrogenase coding region in the Z. mobilis genome. These terms refer to the promoters of strains of Z. mobilis such as the CP4 and ZM4 strains (SEQ ID NOs:1 and 2, respectively) and to variants in sequence and/or length that direct expression at a level that is not substantially different, such as the ZmPgap of pZB4 (SEQ ID NO:3).

The term "heterologous" means not naturally found in the location of interest. For example, a heterologous gene refers to a gene that is not naturally found in the host organism, but that is introduced into the host organism by gene transfer. For example, a heterologous nucleic acid molecule that is present in a chimeric gene is a nucleic acid molecule that is not naturally found associated with the other segments of the chimeric gene, such as the nucleic acid molecules having the coding region and promoter segments not naturally being associated with each other.

As used herein, an "isolated nucleic acid molecule" is a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, 2$^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Altschul, S. F., et al., J. Mol. Biol., 215:403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular fungal proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine.

The terms "homology" and "homologous" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that homologous nucleic acid sequences encompassed by this invention are also defined by their ability to hybridize, under moderately stringent conditions (e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (described by Higgins and Sharp, *CABIOS.* 5:151-153 (1989); Higgins, D. G. et al., *Comput. Appl..,* 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS.* 5:151-153 (1989); Higgins, D. G. et al., *Comput. Appl. Biosci.* 8:189-191 (1992)) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

It is well understood by one skilled in the art that many levels of sequence identity are useful in identifying polypeptides, from other species, wherein such polypeptides have the same or similar function or activity. Useful examples of percent identities include, but are not limited to: 24%, 30%, 35%, 40%, 45%, 50%, 55%, 60%, 65%, 70%, 75%, 80%, 85%, 90%, or 95%, or any integer percentage from 24% to 100% may be useful in describing the present invention, such as 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., J. Mol. Biol., 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, Comput. Methods Genome Res., [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used here are well known in the art and are described by Sambrook, J., Fritsch, E. F. and Maniatis, T. *Molecular Cloning: A Laboratory Manual*, $2^{nd}$ ed.; Cold Spring Harbor Laboratory Cold Spring Harbor, N.Y., 1989 (hereinafter "Maniatis"); and by Silhavy, T. J., Bennan, M. L. and Enquist, L. W. *Experiments with Gene Fusions*; Cold Spring Harbor Laboratory: Cold Spring Harbor, N.Y., 1984; and by Ausubel, F. M. et al., In *Current Protocols in Molecular Biology*, published by Greene Publishing and Wiley-Interscience, 1987.

Discovery of Improved *Z. mobilis* Glyceraldehyde-3-Phosphate Dehydrogenase Gene Promoters The promoter of the *Z. mobilis* glyceraldehyde-3-phosphate dehydrogenase gene (ZmPgap or Pgap) has been used for expression of chimeric genes in *Zymomonas mobilis* and *Zymobacter palmae*. When this promoter has been used to express genes for xylose metabolism, the resulting xylose utilization typically has not been as effective as desired. A recombinant *Z. mobilis* strain engineered to express the four xylose metabolism enzymes (xylose isomerase, xylulokinase, transketolase, and transaldolase) with limited xylose utilizing ability was further adapted on xylose medium for improved xylose utilization (described in commonly owned and co-pending U.S. App. Publication No. US20080286870).

Applicants have discovered, as described in Example 3 herein, that the improved xylose-utilizing strain called ZW658 (ATCC # PTA-7858) has increased expression of the xylose isomerase and xylulokinase enzymes that were integrated into the genome as an operon expressed from ZmPgap (PgapxylAB operon). Applicants have further discovered that there is a single new nucleotide change in the promoter of the PgapxylAB operon that is responsible for the promoter directing increased expression of operably linked coding regions. The nucleotide change is new with respect to the sequence of the Pgap of the PgapxylAB operon in strain ZW658 as compared to the sequence of the ZmPgap of the PgapxylAB operon in a precursor strain to ZW658 that did not have increased xylose isomerase and xylulokinase activities. Thus the Pgap having this single nucleotide change is an improved promoter.

Applicants have in addition discovered that a *Z. mobilis* strain that was separately engineered with the genes encoding the four xylose utilization enzymes and separately adapted for improved xylose utilization (strain 8b, described in U.S. Pat. No. 7,223,575) also has increased expression of the xylose isomerase and xylulokinase enzymes that were integrated into the genome as a PgapxylAB operon. Applicants have further discovered that there is a single new nucleotide change in the Pgap of the PgapxylAB operon in the 8b strain that is at a different position than the nucleotide change of the ZW658 Pgap. Based on the increased expression of the xylose isomerase and xylulokinase enzymes encoded by the PgapxylAB operon, the mutant Pgap of the PgapxylAB operon also provides an improved promoter.

The identified new nucleotide changes in the Pgap of the ZW658 and 8b strain PgapxylAB operons are at positions −190 and −89, respectively, with respect to the natural ATG translation initiation codon for glyceraldehyde-3-phosphate dehydrogenase in the CP4 and ZM4 strains of *Z. mobilis*. The discovered nucleotide change at position −190 is from G to T, and at position −89 is from C to T.

The sequence context of the base changes are the important factor, as the position number may change due to sequence variations.

The −190 position is in the sequence context:
AACGGTATACT
GGAATAAATGGTCTTCGTTATGGTATTGATGTTTTT,
which is a portion of ZmPgap of CP4, ZM4, and pZB4 with SEQ ID NOs:1, 2, and 3, respectively,
where the bold and underlined G is the base changed to T by the mutation. This position is −190 in the ZmPgap sequence of the CP4 and ZM4 strains, but position −189 in pZB4 since in the promoter sequence in pZB4 there is a deletion of T at position −21.

The −89 position is in the sequence context:
CGGCATCACGAA
CAAGGTGTTGGCCGCGATCGCCGGTAAGTCGGC,
which is a portion of ZmPgap of CP4, ZM4, and pZB4 with SEQ ID NOs:1, 2, and 3, respectively,
where the bold and underlined C is the base changed to T by the mutation. This position is −89 in the ZmPgap sequence of the CP4 and ZM4 strains, but position −88 in pZB4 since in the promoter sequence in pZB4 there is a deletion of T at position −21. Promoters of the present invention have a nucleotide change in ZmPgap at position −190, at position −89, or at both of these positions. Preferably the changes are a G to T change at position −190 and a C to T change at position −89. The present promoters comprising these modifications are improved Pgaps.

Changes to other nucleotides at the −190 and −89 positions may provide improved activity of ZmPgap. In addition, nucleotide changes at other positions within ZmPgap may provide improved activity of ZmPgap.

The naturally occurring sequence of ZmPgap is not a single sequence, but may have some variation in sequence that has no substantial effect on promoter function. Having no substantial effect on promoter function means that the promoter sequence directs an expression level that is substantially similar to the level of expression directed by a ZmPgap present in a natural *Zymomonas mobilis* strain. Variation in sequence may naturally occur between different isolates or strains of *Zymomonas mobilis*, such as the difference between the CP4 and ZM4 strains at position −29 with respect to the natural ATG translation initiation codon for glyceraldehyde-3-phosphate dehydrogenase (SEQ ID NOs:1 and 2, respectively), where in CP4 there is an A and in ZM4 there is a G.

In addition to naturally occurring sequence variations, nucleotide changes that do not substantially affect function may occur during routine manipulation procedures including PCR, cloning, transformation, and strain growth as is known to one skilled in the art. An example is the ZmPgap of pZB4, which has a deletion of T at position −21.

Any nucleotide changes in the ZmPgap sequence, occurring in different natural or engineered strains, that do not substantially affect promoter function, may be present in the sequence of a *Z. mobilis* glyceraldehyde-3-phosphate dehydrogenase gene promoter such as the deletion of a T after position −21 that is in the ZmPgap of pZB4 (SEQ ID NO:3). Thus the mutations at positions −190 and −89 described above that do affect promoter function, that is, that substantially improve promoter function, may be made in any of the ZmPgap sequences with substantially similar activity (natural level) and can co-occur with variations not affecting function.

Examples of improved Pgap sequences with the described mutations at positions −190 and/or −89 include the promoter sequence from strain ZW658 (SEQ ID NO:4), from strain 8b (SEQ ID NO:5), and a double mutation of the same ZmPgap variant which is from pZB4 (SEQ ID NO:6). Additional examples of improved Pgap sequences are the −190. −89, or double mutation in the ZmPgap variant from CP4 (SEQ ID NOs:7, 8, and 9, respectively) and the −190. −89, or double mutation in the ZmPgap variant from ZM4 (SEQ ID NOs:10, 11, and 12, respectively).

In addition, variations in the length of the ZmPgap occur that do not substantially affect promoter function. The present invention includes improved Pgaps having the described mutations at position −190 and/or −90 (with respect to the natural ATG translation initiation codon for glyceraldehyde-3-phosphate dehydrogenase in the CP4 and ZM4 strains of *Z.*

*mobilis*) in ZmPgaps of varying length that have no substantial change in activity prior to addition of the −190 and/or −89 mutations.

Preparing an Improved Pgap

The described mutations at positions −190 and/or −89 may be introduced into a ZmPgap nucleic acid molecule by any method known to one skilled in the art. For example, an oligonucleotide having the mutation and surrounding DNA sequence may be synthesized and cloned into a larger promoter DNA fragment, substituting for a segment without the mutation. Primers containing the mutation and some adjacent promoter sequence may be synthesized and used in PCR to prepare the promoter fragment. An entire promoter DNA fragment may be synthesized as multiple oligonucleotides that are ligated together. Site-directed mutagenesis may be used to introduce the mutation(s). In addition, the mutant promoters may be prepared as PCR amplified DNA fragments using DNA from the ZW658 or 8b strain as template.

Expression of Xylose Isomerase Using Improved Pgap

A promoter described herein may be operably linked to a heterologous nucleic molecule that encodes xylose isomerase for directing increased expression of xylose isomerase, as compared to expression from the ZmPgap. The improved Pgap and xylose isomerase coding region form a chimeric gene, which also generally includes a 3' termination control region. Termination control regions may be derived from various genes, and are often taken from genes native to a target host cell. The construction of chimeric genes is well known in the art.

Any xylose isomerase coding region may be used in a chimeric gene to express xylose isomerase from an improved Pgap in the present invention. Xylose isomerase enzymes belong to the group EC5.3.1.5. Examples of suitable xylose isomerase proteins and encoding sequences that may be used are given in Table 1. Particularly suitable examples are those from *E. coli* (SEQ ID NO:42 and 43, respectively), and *Lactobacillus brevis* (SEQ ID NO:44 and 45, respectively).

Many other examples of xylose isomerase proteins and encoding sequences are identified in the literature and in bioinformatics databases well known to the skilled person. Additionally, the encoding sequences described herein or those recited in the art may be used to identify other homologs in nature. For example each of the xylose isomerase encoding nucleic acid fragments described herein may be used to isolate genes encoding homologous proteins from the same or other microbial species. Isolation of homologous genes using sequence-dependent protocols is well known in the art.

Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci.* USA 82:1074 (1985); or strand displacement amplification (SDA), Walker, et al., *Proc. Natl. Acad. Sci. U.S.A.,* 89:392 (1992)]; and 3.) methods of library construction and screening by complementation.

For example, sequences encoding similar proteins or polypeptides to the xylose isomerase coding regions described herein could be isolated directly by using all or a portion of the instant nucleic acid fragments as DNA hybridization probes to screen libraries from any desired bacteria using methodology well known to those skilled in the art. Specific oligonucleotide probes based upon the disclosed nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the described sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the described nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (e.g., BRL, Gaithersburg, Md.), specific 3' or 5' cDNA fragments can be isolated (Ohara et al., *PNAS USA* 86:5673 (1989); Loh et al., *Science* 243:217 (1989)).

Alternatively, these xylose isomerase encoding sequences may be employed as hybridization reagents for the identification of homologs. The basic components of a nucleic acid hybridization test include a probe, a sample suspected of containing the gene or gene fragment of interest, and a specific hybridization method. Probes are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined and known in the art. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide and cesium trifluoroacetate, among others. Typically, the chaotropic agent will be present at a final concentration of about 3 M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Bioinformatic Approaches

Alternatively, because xylose isomerase proteins are so well known and abundant, additional xylose isomerase proteins may be identified on the basis of catalytic site residues and a Profile Hidden Markov Model (HMM) constructed using the Pfam (*Pfam: clans, web tools and services*: R. D. Finn, J. Mistry, B. Schuster-Bockler, S. Griffiths-Jones, V. Hollich, T. Lassmann, S. Moxon, M. Marshall, A. Khanna, R. Durbin, S. R. Eddy, E. L. L. Sonnhammer and A. Bateman, Nucleic Acids Research (2006) Database Issue 34:D247-D251) identified family of xylose isomerase proteins.

The Profile HMM is prepared using the hmmsearch algorithm of the HMMER software package (Janelia Farm Research Campus, Ashburn, Va.). The theory behind Profile HMMs is described in Durbin et al. ((1998) *Biological sequence analysis: probabilistic models of proteins and nucleic acids*, Cambridge University Press) and Krogh et al. ((1994) J. Mol. Biol. 235:1501-1531), which characterizes a set of proteins based on the probability of each amino acid occurring at each position in the alignment of the proteins of the set.

A Profile HMM for xylose isomerases prepared using 32 xylose isomerase protein sequences with experimentally verified function as referenced in the BRENDA database provides a basis for identification of xylose isomerases. BRENDA is a human-curated database that contains detailed information about enzyme kinetic, physical, and biochemical properties extracted from the experimental literature and with links to the relevant databases (Cologne University Bioinformatics Center). The SEQ ID NOs for these 32 proteins are given in Table 1. Using these 32 protein sequences a multiple sequence alignment (MSA) was built using ClustalW with default parameters. The MSA results were used as input data to prepare the Profile HMM that is given in Table 3. In the table, the amino acids are represented by the one letter code. The first line for each position reports the match emission scores: probability for each amino acid to be in that state (highest score is highlighted). The second line reports the insert emission scores, and the third line reports on state transition scores: M→M, M→I, M→D; I→M, I→I; D→M, D→D; B→M; M→E.

In addition to the Profile HMM, four catalytic site amino acids are characteristic of xylose isomerases: histidine 54, aspartic acid 57, glutamic acid 181, and lysine 183, with the position numbers in reference to the *Streptomyces albus* xylose isomerase sequence. Any protein fitting the xylose isomerase Profile HMM with an Evalue <or $=3 \times 10^{-10}$ and having these four catalytic site residues is a xylose isomerase whose coding region may be constructed in a chimeric gene comprising an improved Pgap and transformed into a bacterial strain as described herein. Currently 251 proteins in the Gen Bank sequence database, reduced to a 90% non-redundancy level, match these criteria. These sequences will not all be presented herein with SEQ ID NOs as they can be readily identified by one skilled in the art. Additional sequences fitting these criteria that become available may also be used as described herein.

As known in the art, there may be variations in DNA sequences encoding an amino acid sequence due to the degeneracy of the genetic code. Codons may be optimized for expression of an amino acid sequence in a target host cell to provide for optimal encoded expression.

Engineering Bacterial Cells for Xylose Isomerase Expression

The chimeric genes described herein are typically constructed in or transferred to a vector for further manipulations. Vectors are well known in the art. Certain vectors are capable of replicating in a broad range of host bacteria and can be transferred by conjugation. The complete and annotated sequence of pRK404 and three related vectors: pRK437, pRK442, and pRK442(H) are available. These derivatives have proven to be valuable tools for genetic manipulation in gram-negative bacteria (Scott et al., *Plasmid* 50(1):74-79 (2003)).

Other well-known vectors may be used in different target host cells. Examples of vectors useful for different hosts are described in co-owned and co-pending U.S. App. Pub. No. US20070092957 A1, pp 11-13, which is hereby incorporated herein by reference. Particularly useful for expression in Zymomonas are vectors that can replicate in both *E. coli* and Zymomonas, such as pZB188 which is described in U.S. Pat. No. 5,514,583. Vectors may include plasmids for autonomous replication in a cell, and plasmids for carrying constructs to be integrated into bacterial genomes. Plasmids for DNA integration may include transposons, regions of nucleic acid sequence homologous to the target bacterial genome, or other sequences supporting integration. An additional type of vector may be a transposome produced using, for example, a system that is commercially available from EPICENTRE®. It is well known how to choose an appropriate vector for the desired target host and the desired function.

Bacterial cells may be engineered by introducing a vector having a chimeric gene comprising an improved Pgap and operably linked xylose isomerase coding region by well known methods, such as using freeze-thaw transformation, calcium-mediated transformation, electroporation, or conjugation. Any bacterial cell to be engineered for xylose utilization by expressing a xylose isomerase enzyme is a target host cell for transformation to engineer a strain as described herein. Particularly suitable host cells are Zymomonas and Zymobacter. The introduced chimeric gene may be maintained in the cell on a stably replicating plasmid, or integrated into the genome following introduction.

For engineering a strain with an integrated improved Pgap-xylose isomerase chimeric gene in the bacterial cell genome, methods may be used that are well known in the art such as homologous recombination, transposon insertion, or transposome insertion. In homologous recombination, DNA sequences flanking a target integration site are placed bounding a spectinomycin-resistance gene or other selectable marker, and the improved Pgap-xylose isomerase chimeric gene leading to insertion of the selectable marker and the improved Pgap-xylose isomerase chimeric gene into the target genomic site. In addition, the selectable marker may be bounded by site-specific recombination sites, so that after expression of the corresponding site-specific recombinase, the resistance gene is excised from the genome. Particularly suitable for integration of the improved Pgap-xylose isomerase chimeric gene is transposition using EPICENTRE®'s EZ::Tn in vitro transposition system, which is used here in Examples 1 and 6.

Xylose Isomerase Activity

In the strains described herein, xylose isomerase activity levels are higher than previously described in the art. These strains are engineered to express xylose isomerase at a level to produce at least about 0.1 μmoles product/mg protein/minute, as determined by reacting 20 μL of cell free extract in a reaction mix, at 30° C., comprising 0.256 mM NADH, 50 mM xylose, 10 mM MgSO$_4$, 10 mM triethanolamine, and 1 U/ml sorbitol dehydrogenase, wherein D-xylulose is the product. Strains may express xylose isomerase at a level to produce at least about 0.14, 0.2, or 0.25 μmoles product/mg protein/minute. High expression promoters with the improved Pgap described herein may be used to express a xylose isomerase coding region to obtain these enzyme activity levels. The high xylose isomerase activity levels in the presence of three additional xylose metabolic pathway enzyme activities described below provides a strain with improved growth on xylose-containing medium.

Engineering of Full Xylose Utilization Pathway

In addition to transforming with a chimeric gene comprising an improved Pgap and xylose isomerase coding region, bacterial strains are also engineered for expression of the three other enzymes needed for xylose utilization: xylulokinase, transaldolase and transketolase, as described in U.S. Pat. No. 5,514,583, U.S. Pat. No. 5,712,133, U.S. Pat. No. 6,566,107, WO 95/28476, Feldmann et al. ((1992) Appl Microbiol Biotechnol 38: 354-361), Zhang et al. ((1995) Science 267:240-243)), and Yanase et al. ((2007) Appl. Environ. Mirobiol. 73:2592-2599).

The presence of genes encoding all four enzymes is known to complete the xylose utilization pathway to produce xylose-utilizing strains. The additional three enzymes may be expressed from individual chimeric genes or from operons including more than one coding region.

Chimeric genes may be constructed by operably linking a promoter, coding region, and a 3' termination control region as described above for a xylose isomerase chimeric gene. The promoter is chosen as one that is active in the target host cell, as well known in the art. Promoters that may be used in Zymomonas and Zymobacter include ZmPgap and the promoter of the Zymomonas enolase gene. Coding regions for xylulokinase, transaldolase and transketolase may be from any Gram-negative bacterium capable of utilizing xylose, for example Xanthomonas, Klebsiella, Escherichia, Rhodobacter, Flavobacterium, Acetobacter, Gluconobacter, Rhizobium, Agrobacterium, Salmonella, and Pseudomonas. Examples of protein sequences and their encoding region sequences that may be used are given in Table 2. Preferred are the sequences encoding xylulokinase, transaldolase and transketolase enzymes from E. coli (SEQ ID NOs:107, 119, and 131, respectively). These sequences may also be used to identify additional encoding sequences, as described above for xylose isomerase, that may be used to express the complete xylose utilization pathway.

In addition, bioinformatics methods including Pfam protein families and Profile HMMs as described above for xylose isomerase may be applied to identifying xylulokinase, transaldolase and transketolase enzymes. Sequences encoding these enzyme may have diversity due to codon degeneracy and may be codon optimized for expression in a specific host, also as described above.

Operons may be constructed for expression of xylulokinase, transaldolase and transketolase. One or more of the encoding sequences may be operably linked with the xylose isomerase coding region expressed from an improved Pgap, forming an operon. Typically xylose isomerase and xylulokinase are expressed in one operon, and transaldolase and transketolase are expressed in a second operon, as described in Example 1 herein.

These enzymes may be expressed from chimeric genes or operons located on stably replicating plasmids, or integrated into the genome.

Improved Growth of Bacterial Strains Having Improved Pgap-Xylose Isomerase Chimeric Gene A xylose-utilizing bacterial strain described herein having an improved Pgap-xylose isomerase chimeric gene, for example a Zymomonas mobilis strain, shows improved growth in a medium containing xylose in the absence or presence of other sugars ("mixed sugars"). The mixed sugars include at least one additional sugar to xylose. Any sugar that may provide an energy source for metabolism of the cells, or any sugar that is present in a mixture containing xylose may be included. It is desirable to grow strains of the present invention on sugars that are produced from biomass saccharification. Typically biomass is pretreated, for example as described in Patent Application WO2004/081185 and in co-owned and co-pending U.S. application 60/670,437, and then treated with saccharification enzymes as reviewed in Lynd, L. R., et al. (Microbiol. Mol. Biol. Rev. (2002) 66:506-577). Biomass saccharification produces sugars that may typically include a mixture of xylose with glucose, fructose, sucrose, galactose, mannose, and/or arabinose.

For maximal production and efficiency of fermentation it is desirable to grow a strain described herein in medium containing high levels of sugars, including xylose. This allows the direct use of biomass saccharification sugars, or use with little dilution, thereby reducing fermentation volumes, which is desirable for commercial scale production, such as of ethanol. High sugars concentrations are used so that greater concentrations of product, such as ethanol, may be produced. The mixed sugars concentration in the fermentation medium is typically between about 120 g/L and up to about 300 g/L, more typically between about 150 g/L and about 235 g/L.

In the high concentration mixed sugars conditions desired for commercial production, such as of ethanol, sorbitol may be included in the fermentation medium. Sorbitol (D-sorbitol and/or L-sorbitol) may be present in the medium at concentrations that are between about 2 mM and 200 mM, typically between about 2 mM and 100 mM, or between 5 mM and 20 mM as described in commonly owned and co-pending US Application Publication # 20080286870. Mannitol, galactitol or ribitol may be used in the medium instead of sorbitol, or in combination with sorbitol, as described in commonly owned and co-pending U.S. App. Pub. No. US20080081358.

Under fermentation conditions in xylitol medium, a strain described herein having an improved Pgap-xylose isomerase chimeric gene has improved growth over a strain with xylose isomerase expressed from a ZmPgap. The exact improvement will vary depending on the strain background, medium used, and general growth conditions. For example, when grown in media containing 50 g/L xylose, after one hour strains with the improved Pgap-xylose isomerase chimeric gene grew to an OD600 of between about two and five times higher than that of strains without the improved Pgap, as shown in Example 8, FIG. 13A, herein.

Fermentation of Improved Xylose-Utilizing Strain

An engineered xylose-utilizing strain with an improved Pgap-xylose isomerase chimeric gene and genes or operons for expression of xylulokinase, transaldolase and transketolase may be used in fermentation to produce a product that is a natural product of the strain, or a product that the strain is engineered to produce. For example, *Zymomonas mobilis* and *Zymobacter palmae* are natural ethanolagens. As an example, production of ethanol by a *Z. mobilis* strain of the invention is described.

For production of ethanol, recombinant xylose-utilizing *Z. mobilis* having an improved Pgap-xylose isomerase chimeric gene is brought in contact with medium that contains mixed sugars including xylose. When the mixed sugars concentration is high such that growth is inhibited, the medium includes sorbitol, mannitol, or a mixture thereof. Galactitol or ribitol may replace or be combined with sorbitol or mannitol. The *Z. mobilis* grows in the medium where fermentation occurs and ethanol is produced. The fermentation is run without supplemented air, oxygen, or other gases (which may include conditions such as anaerobic, microaerobic, or microaerophilic fermentation), for at least about 24 hours, and may be run for 30 or more hours. The timing to reach maximal ethanol production is variable, depending on the fermentation conditions. Typically, if inhibitors are present in the medium, a longer fermentation period is required. The fermentations may be run at temperatures that are between about 30° C. and about 37° C., at a pH of about 4.5 to about 7.5.

The present *Z. mobilis* may be grown in medium containing mixed sugars including xylose in laboratory scale fermenters, and in scaled up fermentation where commercial quantities of ethanol are produced. Where commercial production of ethanol is desired, a variety of culture methodologies may be applied. For example, large-scale production from the present *Z. mobilis* strains may be produced by both batch and continuous culture methodologies. A classical batch culturing method is a closed system where the composition of the medium is set at the beginning of the culture and not subjected to artificial alterations during the culturing process. Thus, at the beginning of the culturing process the medium is inoculated with the desired organism and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable for growth of the present *Z. mobilis* strains and comprise a typical batch system with the exception that the substrate is added in increments as the culture progresses. Fed-Batch systems are useful when catabolite repression is apt to inhibit the metabolism of the cells and where it is desirable to have limited amounts of substrate in the medium. Measurement of the actual substrate concentration in Fed-Batch systems is difficult and is therefore estimated on the basis of the changes of measurable factors such as pH and the partial pressure of waste gases such as $CO_2$. Batch and Fed-Batch culturing methods are common and well known in the art and examples may be found in Biotechnology: A Textbook of Industrial Microbiology, Crueger, Crueger, and Brock, Second Edition (1989) Sinauer Associates, Inc., Sunderland, Mass., or Deshpande, Mukund V., *Appl. Biochem. Biotechnol.*, 36, 227, (1992), herein incorporated by reference.

Commercial production of ethanol may also be accomplished with a continuous culture. Continuous cultures are open systems where a defined culture medium is added continuously to a bioreactor and an equal amount of conditioned medium is removed simultaneously for processing. Continuous cultures generally maintain the cells at a constant high liquid phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials as is known to one skilled in the art.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by medium turbidity, is kept constant. Continuous systems strive to maintain steady state growth conditions and thus the cell loss due to medium being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Particularly suitable for ethanol production is a fermentation regime as follows. The desired *Z. mobilis* strain of the present invention is grown in shake flasks in semi-complex medium at about 30° C. to about 37° C. with shaking at about 150 rpm in orbital shakers and then transferred to a 10 L seed fermentor containing similar medium. The seed culture is grown in the seed fermentor anaerobically until $OD_{600}$ is between 3 and 6, when it is transferred to the production fermentor where the fermentation parameters are optimized for ethanol production. Typical inoculum volumes transferred from the seed tank to the production tank range from about 2% to about 20% v/v. Typical fermentation medium contains minimal medium components such as potassium phosphate (1.0-10.0 g/l), ammonium sulfate (0-2.0 g/l), magnesium sulfate (0-5.0 g/l), a complex nitrogen source such as yeast extract or soy based products (0-10 g/l). A final concentration of about 5 mM sorbitol or mannitol is present in the medium. Mixed sugars including xylose and at least one additional sugar such as glucose (or sucrose), providing a carbon source, are continually added to the fermentation vessel on depletion of the initial batched carbon source (50-200 g/l) to maximize ethanol rate and titer. Carbon source feed rates are adjusted dynamically to ensure that the culture is not accumulating glucose in excess, which could lead to build up of toxic byproducts such as acetic acid. In order to maximize yield of ethanol produced from substrate utilized, biomass growth is restricted by the amount of phosphate that is either batched initially or that is fed during the course of the fermentation. The fermentation is controlled at pH 5.0-6.0 using caustic solution (such as ammonium hydroxide, potassium hydroxide, or sodium hydroxide) and either sulfuric or phosphoric acid. The temperature of the fermentor is controlled at 30° C.-35° C. In order to minimize foaming, antifoam agents (any class-silicone based, organic based etc) are added to the vessel as needed. An antibiotic, for which there is an antibiotic resistant marker in the strain, such as kanamycin, may be used optionally to minimize contamination.

Any set of conditions described above, and additionally variations in these conditions that are well known in the art, are suitable conditions for production of ethanol by a xylose-utilizing recombinant *Zymomonas* strain.

EXAMPLES

The Examples illustrate the inventions described herein.
General Methods

Standard recombinant DNA and molecular cloning techniques used here are well known in the art and are described by Sambrook, J., Fritsch, E. F. and Maniatis, T., *Molecular Cloning: A Laboratory Manual*, 2$^{nd}$ ed., Cold Spring Harbor Laboratory: Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

The meaning of abbreviations is as follows: "kb" means kilobase(s), "bp" means base pairs, "nt" means nucleotide(s), "hr" means hour(s), "min" means minute(s), "sec" means second(s), "d" means day(s), "L" means liter(s), "ml" means milliliter(s), "μL" means microliter(s), "μg" means microgram(s), "ng" means nanogram(s), "mM" means millimolar, "μM" means micromolar, "nm" means nanometer(s), "μmol" means micromole(s), "pmol" means picomole(s), "Cm" means chloramphenicol, "Cm$^r$" means chloramphenicol resistant, "Cm$^s$" means chloramphenicol sensitive, "Sp$^r$" means spectinomycin resistance, "Sp$^s$" means spectinomycin sensitive, "XI" is xylose isomerase, "XK" is xylulokinase, "TAL" is transaldolase, "TKT" is transketolase, "EFT" means elapsed fermentation time, "RM" means rich medium containing 10 g/L yeast extract plus 2 g/L $KH_2PO_4$, "MM" means mating medium containing 10 g/L yeast extract, 5 g/L tryptone, 2.5 g/L $(NH_4)_2SO_4$ and 0.2 g/L $KH_2PO_4$.

Preparation of Cell-Free Extracts of *Zymomonas* for Enzymatic Assays

Cells were grown in 50 ml of RM+2% glucose at 30° C. overnight to an $OD_{600}$ of 1.0-1.2. Cells were harvested by centrifugation at 4500 rpm for 10 min at 4° C. The supernatant was discarded and the cell pellet washed with 25 ml ice-cold sonication buffer (10 mM Tris, pH 7.6, 10 mM $MgCl_2$), followed by centrifugation at 4500 rpm for 10 min. The pellet was resuspended in 2.0-2.5 ml sonication buffer plus 1 mM dithiothreitol. A 500 μL aliquot was centrifuged for 1 min in an eppendorf centrifuge at 4° C. Most of supernatant was discarded, leaving about 10-20 μL behind to keep the pellet from drying out. The cells were frozen and stored at about 80° C. until assayed. Prior to assay, the cells were thawed and resuspended with 500 μL of sonication buffer plus 1 mM dithiothreitol. The mix was sonicated 2× for 45 seconds at 62% duty cycle and an output control of 2 using a Branson sonifier 450, letting samples cool about 3-5 min between sonications. Samples were centrifuged at 14,000 rpm for 60 min in a Beckman microfuge at 4° C. The supernatant was transferred to a new tube and kept at 4° C. The Pierce BCA assay was used for determining protein concentrations.

Figure 1A:
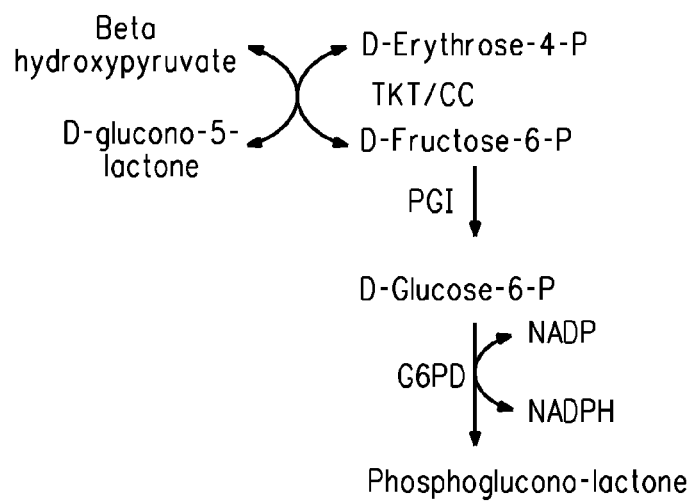
FIG. 1 shows the strategies for enzyme assays of transketolase (A), transaldolase (B), xylose isomerase (C), and xyulokinase (D).

The transketolase (TKT) assay was usually performed first since this enzyme is more labile than the others. A diagram of the TKT assay is shown in FIG. 1A.

In a microplate assay, 20 μL of cell free extract was added to each well in a reaction mix, at 30° C., that included the following final concentrations of components: 0.37 mM NADP, 50 mM TrisHCl pH 7.5, 8.4 mM Mg $Cl_2$, 0.1 mM TPP ((thiamine pyrophosphate chloride), 0.6 mM E4P (erythrose-4-phosphate), 4 mM BHP (betahydroxypyruvate), 4 U/ml PGI (phosphoglucose isomerase), and 4 U/ml G6PD (glucose-6-phosphate dehydrogenase). The $A_{340}$ was read on a plate reader for 3-5 min. TKT activity was calculated as follows:

1 unit corresponds to the formation of 1 μmol of D-fructose 6-phosphate/min at 30° C.

$U$(μmole/min)=slope($dA_{340}$/min)*volume of reaction (μL)/6220/0.55 cm (moles of NADP→NADPH is 6220 $A_{340}$ per mole per L in a 1 cm cuvette)
(pathlength of 200 μL per well in microplate=0.55 cm)

Specific Activity(μmole/min-mg)=μmole/min/protein concentration(mg)

Figure 1B:
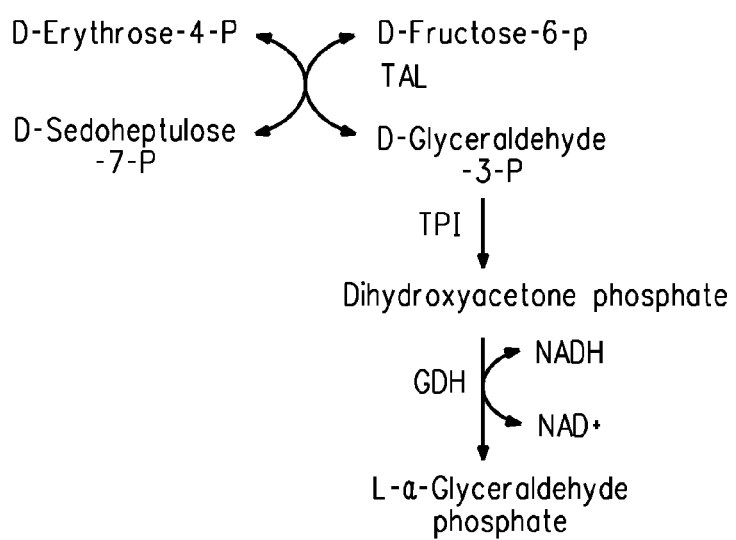

The basis of the transaldolase (TAL) assay is shown in FIG. 1B. In a microplate assay, 20 μL of cell free extract was added to each well in a reaction mix, at 30° C., that included the following final concentrations of components: 0.38 mM NADH, 87 mM triethanolamine, 17 mM EDTA, 33 mM F6P (fructose-6-phosphate), 1.2 mM E4P (erythrose-4-phosphate), 2.0 U/ml GDH (Glycerol-3-phosphate dehydrogenase), and 20 U/ml TPI (Triose phosphate isomerase). The plate was incubated for 5 min., then the $A_{340}$ was read for 3-5 min. TAL activity was calculated as follows:

1 unit corresponds to the formation of 1 μmol of D-glyceraldehyde per minute at 30° C.

$U$(μmole/min)=slope($dA_{340}$/min)*volume of reaction (μL)/6220/0.55 cm (moles of NADH→NAD is 6220 $A_{340}$ per mole per L in a 1 cm cuvette)
(pathlength of 200 μL per well in microplate=0.55 cm)

Specific Activity(μmole/min-mg)=μmole/min/protein

Figure 1C:
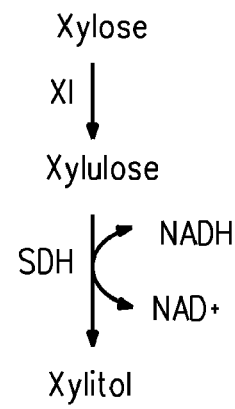

The basis of the xylose isomerase (XI) assay is shown in FIG. 1C. In a microplate assay, 20 μL of cell free extract was added to each well in a reaction mix, at 30° C., that included the following final concentrations of components: 0.256 mM NADH, 50 mM xylose, 10 mM MgSO$_4$, 10 mM triethanolamine, and 1 U/ml SDH (sorbitol dehydrogenase). The A$_{340}$ was read on a plate reader for 3-5 min. XI activity was calculated as follows:
1 unit of XI corresponds to the formation of 1 μmole of D-xylulose per minute at 30° C.

$U$(μmole/min)=slope(dA$_{340}$/min)*volume of reaction (μL)/6220/0.55 cm (moles of NADHP→NAD is 6220 A$_{340}$ per mole per L in a 1 cm cuvette)
(pathlength of 200 μL per well in microplate=0.55 cm)

Specific Activity(μmole/min-mg)=μmole/min/protein concentration(mg)

Figure 1D:
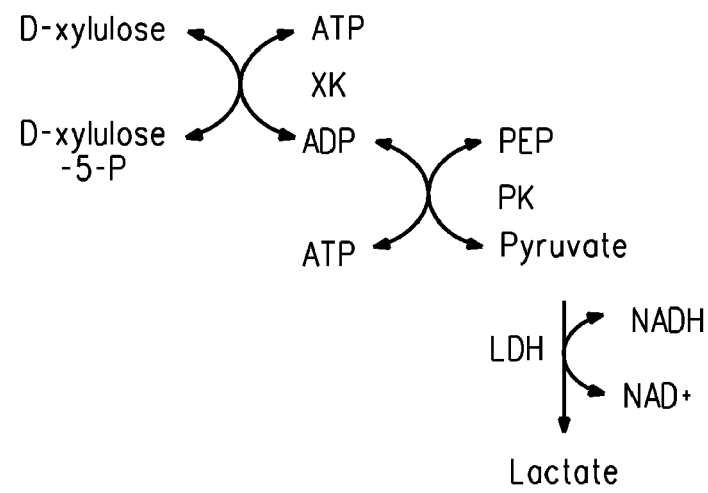

The basis of the xylulokinase (XK) assay is shown in FIG. 1D. In a microplate assay, 20 μL of cell free extract was added to each well in a reaction mix, at 30° C., that included the following final concentrations of components: 0.2 mM NADH, 50 mM Tris HCl pH 7.5, 2.0 mm MgCl$_2$-6H$_2$O, 2.0 M ATP 0.2 M PEP (phosphoenolpyruvate), 8.5 mM D-xylose, 5 U/ml PK (pyruvate kinase), and 5 U/ml LDH (lactate dehydrogenase). The A$_{340}$ was read on a plate reader for 3-5 min. XI activity was calculated as follows:
1 unit corresponds to the formation of 1 μmole of D-xylulose to D-xylulose-5-phosphate per minute at 30° C.

$U$(μmole/min)=slope(dA$_{340}$/min)*volume of reaction (μL)/6220/0.55 cm (moles of NADH→NAD is 6220 A$_{340}$ per mole per L in a 1 cm cuvette)
(pathlength of 200 μL per well in microplate=0.55 cm)

Specific Activity(μmole/min-mg)=μmole/min/protein concentration(mg)

HPLC Method

The analysis was done with an Agilent 1100 series HPLC and Agilent ChemStation software for LC 3D. The column was BioRad Aminex HPX-87H (HPLC Organic Analysis Column 125-0140) with BioRad Micro-Guard Cartridge Cation-H (125-0129). The operating conditions were:

| | |
|---|---|
| Flow | 0.6 ml/min |
| Solvent | 0.01N H$_2$SO$_4$ |
| Stop Time | 25 min |
| Injection Volume | 5 μL |
| Auto Sampler | Temp Control @ 10° C. or 4° C. |
| Column Temp | 55° C. |
| Detector | Refractive Index (40° C.) with External Standard Calibration Curves |

Example 1

Construction of Xylose-Fermenting *Zymomonas mobilis* Strains

As described in commonly owned and co-pending U.S. App. Pub. No. US20080286870, strains of xylose-fermenting *Zymomonas mobilis* were constructed by integrating two operons, PgapxylAB and Pgaptaltkt, containing four xylose-utilizing genes encoding xylose isomerase, xylulokinase, transaldolase and transketolase, into the genome of ZW1 (ATCC #31821) via sequential transposition events, followed by adaptation on selective media containing xylose. Previously, a xylose-fermenting *Zymomonas mobilis* strain called 8b was constructed, as described in U.S. App. Pub. No. 20030162271, by integrating the two operons PgapxylAxylB and Penotaltkt, along with selectable antibiotic markers, into the genome of *Zymomonas mobilis* 5C via a combination of homologous recombination and transposon approaches followed by adaptation and NTG mutagenesis. In the preparation of new strains, transposition (Epicentre's EZ::Tn in vitro transposition system) was used, as opposed to site specific homologous recombination, because this approach offers the advantages of multiple choices of integration sites and relatively high insertion frequency. The four genes encoding the xylose utilization enzymes were arranged and cloned as two separate operons: PgapxylAB and Pgaptaltkt for the integration. An antibiotic resistance marker, a chloramphenicol resistance (Cm$^r$) gene flanked by two P1 phage Cre-recombinase recognition sequences (loxP), was attached to each operon for the selection of integrants. The integration of the two operons was accomplished in a two-step, sequential manner: Pgaptaltkt followed by PgapxylAB. Cm resistance selection was used in both integration events, since it was removed by expressing a Cre recombinase on a plasmid followed by curing of the plasmid after each integration. This process allowed the use of the same antibiotic marker for selection multiple times. More importantly, it allowed the removal of the antibiotic marker introduced for selection of the integration of the operons. This process eliminated the negative impact of antibiotic resistance gene(s) on the fermentation strain for commercial use.

Construction of pMODPqaptaltktCm for Transposition

As described in U.S. App. Pub. No. 20030162271 (Example 9 therein), a 2.2 kb DNA fragment containing the transketolase (tkt) coding region from *E. coli* was isolated from pUCtaltkt (U.S. App. Pub. No. 20030162271) by BgIII/XbaI digestion and cloned in a PMOD (Epicentre Biotechnologies, Madison, Wis.) vector digested with BamHI/XbaI, resulting in pMODtkt. A PCR fragment named Pgaptal was generated by fusing the promoter region of the *Zymomonas mobilis* gap (Pgap; glyceraldehyde-3-phosphate dehydrogenase) gene to the coding region of *E. coli* transaldolase (tal) as follows. A Pgap fragment was amplified from pZB4, the construction of which is described in U.S. Pat. No. 5,514,583 (Example 3), using primers with SEQ ID NOs:13 and 14. pZB4 contains a Pgap-xylA/xylB operon and a Peno-tal/tkt operon. A tal coding region fragment was amplified from pZB4 using primers with SEQ ID NOs: 15 and 16. A Pgaptal fragment was amplified using the Pgap and tal fragments as template using primers with SEQ ID NOs:17 and 18. This fragment was digested with XbaI and cloned into the plasmid pMODtkt, upstream of the tkt coding region. A loxP::Cm fragment was generated by PCR using Cmlox(F,sfi) and Cmlox(R,sfi) primers (SEQ ID NOs:19 and 20) and pZB186 as the template. pZB186 is a combination of a native *Z. mobilis* plasmid and pACYC184, described in U.S. Pat. No. 514,583 (Example 3) and Zhang et al. ((1995) Science 267: 240-243). Finally, the loxP::Cm PCR fragment was inserted in the SfiI site of the plasmid containing Pgaptaltkt to form the integrative plasmid pMODPgaptaltktCm. In this plasmid, the Pgaptaltkt loxP::Cm fragment was inserted between two mosaic ends (transposase binding sites) in the PMOD vector. The complete nucleotide sequence for the pMODPgaptaltktCm plasmid is given as SEQ ID NO:21.

Transposition and Transformation of pMODPgaptaltktCm in ZW1

Plasmid PMOD is a pUC-based vector, and therefore is a non-replicative vector in *Zymomonas*. Plasmid pMODPgaptaltktCm was treated with transposase in the presence of Mg$^{2+}$ at room temperature for one hour and used to transform ZW1 cells by electroporation (using a BioRad Gene Pulser set at 200 ohms, 25 µF and 16 kV/cm). Electroporated cells were incubated in a mating medium (MM), which consists of 10 g/L yeast extract, 5 g/L tryptone, 2.5 g/L (NH$_4$)$_2$SO$_4$, 0.2 g/L K$_2$HPO$_4$) supplemented with 50 g/L glucose and 1 mM MgSO$_4$ for 6 hours at 30° C. The transformation mixture was plated on agar plates containing 15 g/L Bacto agar in MM supplemented with 50 g/L glucose and 120 µg/mL chloramphenicol and incubated anerobically at 30° C. The transformants were visible after about 2 days. The transformation/transposition frequency was approx. $3 \times 10^1$/µg DNA.

A total of 39 Cm$^r$ transformant colonies was obtained. Twenty-one colonies were picked and further analyzed by PCR and enzymatic activity assays. PCR using primers SEQ ID NOs:22 and 23 confirmed the presence of a 3 kb DNA fragment containing tal and tkt coding regions in the transformants. Back transformation with plasmid DNA from the 21 integrant colonies generated no back transformants in *E. coli* suggesting the tal and tkt were integrated in the genome of ZW1. These integrants were tested for transaldolase and transketolase activities using protocols modified for microplates (General Methods). The Pierce BCA protein assay was used for the determination of protein concentrations. The transformants were grown up in RM medium containing 2% (w/v) glucose supplemented with 120 µg/ml chloramphenicol) in 50 ml conical centrifuge tubes at 30° C. The control strains 8b and ZW1 were grown up as well (RM plus 2% glucose was used for ZW1) for enzymatic assays. Cells were harvested when the OD$_{600}$ reached 1.0. Cells were washed once and resuspended in sonication buffer (10 mM Tris-HCl, pH 7.6 and 10 mM MgCl$_2$). Enzymatic assays were conducted as described in U.S. App. Pub. No. 20030162271. Units are given as µmole/min-mg. All samples had transaldolase and transketolase activities except for one.

Southern hybridization was performed on genomic and plasmid DNA of selected integrants digested with PstI using a tkt probe. ZW1 DNA did not hybridize with the tkt probe. A common 1.5 kb band was visible in all integrant genomic DNA samples, which is the expected DNA fragment between a PstI site in tkt and a PstI site in tal. A second visible high molecular weight (6 kb or greater) band was unique between independent lines T2, T3, T4 and T5 indicating a separate genomic integration site in each line. Interestingly, both plasmid and genomic DNA of T5 hybridized with the tkt probe indicating it was likely that Pgaptaltkt was also integrated in T5 on the native plasmid. These four strains (T2, T3, T4 and T5) were selected for further Cre treatment to remove the Cm$^r$ marker.

Cre Treatment to Remove Cm$^r$ Marker from taltkt Integrants

To remove the Cm$^r$ marker from the chromosome, T2, T3, T4 and T5 were transformed with pZB188/Spec-Cre. This plasmid is a derivative of the *Zymomonas-E. coli* shuttle vector pZB188 [Zhang et al. (1995) Science 267:240-243; U.S. Pat. No. 5,514,583] that contains an expression cassette for Cre Recombinase. pZB188/Spec-Cre is identical to the Cre Expression vector that is described In Example 10 (pZB188/Kan-Cre), except that it has a spectinomycin-resistance gene instead of a kanamycin-resistance gene. The transformants were selected on MM agar plates supplemented with 2% glucose and 200 µg/ml spectinomycin). Sp$^r$ resistant colonies were picked onto RM agar plates supplemented with 2% glucose and 200 µg/ml spectinomycin and RM agar plates supplemented with 2% glucose and 120 µg/mL Cm. One hundred percent of the colonies picked were Cm$^s$ indicating the high efficiency excision of Cm$^r$ by Cre. Sp$^r$Cm$^s$ transformants were cultured in RM plus 2% glucose at 37° C. for 2 to 5 daily transfers to cure pZB188aadACreF. At each transfer, cells were diluted and plated on RM plus 2% glucose agar plates for picking onto additional plates of the same medium with or without 200 µg/mL Sp. Sp$^s$ colonies were analyzed by PCR to confirm the loss of pZB188aadACreF. The plasmid-cured descendents of the integrants were named T2C, T3C, T4C and T5C. To examine whether these transposition integrants were stable, these 4 strains were grown in RM plus 2% glucose and then transferred to 10 ml of the same medium and grown at 37° C. in duplicate test tubes. Cells were transferred daily for ten days, or approximately 100 generations. Colonies were diluted and plated onto RMG plates for colony isolation after the 1st and 10th transfers. Twelve colonies from each transfer of each strain tested positive for the presence of Pgaptaltkt by colony PCR using 5' Pgap and 3' tkt primers (SEQ ID NOs; 13 and 23). Transaldolase and transketolase activities were also measured for isolates after the 1st and 10th transfers (as described in General Methods). All 4 integrants had similar levels of both TAL and TKT activities after 100 generations on the non-selective medium, suggesting that these integrants were genetically stable.

Construction of pMODPgapxylABCm for Transposition

The next step was to further integrate the PgapxylAB loxP::Cm operon into the ZW1::Pgaptaltkt integrants (T2C, T3C, T4C and T5C). The integrative plasmid pMODPgapxylABCm was constructed based on the plasmid pMODPgaptaltktCm (described above). The Pgaptaltkt DNA fragment was removed by SacI/SfiI digestion. An adaptor fragment containing SacI, NotI, and SfiI restriction sites was introduced by ligation. A NotI fragment of PgapxylAB, that was isolated from pZB4 (U.S. Pat. No. 5,514,583), was then cloned in the NotI site of the adaptor. Xylose isomerase (XI) is encoded by xylA and xylulokinase (XK) is encoded by xylB. The complete nucleotide sequence for the pMODPgapxylABCm plasmid is given as SEQ ID NO:24.

Transposition and Transformation of pMODPgapxylABCm in T2C, T3C, T4C and T5C

Using a similar approach to the integration of PgaptaltktCm, T2C, T3C, T4C and T5C were transformed/transposed with pMODPgapxylABCm (described above) treated with transposase. Six integrants (T3CCmX1, T3CCmX2, T3CCmX3, T4CCmX1, T5CCmX1, T5CCmX2) were obtained in 2 transformation/transposition experiments following Cm selection. All were confirmed for the presence of xylAB by PCR using two sets of primers: SEQ ID NOs:25, and 26, and SEQ ID NOs:15 and 16 except for T2 CcmX1 and T2 CcmX6 from which no PCR fragment was detected using the primers SEQ ID NOs:25 and 26.

Figure 2:
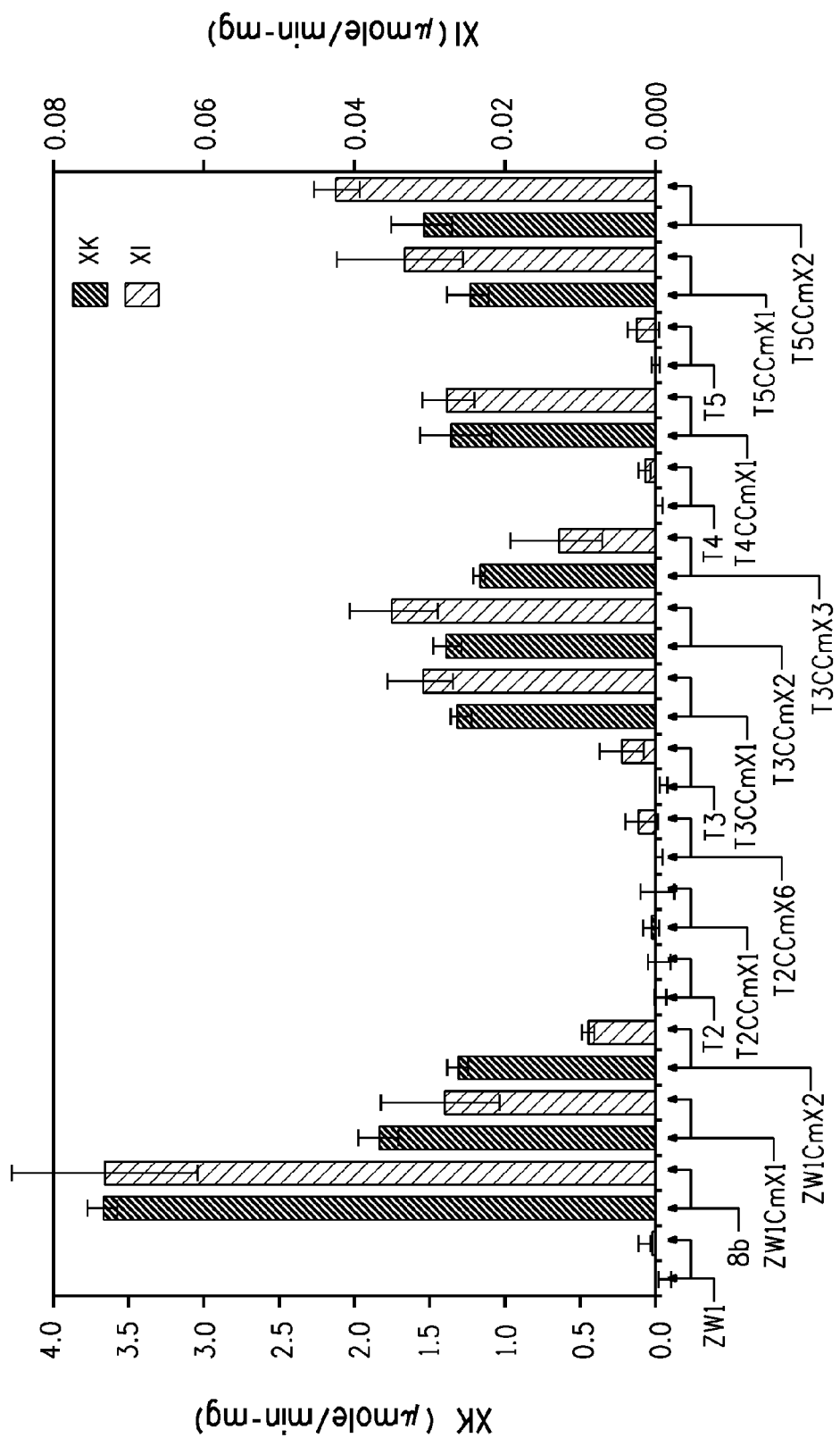
FIG. 2 shows a graph of xylose isomerase (XI) and xylulokinase (XK) activities in T2C, T3C, T4C, and T5C lines transformed with PgapxylAB.
Figure 3:
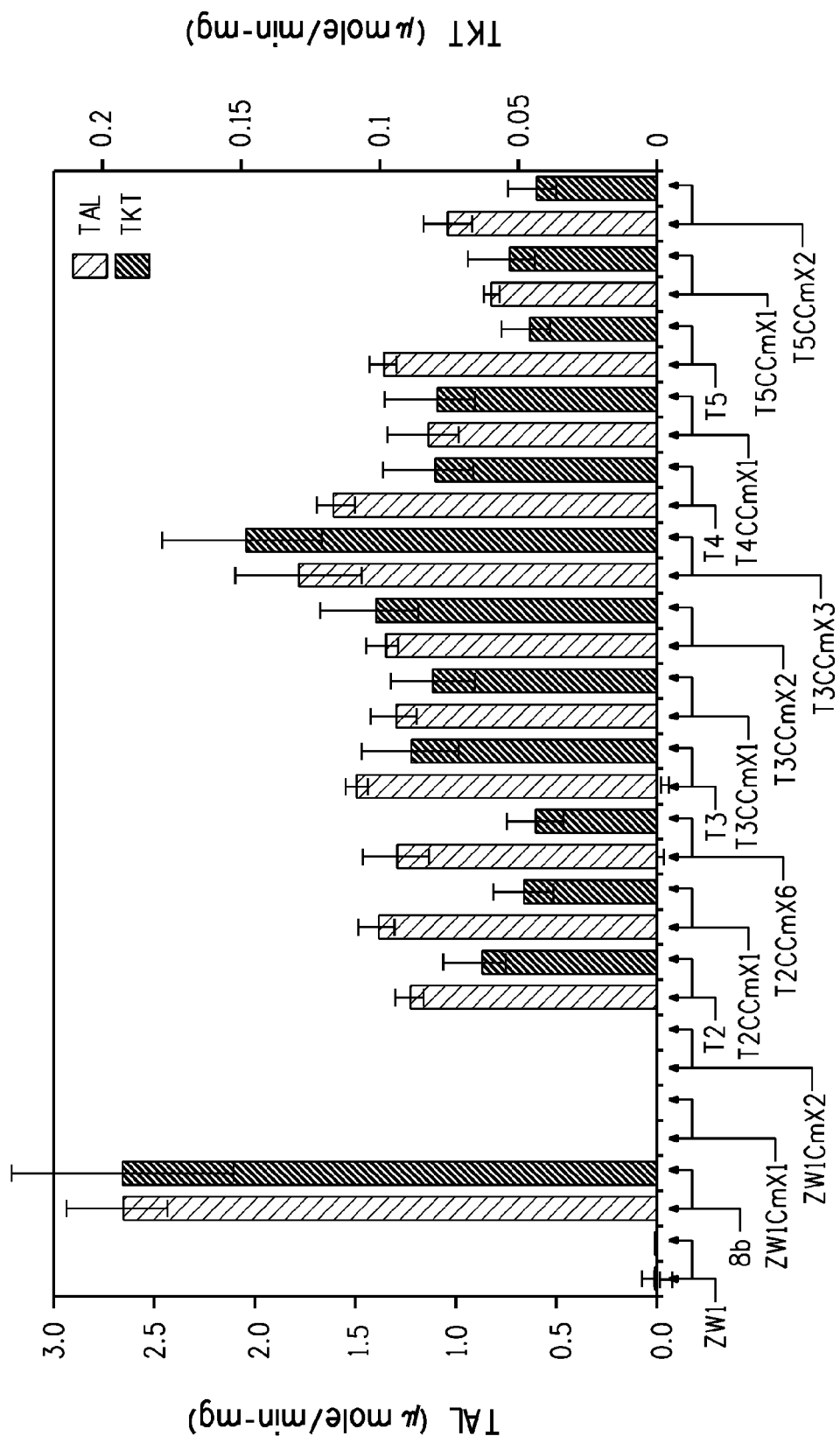
FIG. 3 shows a graph of transaldolse (TAL) and transketolase (TKT) activities in T2C, T3C, T4C, and T5C lines transformed with PgapxylAB.

The integrants, including the 2 PCR negative lines, were assayed for XI, XK, TAL and TKT activities (General Methods). The results shown in FIGS. 2 and 3 indicated that the six xylAB integrants T3CCmX1, T3CCmX2, T3CCmX3, T4CCmX1, T5CCmX1, and T5CCmX2 all had XI, XK, TAL and TKT activities. XI and XK activities were newly acquired as compared to the negative parental controls (FIG. 2). TAL and TKT activities were maintained as in the parental controls. All results indicated that the proteins were made and functional. Enzyme activity levels varied, with TI and XK activities similar to those of ZW1 integrants transformed/transposed with the same plasmid. The levels of activities of XI, XK, TAL and TKT were lower than those in strain 8b.

The integration of the xylAB operon was confirmed by Southern hybridization. Both genomic and plasmid DNA of the 6 lines were digested with SphI and hybridized to a digoxenin labeled xylB probe. A common band of about 3 kb, which is generated from an SphI site in xylB and another SphI site in the adjacent cloning sites on the PMOD vector, was present in all genomic DNA samples, and in addition, higher molecular weight hybridizing bands in the genomic DNA samples indicated that there were four sites of integration for the PgapxylAB operon in the chromosome. T3CCmX1 and T3CCmX2 appear to have the same integration site, T3CCmX3 and T4CCmX1 may have the same integration site, and T5CCmX1 and T5CCmX2 each have a separate integration site. Digestion of the same DNA with PstI followed by Southern hybridization with the tkt probe demonstrated that each integrant had the same hybridization pattern as its respective parental strain.

Adaptation of the ZW1::Pgaptaltkt PgapxylAB Cm Integrants on Xylose Media

Despite the presence of all four enzymatic activities for xylose utilization, previous observations (U.S. App. Pub. No. 20030162271) indicated that the integrants may not grow on xylose immediately. Growth on xylose may occur after prolonged incubation on xylose medium (either in test tubes or on plates), a process called adaptation.

The strains were adapted as follows. ZW1::PgaptaltktPgapxylABCm integrant strains were inoculated into test tubes containing RMX (containing 10 g/l yeast extract, 2 g/l $KH_2PO_4$, 20 g/l or 2% (w/v) xylose as well as onto MMGX or MMX plates (10 g/L yeast extract, 5 g/L of tryptone, 2.5 g/L of $(NH_4)_2SO_4$, 0.2 g/L $K_2HPO_4$, 1 mM $MgSO_4$, 1.5% (w/v) agar, 0.025% (w/v) glucose and 4% (w/v) xylose or just 4% (w/v) xylose). The low level of glucose was used to support initial growth to increase the chance of mutation during adaptation. One of at least five attempts at adaptation on xylose in both cultures and plates was successful. After 10 days of anaerobic incubation at 30° C., 17 and 19 colonies were visible on MMGX plated with T3CCmX1 and T3CCmX2 cells, respectively. The colonies were small and looked unhealthy (transparent) on the plates. Twelve colonies (four from T3CCmX1 plating: T3CCmX11, T3CCmX12, T3CCmX13 and T3CCmX110; eight from T3CCmX2 plating: T3CCmX24, T3CCmX25, T3CCmX26, T3CCmX27, T3CCmX28, T3CCmX29, T3CCmX211 and T3CCmX212) were inoculated in RMGCm120 and transferred into 3 ml RMX for further adaptation to obtain lines that were able to grow faster on xylose.

Adaptation of integrants in test tubes containing 3 ml RMX was conducted at 30° C. $OD_{600}$ was constantly monitored in a Spectronic 601 spectrophotometer. When the growth reached mid-log phase, the cultures were transferred into fresh tubes of RMX. This process was continued for 7 transfers. The growth rates and final ODs (non-linear readings) were improved over the transfers.

Figure 4:
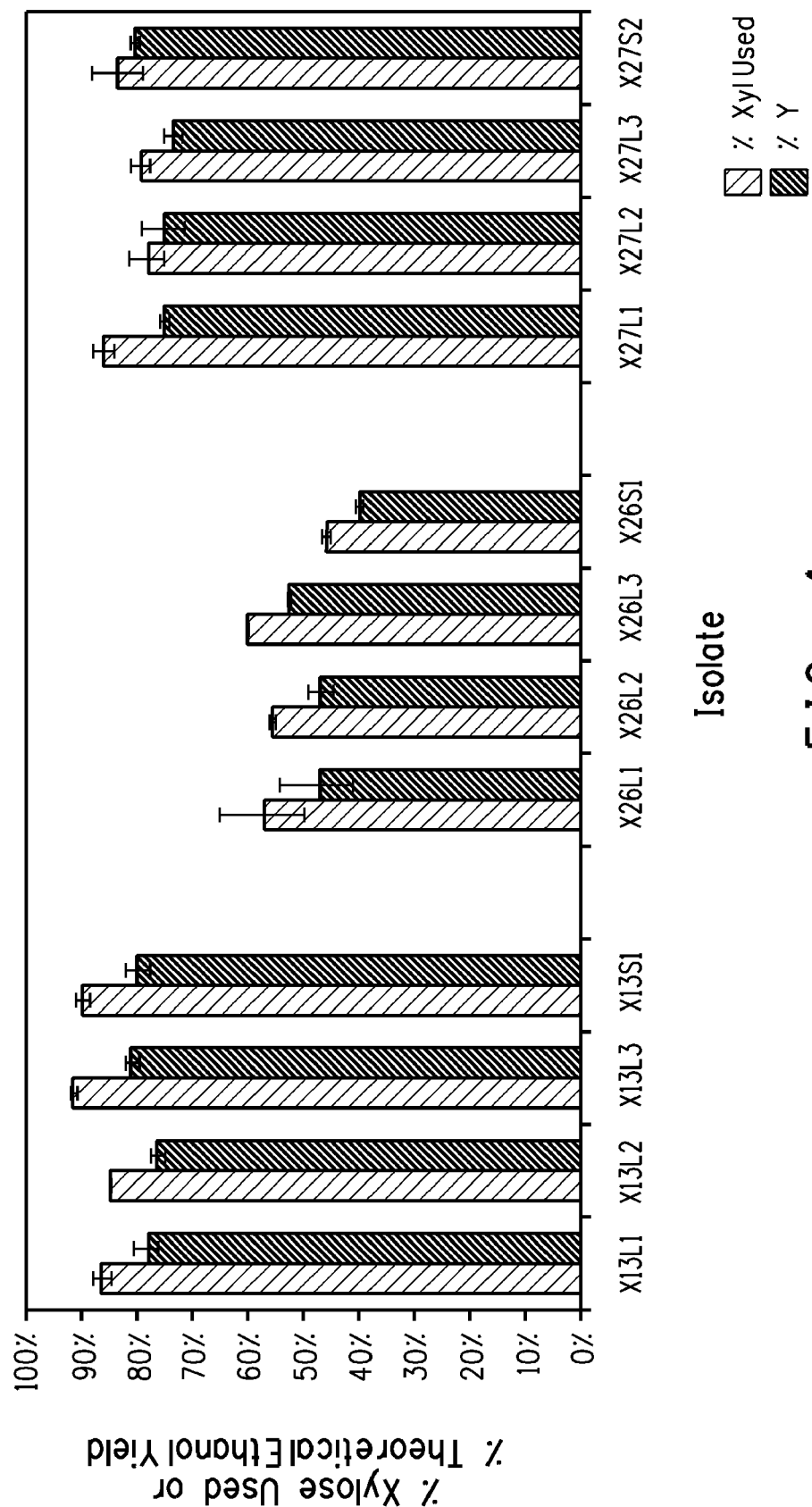
FIG. 4 shows a graph of % theoretical ethanol yield and % xylose utilization of selected adapted xylose-utilizing strain colonies.

At the $6^{th}$ transfer, the cultures were streaked out on RMX plates to isolate single colonies. Three integrants grew faster than others on RMX streaked plates: T3CCmX13, T3CCmX26 and T3CCmX27, which are referred to as X13, X26 and X27 in the tables and discussion below. To screen for the best xylose growers, four large (L1-4) and four small (S1-4) colonies each for TX13, X26 and X27 were selected and grown in RMX test tubes so that growth, sugar utilization, and ethanol production could be monitored. Colonies were grown overnight at 30° C. followed by inoculation of $OD_{600}$=0.05 into 3 ml of RMX in test tubes in duplicates. X27 grew more slowly in RMG than the other cultures and was inoculated again 6.5 hrs later. After 69 hrs (62.5 hrs for X27), samples were taken for HPLC analysis (General Methods). FIG. 4 charts the average ethanol yield (% of theoretical yield) and xylose utilization (%) for cultures at 69 hours (62.5 hr for all X27 cultures). There was no significant difference between the large and small colonies. Although the performance of X27 was better as compared to X26 on xylose, it showed slower growth on glucose. Therefore, the top performers, large colonies of X13 (X13L3) and X26 (X26L1), were chosen for further evaluation in pH-controlled fermentations. The fermentations were conducted in RMG(6% glucose), RMX(6% xylose) and RMGX(8%:4%; glucose:xylose) at 37° C. for strains X13L3 and X26L1, as well as the control strain 8b. Fermentation of glucose by X13L3 and X26L1 grown in RMG(6%) and RMGX(8%:4%) proceeded rather quickly. The fermentation of xylose in the RMGX(8%: 4%) was slower for both X13L3 and X26L1 as compared to that of strain 8b. In addition, growth on RMX(6%) at 37° C. occurred after a long lag for both X13L3 and X26L1. Several isolates, X13b, X13c and X13FL, were recovered from RMX (6%) fermentations. These isolates along with the original strains X13a (an isolate of X13L3) and X26 were subjected to Cre treatment, as described previously in this Example, to remove the $Cm^r$ marker from ZW1::PgaptaltktPgapxylABCm strains. The resulting Cre treated, $Cm^r$-free integrants were named: X13aC, X13bC, X13cC, X13FLC and X26C.

Example 2

Adaptation and Selection of Strain ZW658

As described earlier, adaptation of the initial ZW1::PgaptaltktPgapxylABCm strains on RMX at 30° C. greatly improved the growth of strains in these conditions. However, the adapted strains suffered a long lag during growth and fermentation in RMX(6%) at 37° C. To further improve the integrants for xylose fermentation at preferred process conditions including higher sugar concentration and temperature, the evolutionary or adaptation process was continued in RMX(5%) at 37° C. Serial transfers were conducted and the best growers were selected. Integrants used in this process included X13aC, X13bC, X13cC, X26C and X13FLC. These 5 strains were grown in RMX at 30° C. for 6 transfers before being transferred to RMX(5%) at 37° C. for another 5 to 16 transfers. During and after all the transfers cultures were streaked on RMX plates and incubated at 37° C. to isolate single colonies. Large colonies were further streaked on RMX plates and incubated at 37° C. for 3 to 4 times to purify the colonies. Final large colonies were selected for growth testing in RMX(5%) at 37° C.

Evaluation of Strains from Adaptation in RMX(5%) Medium at 37° C.

Eighteen colonies isolated after adaptation with serial transfers were tested in RMX(5%) test tubes at 37° C. initially. Twelve strains were selected for a 2nd test tube evaluation. Strain 8b was included in all the evaluations for comparison. The 18 colonies were grown up in RMG at 37° C. overnight, centrifuged and the cells were inoculated into 4 ml of RMX(5%) at 37° C., statically in test tubes for the $1^{st}$ evaluation. Based on the growth ($OD_{600}$, non-linear) and end point HPLC results (low residual xylose and high ethanol), 12 strains were selected for the $2^{nd}$ evaluation.

One of the purposes of the $2^{nd}$ evaluation was to test the stability of improved growth on xylose and xylose utilization capability of the strains. All 12 strains were subjected to a stability study to see whether the adapted strains were stable after being exposed to a non-selective medium in which they were serially transferred in at 37° C. for 50 generations. Cultures before and after RMG(5%) transfers were inoculated in RMX(5%) test tubes and grown at 37° C. for evaluation. The non-linear ODs were monitored by direct reading of test tubes in a Spectronic 601 spectrophotometer. The ODs at the 70$^{th}$ hour of growth in RMX(5%) before and after 50 generations of growth in RMG are plotted in FIG. 5. The results indicated that most strains were stable after 50 generations in RMG at 37° C. The endpoint (at stationary phase) supernatants were also analyzed by HPLC for xylose and ethanol concentrations. The low residual xylose and high ethanol concentrations in these cultures supported the fact that the strain grew and fermented xylose well.

Based on the results from the above test tube evaluation (low residual xylose, high ethanol concentration and higher OD) and a subsequent microtiter plate growth screening with high concentrations of glucose and/or xylose (up to 20%) and mixtures of glucose and xylose with acetate to select better growers in high sugars and in the presence of acetate, such as strain #26, designated as ZW658, which exhibited the best overall performance Example 3

Assay of Pentose Phosphate Pathway Enzyme Activities

The activities of the four xylose utilization enzymes encoded by integrated genes (described in Example 1) were measured as described in the General Methods for three of the strains selected for adaptation at high sugar and 37° C. (of Example 1) and were compared to activities of the same enzymes in the further adapted strain ZW658 (of Example 2). The results, expressed as μmoles product/mg protein/minute are shown in Table 4.

TABLE 4

Enzyme activities in different xylose-utilizing adapted *Z. mobilis* strains

| Strain | Xylose isomerase | Xylulokinase | Transaldolase | Transketolase |
|---|---|---|---|---|
| X13bC | 0.033 +/− 0.013 | 1.15 +/− 0.13 | 1.66 +/− 0.5 | 0.22 +/− 0.02 |
| ZW658 | 0.25 +/− 0.033 | 4.41 +/− 0.21 | 2.67 +/− 1.0 | 0.19 +/− 0.05 |

The activity levels for both members of the xylAB operon were increased by about 4 to 8 fold in the further adapted strain ZW658 as compared to levels in the partially adapted precursor strains. There was little or no change in the expression level of enzymes from the tal/tkt operon between ZW658 and the partially adapted precursor strains.

Example 4

Sequence Comparison of the Promoter Regions of the XylAB Operons in a Partially Adapted Strain and in ZW658

Since a clear change in the enzyme activity levels of the products of both genes under the control of the GAP promoter (Pgap) driving xylAB was a noted outcome of the adaptation that led to ZW658, the promoter region of that operon from a partially adapted strain (of Example 1; subsequently given the strain number ZW641) and from ZW658 were amplified by PCR and sequenced. A PCR fragment was prepared using a forward PCR primer (PC11; SEQ ID NO:27) from the recG coding region where the PgapxylAB operon was integrated and a reverse primer from the xylA coding region (PC12; SEQ ID NO:28). The resulting 961 bp PCR product was sequenced using primers LM121, LM122, and LM123 (SEQ ID NOs:29, 30, and 31). The promoter sequence from ZW641 is given in SEQ ID NO:3 and that from ZW658 in SEQ ID NO:4. These promoter sequences were both found to differ at one position from the published sequence of the Pgap in the *Z. mobilis* strain CP4 (SEQ ID NO:1): a 1 base deletion (of a T) after position −21, counting towards the 5' end starting upstream of the ATG start codon for the GAP coding region. This sequence change does not contribute to any difference in expression between the Pgap of ZW641 and Pgap of ZW658 since it is present in both strains. In addition to this common change—there was also a single base pair difference between the ZW641 and ZW658 Pgap sequences. The G at position −189 with respect to the coding region start ATG for XylA in the sequence from the ZW641 strain was replaced by a T in the sequence from ZW658. No other changes between the two sequences were noted and it seemed possible that a change in expression level due to this single base change in the GAP promoter region might be responsible for the increased enzyme activities found for both proteins encoded by genes under the control of that promoter.

Example 5

Construction of a Xylose Isomerase Expression Vector for *Z. mobilis* that has the Same Pgap that Drives the XylA/B Operon in *Z. mobilis* ZW641

Figures 6A, 6B:
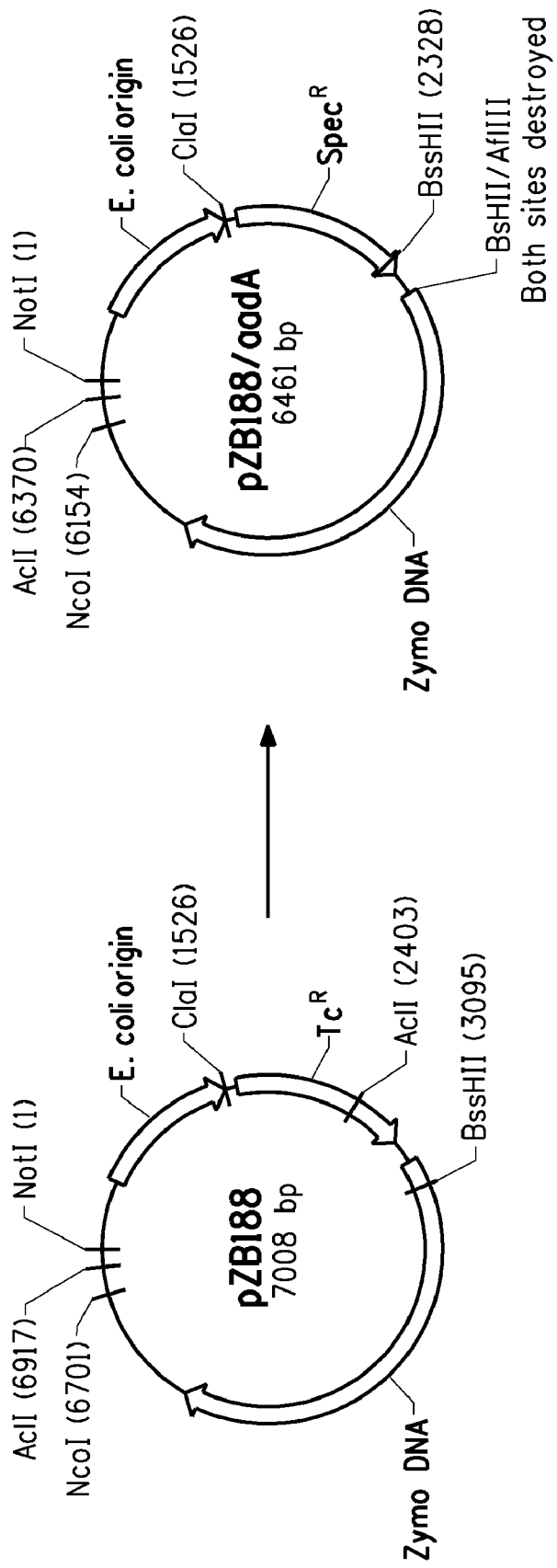

A plasmid construct that confers resistance to spectinomycin and expression of *E. coli* xylose isomerase in *Z. mobilis* (pZB188/aada-GapXylA; where Gap represents the promoter) was generated as described below using an *E. coli/Z. mobilis* shuttle vector (pZB188) as starting material (FIG. 6A). Steps involved in the construction of pZB188 are disclosed in U.S. Pat. No. 5,514,583. Briefly, this 7008 bp plasmid is able to replicate in *E. coli* and *Z. mobilis* because it has two different origins of replication, one for each bacterial species. pZB188 also contains a DNA fragment that confers resistance to tetracycline (i.e. a Tc$^r$-cassette). The first step in the construction of pZB188/aada-GapXylA, was to remove the Tc$^r$-cassette from pZB188 and replace it with a DNA fragment that confers resistance to spectinomycin (i.e. Spec$^r$-cassette). To excise the Tc$^r$-cassette from pZB188, the plasmid was cut with ClaI and BssHII and the resulting large vector fragment was purified by agarose gel electrophoresis as described in more detail below. The Spec$^r$-cassette was generated by PCR using plasmid pHP15578 (Cahoon et al, (2003) Nature Biotechnology 21: 1082-1087) as a template and Primers 1 (SEQ ID NO:32) and 2 (SEQ ID NO:33). Plasmid pHP15578 contains the complete nucleotide sequence for the Spec$^r$-cassette and its promoter, which is based on the published sequence of the Tranposon Tn7 aadA gene (GenBank accession number X03043) that codes for 3' (9)-O-nucleotidyltransferase.

```
Primer 1                              (SEQ ID NO: 32)
CTACTCATTTatcgatGGAGCACAGGATGACGCCT Primer 2                              (SEQ ID NO: 33)
CATCTTACTacgcgtTGGCAGGTCAGCAAGTGCC
```

The underlined bases of Primer 1 (forward primer) hybridize just upstream from the promotor for the Spec$^r$-cassette (to nts 4-22 of GenBank accession number X03043), while the lower case letters correspond to a ClaI site that was added to the 5' end of the primer. The underlined bases of Primer 2 (reverse primer) hybridize about 130 bases downstream from the stop codon for the Spec$^r$-cassette (to nts 1002-1020 of GenBank accession number X03043), while the lower case letters correspond to an AflIII site that was added to the 5' end of the primer. The 1048 bp PCR-generated Spec$^r$-cassette was double-digested with ClaI and AflIII, and the resulting DNA fragment was purified using the QIAquick PCR Purification Kit (Qiagen, Cat. No. 28104) and the vendor's recommended protocol. In the next step, plasmid pZB188 (isolated from *E. coli* SSC110 (dcm$^-$, dam$^-$) in order to obtain non-methylated plasmid DNA for cutting with ClaI, which is sensitive to dam methylation) was double-digested with ClaI and BssHII to remove the Tc$^r$-cassette, and the resulting large vector fragment was purified by agarose gel electrophoresis. This DNA fragment and the cleaned up PCR product were then ligated together, and the transformation reaction mixture was introduced into *E. coli* JM110 using chemically competent cells that were obtained from Stratagene (Cat. No. 200239). Note that BssHII and AflIII generate compatible "sticky ends", but both sites are destroyed when they are ligated together. Transformants were plated on LB medium that contained spectinomycin (100 μg/ml) and grown at 37° C. A spectinomycin-resistant transformant that contained a plasmid with the correct size insert was identified by restriction digestion analysis with NotI, and the plasmid that was selected for further manipulation is referred to below as pZB188/aadA. A circle diagram of this construct is shown in FIG. 6B.

In the next step, an *E. coli* xylose isomerase expression cassette was inserted between the NcoI and AclI sites of pZB188/aadA after cutting the latter with both enzymes, and purifying the large vector fragment by agarose gel electrophoresis. The ~2 Kbp DNA fragment that served as the *E. coli* xylose isomerase expression cassette was isolated from plasmid pZB4 by cutting the latter construct with NcoI and ClaI, and purifying the relevant DNA fragment by agarose gel electrophoresis. Plasmid pZB4 is described in detail in U.S. Pat. No. 5,514,583, and a schematic representation of the *E. coli* xylose isomerase expression cassette PgapXylA (SEQ ID NO:34) is shown in the boxed diagram in FIG. 6D.

The fragment containing the *E. coli* xylose isomerase expression cassette has an NcoI site and a ClaI site at its 5' and 3' ends respectively. As described in more detail in U.S. Pat. No. 5,514,583, this fragment contains the strong, constitutive *Z. mobilis* glyceraldehyde 3-phosphate dehydrogenase (GAP) promoter (nts 316-619), which is precisely fused to the complete open reading frame of the *E. coli* xylA open reading frame (nts 620-1942) that codes for xylose isomerase. It also contains the small stem-loop region that immediately follows the xylose isomerase stop codon (nts 1965-1999). The *E. coli* xylose isomerase expression cassette was inserted between the NcoI and AclI sites of pZB188/aadA in a standard ligation reaction. Note that ClaI and AclI generate compatible "sticky ends", but both sites are destroyed when they are ligated together. The ligation reaction mixture was then electroporated into *E. coli* SSC110 (dcm$^-$, dam$^-$) to obtain non-methylated plasmid DNA for subsequent transformation of *Z. mobilis*, and the transformed cells were plated on LB medium that contained 100 μg/ml of spectinomycin; growth was at 37° C. Spectinomycin-resistant tranformants that had a plasmid with a correct size insert were identified by restriction digestion analysis with NotI, NcoI and AclI. The plasmid that was selected for further manipulation and overexpression of *E. coli* xylose isomerase in the *Z. mobilis* ZW641 strain is referred to below as "pZB188/aadA-641Gap-XylA"; a circle diagram of this plasmid construct is shown in FIG. 6C.

It is important to note that the nucleotide sequence of SEQ ID NO:34 is not identical to the nucleotide sequence that is described in SEQ ID NO:34 in co-owned and co-pending U.S. App. Pub. Nos. US20080286870 and US20080187973, even though it corresponds to the same *E. coli* xylose isomerase expression cassette (PgapXylA). The DNA sequence disclosed in SEQ ID NO: 34 in the present work has a 1-bp deletion in the Pgap that corresponds to nt 599 of SEQ ID NO:34 in U.S. App. Pub. Nos. US20080286870 and US20080187973. The nucleotide sequence that was reported in the earlier patent applications was based on the published DNA sequence of the Pgap for the *Z. mobilis* strain CP4 (Conway et al. J. Bacteriol. 169 (12):5653-5662 (1987)) and the promoter was not resequenced at that time. Recently, however, we have discovered that the Pgap in pZB4 is also missing the same nucleotide, and the *E. coli* xylose isomerase expression cassette (PgapXylA) that was used for all three patent applications was derived from this plasmid as noted above.

Example 6

Generation of an *E. coli* Xylose Isomerase Expression Vector that has the Same Pgap that Drives the XylA/B Operon in *Z. mobilis* ZW658 and ZW801-4

Plasmid pZB188/aadA-801GapXylA is identical to pZB188-aada-641GapXylA (FIG. 6C) but has a single nucleotide substitution in the Pgap that corresponds to the G->T mutation that is present at position −189 in the Pgap that drives expression of the *E. coli* XylA/B operon in ZW658. The same point mutation is also present in strains ZW800 and ZW801-4, which were sequentially derived from ZW658 as described below. The construction and characterization of ZW800 and ZW801-4 are described in great detail in commonly owned and co-pending U.S. App. Pub. No. 11/862, 566. ZW800 is a derivative of ZW658 which has a double-crossover insertion of a spectinomycin resistance cassette in the sequence encoding the glucose-fructose oxidoreductase (GFOR) enzyme that inactivates this activity. ZW801-4 is a derivative of ZW800 in which the spectinomycin resistance cassette was deleted by site-specific recombination leaving an in-frame stop codon that prematurely truncates the protein. None of these manipulations altered the nucleotide sequence of the mutant Pgap promoter that drives the XylA/B operon in ZW658. Thus, the "801GAP promoter" refers to the promoter sequence that is present in the following strains: ZW658, ZW800, and ZW801-4.

The steps and plasmid intermediates that were used to generate pZB188/aadA-801GapXylA are described below in chronological order starting with the plasmid pMOD-Linker.

Construction of pMOD-Linker

Figures 7A, 7B:
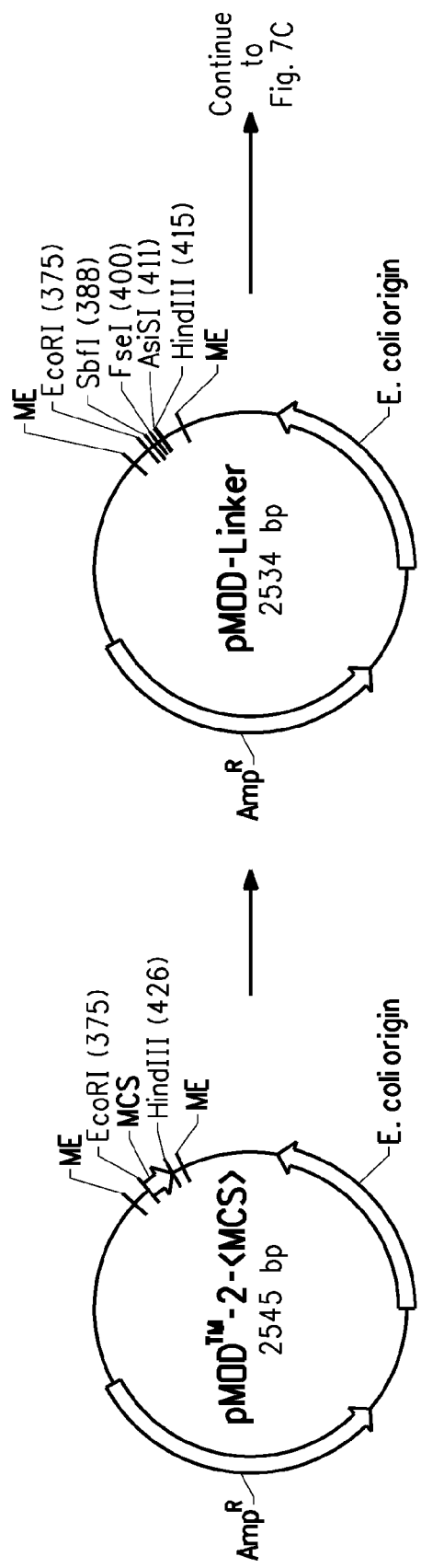

The precursor for plasmid pMOD-Linker was the pMOD™-2<MCS> Transposon Construction Vector (Cat. No. MOD0602) that is commercially available from EPICENTRE®. As shown in FIG. 7A, pMOD™-2<MCS> has an ampicillin resistance gene (ampR), an *E. coli* origin of replication (ori), and a multi-cloning site that is situated between the two mosaic ends (ME) that Tn5 transposase interacts with. The first step in the construction of pMOD-Linker was to remove the original multi-cloning site in pMOD2-<MCS> and replace it with a new multi-cloning site that has unique restriction sites for AsiSi, FseI and SbfI. This was done by cutting the plasmid with EcoRI and HindIII and purifying the large (about 2.5 Kbp) vector fragment by agarose gel electrophoresis. The new multi-cloning site was then generated by annealing together two synthetic oligonucleotides, Linker B (SEQ ID NO:35) and Linker T (SEQ ID NO:36) that were both phosphorylated at their 5' end.

```
Linker B (SEQ ID NO: 35):
aattCTACCTGCAGGAGTAGGCCGGCCATGAGCGATCGCA

Linker T (SEQ ID NO: 36):
agctTGCGATCGCTCATGGCCGGCCTACTCCTGCAGGTAG
```

These oligonucleotides are complimentary to each other, and when annealed together form a double stranded linker that has single-stranded overhangs at both ends (lower case letters), which allow the DNA fragment to be ligated between the EcoRI and HindIII sites of the large pMOD™-2<MCS> vector fragment described above. As noted above this synthetic linker also contains three unique restriction sites (AsiSi, FseI and SbfI) that can be used for subsequent cloning steps. The SbfI site is underlined with a thin line, the FseI site is underlined with a thick line and the AsiSI site is underlined with two thin lines. Linker B and Linker T were annealed together and the resulting DNA fragment was inserted between the EcoRI and HindIII sites of pMOD™-2<MCS> in a standard ligation reaction. The ligation reaction mixture was used to transform *E. Coli* DH10B and the transformed cells were plated on LB media that contained 100 μg/ml of ampicillin. Plasmid DNA was then isolated from a representative ampicillin-resistant colony that contained the new multi-cloning site. A circle diagram of the resulting plasmid construct (referred to below as "pMOD-Linker") is shown in FIG. 7B.

Construction of pMOD-Linker-Spec

A DNA fragment that confers resistance to spectinomycin (Spec$^r$) and has a wild type loxP site at both ends was inserted between the AsiSI and FseI sites of the pMOD-Linker construct described above. The source of the loxP-flanked Spec$^r$ cassette was plasmid pLDH-Sp-9WW (FIG. 8), which is described in great detail in U.S. application Ser. No. 11/862,566. In the first step, MOD-Linker plasmid DNA was sequentially digested with FseI and AsiSI, and the large vector fragment was purified using a DNA Clean & Concentrator™-5 spin column kit that was purchased from Zymo Research Corporation (Cat. No. DO4003). Next, plasmid pLDH-Sp-9WW was also double-digested with the same two enzymes and the small (about 1.1 Kbp) DNA fragment that contained the loxP-flanked Spec$^r$ cassette was purified by agarose gel electrophoresis. The two DNA fragments of interest were then ligated together, and the transformation reaction mixture was introduced into *E. coli* DH10B using electroporation. Transformants were plated on LB media that contained ampicillin (100 μg/ml) and spectinomycin (100 μg/ml) and growth was at 37° C. Plasmid DNA was then isolated from one of the ampicillin-resistant colonies that contained a DNA fragment with the correct size and this was used for subsequent manipulations. A circle diagram of this construct (referred to below as "pMOD-Linker-Spec") is shown in FIG. 7C.

Construction of pMOD-Linker-Spec-801GapXylA and pMOD-Linker-Spec-641GapXylA

A DNA fragment that contains the entire Pgap, the XylA coding region, and the stem-loop region that is between the XylA and XylB open reading frames was PCR-amplified from ZW801-4 using Primers 3 and 4 (SEQ ID NOs:37 and 38, respectively) and resuspended cells as a template. As already noted, DNA sequence analysis has shown that ZW801-4 has the same G->T point mutation at position −189 in the Pgap promoter that drives the expression of the integrated *E. coli* XylA/B operon as ZW658 and that the Pgap in both strains are identical.

```
Primer 3                         (SEQ ID NO: 37)
TCACTCATggccggccGTTCGATCAACAACCCGAATCC Primer 4                         (SEQ ID NO: 38)
CTACTCATcctgcaggCCGATATACTTATCGATCGTTCC
```

The underlined bases of Primer 3 (forward primer) hybridize to the first 22 bases of the Pgap (and to nts 316-337 of SEQ ID NO:34, while the lower case letters correspond to an FseI site that was added to the 5' end of the primer. The underlined bases of Primer 4 (reverse primer) hybridize just downstream from the stem-loop region that is after the XylA stop codon (and to the last 12 nts of SEQ ID NO:34), while the lower case letters correspond to an SbfI site that was added to the 5' end of the primer.

The PCR product was double-digested with FseI and SbfI, and purified using a DNA Clean & Concentrator™-5 spin column kit that was purchased from Zymo Research Corporation (Cat. No. DO4003). Next, plasmid pMOD-Linker-Spec was cut with the same two enzymes and the resulting large vector fragment was purified using the same procedure. The two DNA fragments of interest were then ligated together, and the transformation reaction mixture was introduced into *E. coli* DH10B using electroporation. The cells were plated on LB media that contained ampicillin (100 μg/ml) and spectinomycin (100 μg/ml) and growth was at 37° C. Transformants that contained a plasmid with a correct size insert were identified by PCR using Primers 3 and 4 and resuspended colonies as a template ("colony PCR"). The plasmid that was selected for further manipulation is referred to below as pMOD-Linker-Spec-801GapXylA, and a circle diagram of this construct is shown in FIG. 9.

The same steps described above were used to generate another plasmid that is referred to below as "pMOD-Linker-Spec-641GapXylA", except the template that was used for PCR-amplification of the Pgap-XylA gene DNA fragment was a cell suspension of ZW641. pMOD-Linker-Spec-641GapXylA and pMOD-Linker-Spec-801GapXylA are identical except for the G->T substitution in the Pgap that distinguishes ZW658 (and ZW801-4) from ZW641.

Construction of pZB188-aadA-801GapXylA

Figure 10C:
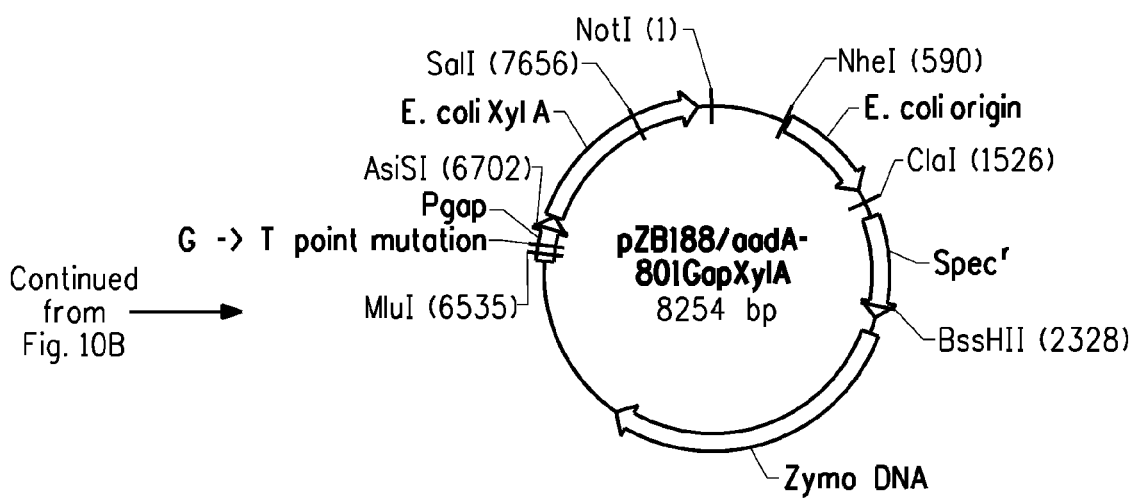

As described in the first paragraph of Example 6, pZB188-aadA-801GapXylA is an *E. Coli* Xylose Isomerase expression vector for *Z. mobilis* that is identical to pZB188-aadA-641GapXylA, but it has the same G->T substitution in the Pgap that drives expression of the integrated Pgap-XylA/B operon in ZW658 (and ZW801-4). To construct this plasmid, pMOD-Linker-Spec-801GapXylA (FIG. 10A) was double digested with MluI and SalI and the smaller DNA fragment (about 1100 bp) was purified using agarose gel electrophoresis and the Zymoclean Gel DNA Recovery Kit (catalog #D4001, Zymo Research). This fragment contains the Pgap G->T substitution and part of the XylA ORF and was used to replace the corresponding fragment in pZB188-aadA-641GapXylA (FIG. 10B), after cutting the latter construct with the same two enzymes and purifying the large vector fragment by agarose gel electrophoresis. The two fragments of interest were then ligated together and the ligation reaction mixture was introduced into *E. Coli* DH10B using electroporation. Transformants were plated on LB media that contained spectinomycin (100 μg/ml) and growth was at 37° C. Plasmid DNA was isolated from a spectinomycin-resistant colony and the presence of the Pgap promoter G->T substitution was confirmed by DNA sequence analysis. The plasmid used for subsequent manipulations, ("pZB188-aadA-801GapXylA") is shown in FIG. 10c.

Example 7

Overexpression of E. coli Xylose Isomerase in ZW641

The enzyme activity measurements in Table 4 show that xylose isomerase and xylulokinase activities increased dramatically during the transition from ZW641 to ZW658. To test the hypothesis that xylose isomerase is the rate-limiting enzyme for growth on xylose in ZW641, the enzyme was overexpressed in this strain using the multicopy plasmid, pZB188/aadA-641GapXylA (FIG. 6C). The control for this experiment was ZW641 transformed with the multicopy plasmid pZB188/aadA, which lacks the Pgap-E. coli xylose isomerase expression cassette (FIG. 6B). The construction of both of these plasmids is described in Example 5, and the transformation protocol was essentially as described in Example 5 of commonly owned and co-pending U.S. App. Pub. No. US20080187973. Briefly, non-methylated plasmid DNA (isolated from E. coli SSC110, which is a dcm$^{-1}$ and dam$^-$ strain) was introduced into ZW641 using electroporation, and the transformed cells were plated on LB media that contained 200 µg/ml spectinomycin. After a 48-hr growth period at 30° C. under anaerobic conditions, three primary transformants were randomly selected for each plasmid, and these were patched (transferred) onto agar plates that contained the same growth media for further characterization.

FIG. 11 shows growth curves (OD600 versus time) in xylose-containing media for the three strains that harbored the 641 Pgap-E. coli xylose isomerase expression plasmid (X1, X2 and X2) and the three strains that harbored the control plasmid (C1, C2 and C3). This experiment was performed at 30° C. in shake flasks (5-ml cultures in 15-ml tubes at 150 rpm), and the growth media was mRM3-X10 (10 g/L yeast extract, 2 g/L KH2PO4, 1 g/L MgSO4 and 100 g/L xylose) that also contained spectinomycin (200 µg/ml). The cultures were started with a loop of cells from the patched plate described in the above paragraph and the initial OD600 in each case was about 0.13. Similar to ZW641, the three strains with the control plasmid barely grew on xylose. In marked contast, both the rate and extent of growth (final OD600 values) on xylose were dramatically improved when ZW641 was transformed with the 641 Pgap-E. coli xylose isomerase expression plasmid, pZB188/aadA-641GapXylA. Since all three strains that had this plasmid behaved the same in the experiment that is shown in FIG. 11, only the X1 strain and C1 strain were subjected to further characterization.

Figure 12A:
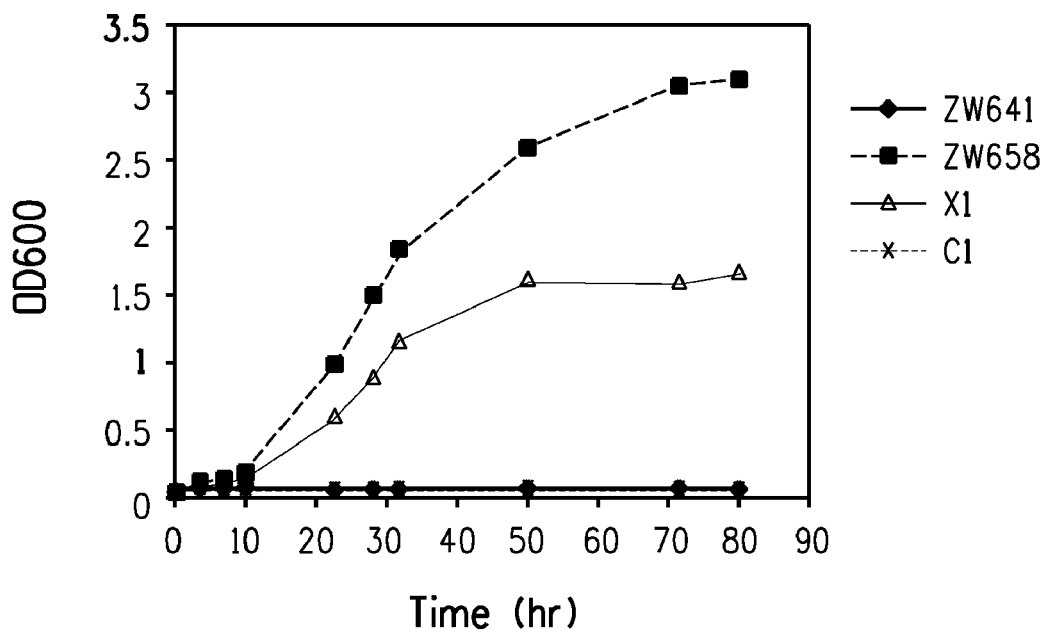
Figure 12B:
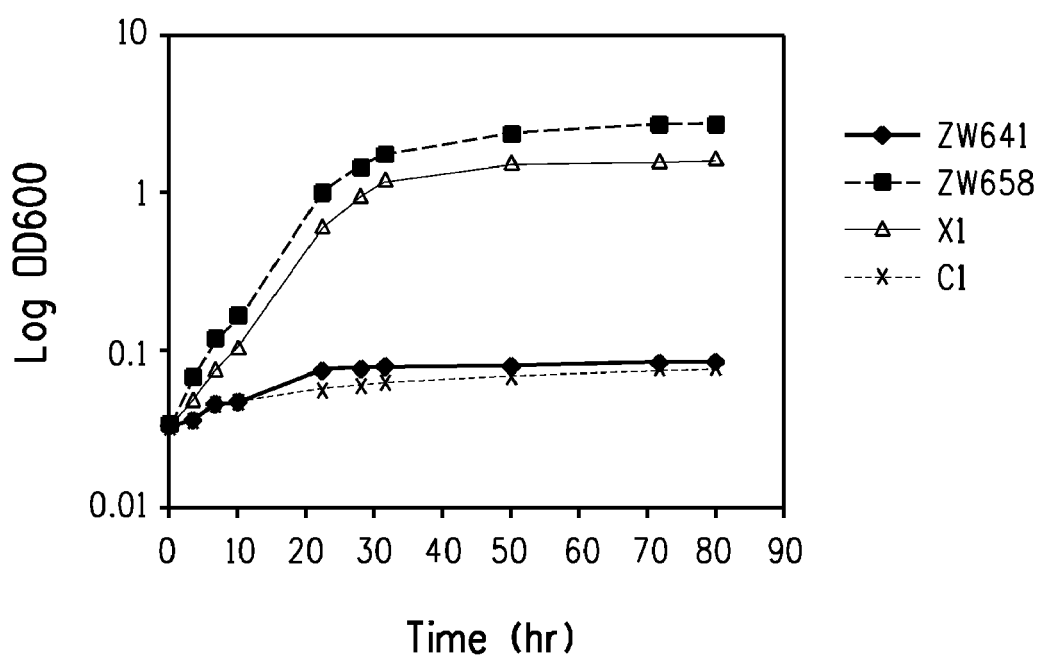

FIG. 12 shows a side-by-side comparison of ZW641, ZW658, X1 and C1 in the same xylose containing growth media without spectinomycin. The conditions for this experiment were identical to those described above but the 20-ml cultures were grown in 50-ml tubes and the initial OD600s were about 4-fold lower (0.035). The growth curves shown in FIG. 12A are plotted on a linear scale (OD600 versus Time), while FIG. 12B shows the same experimental data plotted on a logarithmic scale (logOD600 versus Time) in order to compare exponential growth rates. It is apparent from this experiment that the exponential growth rate of X1 is almost as fast as the xylose-adapted strain ZW658, and that this strain grows much better on xylose than the parent strain ZW641 with or without the control plasmid. Thus, high expression of xylose isomerase in ZW641 (driven by a 641 Pgap promoter from a multicopy plasmid) has a similar effect on growth on xylose as the increase in xylose isomerase activity had on ZW658 (shown in Table 4). Although the final biomass yield for X1 is about 2-fold lower than that obtained with ZW658, it is clear from this data that the rate-limiting enzyme for growth on xylose in ZW641 is xylose isomerase. The experiments shown in FIGS. 11 and 12 further suggest two other interesting possibilities: (1) that the large increase in xylose isomerase activity that occurred during the transition from ZW641 to ZW658 (Table 4) was largely responsible for the better growth on xylose that occurred during the "xylose adaption" process; and 2) that the increase in xylose isomerase activity may have resulted from the G->T substitution in the Pgap promoter that drives expression of the chromosomally-integrated Pgap-XylA/B operon that is present in ZW658.

Example 8

Transposon-Mediated Integration of E. coli Xylose Isomerase in ZW641

ZW641 and two plasmid constructs (pMOD-Linker-Spec-801GapXylA and pMOD-Linker-Spec-641GapXylA) were used to test the hypothesis that the Pgap promoter with the G->T substitution that drives expression of the integrated XylA/B operon in ZW658 (henceforth referred to as the "801GAP promoter") is stronger than the corresponding promoter in ZW641 (henceforth referred to as the "641GAP promoter"). ZW641 was selected for these experiments since it's barely able to grow on xylose, and because overexpression of xylose isomerase in this strain results in faster growth on xylose (Example 7, FIGS. 11 and 12). The basic idea was to introduce an extra copy of the E. coli xylose isomerase gene (driven by the 641GAP promoter or the 801GAP promoter) into the chromosome of ZW641 and see which construct would result in the fastest growth on xylose. Chromosomal integration of the two chimeric genes was accomplished using Epicentre's transposome technology.

As already indicated, pMOD-Linker-Spec-641GapXylA and pMOD-Linker-Spec-801GapXylA are identical plasmids except for the G->T point mutation that is present in the Pgap promoter in the latter construct. The transposable element used for random insertion into DNA in both cases consisted of the two 19-bp mosaic ends (MEs) and the entire DNA fragment that is sandwiched between them. As shown in FIG. 9, this element, which is referred to as the transposon, contains a spectinomycin-resistance cassette (Spec$^r$) and a downstream Pgap-E. coli xylose isomerase expression cassette. The protocol that was used to form the transposomes was essentially the same as that described in Epicentre's instruction manual for the EZ::TN™pMOD™-2<MCS> Transposon Construction Vector (Cat. No. MOD0602). The 8-µL reaction contained 1.5 µL of 5'-phosphorylated, blunt-ended transposon DNA that was free of Mg$^{++}$ ions (about 250 ng/µL), 4 µL of Epicentre's EZ::TN Transposase and 2.5 µL of 80% (v/v) glycerol. The control transposome reaction mixture was identical but 4 µL of sterile water was substituted for the transposase. The reactions were incubated at room temperature for 30 min and were then transferred to 4° C. for a 2- to 7-day incubation period that is required for the slow isomerization step, which results in the formation of the active transposome; using this procedure the transposomes are stable for at least 3 months at −20° C.

The transposomes were electroporated into ZW641 essentially using the same transformation protocol that is described in U.S. Pat. No. 5,514,583. Briefly, the 40 µL transformation reactions contained about 10$^{10}$ cells/ml in 10% (v/v) glycerol, 1 μL of Epicentre's TypeOne™ Restriction Inhibitor (Cat. No. TY0261H) and 1 μL of the control or transposome reaction mixture. The settings for the electroporator were 1.6 kv/cm, 200Ω, and 25 μF, and the gap width of the cuvette was 0.1 cm. Following electroporation, the transformation reactions were diluted with 1.0 ml of MMG media (50 g/L glucose, 10 g/L yeast extract, 5 g/L of tryptone, 2.5 g/L of $(NH_4)_2SO_4$, 0.2 g/L $K_2HPO$, and 1 mM $MgSO_4$) and the cells were allowed to recover for about 3 hours at 30° C. The cells were then harvested by centrifugation at room temperature (13,000×g, 5 min) in sterile 1.5-ml microfuge tubes and the supernatant was carefully removed. Cell pellets were resuspended in 200 μL of liquid MMG media and a 100-μL aliquot of each cell suspension was plated on MMG media that contained 1.5% agar and 200 μg/ml of spectinomycin. After a 72-hr incubation period at 30° C. under anaerobic conditions, 3 colonies were on the control plate, 13 colonies were on the 641GapXylA transposome plate and 18 colonies were on the 801GapXylA transposome plate. Six colonies from both transposome plates were randomly selected for further characterization, and these were patched onto agar plates that contained MMX media and 200 μg/ml of spectinomycin; the growth conditions were as described above. MMX media is the same as MMG media, but contains 50 g/L of xylose instead of glucose. After a second round of growth on a fresh MMX plus spectinomycin plates, the six strains that grew the best on xylose (three for each transposome) were used for the experiment described below.

Figure 13A:
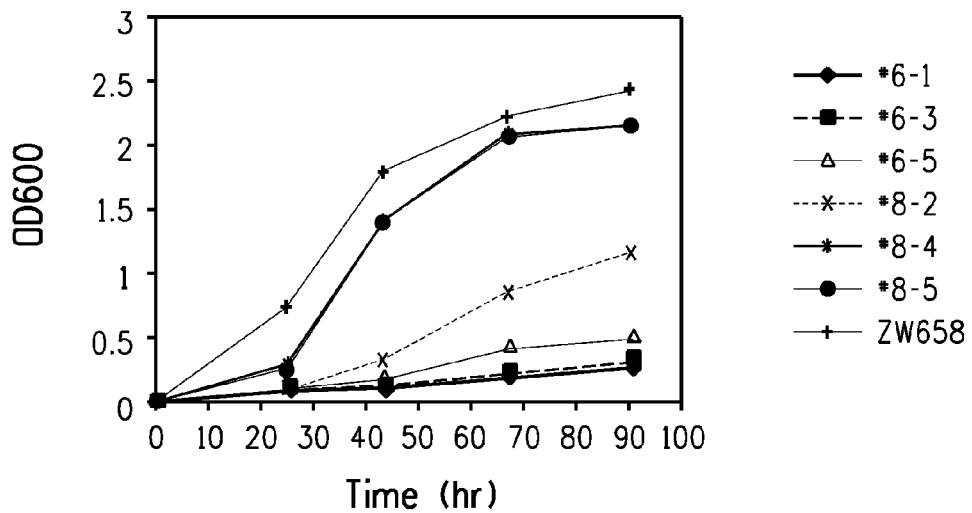

FIG. 13A shows linear growth curves for the three ZW641 strains that were obtained with the 641Gap-XylA transposome (#6-1, #6-3 and #6-5) and the three that received the 801Gap XylA transposome (#8-2, #8-4 and #8-5) in xylose-containing media. The same data is plotted on a log scale in FIG. 13B. This experiment was performed at 30° C. in shake flasks (7-ml cultures in 15-ml tubes at 150 rpm), and mRM3-X10 (10 g/L yeast extract, 2 g/L KH2PO4, 1 g/L MgSO4 and 100 g/L xylose) was the growth media. The cultures were started with a loop of cells from the patched plate described above and the initial ODs were very similar (about 0.02-0.03). The control for this experiment was the xylose-adapted strain ZW658, which has the G->T substitution in the Pgap that drives the chromosomally-integrated E. coli XylA/B operon.

Figure 13B:
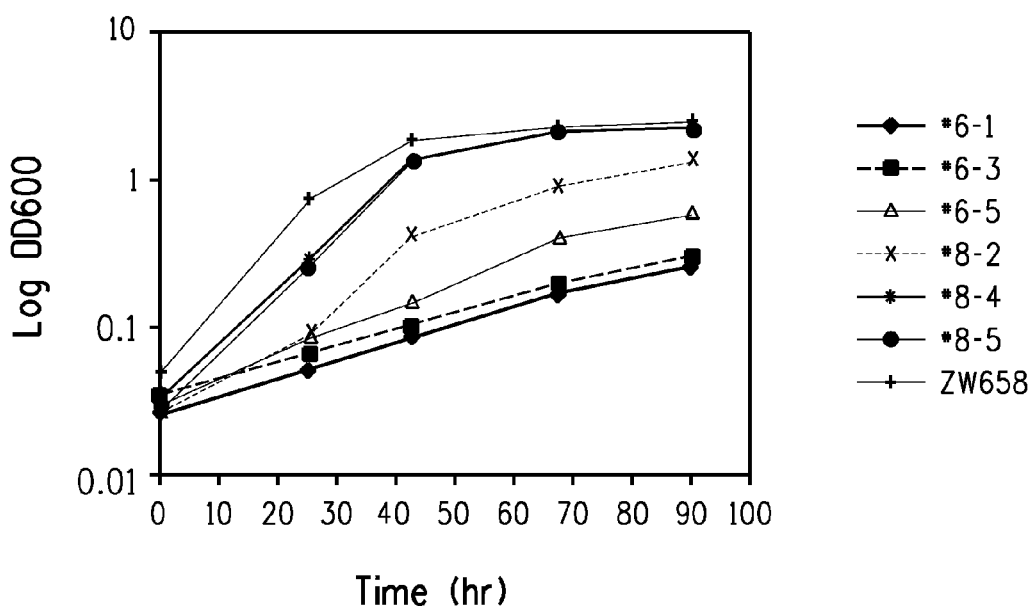

Similar to the parent strain (ZW641) the three strains that had an extra chromosomally-integrated copy of the 641GapXylA expression cassette grew very poorly in xylose-containing media, although it was apparent that there were some minor improvements in both the growth rate and biomass yield (OD600), especially for strain #6-5 (compare FIG. 12A and FIG. 13A). In contrast, all three of the strains that were obtained with the 801GapXylA transposon grew much better on xylose than the parent strain (FIGS. 13A and 13B). In fact, two of the transformants (#8-4 and #8-5) grew almost as well on this sugar as ZW658 and the ZW641 transformants that harbored the multi-copy plasmid pZB188/aadA-GapXylA, which contains a 641GapXylA expression cassette (compare FIG. 12 and FIG. 13). Since transposition is a random event and all six strains have the 641GapXylA or 801GapXylA expression cassette inserted at different locations in the chromosome, differences in foreign gene expression that were observed in this experiment using the same transposome are likely to be due to positional effects. For example, position effects may account for the better growth of #6-5 than of #6-1 and #6-3, and for the poorer growth of #8-2 than of #8-4 and 8-5. Nevertheless, despite the small size of the population that was analyzed, the results that are shown in FIG. 13 strongly support the notion that the G->T mutation that is present in the Pgap promoter that drives the E. coli XylA/B operon in ZW658 and ZW801-4 is responsible for the higher xylose isomerase activity and better growth on xylose that is observed with these strains, compared to the parent strain ZW641.

Example 9

Enzyme Activity and Sequence Comparison of the Transgene Gap Promoter Regions of Independently Adapted Strains of Xylose Utilizing Z. Mobilis Since strain 8b (Example 1 and US App. Pub. No. 20030162271) was obtained using a similar course of gene introduction and strain adaptation as was ZW658, the transgene activities of the pentose phosphate pathway and the sequence of the PgapxylAB operon were also compared in partially and more fully adapted strains of this independent strain production. Enzyme activities for products of the PgapxylAB operon in a partially adapted strain 8XL4 and the final adapted strain 8b were measured using the techniques described in General Methods and the results expressed as μmoles product/mg protein/minute are shown in Table 5.

TABLE 5

Enzyme activities in different xylose-utilizing adapted Z. mobilis strains

| Strain | Xylose isomerase | Xyulose kinase |
|--------|------------------|----------------|
| 8XL4   | 0.027 +/– 0.004  | 1.10 +/– 0.41  |
| 8b     | 0.142 +/– 0.057  | 5.76 +/– 0.43  |

As with the adaptation that occurred when the strains preceding ZW658 picked up mutations that allowed enhanced growth on xylose, strain 8b had increased activity for products of both genes in the xylAB operon over its predecessor strain 8XL4. Once again the increase in measured enzyme activity was about five fold increased over the less adapted strain.

The Pgap directing expression of the xylAB operon was sequenced in the 8b and 8XL4 strains. A PCR fragment was prepared using a forward PCR primer (GAP-F8; SEQ ID NO:39) from the 5' end of the promoter and a reverse primer from the xylA coding region (XylAB851R; SEQ ID NO:5). The resulting PCR product was sequenced using primers GAP-F8, XylAB449R, and XylAB851R (SEQ ID NOs:39, 41, and 40). The promoter sequence from ZW8XL4 is given in SEQ ID NO:3 and that from 8b in SEQ ID NO:5. These promoter sequences also both had the one difference with the published sequence of the Pgap of strain CP4 as in the Pgap of the xylAB operon in ZW641 and ZW658. In addition to these common changes there was also a single base pair difference between the ZW641 and ZW658 Pgap sequences. While the G to T change at −189 to the start ATG was not present in the comparison of 8XL4 and 8b, a C to T change did occur at position −89 with respect to the start ATG.

As with the promoter sequence of the PgapxylAB operon in strain ZW658, the promoter sequence of the PgapxylAB operon in strain 8b changed during adaptation to a new sequence which allowed production of more of the protein from the coding regions under its control than did the sequence of the same promoter from the partially adapted strain.

```
HMMER2.0 [2.3.2]1
NAME  brenda_xylA3_seqs-con2
LENG  4553
ALPH  Amino4
MAP   yes5
COM   hmmbuild brenda-xyla3.hmm brenda_xylA3_seqs-con.aln6
COM   hmmcalibrate brenda-xyla3.hmm7
NSEQ  328
DATE  Wed Mar. 12 21:55:22 20089
XT    -8455 -4 -1000 -1000 -8455 -4 -8455 -4
NULT  -4 -845510
NULE  595 -1558 85 338 -294 453 -1158 197 249 902 -1085 -142 -21 -313 45 531 201 384 -1998 -64411
EVD   -379.726868 0.10545212
```

|       | A       | C       | D       | E       | F       | G       | H       | I       |
|-------|---------|---------|---------|---------|---------|---------|---------|---------|
| HMM   | m→m     | m→i     | m→d     | i→m     | i→i     | d→m     | d→d     | b→m     |
|       | -152    | *       | -3322   |         |         |         |         |         |
| 1(W)  | -204    | 887     | 46      | 246     | -204    | -619    | 891     | -475    |
| —     | -149    | -500    | 233     | 43      | -381    | 399     | 106     | -626    |
| —     | -383    | -8312   | -2119   | -894    | -1115   | -701    | -1378   | -152    |
| 2(I)  | -652    | -1642   | -4507   | -4008   | 395     | -3998   | -3165   | 3129    |
| —     | -149    | -500    | 233     | 43      | -381    | 399     | 106     | -626    |
| —     | -9      | -7937   | -8980   | -894    | -1115   | -1952   | -431    | *       |
| 3(D)  | -60     | -2403   | 1759    | 355     | -2717   | 573     | -526    | -2474   |
| —     | -149    | -500    | 233     | 43      | -381    | 399     | 106     | -626    |
| —     | -9      | -7937   | -8980   | -894    | -1115   | -1952   | -431    | *       |
| 4(K)  | -1273   | -2543   | -1243   | -600    | -2936   | -2186   | -668    | -2589   |
| —     | -149    | -500    | 233     | 43      | -381    | 399     | 106     | -626    |
| —     | -9      | -7937   | -8980   | -894    | -1115   | -1952   | -431    | *       |
| 5(I)  | -2454   | -1957   | -5121   | -4804   | -2568   | -4911   | -4887   | 3182    |
| —     | -149    | -500    | 233     | 43      | -381    | 399     | 106     | -626    |
| —     | -9      | -7937   | -8980   | -894    | -1115   | -1952   | -431    | *       |
| 6(Q)  | -232    | -2237   | -616    | 690     | -2557   | -420    | -400    | -2306   |
| —     | -149    | -500    | 233     | 43      | -381    | 399     | 106     | -626    |
| —     | -9      | -7937   | -8980   | -894    | -1115   | 1952    | -431    | *       |
| 7(Y)  | -4607   | -3566   | -5021   | -5359   | 2754    | -4894   | -1132   | -3491   |
| —     | -149    | -500    | 233     | 43      | -381    | 399     | 106     | -626    |
| —     | -9      | -7937   | -8980   | -894    | -1115   | -1952   | -431    | *       |
| 8(E)  | -1557   | -2509   | -804    | 3253    | -3197   | -2167   | -1540   | -2531   |
| —     | -149    | -500    | 233     | 43      | -381    | 399     | 106     | -626    |
| —     | -9      | -7937   | -8980   | -894    | -1115   | 1952    | -431    | *       |
| 9(G)  | -4079   | -3917   | -4766   | -5131   | -5608   | 3825    | -4746   | -6295   |
| —     | -149    | -500    | 233     | 44      | -381    | 398     | 108     | -625    |
| —     | -284    | -2499   | -8980   | -602    | -1552   | -1952   | -431    | *       |
| 10(K) | -211    | -2265   | -699    | -143    | -2591   | -1802   | -444    | -2325   |
| —     | -149    | -500    | 233     | 43      | -381    | 399     | 106     | -626    |
| —     | -9      | -7937   | -8980   | -894    | -1115   | -1952   | -431    | *       |
| 11(K) | -238    | -2256   | 1519    | 758     | -2576   | -602    | -412    | -2328   |
| —     | -149    | -500    | 233     | 43      | -381    | 399     | 106     | -626    |
| —     | -9      | -7937   | -8980   | -894    | -1115   | -1952   | -431    | *       |
| 12(S) | -24     | -1368   | -1330   | -776    | -1457   | -2006   | -777    | -219    |
| —     | -149    | -500    | 233     | 43      | -381    | 399     | 106     | -626    |
| —     | -9      | -7937   | -8980   | -894    | -1115   | -1952   | -431    | *       |
| 13(K) | -815    | -2291   | 332     | 381     | -2610   | -1764   | -439    | -2362   |
| —     | -149    | -500    | 233     | 43      | -381    | 399     | 106     | -626    |
| —     | -9      | -7937   | -8980   | -894    | -1115   | -1952   | -431    | *       |
| 14(N) | -112    | -2600   | -523    | 381     | -2952   | -1931   | -753    | -2702   |
| —     | -149    | -500    | 233     | 43      | -381    | 399     | 106     | -626    |
| —     | -9      | -7937   | -8980   | -894    | -1115   | -1952   | -431    | *       |
| 15(P) | -67     | -1766   | -1443   | -999    | -2363   | 1282    | -1134   | -1992   |
| —     | -149    | -500    | 233     | 43      | -381    | 399     | 106     | -626    |
| —     | -9      | -7937   | -8980   | -894    | -1115   | -1952   | -431    | *       |
| 16(L) | -1558   | -1364   | -253    | -3026   | 1709    | -3054   | -1523   | -618    |
| —     | -149    | -500    | 233     | 43      | -381    | 399     | 106     | -626    |
| —     | -9      | -7937   | -8980   | -894    | -1115   | -1508   | -625    | *       |
| 17(A) | 2539    | -1340   | -2407   | -1923   | -114    | 254     | -1611   | -1400   |
| —     | -149    | -500    | 233     | 43      | -381    | 399     | 106     | -626    |
| —     | -8      | -8005   | -9047   | -894    | -1115   | -1811   | -484    | *       |
| 18(F) | -3970   | -3283   | -4844   | -4992   | 4163    | -4617   | -1220   | -3051   |
| —     | -149    | -500    | 233     | 43      | -381    | 399     | 106     | -626    |
| —     | -8      | -8005   | -9047   | -894    | -1115   | -1811   | -484    | *       |

-continued

| | | | | | | | | |
|---|---|---|---|---|---|---|---|---|
| 19(K) | | −1512 | −2771 | −1507 | −818 | −3232 | −2385 | 2267 | −2858 |
| — | | −149 | −500 | 233 | 43 | −381 | 399 | 106 | −626 |
| — | | −8 | −8005 | −9047 | −894 | −1115 | −1811 | −484 | * |
| 20(Y) | | −3420 | −2864 | −4689 | −4633 | 1930 | −4361 | 3299 | −2576 |
| — | | −149 | −500 | 233 | 43 | −381 | 399 | 106 | −626 |
| — | | −8 | −8005 | −9047 | −894 | −1115 | −1811 | −484 | * |
| 21(Y) | | −3783 | −3746 | −2646 | −265 | −826 | −3845 | −1884 | −3929 |
| — | | −149 | −500 | 233 | 43 | −381 | 399 | 106 | −626 |
| — | | −8 | −8005 | −9047 | −894 | −1115 | −1811 | −484 | * |
| 22(N) | | −2403 | −4115 | 2160 | −610 | −4589 | −2333 | −1803 | −4558 |
| — | | −149 | −500 | 233 | 43 | −381 | 399 | 106 | −626 |
| — | | −8 | −8005 | −9047 | −894 | −1115 | −1811 | −484 | * |
| 23(P) | | 1749 | −1901 | −2474 | −2677 | −4084 | −2051 | −2900 | −3873 |
| — | | −149 | −500 | 233 | 43 | −381 | 399 | 106 | −626 |
| — | | −8 | −8005 | −9047 | −894 | −1115 | −1811 | 484 | * |
| 24(E) | | −1269 | −2810 | 2039 | 2488 | −3105 | −1980 | −824 | −2879 |
| — | | −149 | −500 | 233 | 43 | −381 | 399 | 106 | −626 |
| — | | −8 | −8005 | −9047 | −894 | −1115 | −1811 | 484 | * |
| 25(E) | | −1569 | −3030 | −675 | 2974 | −3390 | −2199 | −979 | −3118 |
| — | | −149 | −500 | 233 | 43 | −381 | 399 | 106 | −626 |
| — | | −8 | −8005 | −9047 | −894 | −1115 | −1811 | 484 | * |
| 26(V) | | −940 | −874 | −2689 | 438 | 215 | −2419 | −1259 | 1264 |
| — | | −149 | −500 | 233 | 43 | −381 | 399 | 106 | −626 |
| — | | −8 | −8005 | −9047 | −894 | −1115 | −1811 | 484 | * |
| 27(I) | | −2373 | −1909 | −4992 | −4608 | −2445 | −4701 | −4324 | 2910 |
| — | | −149 | −500 | 233 | 43 | −381 | 399 | 106 | −626 |
| — | | −8 | −8005 | −9047 | −894 | −1115 | −1147 | −867 | * |
| 28(M) | | 297 | −2163 | 527 | 293 | −2408 | 1145 | −557 | −2107 |
| — | | −149 | −500 | 233 | 43 | −381 | 399 | 106 | −626 |
| — | | −8 | −8107 | −9149 | −894 | −1115 | −623 | −1512 | * |
| 29(G) | | −858 | −2502 | 613 | −529 | −2936 | 2600 | −948 | −2664 |
| — | | −149 | −500 | 233 | 43 | −381 | 399 | 106 | −626 |
| — | | −7 | −8252 | −9294 | −894 | −1115 | −533 | −1695 | * |
| 30(K) | | −1648 | −2125 | −2186 | −1533 | −1645 | −2748 | 734 | −1787 |
| — | | −149 | −500 | 233 | 43 | −381 | 399 | 106 | −626 |
| — | | −7 | −8312 | −9354 | −894 | −1115 | −701 | −1378 | * |
| 31(T) | | −1046 | −2501 | −897 | 404 | −2830 | −2011 | −653 | −2571 |
| — | | −149 | −500 | 233 | 43 | −381 | 399 | 106 | −626 |
| — | | −7 | −8312 | −9354 | −894 | −1115 | −701 | −1378 | * |
| 32(M) | | −551 | −1875 | −3895 | −3452 | −1627 | −3127 | −2589 | −1019 |
| — | | −149 | −500 | 233 | 43 | −381 | 399 | 106 | −626 |
| — | | −7 | −8312 | −9354 | −894 | −1115 | −701 | −1378 | * |
| 33(K) | | 127 | −2511 | −888 | 1379 | −2865 | −2030 | −726 | −2605 |
| — | | −149 | −500 | 233 | 43 | −381 | 399 | 106 | −626 |
| — | | −7 | −8312 | −9354 | −894 | −1115 | −701 | −1378 | * |
| 34(D) | | −2246 | −3964 | 2730 | 2201 | −4210 | −2482 | −1633 | −4052 |
| — | | −149 | −500 | 233 | 43 | −381 | 399 | 106 | −626 |
| — | | −7 | −8312 | −9354 | −894 | −1115 | −701 | −1378 | * |
| 35(W) | | −307 | −2255 | −1047 | 1375 | −2417 | −2110 | 3282 | −2137 |
| — | | −149 | −500 | 233 | 43 | −381 | 399 | 106 | −626 |
| — | | −7 | −8312 | −9354 | −894 | −1115 | −701 | −1378 | * |
| 36(L) | | −2283 | −2311 | 1522 | −2528 | 661 | −3412 | 1226 | −1601 |
| — | | −149 | −500 | 233 | 43 | −381 | 399 | 106 | −626 |
| — | | −7 | −8312 | −9354 | −894 | −1115 | −701 | −1378 | * |
| 37(R) | | −3325 | −3893 | −4311 | −2623 | −4835 | −3766 | 1845 | −4080 |
| — | | −149 | −500 | 233 | 43 | −381 | 399 | 106 | −626 |
| — | | −7 | −8312 | −9354 | −894 | −1115 | −701 | −1378 | * |
| 38(F) | | −5308 | −4420 | −5610 | −5948 | 4347 | −4921 | −3048 | −4656 |
| — | | −149 | −500 | 233 | 43 | −381 | 399 | 106 | −626 |
| — | | −7 | −8312 | −9354 | −894 | −1115 | −701 | −1378 | * |
| 39(S) | | 2011 | −1975 | −4184 | −4245 | −4465 | −522 | −3670 | −4249 |
| — | | −149 | −500 | 233 | 43 | −381 | 399 | 106 | −626 |
| — | | −7 | −8312 | −9354 | −894 | −1115 | −701 | −1378 | * |
| 40(V) | | −389 | −1555 | −4211 | −3620 | 2221 | −3520 | −2467 | 827 |
| — | | −149 | −500 | 233 | 43 | −381 | 399 | 106 | −626 |
| — | | −7 | −8312 | −9354 | −894 | −1115 | −701 | −1378 | * |
| 41(A) | | 2968 | 1546 | −4577 | −4780 | −4439 | 1767 | −3862 | −4189 |
| — | | −149 | −500 | 233 | 43 | −381 | 399 | 106 | −626 |
| — | | −7 | −8312 | −9354 | −894 | −1115 | −701 | −1378 | * |
| 42(Y) | | −4757 | −3801 | −5352 | −5629 | 2454 | −5193 | −1481 | −3601 |
| — | | −149 | −500 | 233 | 43 | −381 | 399 | 106 | −626 |
| — | | −7 | −8312 | −9354 | −894 | −1115 | −701 | −1378 | * |
| 43(W) | | −6178 | −4896 | −5848 | −6204 | −4109 | −4952 | −4743 | −6650 |
| — | | −149 | −500 | 233 | 43 | −381 | 399 | 106 | −626 |
| — | | −7 | −8312 | −9354 | −894 | −1115 | −701 | −1378 | * |

| | | | | | | | | |
|---|---|---|---|---|---|---|---|---|
| 44(H) | −2390 | −2940 | −3006 | −3167 | −3361 | −3029 | 4890 | −4377 |
| — | | −149 | −500 | 233 | 43 | −381 | 399 | 106 | −626 |
| — | | −383 | −8312 | −2119 | −894 | −1115 | −701 | −1378 | * |
| 45(T) | −1111 | −1722 | −3459 | −3693 | −4071 | −1979 | −3313 | −3836 |
| — | | −149 | −500 | 233 | 43 | −381 | 399 | 106 | −626 |
| — | | −9 | −7937 | −8980 | −894 | −1115 | −254 | −2629 | * |
| 46(F) | −2728 | −2359 | −5136 | −4558 | 3354 | −4572 | −3468 | 910 |
| — | | −149 | −500 | 233 | 43 | −381 | 399 | 106 | −626 |
| — | | −7 | −8312 | −9354 | −894 | −1115 | −701 | −1378 | * |
| 47(C) | −1098 | 2071 | 1338 | −866 | −2368 | 1340 | −1058 | −2007 |
| — | | −149 | −500 | 233 | 43 | −381 | 399 | 106 | −626 |
| — | | −7 | −8312 | −9354 | −894 | −1115 | −701 | −1378 | * |
| 48(W) | 1080 | −2296 | −913 | 535 | −2548 | 415 | −675 | −2251 |
| — | | −149 | −500 | 233 | 43 | −381 | 399 | 106 | −626 |
| — | | −7 | −8312 | −9354 | −894 | −1115 | −701 | −1378 | * |
| 49(D) | −994 | −2466 | 1756 | 978 | −2785 | −1962 | −625 | −2536 |
| — | | −149 | −500 | 233 | 43 | −381 | 399 | 106 | −626 |
| — | | −7 | −8312 | −9354 | −894 | −1115 | −701 | −1378 | * |
| 50(W) | −204 | 887 | 46 | 246 | −204 | −619 | 891 | −475 |
| — | | −149 | −500 | 233 | 43 | −381 | 399 | 106 | −626 |
| — | | −7 | −8312 | −9354 | −894 | −1115 | −701 | −1378 | * |
| 51(G) | −321 | −2099 | −3782 | −3944 | −3733 | 3298 | −3507 | −3250 |
| — | | −149 | −500 | 233 | 43 | −381 | 399 | 106 | −626 |
| — | | −7 | −8312 | −9354 | −894 | −1115 | −701 | −1378 | * |
| 52(R) | 877 | −2295 | −923 | −374 | −2567 | −29 | −672 | −2273 |
| — | | −149 | −500 | 233 | 43 | −381 | 399 | 106 | −626 |
| — | | −7 | −8312 | −9354 | −894 | −1115 | −701 | −1378 | * |
| 53(D) | −4886 | −4905 | 4186 | −3339 | −5949 | −4221 | −4195 | −6666 |
| — | | −149 | −500 | 233 | 43 | −381 | 399 | 106 | −626 |
| — | | −7 | −8312 | −9354 | −894 | −1115 | −701 | −1378 | * |
| 54(P) | −358 | −1704 | −2202 | −1724 | −1995 | −2408 | −1572 | −1504 |
| — | | −149 | −500 | 233 | 43 | −381 | 399 | 106 | −626 |
| — | | −7 | −8312 | −9354 | −894 | −1115 | −701 | −1378 | * |
| 55(F) | −5308 | −4420 | −5610 | −5948 | 4547 | 4921 | −3048 | −4656 |
| — | | −149 | −500 | 233 | 43 | −381 | 399 | 106 | −626 |
| — | | −7 | −8312 | −9354 | −894 | −1115 | −701 | −1378 | * |
| 56(G) | −4740 | −4445 | −5364 | −5738 | −6131 | 3840 | −5265 | −6903 |
| — | | −149 | −500 | 233 | 43 | −381 | 399 | 106 | −626 |
| — | | −7 | −8312 | −9354 | −894 | −1115 | −701 | −1378 | * |
| 57(D) | 674 | −2424 | 2070 | 271 | −2717 | 297 | −669 | −2448 |
| — | | −149 | −500 | 233 | 43 | −381 | 399 | 106 | −626 |
| — | | −7 | −8312 | −9354 | −894 | −1115 | −701 | −1378 | * |
| 58(G) | 2216 | −2048 | −3999 | −4272 | −4632 | 2814 | −3817 | −4443 |
| — | | −149 | −500 | 233 | 43 | −381 | 399 | 106 | −626 |
| — | | −7 | −8312 | −9354 | −894 | −1115 | −701 | −1378 | * |
| 59(T) | −552 | −1875 | −3402 | −3173 | −3341 | −2281 | −2846 | −2926 |
| — | | −149 | −500 | 233 | 43 | −381 | 399 | 106 | −626 |
| — | | −7 | −8312 | −9354 | −894 | −1115 | −701 | −1378 | * |
| 60(M) | 1157 | −1590 | −1704 | −1125 | 650 | −2335 | −1036 | −1217 |
| — | | −149 | −500 | 233 | 43 | −381 | 399 | 106 | −626 |
| — | | −7 | −8312 | −9354 | −894 | −1115 | −701 | −1378 | * |
| 61(Q) | 506 | −2444 | 274 | 1073 | −701 | −1222 | −615 | −365 |
| — | | −149 | −500 | 233 | 43 | −381 | 399 | 106 | −626 |
| — | | −7 | −8312 | −9354 | −894 | −1115 | −701 | −1378 | * |
| 62(R) | 716 | −1736 | −2244 | −1683 | 752 | −2703 | −1193 | −1344 |
| — | | −149 | −500 | 233 | 43 | −381 | 399 | 106 | −626 |
| — | | −7 | −8312 | −9354 | −894 | −1115 | −701 | −1378 | * |
| 63(P) | −625 | −2530 | 60 | −1072 | −2925 | −2398 | −1624 | −2563 |
| — | | −149 | −500 | 233 | 43 | −381 | 399 | 106 | −626 |
| — | | −90 | −8312 | −4120 | −894 | −1115 | −701 | −1378 | * |
| 64(W) | −4762 | −4593 | 2301 | −3636 | −3451 | −4258 | −3708 | −5821 |
| — | | −149 | −500 | 233 | 43 | −381 | 399 | 106 | −626 |
| — | | −130 | −8229 | −3598 | −894 | −1115 | −1121 | −889 | * |
| 65(D) | −1309 | −2840 | 2011 | 494 | −3135 | −2037 | −873 | −2906 |
| — | | −149 | −500 | 233 | 43 | −381 | 399 | 106 | −626 |
| — | | −2311 | −8107 | −331 | −894 | −1115 | −628 | −1503 | * |
| 66(Y) | −635 | −882 | −1209 | −779 | 422 | −1778 | −110 | −454 |
| — | | −149 | −500 | 234 | 43 | −381 | 399 | 106 | −626 |
| — | | −1029 | −988 | −7468 | −137 | −3461 | −571 | −1614 | * |

| | | | | | | | | |
|---|---|---|---|---|---|---|---|---|
| 67(H) | −9 | −2243 | 374 | 1170 | −2564 | 95 | 1478 | −2314 |
| — | −149 | −500 | 233 | 43 | −381 | 399 | 106 | −626 |
| — | −9 | −7937 | −8980 | −894 | −1115 | −1952 | −431 | * |
| 68(Y) | −804 | −1603 | −77 | −470 | −287 | 1328 | −615 | −1330 |
| — | −149 | −500 | 233 | 43 | −381 | 399 | 106 | −626 |
| — | −9 | −7937 | −8980 | −894 | −1115 | −1952 | −431 | * |
| 69(T) | −167 | −2183 | 188 | −187 | −2570 | 677 | −524 | −2303 |
| — | −149 | −500 | 233 | 43 | −381 | 399 | 106 | −626 |
| — | −9 | −7937 | −8980 | −894 | −1115 | −1952 | −431 | * |
| 70(D) | −1090 | −2605 | 2512 | 741 | −2908 | 391 | 837 | −2674 |
| — | −149 | −500 | 233 | 43 | −381 | 399 | 106 | −626 |
| — | −262 | −7937 | −2624 | −894 | −1115 | −1952 | −431 | * |
| 71(P) | 1251 | −2101 | −546 | 596 | −2491 | −1704 | −497 | −2212 |
| — | −149 | −500 | 233 | 43 | −381 | 399 | 106 | −626 |
| — | −10 | −7686 | −8728 | −894 | −1115 | −1200 | −825 | * |
| 72(M) | −1983 | −1721 | −4201 | −671 | −1027 | −3652 | −2508 | 473 |
| — | −149 | −500 | 233 | 43 | −381 | 399 | 106 | −626 |
| — | −9 | −7937 | −8980 | −894 | −1115 | −1952 | −431 | * |
| 73(D) | 325 | −3516 | 2804 | 2034 | −3761 | −2131 | −1242 | −3593 |
| — | −149 | −500 | 233 | 43 | −381 | 399 | 106 | −626 |
| — | −9 | −7937 | −8980 | −894 | −1115 | −1952 | −431 | * |
| 74(M) | −162 | 687 | −1246 | 48 | −1449 | −1992 | −713 | 457 |
| — | −149 | −500 | 233 | 43 | −381 | 399 | 106 | −626 |
| — | −9 | −7937 | −8980 | −894 | −1115 | −1952 | −431 | * |
| 75(A) | 3609 | −2502 | −4177 | −4484 | −4584 | −2730 | −3982 | −4412 |
| — | −149 | −500 | 233 | 43 | −381 | 399 | 106 | −626 |
| — | −9 | −7937 | −8980 | −894 | −1115 | −1952 | −431 | * |
| 76(K) | −1027 | −2025 | −1083 | 321 | −188 | −2040 | 1105 | −1850 |
| — | −149 | −500 | 233 | 43 | −381 | 399 | 106 | −626 |
| — | −9 | −7937 | −8980 | −894 | −1115 | −1952 | −431 | * |
| 77(A) | 2085 | −2164 | −961 | −400 | −2453 | −1963 | −598 | −2122 |
| — | −149 | −500 | 233 | 43 | −381 | 399 | 106 | −626 |
| — | −9 | −7937 | −8980 | −894 | −1115 | −1952 | −431 | * |
| 78(R) | −3027 | −3580 | −3980 | −2342 | −4547 | −3455 | −1266 | −3796 |
| — | −149 | −500 | 233 | 43 | −381 | 399 | 106 | −626 |
| — | −9 | −7937 | −8980 | −894 | −1115 | −1952 | −431 | * |
| 79(V) | 1224 | −1553 | −4145 | −3706 | −1862 | −3327 | −2889 | 214 |
| — | −149 | −500 | 233 | 43 | −381 | 399 | 106 | −626 |
| — | −9 | −7937 | −8980 | −894 | −1115 | −254 | −2629 | * |
| 80(D) | −493 | −3116 | 2767 | 1555 | −3391 | −2262 | −1166 | −3139 |
| — | −149 | −500 | 233 | 43 | −381 | 399 | 106 | −626 |
| — | −7 | −8312 | −9354 | −894 | −1115 | −701 | −1378 | * |
| 81(A) | 2284 | −1391 | −2040 | 1144 | −1397 | −2450 | −1253 | −149 |
| — | −149 | −500 | 233 | 43 | −381 | 399 | 106 | −626 |
| — | −7 | −8312 | −9354 | −894 | −1115 | −701 | −1378 | * |
| 82(A) | 2251 | −1006 | −3057 | −2446 | 931 | −297 | 873 | 186 |
| — | −149 | −500 | 233 | 43 | −381 | 399 | 106 | −626 |
| — | −7 | −8312 | −9354 | −894 | −1115 | −701 | −1378 | * |
| 83(F) | −2224 | −2250 | −4424 | −4264 | 1927 | 1145 | −2398 | −1376 |
| — | −149 | −500 | 233 | 43 | −381 | 399 | 106 | −626 |
| — | −7 | −8312 | −9354 | −894 | −1115 | −701 | −1378 | * |
| 84(E) | −2532 | −3829 | −1248 | 3330 | −4180 | −2869 | 2424 | −3974 |
| — | −149 | −500 | 233 | 43 | −381 | 399 | 106 | −626 |
| — | −7 | −8312 | −9354 | −894 | −1115 | −701 | −1378 | * |
| 85(F) | −1403 | −1396 | −2948 | −2272 | 1386 | −2799 | −1493 | 1022 |
| — | −149 | −500 | 233 | 43 | −381 | 399 | 106 | −626 |
| — | −7 | −8312 | −9354 | −894 | −1115 | −701 | −1378 | * |
| 86(F) | −317 | 889 | −3643 | −3012 | 2565 | −2871 | −1711 | −515 |
| — | −149 | −500 | 233 | 43 | −381 | 399 | 106 | −626 |
| — | −7 | −8312 | −9354 | −894 | −1115 | −701 | −1378 | * |
| 87(E) | 1138 | −2517 | −22 | 2128 | −2834 | −1986 | 953 | −2586 |
| — | −149 | −500 | 233 | 43 | −381 | 399 | 106 | −626 |
| — | −7 | −8312 | −9354 | −894 | −1115 | −701 | −1378 | * |
| 88(K) | −3061 | −4130 | −1699 | 1837 | −4807 | −3224 | −1891 | −4412 |
| — | −149 | −500 | 233 | 43 | −381 | 399 | 106 | −626 |
| — | −7 | −8312 | −9354 | −894 | −1115 | −701 | −1378 | * |
| 89(L) | −3259 | −2823 | −5615 | −5021 | −1437 | −5150 | −3961 | 745 |
| — | −149 | −500 | 233 | 43 | −381 | 399 | 106 | −626 |
| — | −7 | −8312 | −9354 | −894 | −1115 | −701 | −1378 | * |

-continued

| | | | | | | | | |
|---|---|---|---|---|---|---|---|---|
| 90(G) | −1754 | −3293 | 758 | −600 | −3610 | 2854 | 295 | −3395 |
| — | −149 | −500 | 233 | 43 | −381 | 399 | 106 | −626 |
| — | −7 | −8312 | −9354 | −894 | −1115 | −701 | −1378 | * |
| 91(V) | 1814 | −1770 | −4355 | −3892 | −2144 | −3716 | −3087 | 1744 |
| — | −149 | −500 | 233 | 43 | −381 | 399 | 106 | −626 |
| — | −7 | −8312 | −9354 | −894 | −1115 | −701 | −1378 | * |
| 92(P) | −1176 | −2665 | 795 | 1462 | −2975 | −2054 | 1351 | −2732 |
| — | −149 | −500 | 233 | 43 | −381 | 399 | 106 | −626 |
| — | −7 | −8312 | −9354 | −894 | −1115 | −701 | −1378 | * |
| 93(Y) | −3660 | −3259 | −4548 | −4414 | 1974 | 1637 | −1482 | −3075 |
| — | −149 | −500 | 233 | 43 | −381 | 399 | 106 | −626 |
| — | −7 | −8312 | −9354 | −894 | −1115 | −701 | −1378 | * |
| 94(F) | −1766 | −1543 | −3984 | −3431 | 2846 | −3263 | −1648 | 658 |
| — | −149 | −500 | 233 | 43 | −381 | 399 | 106 | −626 |
| — | −7 | −8312 | −9354 | −894 | −1115 | −701 | −1378 | * |
| 95(C) | 367 | 5085 | −4219 | −4291 | −4096 | −2272 | −3593 | −3763 |
| — | −149 | −500 | 233 | 43 | −381 | 399 | 106 | −626 |
| — | −7 | −8312 | −9354 | −894 | −1115 | −701 | −1378 | * |
| 96(F) | −4420 | −3702 | −5536 | −5637 | 4337 | −5230 | −2140 | −2246 |
| — | −149 | −500 | 233 | 43 | −381 | 399 | 106 | −626 |
| — | −7 | −8312 | −9354 | −894 | −1115 | −701 | −1378 | * |
| 97(H) | −5506 | −4764 | −5029 | −5331 | −4362 | −4732 | 5444 | −6634 |
| — | −149 | −500 | 233 | 43 | −381 | 399 | 106 | −626 |
| — | −7 | −8312 | −9354 | −894 | −1115 | −701 | −1378* | * |
| 98(D) | −4886 | −4905 | 4186 | −3339 | −5949 | −4221 | −4195 | −6666 |
| — | −149 | −500 | 233 | 43 | −381 | 399 | 106 | −626 |
| — | −7 | −8312 | −9354 | −894 | −1115 | −701 | −1378 | * |
| 99(R) | −1078 | −2255 | 1071 | 345 | −2468 | −2070 | −762 | 246 |
| — | −149 | −500 | 233 | 43 | −381 | 399 | 106 | −626 |
| — | −7 | −8312 | −9354 | −894 | −1115 | −701 | −1378 | * |
| 100(W) | −204 | 887 | 46 | 246 | −204 | −619 | 891 | −475 |
| — | −149 | −500 | 233 | 43 | −381 | 399 | 106 | −626 |
| — | −7 | −8312 | −9354 | −894 | −1115 | −701 | −1378 | * |
| 101(D) | −4886 | −4905 | 4186 | −3339 | −5949 | −4221 | −4195 | −6666 |
| — | −149 | −500 | 233 | 43 | −381 | 399 | 106 | −626 |
| — | −7 | −8312 | −9354 | −894 | −1115 | −701 | −1378 | * |
| 102(I) | −3148 | −2630 | −5718 | −5282 | −1996 | −5478 | −4785 | 2752 |
| — | −149 | −500 | 233 | 43 | −381 | 399 | 106 | −626 |
| — | −7 | −8312 | −9354 | −894 | −1115 | −701 | −1378 | * |
| 103(A) | 2333 | 880 | −3499 | −2885 | 155 | −2753 | −1687 | 1413 |
| — | −149 | −500 | 233 | 43 | −381 | 399 | 106 | −626 |
| — | −7 | −8312 | −9354 | −894 | −1115 | −701 | −1378 | * |
| 104(P) | −672 | −3716 | 211 | −35 | −4479 | −2521 | −1993 | −4330 |
| — | −149 | −500 | 233 | 43 | −381 | 399 | 106 | −626 |
| — | −7 | −8312 | −9354 | −894 | −1115 | −701 | −1378 | * |
| 105(E) | −1113 | −2563 | 755 | 2544 | 1516 | −2031 | −733 | −2609 |
| — | −149 | −500 | 233 | 43 | −381 | 399 | 106 | −626 |
| — | −7 | −8312 | −9354 | −894 | −1115 | −701 | −1378 | * |
| 106(G) | 299 | −2657 | 34 | −2104 | −4774 | 3464 | −2959 | −4642 |
| — | −149 | −500 | 233 | 43 | −381 | 399 | 106 | −626 |
| — | −7 | −8312 | −9354 | −894 | −1115 | −701 | −1378 | * |
| 107(D) | 940 | −2485 | 1893 | 127 | −2803 | −1971 | 844 | −2554 |
| — | −149 | −500 | 233 | 43 | −381 | 399 | 106 | −626 |
| — | −7 | −8312 | −9354 | −894 | −1115 | −701 | −1378 | * |
| 108(T) | −1565 | −2482 | 739 | −1528 | −3930 | −2299 | −2089 | −3698 |
| — | −149 | −500 | 233 | 43 | −381 | 399 | 106 | −626 |
| — | −7 | −8312 | −9354 | −894 | −1115 | −701 | −1378 | * |
| 109(L) | 183 | −1297 | 530 | −2212 | −1245 | −2705 | −1605 | 1003 |
| — | −149 | −500 | 233 | 43 | −381 | 399 | 106 | −626 |
| — | −7 | −8312 | −9354 | −894 | −1115 | −701 | −1378 | * |
| 110(K) | 640 | −2464 | −846 | 531 | −2786 | −634 | −624 | −2534 |
| — | −149 | −500 | 233 | 43 | −381 | 399 | 106 | −626 |
| — | −7 | −8312 | −9354 | −894 | −1115 | −701 | −1378 | * |
| 111(E) | −2632 | −4118 | −726 | 3650 | −4688 | −2682 | −2003 | −4498 |
| — | −149 | −500 | 233 | 43 | −381 | 399 | 106 | −626 |
| — | −7 | −8312 | −9354 | −894 | −1115 | −701 | −1378 | * |
| 112(T) | −1378 | −1595 | −2330 | −1769 | 970 | 2639 | −1269 | −1211 |
| — | −149 | −500 | 233 | 43 | −381 | 399 | 106 | −626 |
| — | −383 | −8312 | −2119 | −894 | −1115 | −701 | −1378 | * |

-continued

| | | | | | | | | |
|---|---|---|---|---|---|---|---|---|
| 113(N) | −791 | −1832 | 50 | 1047 | −305 | −1841 | −525 | −703 |
| — | −149 | −500 | 233 | 43 | −381 | 399 | 106 | −626 |
| — | −9 | −7937 | −8980 | −894 | −1115 | −1952 | −431 | * |
| 114(K) | 1001 | −2246 | −618 | 864 | −2565 | −1750 | 758 | −2313 |
| — | −149 | −500 | 233 | 43 | −381 | 399 | 106 | −626 |
| — | −9 | −7937 | −8980 | −894 | −1115 | −1952 | −431 | * |
| 115(N) | −2127 | −2452 | −2097 | −2034 | −660 | −2951 | −1368 | −198 |
| — | −149 | −500 | 233 | 43 | −381 | 399 | 106 | −626 |
| — | −9 | −7937 | −8980 | −894 | −1115 | −1952 | −431 | * |
| 116(L) | −3492 | −2924 | −5834 | −5257 | 789 | −5550 | −4102 | 1027 |
| — | −149 | −500 | 233 | 43 | −381 | 399 | 106 | −626 |
| — | −9 | −7937 | −8980 | −894 | −1115 | −254 | −2629 | * |
| 117(D) | 352 | −2696 | 2970 | 584 | −3009 | −2082 | −807 | −2762 |
| — | −149 | −500 | 233 | 43 | −381 | 399 | 106 | −626 |
| — | −7 | −8312 | −9354 | −894 | −1115 | −701 | −1378 | * |
| 118(Q) | −379 | −2417 | −845 | 1254 | −2722 | −784 | 874 | −200 |
| — | −149 | −500 | 233 | 43 | −381 | 399 | 106 | −626 |
| — | −7 | −8312 | −9354 | −894 | −1115 | −701 | −1378 | * |
| 119(M) | −1906 | −1631 | −4282 | −3715 | −1632 | −3659 | 1153 | 2809 |
| — | −149 | −500 | 233 | 43 | −381 | 399 | 106 | −626 |
| — | −7 | −8312 | −9354 | −894 | −1115 | −701 | −1378 | * |
| 120(V) | −1675 | −1428 | −4046 | −3465 | −1535 | −3381 | −2355 | 1345 |
| — | −149 | −500 | 233 | 43 | −381 | 399 | 106 | −626 |
| — | −7 | −8312 | −9354 | −894 | −1115 | −701 | −1378 | * |
| 121(D) | 893 | −2550 | 2186 | 1147 | −2867 | 374 | −691 | −2620 |
| — | −149 | −500 | 233 | 43 | −381 | 399 | 106 | −626 |
| — | −7 | −8312 | −9354 | −894 | −1115 | −701 | −1378 | * |
| 122(M) | −1064 | −1348 | −380 | −1330 | −160 | −875 | 767 | 37 |
| — | −149 | −500 | 233 | 43 | −381 | 399 | 106 | −626 |
| — | −7 | −8312 | −9354 | −894 | −1115 | −701 | −1378 | * |
| 123(I) | 624 | −2059 | −4727 | −4136 | 2069 | −4088 | −2966 | 2565 |
| — | −149 | −500 | 233 | 43 | −381 | 399 | 106 | −626 |
| — | −7 | −8312 | −9354 | −894 | −1115 | −701 | −1378 | * |
| 124(K) | 164 | −2420 | −870 | 864 | −2723 | −1981 | −637 | −2456 |
| — | −149 | −500 | 233 | 43 | −381 | 399 | 106 | −626 |
| — | −7 | −8312 | −9354 | −894 | −1115 | −701 | −1378 | * |
| 125(Q) | −1086 | −2570 | 755 | 2102 | −2887 | −239 | −702 | −2641 |
| — | −149 | −500 | 233 | 43 | −381 | 399 | 106 | −626 |
| — | −7 | −8312 | −9354 | −894 | −1115 | −701 | −1378 | * |
| 126(K) | 1143 | −2138 | −1047 | −491 | −2334 | −1268 | −731 | −1997 |
| — | −149 | −500 | 233 | 43 | −381 | 399 | 106 | −626 |
| — | −7 | −8312 | −9354 | −894 | −1115 | −701 | −1378 | * |
| 127(M) | −3159 | −2791 | −5237 | −4626 | −1375 | −4924 | −3658 | 241 |
| — | −149 | −500 | 233 | 43 | −381 | 399 | 106 | −626 |
| — | −7 | −8312 | −9354 | −894 | −1115 | −701 | −1378 | * |
| 128(K) | 531 | −2467 | 1672 | 432 | −2787 | −1962 | 842 | −2538 |
| — | −149 | −500 | 233 | 43 | −381 | 399 | 106 | −626 |
| — | −7 | −8312 | −9354 | −894 | −1115 | −701 | −1378 | * |
| 129(E) | 608 | −2501 | 1336 | 1866 | −2820 | −1977 | −651 | −2572 |
| — | −149 | −500 | 233 | 43 | −381 | 399 | 106 | −626 |
| — | −7 | −8312 | −9354 | −894 | −1115 | −701 | −1378 | * |
| 130(T) | −1443 | −2096 | −3124 | −3287 | −4401 | −2292 | −3317 | −4200 |
| — | −149 | −500 | 233 | 43 | −381 | 399 | 106 | −626 |
| — | −7 | −8312 | −9354 | −894 | −1115 | −701 | −1378 | * |
| 131(G) | −2342 | −3617 | −1078 | −1138 | −4177 | 3145 | 602 | −3928 |
| — | −149 | −500 | 233 | 43 | −381 | 399 | 106 | −626 |
| — | −7 | −8312 | −9354 | −894 | −1115 | −701 | −1378 | * |
| 132(M) | −1412 | −1211 | −3721 | −3109 | −1195 | −3019 | −1922 | 1936 |
| — | −149 | −500 | 233 | 43 | −381 | 399 | 106 | −626 |
| — | −7 | −8312 | −9354 | −894 | −1115 | −701 | −1378 | * |
| 133(K) | −2382 | −3084 | −2779 | −1906 | −3480 | −3186 | −1412 | −563 |
| — | −149 | −500 | 233 | 43 | −381 | 399 | 106 | −626 |
| — | −7 | −8312 | −9354 | −894 | −1115 | −701 | −1378 | * |
| 134(L) | −2611 | −2332 | −4972 | −4508 | −1725 | −4314 | −3571 | −413 |
| — | −149 | −500 | 233 | 43 | −381 | 399 | 106 | −626 |
| — | −7 | −8312 | −9354 | −894 | −1115 | −701 | −1378 | * |
| 135(L) | −3561 | −3470 | −4972 | −5000 | −2527 | −4319 | −4274 | −2132 |
| — | −149 | −500 | 233 | 43 | −381 | 399 | 106 | −626 |
| — | −7 | −8312 | −9354 | −894 | −1115 | −701 | −1378 | * |
| 136(W) | −4178 | −3738 | −5370 | −5358 | −1338 | −4715 | −2806 | −2734 |
| — | −149 | −500 | 233 | 43 | −381 | 399 | 106 | −626 |
| — | −7 | −8312 | −9354 | −894 | −1115 | −701 | −1378 | * |
| 137(N) | 142 | −1989 | −2878 | −2702 | −3612 | 1917 | −2689 | −3274 |
| — | −149 | −500 | 233 | 43 | −381 | 399 | 106 | −626 |
| — | −7 | −8312 | −9354 | −894 | −1115 | −701 | −1378 | * |

-continued

| | | | | | | | | |
|---|---|---|---|---|---|---|---|---|
| 138(T) | −3014 | −3363 | −4795 | −5109 | −5200 | −3551 | −4612 | −5219 |
| — | −149 | −500 | 233 | 43 | −381 | 399 | 106 | −626 |
| — | −7 | −8312 | −9354 | −894 | −1115 | −701 | −1378 | * |
| 139(A) | 2832 | −1972 | −4244 | −4339 | −4463 | −760 | −3712 | −4243 |
| — | −149 | −500 | 233 | 43 | −381 | 399 | 106 | −626 |
| — | −7 | −8312 | −9354 | −894 | −1115 | −701 | −1378 | * |
| 140(N) | −2239 | −3351 | −994 | −1271 | −4465 | −2566 | −2158 | −4418 |
| — | −149 | −500 | 233 | 43 | −381 | 399 | 106 | −626 |
| — | −7 | −8312 | −9354 | −894 | −1115 | −701 | −1378 | * |
| 141(M) | −1488 | 1901 | −3790 | −3168 | −1094 | −3058 | −1949 | −467 |
| — | −149 | −500 | 233 | 43 | −381 | 399 | 106 | −626 |
| — | −7 | −8312 | −9354 | −894 | −1115 | −701 | −1378 | * |
| 142(F) | −5308 | −4420 | −5610 | −5948 | 4547 | −4921 | −3048 | −4656 |
| — | −149 | −500 | 233 | 43 | −381 | 399 | 106 | −626 |
| — | −7 | −8312 | −9354 | −894 | −1115 | −701 | −1378 | * |
| 143(T) | −1333 | −1921 | −3518 | −3324 | −3642 | 123 | −3003 | −3307 |
| — | −149 | −500 | 233 | 43 | −381 | 399 | 106 | −626 |
| — | −7 | −8312 | −9354 | −894 | −1115 | −701 | −1378 | * |
| 144(H) | −2587 | −4410 | 687 | −793 | −4549 | −2586 | 4208 | −4506 |
| — | −149 | −500 | 233 | 43 | −381 | 399 | 106 | −626 |
| — | −7 | −8312 | −9354 | −894 | −1115 | −701 | −1378 | * |
| 145(P) | −777 | −3430 | −1097 | −93 | −4208 | −2659 | −1777 | −3899 |
| — | −149 | −500 | 233 | 43 | −381 | 399 | 106 | −626 |
| — | −7 | −8312 | −9354 | −894 | −1115 | −701 | −1378 | * |
| 146(R) | −550 | −1933 | −2864 | −2364 | −2830 | −927 | −2070 | −2310 |
| — | −149 | −500 | 233 | 43 | −381 | 399 | 106 | −626 |
| — | −7 | −8312 | −9354 | −894 | −1115 | −701 | −1378 | * |
| 147(F) | −4998 | −3935 | −5388 | −5739 | 3810 | −5262 | −1482 | −3879 |
| — | −149 | −500 | 233 | 43 | −381 | 399 | 106 | −626 |
| — | −7 | −8312 | −9354 | −894 | −1115 | −701 | −1378 | * |
| 148(M) | −1239 | −1212 | −2845 | −2242 | −1184 | −92 | −1512 | −579 |
| — | −149 | −500 | 233 | 43 | −381 | 399 | 106 | −626 |
| — | −7 | −8312 | −9354 | −894 | −1115 | −701 | −1378 | * |
| 149(H) | 593 | −3227 | 1964 | 442 | −3513 | −2264 | 3263 | −3299 |
| — | −149 | −500 | 233 | 43 | −381 | 399 | 106 | −626 |
| — | −7 | −8312 | −9354 | −894 | −1115 | −701 | −1378 | * |
| 150(G) | −4740 | −4445 | −5364 | −5738 | −6131 | 3840 | −5265 | −6903 |
| — | −149 | −500 | 233 | 43 | −381 | 399 | 106 | −626 |
| — | −7 | −8312 | −9354 | −894 | −1115 | −701 | −1378 | * |
| 151(W) | −204 | 887 | 46 | 246 | −204 | −619 | 891 | −475 |
| — | −149 | −500 | 233 | 43 | −381 | 399 | 106 | −626 |
| — | −7 | −8312 | −9354 | −894 | −1115 | −701 | −1378 | * |
| 152(A) | 3079 | −1981 | −4321 | −4534 | −4388 | 1735 | −3806 | −3957 |
| — | −149 | −500 | 233 | 43 | −381 | 399 | 106 | −626 |
| — | −7 | −8312 | −9354 | −894 | −1115 | −701 | −1378 | * |
| 153(A) | 2589 | −1888 | −3886 | −3806 | 2401 | −778 | −3205 | −3235 |
| — | −149 | −500 | 233 | 43 | −381 | 399 | 106 | −626 |
| — | −7 | −8312 | −9354 | −894 | −1115 | −701 | −1378 | * |
| 154(T) | −1493 | −2101 | −3952 | −4245 | −4536 | −2355 | −3794 | −4349 |
| — | −149 | −500 | 233 | 43 | −381 | 399 | 106 | −626 |
| — | −7 | −8312 | −9354 | −894 | −1115 | −701 | −1378 | * |
| 155(S) | 540 | −2055 | −3002 | −2865 | −4153 | −2245 | −2899 | −3915 |
| — | −149 | −500 | 233 | 43 | −381 | 399 | 106 | −626 |
| — | −7 | −8312 | −9354 | −894 | −1115 | −701 | −1378 | * |
| 156(C) | −1362 | 3283 | −2411 | −2080 | −3450 | −2276 | −2150 | −3137 |
| — | −149 | −500 | 233 | 43 | −381 | 399 | 106 | −626 |
| — | −7 | −8312 | −9354 | −894 | −1115 | −701 | −1378 | * |
| 157(D) | −1060 | −2512 | 2344 | 682 | 408 | −2001 | −688 | −2563 |
| — | −149 | −500 | 233 | 43 | −381 | 399 | 106 | −626 |
| — | −7 | −8312 | −9354 | −894 | −1115 | −701 | −1378 | * |
| 158(A) | 2203 | −1406 | −2316 | −1761 | 1179 | −2422 | −1413 | −1077 |
| — | −149 | −500 | 233 | 43 | −381 | 399 | 106 | −626 |
| — | −7 | −8312 | −9354 | −894 | −1115 | −701 | −1378 | * |
| 159(D) | −1108 | −2589 | 2572 | 1474 | −2902 | −2021 | −725 | −2655 |
| — | −149 | −500 | 233 | 43 | −381 | 399 | 106 | −626 |
| — | −7 | −8312 | −9354 | −894 | −1115 | −701 | −1378 | * |
| 160(V) | −2769 | −2275 | −5444 | −5141 | −2907 | −5216 | −5273 | 1475 |
| — | −149 | −500 | 233 | 43 | −381 | 399 | 106 | −626 |
| — | −7 | −8312 | −9354 | −894 | −1115 | −701 | −1378 | * |

| | | | | | | | | |
|---|---|---|---|---|---|---|---|---|
| 161(F) | −3052 | −2695 | −4546 | −4247 | 3203 | −4202 | −1494 | −2262 |
| — | | −149 | −500 | 233 | 43 | −381 | 399 | 106 | −626 |
| — | | −7 | −8312 | −9354 | −894 | −1115 | −701 | −1378 | * |
| 162(A) | 3042 | −2119 | −3426 | −3206 | −4202 | −2348 | −2904 | −3925 |
| — | | −149 | −500 | 233 | 43 | −381 | 399 | 106 | −626 |
| — | | −7 | −8312 | −9354 | −894 | −1115 | −701 | −1378 | * |
| 163(Y) | −3964 | −3336 | −5040 | −5039 | 1445 | −4787 | −1468 | −3083 |
| — | | −149 | −500 | 233 | 43 | −381 | 399 | 106 | −626 |
| — | | −7 | −8312 | −9354 | −894 | −1115 | −701 | −1378 | * |
| 164(A) | 3397 | −1996 | −4237 | −4525 | −4627 | −310 | −3879 | −4438 |
| — | | −149 | −500 | 233 | 43 | −381 | 399 | 106 | −626 |
| — | | −7 | −8312 | −9354 | −894 | −1115 | −701 | −1378 | * |
| 165(A) | 2613 | −1126 | −3505 | −2891 | −69 | −991 | −1733 | 690 |
| — | | −149 | −500 | 233 | 43 | −381 | 399 | 106 | −626 |
| — | | −7 | −8312 | −9354 | −894 | −1115 | −701 | −1378 | * |
| 166(A) | 2450 | −1805 | −2420 | −1934 | −2555 | 164 | −1841 | −2139 |
| — | | −149 | −500 | 233 | 43 | −381 | 399 | 106 | −626 |
| — | | −7 | −8312 | −9354 | −894 | −1115 | −701 | −1378 | * |
| 167(Q) | −3216 | −3916 | −3036 | −2340 | −4750 | −3581 | −1704 | −4191 |
| — | | −149 | −500 | 233 | 43 | −381 | 399 | 106 | −626 |
| — | | −7 | −8312 | −9354 | −894 | −1115 | −701 | −1378 | * |
| 168(V) | −1889 | −1609 | −4294 | −3746 | −1809 | −3673 | −2738 | 1337 |
| — | | −149 | −500 | 233 | 43 | −381 | 399 | 106 | −626 |
| — | | −7 | −8312 | −9354 | −894 | −1115 | −701 | −1378 | * |
| 169(K) | −1988 | −1815 | −3867 | −3265 | −61 | 3579 | −2411 | 608 |
| — | | −149 | −500 | 233 | 43 | −381 | 399 | 106 | −626 |
| — | | −7 | −8312 | −9354 | −894 | −1115 | −701 | −1378 | * |
| 170(H) | −256 | −2524 | −929 | 393 | −2858 | −2038 | 2453 | −2595 |
| — | | −149 | −500 | 233 | 43 | −381 | 399 | 106 | −626 |
| — | | −7 | −8312 | −9354 | −894 | −1115 | −701 | −1378 | * |
| 171(A) | 1760 | −2287 | −1318 | −859 | −3091 | 1259 | −1172 | −2823 |
| — | | −149 | −500 | 233 | 43 | −381 | 399 | 106 | −626 |
| — | | −7 | −8312 | −9354 | −894 | −1115 | −701 | −1378 | * |
| 172(M) | −3851 | −3263 | −6245 | −5660 | −1466 | −5999 | −4689 | 2110 |
| — | | −149 | −500 | 233 | 43 | −381 | 399 | 106 | −626 |
| — | | −7 | −8312 | −9354 | −894 | −1115 | −701 | −1378 | * |
| 173(D) | −2907 | −4984 | 3077 | 2640 | −5091 | −2646 | −2094 | −5089 |
| — | | −149 | −500 | 233 | 43 | −381 | 399 | 106 | −626 |
| — | | −7 | −8312 | −9354 | −894 | −1115 | −701 | −1378 | * |
| 174(I) | 1132 | −1695 | −4439 | −3899 | −1866 | −3834 | −2908 | 2259 |
| — | | −149 | −500 | 233 | 43 | −381 | 399 | 106 | −626 |
| — | | −7 | −8312 | −9354 | −894 | −1115 | −701 | −1378 | * |
| 175(T) | 2228 | −1974 | −4202 | −4278 | −4460 | 1638 | −3685 | −4242 |
| — | | −149 | −500 | 233 | 43 | −381 | 399 | 106 | −626 |
| — | | −7 | −8312 | −9354 | −894 | −1115 | −701 | −1378 | * |
| 176(K) | 692 | −1650 | −1775 | −1196 | −1722 | −2391 | 1742 | 714 |
| — | | −149 | −500 | 233 | 43 | −381 | 399 | 106 | −626 |
| — | | −7 | −8312 | −9354 | −894 | −1115 | −701 | −1378 | * |
| 177(E) | −1319 | −2706 | −1195 | 2572 | −3079 | −2247 | −809 | −2780 |
| — | | −149 | −500 | 233 | 43 | −381 | 399 | 106 | −626 |
| — | | −7 | −8312 | −9354 | −894 | −1115 | −701 | −1378 | * |
| 178(L) | −3875 | −3291 | −6254 | −5672 | −1457 | −5994 | −4687 | −834 |
| — | | −149 | −500 | 233 | 43 | −381 | 399 | 106 | −626 |
| — | | −7 | −8312 | −9354 | −894 | −1115 | −701 | −1378 | * |
| 179(G) | −2536 | −3114 | −2855 | −3225 | −5099 | 3685 | −3752 | −5315 |
| — | | −149 | −500 | 233 | 43 | −381 | 399 | 106 | −626 |
| — | | −7 | −8312 | −9354 | −894 | −1115 | −701 | −1378 | * |
| 180(A) | 2480 | −2007 | −3784 | −3834 | −4416 | 2311 | −3496 | −4197 |
| — | | −149 | −500 | 233 | 43 | −381 | 399 | 106 | −626 |
| — | | −7 | −8312 | −9354 | −894 | −1115 | −701 | −1378 | * |
| 181(E) | −2358 | −3954 | −688 | 3489 | −4290 | −2588 | −1658 | −4076 |
| — | | −149 | −500 | 233 | 43 | −381 | 399 | 106 | −626 |
| — | | −7 | −8312 | −9354 | −894 | −1115 | −701 | −1378 | * |
| 182(N) | −1197 | −1819 | −2024 | −1565 | −2415 | −764 | −1594 | −14 |
| — | | −149 | −500 | 233 | 43 | −381 | 399 | 106 | −626 |
| — | | −7 | −8312 | −9354 | −894 | −1115 | −701 | −1378 | * |
| 183(Y) | −4914 | −3888 | −5384 | −5705 | 1863 | −5254 | −1485 | −3696 |
| — | | −149 | −500 | 233 | 43 | −381 | 399 | 106 | −626 |
| — | | −7 | −8312 | −9354 | −894 | −1115 | −701 | −1378 | * |

| | | | | | | | | |
|---|---|---|---|---|---|---|---|---|
| 184(V) | -3382 | -3135 | -5319 | -5407 | -3802 | -4379 | -4923 | -1179 |
| — | -149 | -500 | 233 | 43 | -381 | 399 | 106 | -626 |
| — | -7 | -8312 | -9354 | -894 | -1115 | -701 | -1378 | * |
| 185(F) | -245 | -1976 | -4569 | -3955 | 3611 | -3896 | -2734 | -630 |
| — | -149 | -500 | 233 | 43 | -381 | 399 | 106 | -626 |
| — | -7 | -8312 | -9354 | -894 | -1115 | -701 | -1378 | * |
| 186(W) | -6178 | -4896 | -5848 | -6204 | -4109 | -4952 | -4743 | -6650 |
| — | -149 | -500 | 233 | 43 | -381 | 399 | 106 | -626 |
| — | -7 | -8312 | -9354 | -894 | -1115 | -701 | -1378 | * |
| 187(G) | -3000 | -3383 | -4355 | -4713 | -5554 | 3708 | -4577 | -5789 |
| — | -149 | -500 | 233 | 43 | -381 | 399 | 106 | -626 |
| — | -7 | -8312 | -9354 | -894 | -1115 | -701 | -1378 | * |
| 188(G) | -4740 | -4445 | -5364 | -5738 | -6131 | 3840 | -5265 | -6903 |
| — | -149 | -500 | 233 | 43 | -381 | 399 | 106 | -626 |
| — | -7 | -8312 | -9354 | -894 | -1115 | -701 | -1378 | * |
| 189(R) | -5156 | -4675 | -5377 | -4998 | -5777 | -4641 | -4103 | -6271 |
| — | -149 | -500 | 233 | 43 | -381 | 399 | 106 | -626 |
| — | -7 | -8312 | -9354 | -894 | -1115 | -701 | -1378 | * |
| 190(E) | -4894 | -4877 | -3044 | 3932 | -5916 | -4252 | -4190 | -6541 |
| — | -149 | -500 | 233 | 43 | -381 | 399 | 106 | -626 |
| — | -7 | -8312 | -9354 | -894 | -1115 | -701 | -1378 | * |
| 191(G) | -4740 | -4445 | -5364 | -5738 | -6131 | 3840 | -5265 | -6903 |
| — | -149 | -500 | 233 | 43 | -381 | 399 | 106 | -626 |
| — | -7 | -8312 | -9354 | -894 | -1115 | -701 | -1378 | * |
| 192(Y) | 1128 | -2151 | -3615 | -3697 | -2169 | -2532 | -2750 | -3414 |
| — | -149 | -500 | 233 | 43 | -381 | 399 | 106 | -626 |
| — | -7 | -8312 | -9354 | -894 | -1115 | -701 | -1378 | * |
| 193(E) | -380 | -3053 | 283 | 1153 | -3334 | -2232 | -1107 | -3096 |
| — | -149 | -500 | 233 | 43 | -381 | 399 | 106 | -626 |
| — | -7 | -8312 | -9354 | -894 | -1115 | -701 | -1378 | * |
| 194(T) | -1103 | 1142 | -2635 | -2048 | 226 | -2529 | -1370 | -640 |
| — | -149 | -500 | 233 | 43 | -381 | 399 | 106 | -626 |
| — | -7 | -8312 | -9354 | -894 | -1115 | -701 | -1378 | * |
| 195(L) | -2451 | -3826 | 1344 | 380 | -3974 | -118 | -1886 | -3714 |
| — | -149 | -500 | 233 | 43 | -381 | 399 | 106 | -626 |
| — | -7 | -8312 | -9354 | -894 | -1115 | -701 | -1378 | * |
| 196(W) | 386 | -1134 | -2676 | -2101 | -1119 | -347 | 779 | -682 |
| — | -149 | -500 | 233 | 43 | -381 | 399 | 106 | -626 |
| — | -7 | -8312 | -9354 | -894 | -1115 | -701 | -1378 | * |
| 197(N) | 1013 | -2090 | -2983 | -3038 | -4320 | -2272 | -3125 | -4091 |
| — | -149 | -500 | 233 | 43 | -381 | 399 | 106 | -626 |
| — | -7 | -8312 | -9354 | -894 | -1115 | -701 | -1378 | * |
| 198(T) | -1798 | -2527 | -2472 | -2321 | -4196 | -165 | -2323 | -3864 |
| — | -149 | -500 | 233 | 43 | -381 | 399 | 106 | -626 |
| — | -7 | -8312 | -9354 | -894 | -1115 | -701 | -1378 | * |
| 199(D) | -2628 | -4493 | 3630 | -795 | -4689 | -2595 | -1891 | -4588 |
| — | -149 | -500 | 233 | 43 | -381 | 399 | 106 | -626 |
| — | -7 | -8312 | -9354 | -894 | -1115 | -701 | -1378 | * |
| 200(M) | -97 | -1073 | -3318 | -2701 | -998 | -2739 | -1606 | -472 |
| — | -149 | -500 | 233 | 43 | -381 | 399 | 106 | -626 |
| — | -7 | -8312 | -9354 | -894 | -1115 | -701 | -1378 | * |
| 201(K) | -294 | -2512 | -898 | 178 | -2843 | -95 | -659 | -2584 |
| — | -149 | -500 | 233 | 43 | -381 | 399 | 106 | -626 |
| — | -7 | -8312 | -9354 | -894 | -1115 | -701 | -1378 | * |
| 202(W) | -204 | 887 | 46 | 246 | -204 | -619 | 891 | -475 |
| — | -149 | -500 | 233 | 43 | -381 | 399 | 106 | -626 |
| — | -7 | -8312 | -9354 | -894 | -1115 | -701 | -1378 | * |
| 203(R) | 515 | -2100 | -67 | -484 | 1101 | -2050 | -726 | -1947 |
| — | -149 | -500 | 233 | 43 | -381 | 399 | 106 | -626 |
| — | -7 | -8312 | -9354 | -894 | -1115 | -701 | -1378 | * |
| 204(E) | 1191 | -2588 | -1433 | 3261 | -3616 | -2449 | -2074 | -2773 |
| — | -149 | -500 | 233 | 43 | -381 | 399 | 106 | -626 |
| — | -7 | -8312 | -9354 | -894 | -1115 | -701 | -1378 | * |
| 205(L) | -1513 | -1884 | -2260 | -1562 | -1940 | -2676 | -1221 | -1499 |
| — | -149 | -500 | 233 | 43 | -381 | 399 | 106 | -626 |
| — | -7 | -8312 | -9354 | -894 | -1115 | -701 | -1378 | * |
| 206(D) | -745 | -4362 | 3177 | 2316 | -4570 | -2552 | -1843 | -4464 |
| — | -149 | -500 | 233 | 43 | -381 | 399 | 106 | -626 |
| — | -7 | -8312 | -9354 | -894 | -1115 | -701 | -1378 | * |
| 207(H) | -1159 | -2582 | -194 | -438 | -2895 | -2097 | 3162 | -2638 |
| — | -149 | -500 | 233 | 43 | -381 | 399 | 106 | -626 |
| — | -7 | -8312 | -9354 | -894 | -1115 | -701 | -1378 | * |

-continued

| | | | | | | | | |
|---|---|---|---|---|---|---|---|---|
| 208(M) | −667 | −1277 | −3818 | −3186 | 164 | −3048 | −1914 | 1188 |
| — | −149 | −500 | 233 | 43 | −381 | 399 | 106 | −626 |
| — | −7 | −8312 | −9354 | −894 | −1115 | −701 | −1378 | * |
| 209(A) | 2605 | −2502 | −1660 | −1121 | −3271 | 74 | −1239 | −2944 |
| — | −149 | −500 | 233 | 43 | −381 | 399 | 106 | −626 |
| — | −7 | −8312 | −9354 | −894 | −1115 | −701 | −1378 | * |
| 210(R) | −254 | −2474 | −853 | 1591 | −2798 | −1977 | −630 | −2545 |
| — | −149 | −500 | 233 | 43 | −381 | 399 | 106 | −626 |
| — | −7 | −8312 | −9354 | −894 | −1115 | −701 | −1378 | * |
| 211(F) | 948 | −1050 | −3245 | −2644 | 1385 | −798 | −1571 | 28 |
| — | −149 | −500 | 233 | 43 | −381 | 399 | 106 | −626 |
| — | −7 | −8312 | −9354 | −894 | −1115 | −701 | −1378 | * |
| 212(F) | −2629 | −2312 | −4914 | −4321 | 2717 | −4278 | −2852 | −858 |
| — | −149 | −500 | 233 | 43 | −381 | 399 | 106 | −626 |
| — | −7 | −8312 | −9354 | −894 | −1115 | −701 | −1378 | * |
| 213(H) | −1020 | −2488 | 1097 | −309 | −2812 | −1983 | 2931 | −2560 |
| — | −149 | −500 | 233 | 43 | −381 | 399 | 106 | −626 |
| — | −7 | −8312 | −9354 | −894 | −1115 | −701 | −1378 | * |
| 214(M) | −359 | −1579 | −4116 | −3488 | 569 | −3396 | −2253 | 143 |
| — | −149 | −500 | 233 | 43 | −381 | 399 | 106 | −626 |
| — | −7 | −8312 | −9354 | −894 | −1115 | −701 | −1378 | * |
| 215(A) | 2548 | 947 | −3783 | −3180 | −1231 | −3043 | −2001 | −310 |
| — | −149 | −500 | 233 | 43 | −381 | 399 | 106 | −626 |
| — | −7 | −8312 | −9354 | −894 | −1115 | −701 | −1378 | * |
| 216(V) | 787 | 844 | −1857 | −1289 | −1397 | −389 | 570 | 555 |
| — | −149 | −500 | 233 | 43 | −381 | 399 | 106 | −626 |
| — | −7 | −8312 | −9354 | −894 | −1115 | −701 | −1378 | * |
| 217(D) | −208 | −3213 | 3902 | 1429 | −3501 | −609 | −1166 | −3288 |
| — | −149 | −500 | 233 | 43 | −381 | 399 | 106 | −626 |
| — | −7 | −8312 | −9354 | −894 | −1115 | −701 | −1378 | * |
| 218(Y) | −4881 | −3957 | −5031 | −5318 | −128 | −5096 | 2506 | −3985 |
| — | −149 | −500 | 233 | 43 | −381 | 399 | 106 | −626 |
| — | −7 | −8312 | −9354 | −894 | −1115 | −701 | −1378 | * |
| 219(A) | 2495 | −1569 | −1878 | −1335 | −1756 | −621 | −1246 | −153 |
| — | −149 | −500 | 233 | 43 | −381 | 399 | 106 | −626 |
| — | −7 | −8312 | −9354 | −894 | −1115 | −701 | −1378 | * |
| 220(K) | −986 | −2457 | −27 | 762 | −2778 | −1959 | 1449 | −834 |
| — | −149 | −500 | 233 | 43 | −381 | 399 | 106 | −626 |
| — | −7 | −8312 | −9354 | −894 | −1115 | −701 | −1378 | * |
| 221(E) | −254 | −2564 | 1369 | 2076 | −2882 | −2009 | −700 | −2635 |
| — | −149 | −500 | 233 | 43 | −381 | 399 | 106 | −626 |
| — | −7 | −8312 | −9354 | −894 | −1115 | −701 | −1378 | * |
| 222(I) | −2688 | −3306 | −3275 | −2169 | −3815 | −3397 | −1438 | 3178 |
| — | −149 | −500 | 233 | 43 | −381 | 399 | 106 | −626 |
| — | −7 | −8312 | −9354 | −894 | −1115 | −701 | −1378 | * |
| 223(G) | −2637 | −3974 | 390 | −1153 | −5020 | 3488 | −2357 | −5035 |
| — | −149 | −500 | 233 | 43 | −381 | 399 | 106 | −626 |
| — | −7 | −8312 | −9354 | −894 | −1115 | −701 | −1378 | * |
| 224(Y) | −4400 | −3612 | −5188 | −5335 | 3494 | −5009 | 1099 | −3457 |
| — | −149 | −500 | 233 | 43 | −381 | 399 | 106 | −626 |
| — | −7 | −8312 | −9354 | −894 | −1115 | −701 | −1378 | * |
| 225(D) | −991 | −2464 | 1721 | 213 | −2784 | 477 | 823 | −2534 |
| — | −149 | −500 | 233 | 43 | −381 | 399 | 106 | −626 |
| — | −7 | −8312 | −9354 | −894 | −1115 | −701 | −1378 | * |
| 226(G) | 624 | −1134 | −2638 | −2059 | −1134 | 2287 | −1399 | −199 |
| — | −149 | −500 | 233 | 43 | −381 | 399 | 106 | −626 |
| — | −7 | −8312 | −9354 | −894 | −1115 | −701 | −1378 | * |
| 227(Q) | −1134 | −2497 | −1028 | −462 | −2811 | −2101 | −720 | −622 |
| — | −149 | −500 | 233 | 43 | −381 | 399 | 106 | −626 |
| — | −7 | −8312 | −9354 | −894 | −1115 | −701 | −1378 | * |
| 228(F) | −3742 | −3197 | −6068 | −5484 | 3900 | −5732 | −4235 | 207 |
| — | −149 | −500 | 233 | 43 | −381 | 399 | 106 | −626 |
| — | −7 | −8312 | −9354 | −894 | −1115 | −701 | −1378 | * |
| 229(L) | 1551 | −2659 | −4811 | −4712 | −2094 | −3608 | −3887 | −1436 |
| — | −149 | −500 | 233 | 43 | −381 | 399 | 106 | −626 |
| — | −7 | −8312 | −9354 | −894 | −1115 | −701 | −1378 | * |

-continued

| | | | | | | | | |
|---|---|---|---|---|---|---|---|---|
| 230(I) | −3359 | −2829 | −5847 | −5421 | −1855 | −5595 | −4779 | 3551 |
| — | −149 | −500 | 233 | 43 | −381 | 399 | 106 | −626 |
| — | −7 | −8312 | −9354 | −894 | −1115 | −701 | −1378 | * |
| 231(E) | −4894 | −4877 | −3044 | 3932 | −5916 | −4252 | −4190 | −6541 |
| — | −149 | −500 | 233 | 43 | −381 | 399 | 106 | −626 |
| — | −7 | −8312 | −9354 | −894 | −1115 | −701 | −1378 | * |
| 232(P) | −5161 | −4627 | −5479 | −5844 | −6102 | −4639 | −5314 | −6971 |
| — | −149 | −500 | 233 | 43 | −381 | 399 | 106 | −626 |
| — | −7 | −8312 | −9354 | −894 | −1115 | −701 | −1378 | * |
| 233(K) | −4797 | −4587 | −4692 | −4321 | −5682 | −3615 | −4474 | −5879 |
| — | −149 | −500 | 233 | 43 | −381 | 399 | 106 | −626 |
| — | −7 | −8312 | −9354 | −894 | −1115 | −701 | −1378 | * |
| 234(P) | −513 | −2636 | −4047 | −4375 | −4929 | −2842 | −4112 | −4853 |
| — | −149 | −500 | 233 | 43 | −381 | 399 | 106 | −626 |
| — | −7 | −8312 | −9354 | −894 | −1115 | −701 | −1378 | * |
| 235(K) | −1854 | −3064 | −1724 | −1121 | −3517 | −2674 | −1100 | −3136 |
| — | −149 | −500 | 233 | 43 | −381 | 399 | 106 | −626 |
| — | −7 | −8312 | −9354 | −894 | −1115 | −701 | −1378 | * |
| 236(E) | −4894 | −4877 | −3044 | 3932 | −5916 | −4252 | −4190 | −6541 |
| — | −149 | −500 | 233 | 43 | −381 | 399 | 106 | −626 |
| — | −7 | −8312 | −9354 | −894 | −1115 | −701 | −1378 | * |
| 237(P) | −5161 | −4627 | −5479 | −5844 | −6102 | −4639 | −5314 | −6971 |
| — | −149 | −500 | 233 | 43 | −381 | 399 | 106 | −626 |
| — | −7 | −8312 | −9354 | −894 | −1115 | −701 | −1378 | * |
| 238(T) | −1947 | −2421 | −3165 | −2413 | −2978 | −2880 | −1827 | −2467 |
| — | −149 | −500 | 233 | 43 | −381 | 399 | 106 | −626 |
| — | −7 | −8312 | −9354 | −894 | −1115 | −701 | −1378 | * |
| 239(K) | −484 | −2389 | −1045 | −493 | −2703 | 1249 | −755 | −2401 |
| — | −149 | −500 | 233 | 43 | −381 | 399 | 106 | −626 |
| — | −7 | −8312 | −9354 | −894 | −1115 | −701 | −1378 | * |
| 240(H) | −3186 | −4015 | 2118 | −1712 | 238 | −3267 | 4734 | −4101 |
| — | −149 | −500 | 233 | 43 | −381 | 399 | 106 | −626 |
| — | −7 | −8312 | −9354 | −894 | −1115 | −701 | −1378 | * |
| 241(Q) | −2896 | −3052 | −3270 | −3166 | −2696 | −3713 | −2865 | 2002 |
| — | −149 | −500 | 233 | 43 | −381 | 399 | 106 | −626 |
| — | −7 | −8312 | −9354 | −894 | −1115 | −701 | −1378 | * |
| 242(Y) | −4742 | −3801 | −5383 | −5639 | 926 | −5232 | −1545 | −3295 |
| — | −149 | −500 | 233 | 43 | −381 | 399 | 106 | −626 |
| — | −7 | −8312 | −9354 | −894 | −1115 | −701 | −1378 | * |
| 243(D) | −3103 | −3191 | 3532 | −2696 | 707 | −3852 | −2334 | −1817 |
| — | −149 | −500 | 233 | 43 | −381 | 399 | 106 | −626 |
| — | −7 | −8312 | −9354 | −894 | −1115 | −701 | −1378 | * |
| 244(F) | −78 | −1005 | −3333 | −2714 | 2786 | −2679 | −1509 | −502 |
| — | −149 | −500 | 233 | 43 | −381 | 399 | 106 | −626 |
| — | −7 | −8312 | −9354 | −894 | −1115 | −701 | −1378 | * |
| 245(D) | −2674 | −3777 | 3647 | −1466 | −4960 | −2802 | −2593 | −4914 |
| — | −149 | −500 | 233 | 43 | −381 | 399 | 106 | −626 |
| — | −7 | −8312 | −9354 | −894 | −1115 | −701 | −1378 | * |
| 246(V) | 1871 | −1480 | −3615 | −3153 | −1890 | −2627 | −2297 | −306 |
| — | −149 | −500 | 233 | 43 | −381 | 399 | 106 | −626 |
| — | −7 | −8312 | −9354 | −894 | −1115 | −701 | −1378 | * |
| 247(A) | 2611 | −2786 | −991 | 446 | −3556 | 1526 | −1508 | −3306 |
| — | −149 | −500 | 233 | 43 | −381 | 399 | 106 | −626 |
| — | −7 | −8312 | −9354 | −894 | −1115 | −701 | −1378 | * |
| 248(T) | −1575 | −2397 | −1716 | −1668 | −3555 | −2353 | 2795 | −3355 |
| — | −149 | −500 | 233 | 43 | −381 | 399 | 106 | −626 |
| — | −7 | −8312 | −9354 | −894 | −1115 | −701 | −1378 | * |
| 249(A) | 1906 | −1213 | −2611 | −2044 | −1274 | −749 | −1459 | −806 |
| — | −149 | −500 | 233 | 43 | −381 | 399 | 106 | −626 |
| — | −7 | −8312 | −9354 | −894 | −1115 | −701 | −1378 | * |
| 250(I) | −1289 | −1106 | −3622 | −2990 | 447 | −2843 | 556 | 2280 |
| — | −149 | −500 | 233 | 43 | −381 | 399 | 106 | −626 |
| — | −7 | −8312 | −9354 | −894 | −1115 | −701 | −1378 | * |
| 251(A) | 3994 | −2060 | −3318 | −3466 | −4480 | 1477 | −3420 | −4277 |
| — | −149 | −500 | 233 | 43 | −381 | 399 | 106 | −626 |
| — | −7 | −8312 | −9354 | −894 | −1115 | −701 | −1378 | * |
| 252(F) | −4510 | −3775 | −5456 | −5636 | 4401 | −5131 | −2010 | −2624 |
| — | −149 | −500 | 233 | 43 | −381 | 399 | 106 | −626 |
| — | −7 | −8312 | −9354 | −894 | −1115 | −701 | −1378 | * |

-continued

| | | | | | | | | |
|---|---|---|---|---|---|---|---|---|
| 253(W) | −204 | 887 | 46 | 246 | −204 | −619 | 891 | −475 |
| — | −149 | −500 | 233 | 43 | −381 | 399 | 106 | −626 |
| — | −7 | −8312 | −9354 | −894 | −1115 | −701 | −1378 | * |
| 254(L) | −3584 | −3041 | −6020 | −5465 | −1547 | −5724 | −4559 | 2056 |
| — | −149 | −500 | 233 | 43 | −381 | 399 | 106 | −626 |
| — | −7 | −8312 | −9354 | −894 | −1115 | −701 | −1378 | * |
| 255(Q) | −1021 | 248 | 260 | 920 | −2812 | −1989 | 1097 | −2558 |
| — | −149 | −500 | 233 | 43 | −381 | 399 | 106 | −626 |
| — | −7 | −8312 | −9354 | −894 | −1115 | −701 | −1378 | * |
| 256(Q) | −387 | −2464 | −846 | 769 | −2785 | −1226 | −626 | −2533 |
| — | −149 | −500 | 233 | 43 | −381 | 399 | 106 | −626 |
| — | −7 | −8312 | −9354 | −894 | −1115 | −701 | −1378 | * |
| 257(Y) | −4615 | −3726 | −5293 | −5520 | 1958 | −5121 | 2666 | −3552 |
| — | −149 | −500 | 233 | 43 | −381 | 399 | 106 | −626 |
| — | −7 | −8312 | −9354 | −894 | −1115 | −701 | −1378 | * |
| 258(G) | −747 | −4382 | 2188 | 1513 | −4595 | 2379 | −1856 | −4494 |
| — | −149 | −500 | 233 | 43 | −381 | 399 | 106 | −626 |
| — | −7 | −8312 | −9354 | −894 | −1115 | −701 | −1378 | * |
| 259(L) | −2849 | −3066 | −3826 | −2761 | −2395 | −3664 | 902 | −2487 |
| — | −149 | −500 | 233 | 43 | −381 | 399 | 106 | −626 |
| — | −7 | −8312 | −9354 | −894 | −1115 | −701 | −1378 | * |
| 260(D) | −1081 | −2552 | 2320 | 1262 | −2865 | −682 | −702 | −2615 |
| — | −149 | −500 | 233 | 43 | −381 | 399 | 106 | −626 |
| — | −7 | −8312 | −9354 | −894 | −1115 | −701 | −1378 | * |
| 261(K) | −1509 | −3060 | 1864 | 1703 | −3356 | −449 | −1058 | −3134 |
| — | −149 | −500 | 233 | 43 | −381 | 399 | 106 | −626 |
| — | −7 | −8312 | −9354 | −894 | −1115 | −701 | −1378 | * |
| 262(H) | −1002 | −2068 | 1504 | 952 | −2245 | −2050 | 1617 | −504 |
| — | −149 | −500 | 233 | 43 | −381 | 399 | 106 | −626 |
| — | −7 | −8312 | −9354 | −894 | −1115 | −701 | −1378 | * |
| 263(F) | −2939 | −2542 | −4828 | −4519 | 3955 | −4337 | −1860 | 649 |
| — | −149 | −500 | 233 | 43 | −381 | 399 | 106 | −626 |
| — | −7 | −8312 | −9354 | −894 | −1115 | −701 | −1378 | * |
| 264(K) | −3285 | −3787 | −3212 | −3069 | −5220 | 1761 | −2834 | −5042 |
| — | −149 | −500 | 233 | 43 | −381 | 399 | 106 | −626 |
| — | −7 | −8312 | −9354 | −894 | −1115 | −701 | −1378 | * |
| 265(L) | −3149 | −2690 | −5597 | −5054 | 1255 | −5177 | −4100 | 997 |
| — | −149 | −500 | 233 | 43 | −381 | 399 | 106 | −626 |
| — | −7 | −8312 | −9354 | −894 | −1115 | −701 | −1378 | * |
| 266(N) | −4313 | −4359 | −3728 | −4093 | −5358 | −4169 | −4424 | −6344 |
| — | −149 | −500 | 233 | 43 | −381 | 399 | 106 | −626 |
| — | −7 | −8312 | −9354 | −894 | −1115 | −701 | −1378 | * |
| 267(I) | −2513 | −2147 | −4957 | −4435 | −1823 | −4442 | −3529 | 2351 |
| — | −149 | −500 | 233 | 43 | −381 | 399 | 106 | −626 |
| — | −7 | −8312 | −9354 | −894 | −1115 | −701 | −1378 | * |
| 268(E) | −4894 | −4877 | −3044 | 3932 | −5916 | −4252 | −4190 | −6541 |
| — | −149 | −500 | 233 | 43 | −381 | 399 | 106 | −626 |
| — | −7 | −8312 | −9354 | −894 | −1115 | −701 | −1378 | * |
| 269(A) | 2088 | 1365 | −3378 | −2828 | 487 | 698 | −1799 | −836 |
| — | −149 | −500 | 233 | 43 | −381 | 399 | 106 | −626 |
| — | −7 | −8312 | −9354 | −894 | −1115 | −701 | −1378 | * |
| 270(N) | 11 | −2335 | −2305 | −2622 | −4638 | 1373 | −3163 | −4488 |
| — | −149 | −500 | 233 | 43 | −381 | 399 | 106 | −626 |
| — | −7 | −8312 | −9354 | −894 | −1115 | −701 | −1378 | * |
| 271(H) | −5506 | −4764 | −5029 | −5331 | −4362 | −4732 | 5444 | −6634 |
| — | −149 | −500 | 233 | 43 | −381 | 399 | 106 | −626 |
| — | −7 | −8312 | −9354 | −894 | −1115 | −701 | −1378 | * |
| 272(A) | 3116 | −3101 | −1551 | 1884 | −4671 | −2707 | −2717 | −4449 |
| — | −149 | −500 | 233 | 43 | −381 | 399 | 106 | −626 |
| — | −7 | −8312 | −9354 | −894 | −1115 | −701 | −1378 | * |
| 273(T) | −1255 | −2072 | −1391 | −875 | −1774 | −2311 | −946 | −1843 |
| — | −149 | −500 | 233 | 43 | −381 | 399 | 106 | −626 |
| — | −7 | −8312 | −9354 | −894 | −1115 | −701 | −1378 | * |
| 274(M) | −4049 | −3435 | −6360 | −5790 | −1437 | −6127 | −4754 | −942 |
| — | −149 | −500 | 233 | 43 | −381 | 399 | 106 | −626 |
| — | −7 | −8312 | −9354 | −894 | −1115 | −701 | −1378 | * |
| 275(A) | 3290 | −2018 | −4238 | −4530 | −4608 | −2288 | −3883 | −4417 |
| — | −149 | −500 | 233 | 43 | −381 | 399 | 106 | −626 |
| — | −7 | −8312 | −9354 | −894 | −1115 | −701 | −1378 | * |

-continued

| | | | | | | | | |
|---|---|---|---|---|---|---|---|---|
| 276(G) | −2006 | −2603 | −2686 | −2983 | −51 | 3566 | −2982 | −4201 |
| — | | −149 | −500 | 233 | 43 | −381 | 399 | 106 | −626 |
| — | | −7 | −8312 | −9354 | −894 | −1115 | −701 | −1378 | * |
| 277(H) | −3898 | −3709 | −4252 | −4240 | −1538 | −4376 | 4892 | −2923 |
| — | | −149 | −500 | 233 | 43 | −381 | 399 | 106 | −626 |
| — | | −7 | −8312 | −9354 | −894 | −1115 | −701 | −1378 | * |
| 278(T) | −1794 | −2944 | 99 | −1062 | −3953 | −2361 | −1803 | −3744 |
| — | | −149 | −500 | 233 | 43 | −381 | 399 | 106 | −626 |
| — | | −7 | −8312 | −9354 | −894 | −1115 | −701 | −1378 | * |
| 279(F) | −4666 | 1469 | −5329 | −5600 | 4144 | −5120 | −1487 | −3637 |
| — | | −149 | −500 | 233 | 43 | −381 | 399 | 106 | −626 |
| — | | −7 | −8312 | −9354 | −894 | −1115 | −701 | −1378 | * |
| 280(E) | −993 | −2363 | −876 | 2071 | −2644 | −1981 | 2018 | −2365 |
| — | | −149 | −500 | 233 | 43 | −381 | 399 | 106 | −626 |
| — | | −7 | −8312 | −9354 | −894 | −1115 | −701 | −1378 | * |
| 281(H) | −3635 | −4141 | −2481 | −2626 | −2997 | −3692 | 5257 | −4886 |
| — | | −149 | −500 | 233 | 43 | −381 | 399 | 106 | −626 |
| — | | −7 | −8312 | −9354 | −894 | −1115 | −701 | −1378 | * |
| 282(E) | −310 | −4317 | 520 | 3226 | −4661 | 1262 | −1926 | −4565 |
| — | | −149 | −500 | 233 | 43 | −381 | 399 | 106 | −626 |
| — | | −7 | −8312 | −9354 | −894 | −1115 | −701 | −1378 | * |
| 283(I) | −3109 | −2594 | −5687 | −5258 | −2040 | −5447 | −4789 | 2687 |
| — | | −149 | −500 | 233 | 43 | −381 | 399 | 106 | −626 |
| — | | −7 | −8312 | −9354 | −894 | −1115 | −701 | −1378 | * |
| 284(R) | 1930 | −2801 | −1080 | 241 | −3166 | −2275 | −912 | −2874 |
| — | | −149 | −500 | 233 | 43 | −381 | 399 | 106 | −626 |
| — | | −7 | −8312 | −9354 | −894 | −1115 | −701 | −1378 | * |
| 285(Q) | −1119 | 867 | −3256 | −2635 | 296 | −2643 | −1503 | −469 |
| — | | −149 | −500 | 233 | 43 | −381 | 399 | 106 | −626 |
| — | | −7 | −8312 | −9354 | −894 | −1115 | −701 | −1378 | * |
| 286(A) | 3647 | −2999 | −4758 | −5092 | −5144 | −3219 | −4514 | −5091 |
| — | | −149 | −500 | 233 | 43 | −381 | 399 | 106 | −626 |
| — | | −7 | −8312 | −9354 | −894 | −1115 | −701 | −1378 | * |
| 287(R) | −438 | −1218 | −2385 | −1792 | −1208 | −2507 | −1291 | 204 |
| — | | −149 | −500 | 233 | 43 | −381 | 399 | 106 | −626 |
| — | | −7 | −8312 | −9354 | −894 | −1115 | −701 | −1378 | * |
| 288(W) | 180 | −1750 | 1481 | 940 | −1841 | −2159 | −866 | 977 |
| — | | −149 | −500 | 233 | 43 | −381 | 399 | 106 | −626 |
| — | | −7 | −8312 | −9354 | −894 | −1115 | −701 | −1378 | * |
| 289(H) | 1869 | −1372 | −1935 | −1371 | 128 | −2386 | 2326 | −951 |
| — | | −149 | −500 | 233 | 43 | −381 | 399 | 106 | −626 |
| — | | −7 | −8312 | −9354 | −894 | −1115 | −701 | −1378 | * |
| 290(G) | −2602 | −4486 | 1035 | 201 | −4670 | 3031 | −1891 | −4579 |
| — | | −149 | −500 | 233 | 43 | −381 | 399 | 106 | −626 |
| — | | −7 | −8312 | −9354 | −894 | −1115 | −701 | −1378 | * |
| 291(M) | 251 | −1162 | −3387 | −2773 | −1077 | −2851 | −1716 | 431 |
| — | | −149 | −500 | 233 | 43 | −381 | 399 | 106 | −626 |
| — | | −7 | −8312 | −9354 | −894 | −1115 | −701 | −1378 | * |
| 292(L) | −4115 | −3482 | −6205 | −5777 | 1065 | −5951 | −3943 | −1092 |
| — | | −149 | −500 | 233 | 43 | −381 | 399 | 106 | −626 |
| — | | −7 | −8312 | −9354 | −894 | −1115 | −701 | −1378 | * |
| 293(G) | −2777 | −2893 | −4388 | −4459 | 2368 | 3236 | −2287 | −2772 |
| — | | −149 | −500 | 233 | 43 | −381 | 399 | 106 | −626 |
| — | | −7 | −8312 | −9354 | −894 | −1115 | −701 | −1378 | * |
| 294(H) | −1953 | −2855 | −1413 | −1605 | −3687 | −2513 | 3228 | −4087 |
| — | | −149 | −500 | 233 | 43 | −381 | 399 | 106 | −626 |
| — | | −7 | −8312 | −9354 | −894 | −1115 | −701 | −1378 | * |
| 295(I) | −2891 | −2384 | −5528 | −5155 | −2443 | −5319 | −4964 | 3155 |
| — | | −149 | −500 | 233 | 43 | −381 | 399 | 106 | −626 |
| — | | −7 | −8312 | −9354 | −894 | −1115 | −701 | −1378 | * |
| 296(D) | −4886 | −4905 | 4186 | −3339 | −5949 | −4221 | −4195 | −6666 |
| — | | −149 | −500 | 233 | 43 | −381 | 399 | 106 | −626 |
| — | | −7 | −8312 | −9354 | −894 | −1115 | −701 | −1378 | * |
| 297(A) | 3106 | −2388 | −4425 | −4439 | −2714 | −3005 | −3693 | −1978 |
| — | | −149 | −500 | 233 | 43 | −381 | 399 | 106 | −626 |
| — | | −7 | −8312 | −9354 | −894 | −1115 | −701 | −1378 | * |

-continued

| | | | | | | | | |
|---|---|---|---|---|---|---|---|---|
| 298(N) | −4313 | −4359 | −3728 | −4093 | −5358 | −4169 | −4424 | −6344 |
| — | −149 | −500 | 233 | 43 | −381 | 399 | 106 | −626 |
| — | −7 | −8312 | −9354 | −894 | −1115 | −701 | −1378 | * |
| 299(Q) | −1050 | −2442 | −224 | −369 | −2747 | 1053 | −681 | −2473 |
| — | −149 | −500 | 233 | 43 | −381 | 399 | 106 | −626 |
| — | −7 | −8312 | −9354 | −894 | −1115 | −701 | −1378 | * |
| 300(G) | −2973 | −3542 | −2659 | −2952 | −5121 | 1336 | −3467 | −5361 |
| — | −149 | −500 | 233 | 43 | −381 | 399 | 106 | −626 |
| — | −7 | −8312 | −9354 | −894 | −1115 | −701 | −1378 | * |
| 301(D) | −1715 | −3268 | 3029 | −581 | −3564 | −2306 | 1979 | −3347 |
| — | −149 | −500 | 233 | 43 | −381 | 399 | 106 | −626 |
| — | −7 | −8312 | −9354 | −894 | −1115 | −701 | −1378 | * |
| 302(M) | −558 | −1400 | −1835 | −1269 | −1420 | 890 | −1097 | −990 |
| — | −149 | −500 | 233 | 43 | −381 | 399 | 106 | −626 |
| — | −7 | −8312 | −9354 | −894 | −1115 | −701 | −1378 | * |
| 303(Q) | −1128 | −1286 | −2178 | −1630 | −1284 | −2459 | −1259 | 1117 |
| — | −149 | −500 | 233 | 43 | −381 | 399 | 106 | −626 |
| — | −7 | −8312 | −9354 | −894 | −1115 | −701 | −1378 | * |
| 304(W) | −204 | 887 | 46 | 246 | −204 | −619 | 891 | −475 |
| — | −149 | −500 | 233 | 43 | −381 | 399 | 106 | −626 |
| — | −7 | −8312 | −9354 | −894 | −1115 | −701 | −1378 | * |
| 305(L) | −1103 | −1400 | −1916 | −1340 | −1417 | −2382 | −1126 | 637 |
| — | −149 | −500 | 233 | 43 | −381 | 399 | 106 | −626 |
| — | −7 | −8312 | −9354 | −894 | −1115 | −701 | −1378 | * |
| 306(G) | −4196 | −3631 | −4960 | −5174 | 1957 | 1236 | −1563 | −3645 |
| — | −149 | −500 | 233 | 43 | −381 | 399 | 106 | −626 |
| — | −7 | −8312 | −9354 | −894 | −1115 | −701 | −1378 | * |
| 307(W) | −4933 | −4706 | 2215 | −3821 | −3602 | −4386 | −3866 | −6001 |
| — | −149 | −500 | 233 | 43 | −381 | 399 | 106 | −626 |
| — | −7 | −8312 | −9354 | −894 | −1115 | −701 | −1378 | * |
| 308(D) | −3069 | −4812 | 3638 | −1083 | −5072 | −2828 | −2301 | −5194 |
| — | −149 | −500 | 233 | 43 | −381 | 399 | 106 | −626 |
| — | −7 | −8312 | −9354 | −894 | −1115 | −701 | −1378 | * |
| 309(T) | −1461 | −1742 | 1783 | −1718 | −1846 | −2672 | −1664 | 872 |
| — | −149 | −500 | 233 | 43 | −381 | 399 | 106 | −626 |
| — | −7 | −8312 | −9354 | −894 | −1115 | −701 | −1378 | * |
| 310(D) | −3546 | −4222 | 3684 | −2153 | −3783 | −3505 | −3081 | −3676 |
| — | −149 | −500 | 233 | 43 | −381 | 399 | 106 | −626 |
| — | −7 | −8312 | −9354 | −894 | −1115 | −701 | −1378 | * |
| 311(E) | −1512 | −2828 | −1244 | 2417 | −3192 | −2375 | −959 | −2865 |
| — | −149 | −500 | 233 | 43 | −381 | 399 | 106 | −626 |
| — | −7 | −8312 | −9354 | −894 | −1115 | −701 | −1378 | * |
| 312(F) | −4608 | −3778 | −5235 | −5513 | 4303 | −5053 | −1486 | −3725 |
| — | −149 | −500 | 233 | 43 | −381 | 399 | 106 | −626 |
| — | −61 | −8312 | −4703 | −894 | −1115 | −701 | −1378 | * |
| 313(P) | −1888 | −2446 | −3444 | −3643 | −4185 | 1827 | −3530 | −4064 |
| — | −149 | −500 | 233 | 43 | −381 | 399 | 106 | −626 |
| — | −7 | −8258 | −9300 | −894 | −1115 | −545 | −1668 | * |
| 314(T) | −273 | −2001 | −1163 | −623 | −2217 | −2089 | 1932 | 12 |
| — | −149 | −500 | 233 | 43 | −381 | 399 | 106 | −626 |
| — | −7 | −8312 | −9354 | −894 | −1115 | −701 | −1378 | * |
| 315(D) | −1847 | −3447 | 2925 | 425 | −3721 | 1133 | −1341 | −3520 |
| — | −149 | −500 | 233 | 43 | −381 | 399 | 106 | −626 |
| — | −7 | −8312 | −9354 | −894 | −1115 | −701 | −1378 | * |
| 316(V) | −1151 | −1254 | 1271 | −1753 | −1247 | −2524 | −1330 | 1068 |
| — | −149 | −500 | 233 | 43 | −381 | 399 | 106 | −626 |
| — | −7 | −8312 | −9354 | −894 | −1115 | −701 | −1378 | * |
| 317(Y) | −1131 | −1223 | −2356 | 151 | −1178 | −2505 | −1285 | 128 |
| — | −149 | −500 | 233 | 43 | −381 | 399 | 106 | −626 |
| — | −7 | −8312 | −9354 | −894 | −1115 | −701 | −1378 | * |
| 318(E) | −66 | −2443 | 1230 | 1971 | −2759 | −1957 | −616 | −2506 |
| — | −149 | −500 | 233 | 43 | −381 | 399 | 106 | −626 |
| — | −7 | −8312 | −9354 | −894 | −1115 | −701 | −1378 | * |
| 319(T) | 1585 | −1443 | −1997 | −1450 | −1562 | −2339 | −1262 | −37 |
| — | −149 | −500 | 233 | 43 | −381 | 399 | 106 | −626 |
| — | −7 | −8312 | −9354 | −894 | −1115 | −701 | −1378 | * |
| 320(T) | 1918 | −1866 | −4124 | −4033 | −3557 | −2298 | −3314 | −2998 |
| — | −149 | −500 | 233 | 43 | −381 | 399 | 106 | −626 |
| — | −7 | −8312 | −9354 | −894 | −1115 | −701 | −1378 | * |

| | | | | | | | | |
|---|---|---|---|---|---|---|---|---|
| 321(F) | −55 | −1078 | −2947 | −2361 | 2116 | −724 | −1483 | −590 |
| — | −149 | −500 | 233 | 43 | −381 | 399 | 106 | −626 |
| — | −7 | −8312 | −9354 | −894 | −1115 | −701 | −1378 | * |
| 322(A) | 2342 | −969 | −3431 | −2800 | 739 | −2681 | −1551 | 746 |
| — | −149 | −500 | 233 | 43 | −381 | 399 | 106 | −626 |
| — | −7 | −8312 | −9354 | −894 | −1115 | −701 | −1378 | * |
| 323(M) | −2508 | −2232 | −4761 | −4150 | −1237 | −4143 | −2920 | −798 |
| — | −149 | −500 | 233 | 43 | −381 | 399 | 106 | −626 |
| — | −7 | −8312 | −9354 | −894 | −1115 | −701 | −1378 | * |
| 324(Y) | −1183 | −1021 | −3411 | −2790 | −854 | −2712 | 739 | −517 |
| — | −149 | −500 | 233 | 43 | −381 | 399 | 106 | −626 |
| — | −7 | −8312 | −9354 | −894 | −1115 | −701 | −1378 | * |
| 325(E) | −1745 | −3328 | 1991 | 2779 | −3608 | −2301 | −1256 | −3398 |
| — | −149 | −500 | 233 | 43 | −381 | 399 | 106 | −626 |
| — | −7 | −8312 | −9354 | −894 | −1115 | −701 | −1378 | * |
| 326(I) | −2844 | −2383 | −5395 | −4937 | 151 | −5038 | −4287 | 2475 |
| — | −149 | −500 | 233 | 43 | −381 | 399 | 106 | −626 |
| — | −7 | −8312 | −9354 | −894 | −1115 | −701 | −1378 | * |
| 327(L) | −3363 | −2830 | −5881 | −5398 | −1770 | −5628 | −4722 | 1688 |
| — | −149 | −500 | 233 | 43 | −381 | 399 | 106 | −626 |
| — | −7 | −8312 | −9354 | −894 | −1115 | −701 | −1378 | * |
| 328(K) | −365 | −2488 | 41 | 1718 | −2813 | −1989 | −641 | −2559 |
| — | −149 | −500 | 233 | 43 | −381 | 399 | 106 | −626 |
| — | −7 | −8312 | −9354 | −894 | −1115 | −701 | −1378 | * |
| 329(N) | 716 | −2390 | −858 | 192 | −377 | −873 | 712 | −2414 |
| — | −149 | −500 | 233 | 43 | −381 | 399 | 106 | −626 |
| — | −7 | −8312 | −9354 | −894 | −1115 | −701 | −1378 | * |
| 330(G) | 66 | −2442 | 172 | −2179 | −4601 | 3363 | −2899 | −4434 |
| — | −149 | −500 | 233 | 43 | −381 | 399 | 106 | −626 |
| — | −244 | −8312 | −2711 | −894 | −1115 | −701 | −1378 | * |
| 331(G) | −1329 | −1980 | −1953 | −1910 | 214 | 3238 | −2065 | −2824 |
| — | −149 | −500 | 233 | 43 | −381 | 399 | 106 | −626 |
| — | −8 | −8076 | −9118 | −894 | −1115 | −1192 | −831 | * |
| 332(F) | −2519 | −2199 | −4819 | −4218 | 2372 | −4220 | −2969 | 1473 |
| — | −149 | −500 | 233 | 43 | −381 | 399 | 106 | −626 |
| — | −1585 | −8137 | −593 | −894 | −1115 | −1458 | −653 | * |
| 333(D) | −901 | −2417 | 2169 | 499 | −2834 | 1682 | −424 | −2665 |
| — | −149 | −500 | 233 | 43 | −381 | 399 | 106 | −626 |
| — | −555 | −6574 | −1696 | −894 | −1115 | −3087 | −181 | * |
| 334(G) | −771 | −1114 | −1327 | −1503 | −2474 | 3336 | −1576 | −2519 |
| — | −148 | −500 | 233 | 43 | −381 | 399 | 106 | −626 |
| — | −1217 | −830 | −7094 | −156 | −3286 | −3231 | −162 | * |
| 335(P) | −947 | −1231 | −1366 | −1466 | −2201 | −1324 | −1470 | −2177 |
| — | −149 | −500 | 233 | 43 | −381 | 399 | 106 | −626 |
| — | −33 | −6052 | −7094 | −894 | −1115 | −2145 | −370 | * |
| 336(G) | 1354 | −1173 | −535 | −238 | −2069 | 1779 | −486 | −1725 |
| — | −149 | −500 | 233 | 43 | −381 | 399 | 106 | −626 |
| — | −21 | −6683 | −7725 | −894 | −1115 | −113 | −3725 | * |
| 337(Y) | 923 | −2098 | −152 | −490 | −2292 | 773 | −737 | −1954 |
| — | −149 | −500 | 233 | 43 | −381 | 399 | 106 | −626 |
| — | −7 | −8312 | −9354 | −894 | −1115 | −701 | −1378 | * |
| 338(T) | −596 | −2454 | −27 | 443 | −2775 | −1955 | 675 | −2525 |
| — | −149 | −500 | 233 | 43 | −381 | 399 | 106 | −626 |
| — | −7 | −8312 | −9354 | −894 | −1115 | −701 | −1378 | * |
| 339(G) | −4740 | −5364 | −4445 | −5738 | −6131 | 3840 | −5265 | −6903 |
| — | −149 | −500 | 233 | 43 | −381 | 399 | 106 | −626 |
| — | −7 | −8312 | −9354 | −894 | −1115 | −701 | −1378 | * |
| 340(G) | −2931 | −3331 | −4304 | −4658 | −5520 | 3378 | −4536 | −5732 |
| — | −149 | −500 | 233 | 43 | −381 | 399 | 106 | −626 |
| — | −7 | −8312 | −9354 | −894 | −1115 | −701 | −1378 | * |
| 341(L) | −1644 | −1468 | −3782 | −3157 | 438 | −3201 | −2041 | 710 |
| — | −149 | −500 | 233 | 43 | −381 | 399 | 106 | −626 |
| — | −7 | −8312 | −9354 | −894 | −1115 | −701 | −1378 | * |
| 342(N) | −3133 | −4000 | −1625 | −1938 | −3244 | −3217 | 3075 | −4941 |
| — | −149 | −500 | 233 | 43 | −381 | 399 | 106 | −626 |
| — | −7 | −8312 | −9354 | −894 | −1115 | −701 | −1378 | * |
| 343(F) | −5308 | −4420 | −5610 | −5948 | 4547 | −4921 | −3048 | −4656 |
| — | −149 | −500 | 233 | 43 | −381 | 399 | 106 | −626 |
| — | −7 | −8312 | −9354 | −894 | −1115 | −701 | −1378 | * |

-continued

| | | | | | | | | |
|---|---|---|---|---|---|---|---|---|
| 344(D) | −3598 | −4594 | 4015 | −1825 | −3014 | −3354 | −2628 | −5167 |
| — | −149 | −500 | 233 | 43 | −381 | 399 | 106 | −626 |
| — | −7 | −8312 | −9354 | −894 | −1115 | −701 | −1378 | * |
| 345(A) | 3015 | −2000 | −3678 | −3337 | 863 | −3026 | −1786 | −1924 |
| — | −149 | −500 | 233 | 43 | −381 | 399 | 106 | −626 |
| — | −7 | −8312 | −9354 | −894 | −1115 | −701 | −1378 | * |
| 346(K) | −3437 | −3998 | −3427 | −2630 | −4447 | −3747 | 1328 | −4350 |
| — | −149 | −500 | 233 | 43 | −381 | 399 | 106 | −626 |
| — | −7 | −8312 | −9354 | −894 | −1115 | −701 | −1378 | * |
| 347(V) | 467 | −1371 | −3451 | −2935 | −1595 | −2710 | −2060 | −662 |
| — | −149 | −500 | 233 | 43 | −381 | 399 | 106 | −626 |
| — | −7 | −8312 | −9354 | −894 | −1115 | −701 | −1378 | * |
| 348(R) | −1896 | −2633 | −2566 | −1895 | −3409 | −2759 | −1580 | −3013 |
| — | −149 | −500 | 233 | 43 | −381 | 399 | 106 | −626 |
| — | −7 | −8312 | −9354 | −894 | −1115 | −701 | −1378 | * |
| 349(R) | −5156 | −4675 | −5377 | −4998 | −5777 | −4641 | −4103 | −6271 |
| — | −149 | −500 | 233 | 43 | −381 | 399 | 106 | −626 |
| — | −7 | −8312 | −9354 | −894 | −1115 | −701 | −1378 | * |
| 350(T) | 361 | −2459 | −832 | 770 | −2780 | −972 | −644 | −2526 |
| — | −149 | −500 | 233 | 43 | −381 | 399 | 106 | −626 |
| — | −7 | −8312 | −9354 | −894 | −1115 | −701 | −1378 | * |
| 351(S) | −2650 | −4418 | 471 | 1677 | −4792 | −2597 | −2009 | −4725 |
| — | −149 | −500 | 233 | 43 | −381 | 399 | 106 | −626 |
| — | −383 | −8312 | −2119 | −894 | −1115 | −701 | −1378 | * |
| 352(F) | −1686 | −1643 | −3313 | −2900 | 3471 | −2934 | −1275 | −1319 |
| — | −149 | −500 | 233 | 43 | −381 | 399 | 106 | −626 |
| — | −9 | −7937 | −8980 | −894 | −1115 | −254 | −2629 | * |
| 353(D) | 395 | −2586 | 2498 | 794 | −2902 | −678 | −718 | −2657 |
| — | −149 | −500 | 233 | 43 | −381 | 399 | 106 | −626 |
| — | −7 | −8312 | −9354 | −894 | −1115 | −701 | −1378 | * |
| 354(W) | −204 | 887 | 46 | 246 | −204 | −619 | 891 | −475 |
| — | −149 | −500 | 233 | 43 | −381 | 399 | 106 | −626 |
| — | −7 | −8312 | −9354 | −894 | −1115 | −701 | −1378 | * |
| 355(P) | 574 | −1802 | 174 | 209 | 242 | −2139 | −841 | −414 |
| — | −149 | −500 | 233 | 43 | −381 | 399 | 106 | −626 |
| — | −7 | −8312 | −9354 | −894 | −1115 | −701 | −1378 | * |
| 356(E) | −1666 | −3205 | 2244 | 2653 | −3457 | −2276 | −1194 | −3250 |
| — | −149 | −500 | 233 | 43 | −381 | 399 | 106 | −626 |
| — | −7 | −8312 | −9354 | −894 | −1115 | −701 | −1378 | * |
| 357(D) | −3359 | −4413 | 3698 | −1801 | −5459 | 1768 | −2962 | −5658 |
| — | −149 | −500 | 233 | 43 | −381 | 399 | 106 | −626 |
| — | −7 | −8312 | −9354 | −894 | −1115 | −701 | −1378 | * |
| 358(L) | −3209 | −2692 | −5753 | −5295 | −1892 | −5491 | −4700 | 887 |
| — | −149 | −500 | 233 | 43 | −381 | 399 | 106 | −626 |
| — | −7 | −8312 | −9354 | −894 | −1115 | −701 | −1378 | * |
| 359(W) | −3018 | −2633 | −4761 | −4491 | 3489 | −4266 | −1661 | 1631 |
| — | −149 | −500 | 233 | 43 | −381 | 399 | 106 | −626 |
| — | −7 | −8312 | −9354 | −894 | −1115 | −701 | −1378 | * |
| 360(Y) | 828 | −1415 | −340 | −305 | −1437 | −2319 | 1172 | 1116 |
| — | −149 | −500 | 233 | 43 | −381 | 399 | 106 | −626 |
| — | −7 | −8312 | −9354 | −894 | −1115 | −701 | −1378 | * |
| 361(A) | 2490 | −1883 | −3530 | −3268 | 392 | 1317 | −2915 | −3137 |
| — | −149 | −500 | 233 | 43 | −381 | 399 | 106 | −626 |
| — | −7 | −8312 | −9354 | −894 | −1115 | −701 | −1378 | * |
| 362(H) | 1671 | −2732 | −3104 | −3318 | −3618 | −2860 | 4899 | −4439 |
| — | −149 | −500 | 233 | 43 | −381 | 399 | 106 | −626 |
| — | −7 | −8312 | −9354 | −894 | −1115 | −701 | −1378 | * |
| 363(I) | 372 | −1510 | −2804 | −2153 | −1581 | −2814 | −1570 | 3136 |
| — | −149 | −500 | 233 | 43 | −381 | 399 | 106 | −626 |
| — | −7 | −8312 | −9354 | −894 | −1115 | −701 | −1378 | * |
| 364(A) | 2824 | −1953 | −4254 | −4336 | −4278 | 1795 | −3663 | −3992 |
| — | −149 | −500 | 233 | 43 | −381 | 399 | 106 | −626 |
| — | −7 | −8312 | −9354 | −894 | −1115 | −701 | −1378 | * |
| 365(G) | 440 | 2735 | −4017 | −4164 | −4414 | 3094 | −3664 | −4182 |
| — | −149 | −500 | 233 | 43 | −381 | 399 | 106 | −626 |
| — | −7 | −8312 | −9354 | −894 | −1115 | −701 | −1378 | * |
| 366(M) | −3435 | −3070 | −5645 | −5292 | −1686 | −5048 | −4285 | 177 |
| — | −149 | −500 | 233 | 43 | −381 | 399 | 106 | −626 |
| — | −7 | −8312 | −9354 | −894 | −1115 | −701 | −1378 | * |

-continued

| | | | | | | | | |
|---|---|---|---|---|---|---|---|---|
| 367(D) | −2500 | −3942 | 3572 | −1015 | −4586 | −2633 | −1974 | −4469 |
| — | −149 | −500 | 233 | 43 | −381 | 399 | 106 | −626 |
| — | −7 | −8312 | −9354 | −894 | −1115 | −701 | −1378 | * |
| 368(T) | 1100 | −1830 | −2203 | −1732 | −2569 | −2230 | −1735 | −2187 |
| — | −149 | −500 | 233 | 43 | −381 | 399 | 106 | −626 |
| — | −7 | −8312 | −9354 | −894 | −1115 | −701 | −1378 | * |
| 369(Y) | −4358 | −3577 | −5299 | −5430 | 3019 | −5078 | −1573 | −2961 |
| — | −149 | −500 | 233 | 43 | −381 | 399 | 106 | −626 |
| — | −7 | −8312 | −9354 | −894 | −1115 | −701 | −1378 | * |
| 370(A) | 3106 | −2388 | −4425 | −4439 | −2714 | −3005 | −3693 | −1978 |
| — | −149 | −500 | 233 | 43 | −381 | 399 | 106 | −626 |
| — | −7 | −8312 | −9354 | −894 | −1115 | −701 | −1378 | * |
| 371(R) | 722 | −1126 | −2287 | −2900 | −1095 | −2649 | −1470 | 1035 |
| — | −149 | −500 | 233 | 43 | −381 | 399 | 106 | −626 |
| — | −7 | −8312 | −9354 | −894 | −1115 | −701 | −1378 | * |
| 372(G) | 1248 | −1889 | −3801 | −3776 | −3523 | 2775 | −3223 | −3143 |
| — | −149 | −500 | 233 | 43 | −381 | 399 | 106 | −626 |
| — | −7 | −8312 | −9354 | −894 | −1115 | −701 | −1378 | * |
| 373(L) | −2143 | −2281 | −3312 | −2427 | 697 | −3298 | −1645 | −1581 |
| — | −149 | −500 | 233 | 43 | −381 | 399 | 106 | −626 |
| — | −7 | −8312 | −9354 | −894 | −1115 | −701 | −1378 | * |
| 374(K) | −1243 | −2663 | −484 | 1864 | −3023 | −2175 | −770 | −2741 |
| — | −149 | −500 | 233 | 43 | −381 | 399 | 106 | −626 |
| — | −7 | −8312 | −9354 | −894 | −1115 | −701 | −1378 | * |
| 375(V) | 135 | −1595 | −1634 | −1081 | −1703 | −685 | −1060 | −548 |
| — | −149 | −500 | 233 | 43 | −381 | 399 | 106 | −626 |
| — | −7 | −8312 | −9354 | −894 | −1115 | −701 | −1378 | * |
| 376(A) | 1481 | −2081 | −4434 | −4657 | −4120 | −2450 | −3905 | −2895 |
| — | −149 | −500 | 233 | 43 | −381 | 399 | 106 | −626 |
| — | −7 | −8312 | −9354 | −894 | −1115 | −701 | −1378 | * |
| 377(A) | 1962 | −2221 | −948 | 716 | −2449 | −2010 | 1143 | −2137 |
| — | −149 | −500 | 233 | 43 | −381 | 399 | 106 | −626 |
| — | −7 | −8312 | −9354 | −894 | −1115 | −701 | −1378 | * |
| 378(K) | 2235 | −3511 | −3265 | −2182 | −4396 | −3362 | −1483 | −3787 |
| — | −149 | −500 | 233 | 43 | −381 | 399 | 106 | −626 |
| — | −7 | −8312 | −9354 | −894 | −1115 | −701 | −1378 | * |
| 379(M) | −3847 | −3277 | −6201 | −5593 | 2394 | −5898 | −4497 | 240 |
| — | −149 | −500 | 233 | 43 | −381 | 399 | 106 | −626 |
| — | −7 | −8312 | −9354 | −894 | −1115 | −701 | −1378 | * |
| 380(I) | −1275 | −1329 | −2647 | −1990 | −1321 | −2643 | 565 | 2202 |
| — | −149 | −500 | 233 | 43 | −381 | 399 | 106 | −626 |
| — | −7 | −8312 | −9354 | −894 | −1115 | −701 | −1378 | * |
| 381(E) | 944 | −2571 | 656 | 2380 | −2887 | −2009 | −705 | −2642 |
| — | −149 | −500 | 233 | 43 | −381 | 399 | 106 | −626 |
| — | −7 | −8312 | −9354 | −894 | −1115 | −701 | −1378 | * |
| 382(D) | −598 | −4837 | 3833 | 578 | −5072 | −2648 | −2116 | −5055 |
| — | −149 | −500 | 233 | 43 | −381 | 399 | 106 | −626 |
| — | −7 | −8312 | −9354 | −894 | −1115 | −701 | −1378 | * |
| 383(P) | −1003 | −2474 | −144 | −294 | −2795 | 1002 | −631 | −2545 |
| — | −149 | −500 | 233 | 43 | −381 | 399 | 106 | −626 |
| — | −7 | −8312 | −9354 | −894 | −1115 | −701 | −1378 | * |
| 384(F) | 81 | −1956 | −1130 | 1500 | 1552 | −2090 | −781 | −1736 |
| — | −149 | −500 | 233 | 43 | −381 | 399 | 106 | −626 |
| — | −7 | −8312 | −9354 | −894 | −1115 | −701 | −1378 | * |
| 385(F) | −2039 | −1782 | −4382 | −3777 | 2108 | −3679 | −2463 | 807 |
| — | −149 | −500 | 233 | 43 | −381 | 399 | 106 | −626 |
| — | −7 | −8312 | −9354 | −894 | −1115 | −701 | −1378 | * |
| 386(D) | −987 | 436 | 2031 | 1591 | −2780 | −1958 | −618 | −2531 |
| — | −149 | −500 | 233 | 43 | −381 | 399 | 106 | −626 |
| — | −7 | −8312 | −9354 | −894 | −1115 | −701 | −1378 | * |
| 387(E) | −507 | −2601 | 840 | 1955 | −2917 | −2021 | −726 | −2673 |
| — | −149 | −500 | 233 | 43 | −381 | 399 | 106 | −626 |
| — | −7 | −8312 | −9354 | −894 | −1115 | −701 | −1378 | * |
| 388(M) | 1019 | −961 | −3469 | −2834 | 1400 | −2682 | −1552 | 1329 |
| — | −149 | −500 | 233 | 43 | −381 | 399 | 106 | −626 |
| — | −7 | −8312 | −9354 | −894 | −1115 | −701 | −1378 | * |
| 389(M) | −1149 | −1013 | −3253 | −2628 | −962 | −2671 | −1525 | 2021 |
| — | −149 | −500 | 233 | 43 | −381 | 399 | 106 | −626 |
| — | −7 | −8312 | −9354 | −894 | −1115 | −701 | −1378 | * |

-continued

| | | | | | | | | |
|---|---|---|---|---|---|---|---|---|
| 390(A) | 1814 | −2486 | 567 | 1223 | −2807 | −1975 | −640 | −2557 |
| — | −149 | −500 | 233 | 43 | −381 | 399 | 106 | −626 |
| — | −7 | −8312 | −9354 | −894 | −1115 | −701 | −1378 | * |
| 391(E) | 1007 | −2465 | 333 | 2274 | −2786 | −1961 | 536 | −2537 |
| — | −149 | −500 | 233 | 43 | −381 | 399 | 106 | −626 |
| — | −7 | −8312 | −9354 | −894 | −1115 | −701 | −1378 | * |
| 392(R) | 73 | −2800 | −1762 | −1095 | −3205 | −2591 | −1056 | −2829 |
| — | −149 | −500 | 233 | 43 | −381 | 399 | 106 | −626 |
| — | −7 | −8312 | −9354 | −894 | −1115 | −701 | −1378 | * |
| 393(Y) | −2721 | −3376 | −2973 | −2154 | −3188 | −727 | −1495 | −3439 |
| — | −149 | −500 | 233 | 43 | −381 | 399 | 106 | −626 |
| — | −7 | −8312 | −9354 | −894 | −1115 | −701 | −1378 | * |
| 394(A) | 1285 | −2377 | −872 | 585 | −2664 | −1977 | −638 | −2390 |
| — | −149 | −500 | 233 | 43 | −381 | 399 | 106 | −626 |
| — | −7 | −8312 | −9354 | −894 | −1115 | −701 | −1378 | * |
| 395(S) | 131 | −2423 | 336 | 386 | −341 | −50 | −762 | −2464 |
| — | −149 | −500 | 233 | 43 | −381 | 399 | 106 | −626 |
| — | −7 | −8312 | −9354 | −894 | −1115 | −701 | −1378 | * |
| 396(F) | −3512 | −3303 | 10 | 1365 | 1217 | −4329 | −1411 | −3102 |
| — | −149 | −500 | 233 | 43 | −381 | 399 | 106 | −626 |
| — | −7 | −8312 | −9354 | −894 | −1115 | −701 | −1378 | * |
| 397(D) | −990 | −2441 | 1836 | −293 | −2754 | −1964 | −625 | −2498 |
| — | −147 | −500 | 233 | 43 | −381 | 399 | 105 | −627 |
| — | −466 | −1865 | −9354 | −73 | −4335 | −701 | −1378 | * |
| 398(E) | −84 | −2457 | −258 | 1626 | −2777 | −455 | −617 | −2527 |
| — | −149 | −500 | 233 | 43 | −381 | 399 | 106 | −626 |
| — | −7 | −8312 | −9354 | −894 | −1115 | −701 | −1378 | * |
| 399(G) | −1414 | −2476 | −1090 | 1358 | −2997 | 2543 | −1296 | −2678 |
| — | −149 | −500 | 233 | 43 | −381 | 399 | 106 | −626 |
| — | −7 | −8312 | −9354 | −894 | −1115 | −701 | −1378 | * |
| 400(I) | 128 | −1033 | −3266 | −2651 | −1007 | −2701 | −1569 | 2545 |
| — | −149 | −500 | 233 | 43 | −381 | 399 | 106 | −626 |
| — | −7 | −8312 | −9354 | −894 | −1115 | −701 | −1378 | * |
| 401(G) | 129 | −2062 | −3816 | −3956 | −3724 | 3250 | −3484 | −3244 |
| — | −149 | −500 | 233 | 43 | −381 | 399 | 106 | −626 |
| — | −79 | −8312 | −4317 | −894 | −1115 | −701 | −1378 | * |
| 402(Q) | 1462 | −2384 | −811 | 38 | −2692 | −1184 | −584 | −2431 |
| — | −149 | −500 | 233 | 43 | −381 | 399 | 106 | −626 |
| — | −7 | −8240 | −9282 | −894 | −1115 | −509 | −1750 | * |
| 403(D) | 286 | −2477 | 2128 | 1000 | −2797 | −1001 | −633 | −2548 |
| — | −149 | −500 | 233 | 43 | −381 | 399 | 106 | −626 |
| — | −7 | −8312 | −9354 | −894 | −1115 | −701 | −1378 | * |
| 404(W) | −204 | 887 | 46 | 246 | −204 | −619 | 891 | −475 |
| — | −149 | −500 | 233 | 43 | −381 | 399 | 106 | −626 |
| — | −7 | −8312 | −9354 | −894 | −1115 | −701 | −1378 | * |
| 405(I) | −1225 | −1056 | −3499 | −2876 | 1632 | 939 | −1661 | 2615 |
| — | −149 | −500 | 233 | 43 | −381 | 399 | 106 | −626 |
| — | −183 | −8312 | −3109 | −894 | −1115 | −701 | −1378 | * |
| 406(E) | −156 | −1264 | −2093 | 2168 | −1299 | −2445 | −1234 | 765 |
| — | −149 | −500 | 233 | 43 | −381 | 399 | 106 | −626 |
| — | −8 | −8137 | −9179 | −894 | −1115 | −1458 | −653 | * |
| 407(E) | 360 | −2380 | 448 | 1932 | −2699 | −673 | −533 | −2451 |
| — | −149 | −500 | 233 | 43 | −381 | 399 | 106 | −626 |
| — | −8 | −8137 | −9179 | −894 | −1115 | −373 | −2136 | * |
| 408(G) | −306 | −1754 | −2167 | −1874 | −1807 | 2904 | −1682 | −1676 |
| — | −149 | −500 | 233 | 43 | −381 | 399 | 106 | −626 |
| — | −7 | −8312 | −9354 | −894 | −1115 | −701 | −1378 | * |
| 409(K) | 356 | −2456 | −833 | 230 | −2777 | −1959 | 716 | −2527 |
| — | −149 | −500 | 233 | 43 | −381 | 399 | 106 | −626 |
| — | −7 | −8312 | −9354 | −894 | −1115 | −701 | −1378 | * |
| 410(A) | 1618 | −2218 | 495 | 834 | −2445 | −2009 | 454 | −2132 |
| — | −149 | −500 | 233 | 43 | −381 | 399 | 106 | −626 |
| — | −7 | −8312 | −9354 | −894 | −1115 | −701 | −1378 | * |
| 411(D) | −1190 | −2605 | 1765 | 410 | −2890 | −2073 | −813 | −2627 |
| — | −149 | −500 | 233 | 43 | −381 | 399 | 106 | −626 |
| — | −7 | −8312 | −9354 | −894 | −1115 | −701 | −1378 | * |

| | | | | | | | | |
|---|---|---|---|---|---|---|---|---|
| 412(F) | −2934 | −2588 | −5133 | −4524 | 2695 | −4635 | −3270 | −872 |
| — | −149 | −500 | 233 | 43 | −381 | 399 | 106 | −626 |
| — | −7 | −8312 | −9354 | −894 | −1115 | −701 | −1378 | * |
| 413(E) | 1449 | −2456 | −323 | 1515 | −2776 | −1957 | 1150 | −2526 |
| — | −149 | −500 | 233 | 43 | −381 | 399 | 106 | −626 |
| — | −7 | −8312 | −9354 | −894 | −1115 | −701 | −1378 | * |
| 414(D) | −185 | −2555 | 2037 | 1092 | −2872 | −2002 | −694 | −2626 |
| — | −149 | −500 | 233 | 43 | −381 | 399 | 106 | −626 |
| — | −7 | −8312 | −9354 | −894 | −1115 | −701 | −1378 | * |
| 415(L) | −76 | −1139 | −2558 | −1967 | −1115 | −2532 | −1344 | −133 |
| — | −149 | −500 | 233 | 43 | −381 | 399 | 106 | −626 |
| — | −7 | −8312 | −9354 | −894 | −1115 | −701 | −1378 | * |
| 416(E) | 1511 | 1129 | −1595 | 1751 | −1576 | −2259 | −999 | −1157 |
| — | −149 | −500 | 233 | 43 | −381 | 399 | 106 | −626 |
| — | −7 | −8312 | −9354 | −894 | −1115 | −701 | −1378 | * |
| 417(K) | 1530 | −2471 | −17 | 1044 | −2791 | −1963 | −628 | −2542 |
| — | −149 | −500 | 233 | 43 | −381 | 399 | 106 | −626 |
| — | −7 | −8312 | −9354 | −894 | −1115 | −701 | −1378 | * |
| 418(Y) | −3642 | −3323 | −4353 | −3980 | 2403 | −4454 | 1728 | −3120 |
| — | −149 | −500 | 233 | 43 | −381 | 399 | 106 | −626 |
| — | −7 | −8312 | −9354 | −894 | −1115 | −701 | −1378 | * |
| 419(A) | 2435 | −1847 | −629 | 808 | −1986 | −901 | −1033 | 1094 |
| — | −149 | −500 | 233 | 43 | −381 | 399 | 106 | −626 |
| — | −7 | −8312 | −9354 | −894 | −1115 | −701 | −1378 | * |
| 420(E) | 67 | −2239 | 224 | 1346 | −452 | −709 | −673 | 230 |
| — | −149 | −500 | 233 | 43 | −381 | 399 | 106 | −626 |
| — | −7 | −8312 | −9354 | −894 | −1115 | −701 | −1378 | * |
| 421(D) | −160 | −2437 | 1202 | 1064 | 1123 | −1958 | −618 | −2495 |
| — | −149 | −500 | 233 | 43 | −381 | 399 | 106 | −626 |
| — | −7 | −8312 | −9354 | −894 | −1115 | −701 | −1378 | * |
| 422(H) | −986 | −2410 | 1343 | −303 | −2711 | −1966 | 2413 | −86 |
| — | −149 | −500 | 233 | 43 | −381 | 399 | 106 | −626 |
| — | −72 | −8312 | −4460 | −894 | −1115 | −701 | −1378 | * |
| 423(N) | 209 | −2403 | −80 | 227 | −2718 | 589 | 404 | −2465 |
| — | −149 | −500 | 233 | 43 | −381 | 399 | 106 | −626 |
| — | −110 | −8247 | −3828 | −894 | −1115 | −1040 | −961 | * |
| 424(Q) | −887 | −2330 | 1492 | 1492 | −2638 | −585 | 686 | −431 |
| — | −149 | −500 | 233 | 43 | −381 | 399 | 106 | −626 |
| — | −848 | −8144 | −1181 | −894 | −1115 | −1434 | −667 | * |
| 425(A) | 2076 | −2279 | 957 | 892 | −2676 | −1567 | −534 | −2428 |
| — | −149 | −500 | 233 | 43 | −381 | 399 | 106 | −626 |
| — | −942 | −7310 | −1080 | −894 | −1115 | −2709 | −239 | * |
| 426(E) | −381 | −1604 | 25 | 1852 | −1759 | −1234 | 69 | −1535 |
| — | −149 | −500 | 233 | 43 | −381 | 399 | 106 | −626 |
| — | −246 | −6394 | −2788 | −894 | −1115 | −3145 | −173 | * |
| 427(L) | −1340 | −1019 | −3303 | −2788 | −110 | −3122 | −2028 | 1936 |
| — | −149 | −500 | 233 | 43 | −381 | 399 | 106 | −626 |
| — | −30 | −6178 | −7220 | −894 | −1115 | −1475 | −643 | * |
| 428(A) | 996 | −971 | −924 | 841 | −1028 | −1637 | −368 | 796 |
| — | −149 | −500 | 233 | 43 | −381 | 399 | 106 | −626 |
| — | −15 | −7202 | −8244 | −894 | −1115 | −137 | −3462 | * |
| 429(I) | 1151 | −1159 | −2438 | −631 | 77 | −2505 | −1313 | 1931 |
| — | −149 | −500 | 233 | 43 | −381 | 399 | 106 | −626 |
| — | −7 | −8312 | −9354 | −894 | −1115 | −701 | −1378 | * |
| 430(Q) | 1025 | −2430 | −838 | 1164 | −2741 | −144 | −619 | −1061 |
| — | −149 | −500 | 233 | 43 | −381 | 399 | 106 | −626 |
| — | −7 | −8312 | −9354 | −894 | −1115 | −701 | −1378 | * |
| 431(N) | 351 | −2447 | 158 | 275 | −2764 | −782 | 1793 | −2512 |
| — | −149 | −500 | 233 | 43 | −381 | 399 | 106 | −626 |
| — | −7 | −8312 | −9354 | −894 | −1115 | −701 | −1378 | * |
| 432(K) | −983 | −2449 | 67 | 142 | −2768 | −1958 | 1110 | −2516 |
| — | −149 | −500 | 233 | 43 | −381 | 399 | 106 | −626 |
| — | −7 | −8312 | −9354 | −894 | −1115 | −701 | −1378 | * |
| 433(S) | −1458 | −2150 | −2472 | −2476 | −3880 | 1432 | −2696 | −3646 |
| — | −149 | −500 | 233 | 43 | −381 | 399 | 106 | −626 |
| — | −7 | −8312 | −9354 | −894 | −1115 | −701 | −1378 | * |

-continued

| | | | | | | | | |
|---|---|---|---|---|---|---|---|---|
| 434(G) | −1089 | 904 | 851 | −1707 | 768 | 2205 | −1253 | −740 |
| — | −149 | −500 | 233 | 43 | −381 | 399 | 106 | −626 |
| — | −7 | −8312 | −9354 | −894 | −1115 | −701 | −1378 | * |
| 435(H) | 818 | −2554 | −999 | −433 | −2894 | −123 | 2729 | −2621 |
| — | −149 | −500 | 233 | 43 | −381 | 399 | 106 | −626 |
| — | −7 | −8312 | −9354 | −894 | −1115 | −701 | −1378 | * |
| 436(Q) | −344 | −1587 | −3692 | −3091 | 1883 | −3276 | −2091 | 243 |
| — | −149 | −500 | 233 | 43 | −381 | 399 | 106 | −626 |
| — | −7 | −8312 | −9354 | −894 | −1115 | −701 | −1378 | * |
| 437(E) | −2248 | −2420 | −2316 | 3402 | −2671 | −3394 | −2628 | 379 |
| — | −149 | −500 | 233 | 43 | −381 | 399 | 106 | −626 |
| — | −7 | −8312 | −9354 | −894 | −1115 | −701 | −1378 | * |
| 438(R) | 204 | −2356 | −880 | 414 | −2634 | −1980 | 1194 | −2355 |
| — | −149 | −500 | 233 | 43 | −381 | 399 | 106 | −626 |
| — | −7 | −8312 | −9354 | −894 | −1115 | −701 | −1378 | * |
| 439(L) | −358 | −1562 | −4144 | −3535 | −1264 | −3440 | −2330 | 1655 |
| — | −149 | −500 | 233 | 43 | −381 | 399 | 106 | −626 |
| — | −7 | −8312 | −9354 | −894 | −1115 | −701 | −1378 | * |
| 440(K) | −1751 | −3345 | 1209 | 2128 | −3630 | −2309 | −1249 | −3421 |
| — | −149 | −500 | 233 | 43 | −381 | 399 | 106 | −626 |
| — | −7 | −8312 | −9354 | −894 | −1115 | −701 | −1378 | * |
| 441(Q) | 854 | −2432 | 264 | −308 | −2743 | −1971 | −641 | −2483 |
| — | −149 | −500 | 233 | 43 | −381 | 399 | 106 | −626 |
| — | −7 | −8312 | −9354 | −894 | −1115 | −701 | −1378 | * |
| 442(L) | −1684 | −1481 | −3911 | −3303 | −1234 | −3289 | −2179 | 1310 |
| — | −149 | −500 | 233 | 43 | −381 | 399 | 106 | −626 |
| — | −7 | −8312 | −9354 | −894 | −1115 | −701 | −1378 | * |
| 443(I) | 1388 | −1660 | −4350 | −3774 | 339 | −3691 | −2667 | 1808 |
| — | −149 | −500 | 233 | 43 | −381 | 399 | 106 | −626 |
| — | −7 | −8312 | −9354 | −894 | −1115 | −701 | −1378 | * |
| 444(N) | −429 | −1301 | −2255 | −1692 | −1310 | −2510 | −1317 | 965 |
| — | −149 | −500 | 233 | 43 | −381 | 399 | 106 | −626 |
| — | −7 | −8312 | −9354 | −894 | −1115 | −701 | −1378 | * |
| 445(H) | −989 | −2462 | 1140 | 1287 | −2782 | −1959 | 2073 | −2533 |
| — | −149 | −500 | 233 | 43 | −381 | 399 | 106 | −626 |
| — | −7 | −8312 | −9354 | −894 | −1115 | −701 | −1378 | * |
| 446(Y) | −570 | −3515 | −4109 | −4216 | −224 | −4378 | 3141 | −3593 |
| — | −149 | −500 | 233 | 43 | −381 | 399 | 106 | −626 |
| — | −7 | −8312 | −9354 | −894 | −1115 | −701 | −1378 | * |
| 447(L) | −2249 | 853 | −4575 | −3952 | −1251 | −3905 | −2751 | 1774 |
| — | −149 | −500 | 233 | 43 | −381 | 399 | 106 | −626 |
| — | −183 | −8312 | −3108 | −894 | −1115 | −701 | −1378 | * |
| 448(F) | −1766 | −1521 | −4129 | −3513 | 1880 | −3413 | −2296 | 1109 |
| — | −149 | −500 | 233 | 43 | −381 | 399 | 106 | −626 |
| — | −152 | −8137 | −3370 | −894 | −1115 | −1459 | −652 | * |
| 449(G) | −169 | −2301 | 1066 | 908 | −2620 | 1545 | −453 | −2372 |
| — | −149 | −500 | 233 | 43 | −381 | 399 | 106 | −626 |
| — | −149 | −7993 | −3412 | −894 | −1115 | −1838 | −473 | * |
| 450(A) | 1384 | −1474 | −1057 | 562 | −1568 | −1895 | −607 | −94 |
| — | −149 | −500 | 233 | 43 | −381 | 399 | 106 | −626 |
| — | −253 | −7853 | −2678 | −894 | −1115 | −2104 | −382 | * |
| 451(R) | −58 | 1062 | −1873 | −1289 | −813 | −2052 | −847 | 394 |
| — | −149 | −500 | 233 | 43 | −381 | 399 | 106 | −626 |
| — | −368 | −7612 | −2186 | −894 | −1115 | −2433 | −295 | * |
| 452(G) | 887 | −1428 | −559 | −11 | −1592 | 1139 | −219 | −1235 |
| — | −149 | −500 | 233 | 43 | −381 | 399 | 106 | −626 |
| — | −296 | −7258 | −2484 | −894 | −1115 | −2747 | −233 | * |
| 453(K) | 359 | −1852 | −165 | 1529 | −2167 | −1348 | −26 | −1905 |
| — | −147 | −500 | 233 | 43 | −381 | 398 | 105 | −626 |
| — | −1078 | −936 | −8022 | −95 | −3976 | −125 | −3592 | * |
| 454(W) | −204 | 887 | 46 | 246 | −204 | −619 | 891 | −475 |
| — | −148 | −500 | 233 | 43 | −381 | 399 | 107 | −627 |
| — | −166 | −3224 | −9354 | −1658 | −550 | −701 | −1378 | * |
| 455(W) | −204 | 887 | 46 | 246 | −204 | −619 | 891 | −475 |
| — | * | * | * | * | * | * | * | * |
| — | * | * | * | * | * | * | * | * |

| m ->e | K | L | M | N | P | O | R | S | T |
|---|---|---|---|---|---|---|---|---|---|
| | 338 | −941 | 659 | 291 | −334 | 598 | 147 | −143 | 7 |
| | 210 | −466 | −720 | 275 | 394 | 45 | 96 | 359 | 117 |
| * | | | | | | | | | |
| | −3750 | 38 | −736 | −3643 | −3893 | −3438 | −3659 | −3185 | −1974 |
| | 210 | −466 | −720 | 275 | 394 | 45 | 96 | 359 | 117 |
| * | | | | | | | | | |
| | −145 | −2417 | −1502 | 888 | 1044 | 650 | −666 | 634 | −860 |
| | 210 | −466 | −720 | 275 | 394 | 45 | 96 | 359 | 117 |
| * | | | | | | | | | |
| | 2995 | −2503 | 541 | −838 | −82 | 803 | 733 | −1166 | −210 |
| | 210 | −466 | −720 | 275 | 394 | 45 | 96 | 359 | 117 |
| * | | | | | | | | | |
| | −4747 | −1338 | −1282 | −4599 | −4682 | −4674 | −4889 | −4283 | −2449 |
| | 210 | −466 | −720 | 275 | 394 | 45 | 96 | 359 | 117 |
| * | | | | | | | | | |
| | 1437 | −2253 | −1327 | 1063 | −363 | 1500 | 815 | −649 | 560 |
| | 210 | −466 | −720 | 275 | 394 | 45 | 96 | 359 | 117 |
| * | | | | | | | | | |
| | −4922 | −2814 | −2904 | −3541 | −4763 | −3674 | −4302 | −4158 | −4468 |
| | 210 | −466 | −720 | 275 | 394 | 45 | 96 | 359 | 117 |
| * | | | | | | | | | |
| | −1429 | −2964 | −2264 | −1142 | −2608 | −1221 | −1910 | −404 | −1676 |
| | 210 | −466 | −720 | 275 | 394 | 45 | 96 | 359 | 117 |
| * | | | | | | | | | |
| | −5445 | −6007 | −5654 | −4803 | −4532 | −5224 | −5099 | −4361 | −4464 |
| | 210 | −466 | −721 | 275 | 394 | 45 | 97 | 359 | 117 |
| * | | | | | | | | | |
| | 2070 | −2275 | −1362 | −444 | 1490 | 1183 | 432 | 193 | 169 |
| | 210 | −466 | −720 | 275 | 394 | 45 | 96 | 359 | 117 |
| * | | | | | | | | | |
| | 1550 | −2272 | −1346 | 498 | −1845 | 1040 | −505 | 399 | 267 |
| | 210 | −466 | −720 | 275 | 394 | 45 | 96 | 359 | 117 |
| * | | | | | | | | | |
| | 3 | −20 | −569 | −944 | −366 | −548 | −1012 | 2341 | 203 |
| | 210 | −466 | −720 | 275 | 394 | 45 | 96 | 359 | 117 |
| * | | | | | | | | | |
| | 2248 | −2306 | −1383 | 929 | −1870 | 1259 | −537 | 203 | 744 |
| | 210 | −466 | −720 | 275 | 394 | 45 | 96 | 359 | 117 |
| * | | | | | | | | | |
| | 541 | −2657 | −1773 | 3112 | −2133 | −322 | −907 | 983 | −1121 |
| | 210 | −466 | −720 | 275 | 394 | 45 | 96 | 359 | 117 |
| * | | | | | | | | | |
| | 272 | −2170 | 1037 | −1129 | 2920 | −813 | −1183 | −1074 | −1062 |
| | 210 | −466 | −720 | 275 | 394 | 45 | 96 | 359 | 117 |
| * | | | | | | | | | |
| | −2677 | 2198 | 1130 | −2548 | −3046 | −2242 | −2517 | −2147 | −1490 |
| | 210 | −466 | −720 | 275 | 394 | 45 | 96 | 359 | 117 |
| * | | | | | | | | | |
| | −1746 | −1704 | 967 | −1746 | −2462 | −1570 | −1957 | 1232 | −1093 |
| | 210 | −466 | −720 | 275 | 394 | 45 | 96 | 359 | 117 |
| * | | | | | | | | | |
| | −4579 | −2594 | −2558 | −3472 | −4567 | −3555 | −4097 | −3851 | −332 |
| | 210 | −466 | −720 | 275 | 394 | 45 | 96 | 359 | 117 |
| * | | | | | | | | | |
| | 2388 | −2715 | −1873 | 46 | −2431 | 989 | 2056 | −1394 | −1391 |
| | 210 | −466 | −720 | 275 | 394 | 45 | 96 | 359 | 117 |
| * | | | | | | | | | |
| | −4223 | −668 | −2142 | −3313 | −4295 | −3326 | −3804 | −3534 | −3326 |
| | 210 | −466 | −720 | 275 | 394 | 45 | 96 | 359 | 117 |
| * | | | | | | | | | |
| | −3309 | −3512 | −3401 | −2873 | −4182 | −3050 | −3402 | −3623 | −3828 |
| | 210 | −466 | −720 | 275 | 394 | 45 | 96 | 359 | 117 |
| * | | | | | | | | | |
| | −2130 | −4439 | −3800 | 3631 | −2908 | −1490 | −3023 | −352 | −2529 |
| | 210 | −466 | −720 | 275 | 394 | 45 | 96 | 359 | 117 |
| * | | | | | | | | | |

| m ->e | K | L | M | N | P | O | R | S | T |
|---|---|---|---|---|---|---|---|---|---|
|  | −3079 | −4087 | −3221 | 194 | 3510 | −2758 | −3227 | −1440 | −1653 |
|  | 210 | −466 | −720 | 275 | 394 | 45 | 96 | 359 | 117 |
| * | | | | | | | | | |
|  | 132 | −2814 | −1924 | 557 | −2199 | 462 | −1082 | −1105 | −1230 |
|  | 210 | −466 | −720 | 275 | 394 | 45 | 96 | 359 | 117 |
| * | | | | | | | | | |
|  | 1545 | −3013 | −2167 | −824 | −2424 | 431 | −850 | −255 | −1514 |
|  | 210 | −466 | −720 | 275 | 394 | 45 | 96 | 359 | 117 |
| * | | | | | | | | | |
|  | 196 | 312 | −72 | −1852 | −2473 | −1538 | −1814 | −1476 | 712 |
|  | 210 | −466 | −720 | 275 | 394 | 45 | 96 | 359 | 117 |
| * | | | | | | | | | |
|  | −4485 | −353 | −1224 | −4353 | −4509 | −4336 | −4547 | −3996 | −278 |
|  | 210 | −466 | −720 | 275 | 394 | 45 | 96 | 359 | 117 |
| * | | | | | | | | | |
|  | 444 | 404 | 2320 | 222 | −1978 | −127 | −668 | −804 | −824 |
|  | 210 | −466 | −720 | 275 | 394 | 45 | 96 | 359 | 117 |
| * | | | | | | | | | |
|  | −620 | −2675 | 970 | 838 | −430 | −525 | −1133 | 25 | −1200 |
|  | 210 | −466 | −720 | 275 | 394 | 45 | 96 | 359 | 117 |
| * | | | | | | | | | |
|  | 3106 | −865 | −1291 | −1622 | −2796 | −1038 | −912 | −1781 | −1555 |
|  | 210 | −466 | −720 | 275 | 394 | 45 | 96 | 359 | 117 |
| * | | | | | | | | | |
|  | 1787 | −2511 | −1591 | −648 | 227 | 1574 | 636 | −249 | 1801 |
|  | 210 | −466 | −720 | 275 | 394 | 45 | 96 | 359 | 117 |
| * | | | | | | | | | |
|  | −3062 | 172 | 4465 | −3001 | 1725 | −2776 | −2984 | −2338 | −1912 |
|  | 210 | −466 | −720 | 275 | 394 | 45 | 96 | 359 | 117 |
| * | | | | | | | | | |
|  | 2447 | −2560 | −1648 | −691 | −2148 | −275 | −785 | 270 | 1004 |
|  | 210 | −466 | −720 | 275 | 394 | 45 | 96 | 359 | 117 |
| * | | | | | | | | | |
|  | −1600 | −3950 | −3164 | −1082 | 1471 | −1258 | 488 | −1984 | −2261 |
|  | 210 | −466 | −720 | 275 | 394 | 45 | 96 | 359 | 117 |
| * | | | | | | | | | |
|  | −380 | −1097 | −1379 | −803 | −2206 | 929 | −826 | −1054 | −1045 |
|  | 210 | −466 | −720 | 275 | 394 | 45 | 96 | 359 | 117 |
| * | | | | | | | | | |
|  | −2637 | 2573 | −1135 | −2460 | −3499 | −2296 | −2785 | −2587 | −2228 |
|  | 210 | −466 | −720 | 275 | 394 | 45 | 96 | 359 | 117 |
| * | | | | | | | | | |
|  | 1753 | −3674 | −3032 | −2431 | −3666 | −1120 | 3594 | −3191 | −2938 |
|  | 210 | −466 | −720 | 275 | 394 | 45 | 96 | 359 | 117 |
| * | | | | | | | | | |
|  | −5852 | −3992 | −4112 | −4995 | −5217 | −5110 | −5315 | −5363 | −5399 |
|  | 210 | −466 | −720 | 275 | 394 | 45 | 96 | 359 | 117 |
| * | | | | | | | | | |
|  | −4052 | −4495 | −3559 | −2916 | −3035 | −3647 | −3928 | 2570 | 1512 |
|  | 210 | −466 | −720 | 275 | 394 | 45 | 96 | 359 | 117 |
| * | | | | | | | | | |
|  | −3266 | −146 | 1500 | −3166 | −3495 | −2880 | −3090 | −2639 | −1760 |
|  | 210 | −466 | −720 | 275 | 394 | 45 | 96 | 359 | 117 |
| * | | | | | | | | | |
|  | −4447 | −4480 | −3561 | −3040 | −3058 | −3946 | −4144 | −1616 | −19 |
|  | 210 | −466 | −720 | 275 | 394 | 45 | 96 | 359 | 117 |
| * | | | | | | | | | |
|  | −5191 | 1280 | −3022 | −3865 | −5051 | −3974 | −4590 | −4428 | −4620 |
|  | 210 | −466 | −720 | 275 | 394 | 45 | 96 | 359 | 117 |
| * | | | | | | | | | |
|  | −6203 | −5992 | −6031 | −5971 | −5371 | −6028 | −5699 | −6531 | −6329 |
|  | 210 | −466 | −720 | 275 | 394 | 45 | 96 | 359 | 117 |
| * | | | | | | | | | |
|  | −2892 | −4385 | −3795 | −2928 | −3660 | −3087 | −2954 | −2556 | 2015 |
|  | 210 | −466 | −720 | 275 | 394 | 45 | 96 | 359 | 117 |
| * | | | | | | | | | |
|  | −3645 | −4141 | −3273 | −2568 | −2762 | −3316 | −3519 | 182 | 3789 |
|  | 210 | −466 | −720 | 275 | 394 | 45 | 96 | 359 | 117 |

-continued

| m −>e | K | L | M | N | P | O | R | S | T |
|---|---|---|---|---|---|---|---|---|---|
| * | | | | | | | | | |
| | −4252 | 475 | 1893 | −4231 | −4294 | −3617 | −3993 | −3745 | −2649 |
| | 210 | −466 | −720 | 275 | 394 | 45 | 96 | 359 | 117 |
| * | | | | | | | | | |
| | −774 | −2171 | −1369 | −1075 | −2324 | −705 | 113 | −1140 | 1757 |
| | 210 | −466 | −720 | 275 | 394 | 45 | 96 | 359 | 117 |
| * | | | | | | | | | |
| | −288 | −2283 | 573 | 864 | −2098 | 1523 | −780 | −923 | −946 |
| | 210 | −466 | −720 | 275 | 394 | 45 | 96 | 359 | 117 |
| * | | | | | | | | | |
| | −208 | −2481 | −1556 | 1471 | −2058 | 1356 | 818 | −349 | 553 |
| | 210 | −466 | −720 | 275 | 394 | 45 | 96 | 359 | 117 |
| * | | | | | | | | | |
| | 338 | −941 | 659 | 291 | −334 | 598 | 147 | −143 | 7 |
| | 210 | −466 | −720 | 275 | 394 | 45 | 96 | 359 | 117 |
| * | | | | | | | | | |
| | −3871 | 860 | −2925 | −2956 | −3185 | −3562 | −3763 | −1823 | −1971 |
| | 210 | −466 | −720 | 275 | 394 | 45 | 96 | 359 | 117 |
| * | | | | | | | | | |
| | 201 | −2299 | −1418 | 171 | −2092 | −237 | 1473 | 1037 | 601 |
| | 210 | −466 | −720 | 275 | 394 | 45 | 96 | 359 | 117 |
| * | | | | | | | | | |
| | −4787 | −6283 | −6022 | −3676 | −4750 | −4186 | −5191 | −4762 | −5055 |
| | 210 | −466 | −720 | 275 | 394 | 45 | 96 | 359 | 117 |
| * | | | | | | | | | |
| | −1467 | −1768 | 1554 | −1730 | 3367 | 1187 | −1721 | −1521 | −1336 |
| | 210 | −466 | −720 | 275 | 394 | 45 | 96 | 359 | 117 |
| * | | | | | | | | | |
| | −5852 | −3992 | −4112 | −4995 | −5217 | −5110 | −5315 | −5363 | −5399 |
| | 210 | −466 | −720 | 275 | 394 | 45 | 96 | 359 | 117 |
| * | | | | | | | | | |
| | −6030 | −6539 | −6235 | −5426 | −5034 | −5814 | −5624 | −5041 | −5115 |
| | 210 | −466 | −720 | 275 | 394 | 45 | 96 | 359 | 117 |
| * | | | | | | | | | |
| | 257 | −2431 | −1527 | −639 | −352 | −221 | −775 | −916 | −171 |
| | 210 | −466 | −720 | 275 | 394 | 45 | 96 | 359 | 117 |
| * | | | | | | | | | |
| | −4322 | −4692 | −3754 | −2971 | 778 | −3836 | −4128 | −1679 | −1899 |
| | 210 | −466 | −720 | 275 | 394 | 45 | 96 | 359 | 117 |
| * | | | | | | | | | |
| | −3030 | −3256 | −2480 | −431 | −2933 | −2784 | −3135 | 445 | 3459 |
| | 210 | −466 | −720 | 275 | 394 | 45 | 96 | 359 | 117 |
| * | | | | | | | | | |
| | 1096 | −1475 | 2399 | −1271 | −2407 | −836 | 1972 | −1316 | −1065 |
| | 210 | −466 | −720 | 275 | 394 | 45 | 96 | 359 | 117 |
| * | | | | | | | | | |
| | 270 | −2458 | −1534 | 700 | −532 | 2051 | −444 | −279 | 33 |
| | 210 | −466 | −720 | 275 | 394 | 45 | 96 | 359 | 117 |
| * | | | | | | | | | |
| | −1412 | −1580 | −929 | −63 | −2766 | −1328 | 3068 | −1710 | −1403 |
| | 210 | −466 | −720 | 275 | 394 | 45 | 96 | 359 | 117 |
| * | | | | | | | | | |
| | −1584 | 1086 | −2026 | 184 | 3237 | −1340 | −2075 | −1705 | −1751 |
| | 210 | −466 | −720 | 275 | 394 | 45 | 96 | 359 | 117 |
| * | | | | | | | | | |
| | −4679 | −5395 | −5229 | −3844 | −4736 | −4222 | −4864 | −4710 | −4913 |
| | 210 | −466 | −720 | 275 | 394 | 45 | 96 | 359 | 117 |
| * | | | | | | | | | |
| | −572 | −2846 | −1955 | 2010 | 1717 | 1170 | −1125 | −1150 | −1269 |
| | 210 | −466 | −720 | 275 | 394 | 45 | 96 | 359 | 117 |
| * | | | | | | | | | |
| | −556 | 590 | −63 | 1215 | −1869 | −452 | −785 | −844 | −583 |
| | 210 | −466 | −721 | 275 | 394 | 46 | 96 | 359 | 117 |
| * | | | | | | | | | |
| | 1276 | −2259 | −1332 | −378 | −1836 | 1253 | 987 | −8 | −709 |
| | 210 | −466 | −720 | 275 | 394 | 45 | 96 | 359 | 117 |
| * | | | | | | | | | |
| | 378 | −176 | −755 | −707 | −70 | −291 | −797 | −226 | −744 |
| | 210 | −466 | −720 | 275 | 394 | 45 | 96 | 359 | 117 |
| * | | | | | | | | | |

-continued

| m ->e | K | L | M | N | P | O | R | S | T |
|---|---|---|---|---|---|---|---|---|---|
| | 362 | −2287 | −1382 | −483 | −141 | −80 | −634 | 985 | 2088 |
| * | 210 | −466 | −720 | 275 | 394 | 45 | 96 | 359 | 117 |
| | −342 | −2615 | −1713 | 665 | −2065 | −234 | −883 | 9 | 769 |
| * | 210 | −466 | −720 | 275 | 394 | 45 | 96 | 359 | 117 |
| | 497 | −2217 | −1335 | −424 | 2156 | −66 | −607 | 788 | −767 |
| * | 210 | −466 | −720 | 275 | 394 | 45 | 96 | 359 | 117 |
| | −3258 | 1831 | 3893 | −3253 | −3511 | −2756 | −3069 | −2772 | −1908 |
| * | 210 | −466 | −720 | 275 | 394 | 45 | 96 | 359 | 117 |
| | −1187 | −3502 | −2691 | 664 | −2522 | 465 | −1858 | −1573 | −1824 |
| * | 210 | −466 | −720 | 275 | 394 | 45 | 96 | 359 | 117 |
| | 968 | 807 | 1568 | −876 | −2071 | 590 | 824 | −952 | 177 |
| * | 210 | −466 | −720 | 275 | 394 | 45 | 96 | 359 | 117 |
| | −4488 | −4693 | −4043 | −3432 | −3468 | −4163 | −4245 | −2287 | −2480 |
| * | 210 | −466 | −720 | 275 | 394 | 45 | 96 | 359 | 117 |
| | | 477 | −1152 | −762 | −2121 | −270 | −504 | −1005 | −952 |
| * | 210 | −466 | −720 | 275 | 394 | 45 | 96 | 359 | 117 |
| | −76 | −2158 | 472 | 939 | −2059 | 608 | 1792 | −921 | −920 |
| * | 210 | −466 | −720 | 275 | 394 | 45 | 96 | 359 | 117 |
| | 2824 | −3394 | −2754 | −2150 | −3372 | −849 | 3133 | −2900 | −2653 |
| * | 210 | −466 | −720 | 275 | 394 | 45 | 96 | 359 | 117 |
| | −3415 | −1131 | 2011 | −3214 | −3508 | −3137 | −3344 | −2552 | −1771 |
| * | 210 | −466 | −720 | 275 | 394 | 45 | 96 | 359 | 117 |
| | 191 | −3116 | −2255 | −888 | −2518 | −751 | −1483 | −1454 | −1589 |
| * | 210 | −466 | −720 | 275 | 394 | 45 | 96 | 359 | 117 |
| | −1343 | −1258 | −592 | −1560 | −2537 | −1201 | −1606 | −1469 | −1103 |
| * | 210 | −466 | −720 | 275 | 394 | 45 | 96 | 359 | 117 |
| | −2124 | 136 | −207 | −2119 | −2664 | −1821 | −2064 | −199 | −1051 |
| * | 210 | −466 | −720 | 275 | 394 | 45 | 96 | 359 | 117 |
| | −3976 | −1984 | −1709 | −3372 | −3765 | −3490 | −3760 | −2682 | −2389 |
| * | 210 | −466 | −720 | 275 | 394 | 45 | 96 | 359 | 117 |
| | −839 | −3774 | −3045 | −1508 | −3153 | −1222 | 558 | −2322 | −2451 |
| * | 210 | −466 | −720 | 275 | 394 | 45 | 96 | 359 | 117 |
| | 1260 | −1060 | 686 | −2099 | −2836 | −1618 | 230 | −1871 | −1330 |
| * | 210 | −466 | −720 | 275 | 394 | 45 | 96 | 359 | 117 |
| | −2614 | 1586 | 2444 | −2508 | −2900 | −2216 | −2412 | −1959 | −1257 |
| * | 210 | −466 | −720 | 275 | 394 | 45 | 96 | 359 | 117 |
| | −260 | −2532 | −1609 | 47 | −2094 | 1725 | −772 | −522 | −30 |
| * | 210 | −466 | −720 | 275 | 394 | 45 | 96 | 359 | 117 |
| | 3434 | −4126 | −3469 | −1918 | −3509 | −1513 | −1024 | −2841 | −2941 |
| * | 210 | −466 | −720 | 275 | 394 | 45 | 96 | 359 | 117 |
| | −4731 | 2913 | 1019 | −4827 | −4647 | −3875 | −4383 | −4368 | 365 |
| * | 210 | −466 | −720 | 275 | 394 | 45 | 96 | 359 | 117 |
| | −1059 | −3333 | −2477 | 1368 | −2611 | −871 | −192 | −608 | −1738 |
| * | 210 | −466 | −720 | 275 | 394 | 45 | 96 | 359 | 117 |
| | −3628 | −1521 | −1158 | −748 | −3817 | −3368 | −3576 | −2912 | −2012 |
| * | 210 | −466 | −720 | 275 | 394 | 45 | 96 | 359 | 117 |
| | 293 | −2676 | −1764 | 301 | 2104 | −333 | −927 | −1042 | −1122 |

-continued

| m −>e | K | L | M | N | P | O | R | S | T |
|---|---|---|---|---|---|---|---|---|---|
|  | 210 | −466 | −720 | 275 | 394 | 45 | 96 | 359 | 117 |
| * |  |  |  |  |  |  |  |  |  |
|  | −3905 | −2811 | −2599 | −3440 | −4500 | −3380 | −86 | −3688 | −3603 |
|  | 210 | −466 | −720 | 275 | 394 | 45 | 96 | 359 | 117 |
| * |  |  |  |  |  |  |  |  |  |
|  | −3029 | 322 | −605 | −2801 | −3277 | −2560 | −2795 | −2362 | −1702 |
|  | 210 | −466 | −720 | 275 | 394 | 45 | 96 | 359 | 117 |
| * |  |  |  |  |  |  |  |  |  |
|  | −4037 | −4088 | −3236 | 350 | −3041 | −3643 | −3867 | −1621 | 1654 |
|  | 210 | −466 | −720 | 275 | 394 | 45 | 96 | 359 | 117 |
| * |  |  |  |  |  |  |  |  |  |
|  | −5268 | −125 | −1647 | −4338 | −5053 | −4174 | −4736 | −4670 | −4342 |
|  | 210 | −466 | −720 | 275 | 394 | 45 | 96 | 359 | 117 |
| * |  |  |  |  |  |  |  |  |  |
|  | −5266 | −6082 | −5977 | −5274 | −5186 | −5341 | −5054 | −5722 | −5705 |
|  | 210 | −466 | −720 | 275 | 394 | 45 | 96 | 359 | 117 |
| * |  |  |  |  |  |  |  |  |  |
|  | −4787 | −6283 | −6022 | −3676 | −4750 | −4186 | −5191 | −4762 | −5055 |
|  | 210 | −466 | −720 | 275 | 394 | 45 | 96 | 359 | 117 |
| * |  |  |  |  |  |  |  |  |  |
|  | −400 | −2220 | −1378 | 214 | −2175 | −352 | 2115 | −1018 | −1019 |
|  | 210 | −466 | −720 | 275 | 394 | 45 | 96 | 359 | 117 |
| * |  |  |  |  |  |  |  |  |  |
|  | 338 | −941 | 659 | 291 | −334 | 598 | 147 | −143 | 7 |
|  | 210 | −466 | −720 | 275 | 394 | 45 | 96 | 359 | 117 |
| * |  |  |  |  |  |  |  |  |  |
|  | −4787 | −6283 | −6022 | −3676 | −4750 | −4186 | −5191 | −4762 | −5055 |
|  | 210 | −466 | −720 | 275 | 394 | 45 | 96 | 359 | 117 |
| * |  |  |  |  |  |  |  |  |  |
|  | −5148 | 2210 | −760 | −5155 | −4982 | −4511 | −4983 | −4815 | −3092 |
|  | 210 | −466 | −720 | 275 | 394 | 45 | 96 | 359 | 117 |
| * |  |  |  |  |  |  |  |  |  |
|  | −2507 | −912 | −290 | −2404 | −2824 | −2151 | −2344 | 131 | −1170 |
|  | 210 | −466 | −720 | 275 | 394 | 45 | 96 | 359 | 117 |
| * |  |  |  |  |  |  |  |  |  |
|  | −2167 | −4293 | −3563 | −1294 | 3795 | −1666 | −2911 | −671 | −2463 |
|  | 210 | −466 | −720 | 275 | 394 | 45 | 96 | 359 | 117 |
| * |  |  |  |  |  |  |  |  |  |
|  | −341 | −2569 | −1661 | −668 | −2154 | 563 | 301 | −991 | −66 |
|  | 210 | −466 | −720 | 275 | 394 | 45 | 96 | 359 | 117 |
| * |  |  |  |  |  |  |  |  |  |
|  | −3376 | −4771 | −3958 | −2126 | −3197 | −2757 | −3854 | −1993 | −2272 |
|  | 210 | −466 | −720 | 275 | 394 | 45 | 96 | 359 | 117 |
| * |  |  |  |  |  |  |  |  |  |
|  | 764 | −2500 | −1576 | 1057 | −2071 | −182 | −737 | 809 | 137 |
|  | 210 | −466 | −720 | 275 | 394 | 45 | 96 | 359 | 117 |
| * |  |  |  |  |  |  |  |  |  |
|  | −2004 | −3773 | −2913 | −1652 | 144 | −1753 | −2486 | 2008 | 2860 |
|  | 210 | −466 | −720 | 275 | 394 | 45 | 96 | 359 | 117 |
| * |  |  |  |  |  |  |  |  |  |
|  | −2029 | 2269 | −425 | −2074 | −99 | −1781 | −2114 | −1784 | −1252 |
|  | 210 | −466 | −720 | 275 | 394 | 45 | 96 | 359 | 117 |
| * |  |  |  |  |  |  |  |  |  |
|  | 1804 | −2478 | −1554 | −606 | −2062 | 1184 | 1680 | −183 | 159 |
|  | 210 | −466 | −720 | 275 | 394 | 45 | 96 | 359 | 117 |
| * |  |  |  |  |  |  |  |  |  |
|  | −1128 | −4407 | −3745 | −1375 | −3200 | −1672 | −2399 | −2379 | −470 |
|  | 210 | −466 | −720 | 275 | 394 | 45 | 96 | 359 | 117 |
| * |  |  |  |  |  |  |  |  |  |
|  | −1461 | −1477 | −820 | −1762 | −2729 | −1384 | 1813 | −551 | 2331 |
|  | 210 | −466 | −720 | 275 | 394 | 45 | 96 | 359 | 117 |
| * |  |  |  |  |  |  |  |  |  |
|  | −197 | −251 | −964 | 2489 | −1931 | −140 | −666 | −283 | −731 |
|  | 210 | −466 | −720 | 275 | 394 | 45 | 96 | 359 | 117 |
| * |  |  |  |  |  |  |  |  |  |
|  | 2093 | −2260 | −1336 | 584 | −1845 | 635 | −493 | −69 | −7 |
|  | 210 | −466 | −720 | 275 | 394 | 45 | 96 | 359 | 117 |
| * |  |  |  |  |  |  |  |  |  |
|  | −1982 | −2230 | −1833 | 3905 | −3222 | −1904 | −2179 | −2236 | −2170 |
|  | 210 | −466 | −720 | 275 | 394 | 45 | 96 | 359 | 117 |

-continued

| m ->e | K | L | M | N | P | O | R | S | T |
|---|---|---|---|---|---|---|---|---|---|
| * | | | | | | | | | |
| | | −5024 | 2950 | 84 | −5225 | −4707 | −3869 | −4541 | −4869 | −3343 |
| | 210 | −466 | −720 | 275 | 394 | 45 | 96 | 359 | 117 |
| * | | | | | | | | | |
| | 980 | −2704 | −1796 | −713 | −2225 | −360 | 0 | −1079 | −1159 |
| | 210 | −466 | −720 | 275 | 394 | 45 | 96 | 359 | 117 |
| * | | | | | | | | | |
| | 1175 | −2426 | 150 | −604 | −2055 | 1667 | 717 | −495 | −154 |
| | 210 | −466 | −720 | 275 | 394 | 45 | 96 | 359 | 117 |
| * | | | | | | | | | |
| | −3369 | −1030 | 2854 | −3290 | −3631 | −3031 | −3229 | −2790 | −1858 |
| | 210 | −466 | −720 | 275 | 394 | 45 | 96 | 359 | 117 |
| * | | | | | | | | | |
| | −3118 | −355 | 657 | −3016 | −3390 | −2785 | −2974 | −980 | 862 |
| | 210 | −466 | −720 | 275 | 394 | 45 | 96 | 359 | 117 |
| * | | | | | | | | | |
| | 533 | −2564 | −1644 | −634 | −2116 | −235 | 310 | −332 | −1012 |
| | 210 | −466 | −720 | 275 | 394 | 45 | 96 | 359 | 117 |
| * | | | | | | | | | |
| | 931 | 35 | 2022 | −1413 | −2427 | −1031 | 1430 | −1349 | −1004 |
| | 210 | −466 | −720 | 275 | 394 | 45 | 96 | 359 | 117 |
| * | | | | | | | | | |
| | −3797 | 1421 | −374 | −3739 | −3937 | −3261 | −3569 | −3229 | −2291 |
| | 210 | −466 | −720 | 275 | 394 | 45 | 96 | 359 | 117 |
| * | | | | | | | | | |
| | 2548 | −1107 | −1515 | 258 | −2073 | −184 | 396 | −892 | −135 |
| | 210 | −466 | −720 | 275 | 394 | 45 | 96 | 359 | 117 |
| * | | | | | | | | | |
| | 579 | −2583 | −1663 | −642 | −2127 | 2335 | −145 | −259 | −1028 |
| | 210 | −466 | −720 | 275 | 394 | 45 | 96 | 359 | 117 |
| * | | | | | | | | | |
| | 1991 | −845 | 321 | 94 | −2151 | −329 | 582 | −988 | −966 |
| | 210 | −466 | −720 | 275 | 394 | 45 | 96 | 359 | 117 |
| * | | | | | | | | | |
| | −4242 | 1751 | 3339 | −4479 | −4487 | 2834 | −4010 | −4102 | −3045 |
| | 210 | −466 | −720 | 275 | 394 | 45 | 96 | 359 | 117 |
| * | | | | | | | | | |
| | 1945 | −2482 | −1556 | −597 | −2058 | 764 | −60 | 337 | −933 |
| | 210 | −466 | −720 | 275 | 394 | 45 | 96 | 359 | 117 |
| * | | | | | | | | | |
| | 350 | −2516 | −1592 | 79 | −2081 | 847 | −752 | −263 | 1096 |
| | 210 | −466 | −720 | 275 | 394 | 45 | 96 | 359 | 117 |
| * | | | | | | | | | |
| | −3525 | −4417 | −3519 | −111 | −3045 | −3199 | −3603 | 2044 | |
| | 210 | −466 | −720 | 275 | 394 | 45 | 96 | 359 | 117 |
| * | | | | | | | | | |
| | 852 | −3793 | −3046 | 937 | −3065 | −1284 | −1318 | −2168 | −2338 |
| | 210 | −466 | −720 | 275 | 394 | 45 | 96 | 359 | 117 |
| * | | | | | | | | | |
| | 153 | 636 | 2441 | −2644 | −3047 | −2378 | −2570 | −2115 | 254 |
| | 210 | −466 | −720 | 275 | 394 | 45 | 96 | 359 | 117 |
| * | | | | | | | | | |
| | 3569 | −2849 | −2226 | −1941 | −3205 | 185 | −333 | −2373 | −2209 |
| | 210 | −466 | −720 | 275 | 394 | 45 | 96 | 359 | 117 |
| * | | | | | | | | | |
| | −4186 | 2461 | −619 | −4123 | −180 | −3692 | −3999 | −3552 | −2603 |
| | 210 | −466 | −720 | 275 | 394 | 45 | 96 | 359 | 117 |
| * | | | | | | | | | |
| | −4722 | 2904 | −1522 | −4638 | 2196 | −4380 | −4502 | −4088 | −3732 |
| | 210 | −466 | −720 | 275 | 394 | 45 | 96 | 359 | 117 |
| * | | | | | | | | | |
| | −4647 | −2000 | 3289 | −4520 | −4875 | −4300 | −4355 | −4520 | −4225 |
| | 210 | −466 | −720 | 275 | 394 | 45 | 96 | 359 | 117 |
| * | | | | | | | | | |
| | −2730 | −3523 | −2701 | 2927 | −2900 | −2506 | −2962 | −414 | −1684 |
| | 210 | −466 | −720 | 275 | 394 | 45 | 96 | 359 | 117 |
| * | | | | | | | | | |

-continued

| m -> e | K | L | M | N | P | O | R | S | T |
|---|---|---|---|---|---|---|---|---|---|
|  | −5081 | −5386 | −4862 | −4270 | −4241 | −4876 | −4829 | −3277 | 4049 |
|  | 210 | −466 | −720 | 275 | 394 | 45 | 96 | 359 | 117 |
| * |  |  |  |  |  |  |  |  |  |
|  | −4136 | −4497 | −3564 | −2941 | −3041 | −3711 | −3978 | 1060 | 1917 |
|  | 210 | −466 | −720 | 275 | 394 | 45 | 96 | 359 | 117 |
| * |  |  |  |  |  |  |  |  |  |
|  | −2073 | −4368 | −3639 | 3979 | −3136 | 445 | −2533 | 245 | −2444 |
|  | 210 | −466 | −720 | 275 | 394 | 45 | 96 | 359 | 117 |
| * |  |  |  |  |  |  |  |  |  |
|  | −2783 | 2250 | 2832 | −414 | −3076 | −2387 | −2597 | −2155 | −1430 |
|  | 210 | −466 | −720 | 275 | 394 | 45 | 96 | 359 | 117 |
| * |  |  |  |  |  |  |  |  |  |
|  | −5852 | −3992 | −4112 | −4995 | −5217 | −5110 | −5315 | −5363 | −5399 |
|  | 210 | −466 | −720 | 275 | 394 | 45 | 96 | 359 | 117 |
| * |  |  |  |  |  |  |  |  |  |
|  | −3160 | −3578 | 1028 | −2602 | −2954 | −2918 | −3250 | 1815 | 3158 |
|  | 210 | −466 | −720 | 275 | 394 | 45 | 96 | 359 | 117 |
| * |  |  |  |  |  |  |  |  |  |
|  | −1989 | −4378 | −3682 | 2832 | −3090 | 194 | −2726 | −2268 | −2637 |
|  | 210 | −466 | −720 | 275 | 394 | 45 | 96 | 359 | 117 |
| * |  |  |  |  |  |  |  |  |  |
|  | 593 | −3828 | −3084 | −1470 | 3745 | −1415 | −1541 | −2135 | −2319 |
|  | 210 | −466 | −720 | 275 | 394 | 45 | 96 | 359 | 117 |
| * |  |  |  |  |  |  |  |  |  |
|  | −1691 | −2646 | −1918 | −2140 | −2867 | −1879 | 3417 | −1633 | −92 |
|  | 210 | −466 | −720 | 275 | 394 | 45 | 96 | 359 | 117 |
| * |  |  |  |  |  |  |  |  |  |
|  | −5300 | −3188 | −3284 | −3899 | −5127 | −4036 | −4670 | −4527 | −4855 |
|  | 210 | −466 | −720 | 275 | 394 | 45 | 96 | 359 | 117 |
| * |  |  |  |  |  |  |  |  |  |
|  | 1562 | 39 | 2941 | −2060 | −2743 | −1703 | −1901 | −1745 | −1181 |
|  | 210 | −466 | −720 | 275 | 394 | 45 | 96 | 359 | 117 |
| * |  |  |  |  |  |  |  |  |  |
|  | −948 | −3231 | −2358 | 1914 | −2532 | −764 | −1529 | −462 | −1628 |
|  | 210 | −466 | −720 | 275 | 394 | 45 | 96 | 359 | 117 |
| * |  |  |  |  |  |  |  |  |  |
|  | −6030 | −6539 | −6235 | −5426 | −5034 | −5814 | −5624 | −5041 | −5115 |
|  | 210 | −466 | −720 | 275 | 394 | 45 | 96 | 359 | 117 |
| * |  |  |  |  |  |  |  |  |  |
|  | 338 | −941 | 659 | 291 | −334 | 598 | 147 | −143 | 7 |
|  | 210 | −466 | −720 | 275 | 394 | 45 | 96 | 359 | 117 |
| * |  |  |  |  |  |  |  |  |  |
|  | −4337 | −4384 | −3516 | −3010 | −3078 | −3869 | −4090 | −1647 | −1847 |
|  | 210 | −466 | −720 | 275 | 394 | 45 | 96 | 359 | 117 |
| * |  |  |  |  |  |  |  |  |  |
|  | −3632 | −3529 | −2743 | −2783 | −3003 | −3276 | −3573 | 1465 | −1739 |
|  | 210 | −466 | −720 | 275 | 394 | 45 | 96 | 359 | 117 |
| * |  |  |  |  |  |  |  |  |  |
|  | −4195 | −4644 | −3761 | −2999 | −3149 | −3828 | −4010 | −557 | 3992 |
|  | 210 | −466 | −720 | 275 | 394 | 45 | 96 | 359 | 117 |
| * |  |  |  |  |  |  |  |  |  |
|  | −2898 | −4091 | −3185 | 1991 | −2931 | −2672 | −3128 | 2781 | 1118 |
|  | 210 | −466 | −720 | 275 | 394 | 45 | 96 | 359 | 117 |
| * |  |  |  |  |  |  |  |  |  |
|  | −1861 | −3298 | −2470 | 2369 | 2823 | −1857 | −547 | −338 | −1614 |
|  | 210 | −466 | −720 | 275 | 394 | 45 | 96 | 359 | 117 |
| * |  |  |  |  |  |  |  |  |  |
|  | −290 | −2522 | −1608 | 1941 | −2113 | −236 | 126 | 73 | −1002 |
|  | 210 | −466 | −720 | 275 | 394 | 45 | 96 | 359 | 117 |
| * |  |  |  |  |  |  |  |  |  |
|  | −1508 | −1393 | −717 | −1726 | 1050 | −1393 | 1435 | −1489 | −1163 |
|  | 210 | −466 | −720 | 275 | 394 | 45 | 96 | 359 | 117 |
| * |  |  |  |  |  |  |  |  |  |
|  | 395 | −2602 | −1685 | 326 | −2145 | −272 | −851 | 251 | −169 |
|  | 210 | −466 | −720 | 275 | 394 | 45 | 96 | 359 | 117 |
| * |  |  |  |  |  |  |  |  |  |
|  | −5092 | −1669 | −1617 | −4931 | −5004 | −5033 | −5244 | −4603 | −2770 |

-continued

| m −>e | K | L | M | N | P | O | R | S | T |
|---|---|---|---|---|---|---|---|---|---|
|  | 210 | −466 | −720 | 275 | 394 | 45 | 96 | 359 | 117 |
| * |  |  |  |  |  |  |  |  |  |
|  | −3699 | −2242 | −1900 | −3317 | −4178 | −3190 | 2010 | −3345 | −2975 |
|  | 210 | −466 | −720 | 275 | 394 | 45 | 96 | 359 | 117 |
| * |  |  |  |  |  |  |  |  |  |
|  | −2474 | −4083 | −3222 | −2583 | −3032 | −2685 | 1719 | 534 | −1849 |
|  | 210 | −466 | −720 | 275 | 394 | 45 | 96 | 359 | 117 |
| * |  |  |  |  |  |  |  |  |  |
|  | −4580 | −2777 | 836 | −3655 | −4704 | −3678 | 1014 | −3973 | −3862 |
|  | 210 | −466 | −720 | 275 | 394 | 45 | 96 | 359 | 117 |
| * |  |  |  |  |  |  |  |  |  |
|  | −4443 | −4696 | −3743 | −3000 | −3071 | −3927 | −4178 | 218 | −1854 |
|  | 210 | −466 | −720 | 275 | 394 | 45 | 96 | 359 | 117 |
| * |  |  |  |  |  |  |  |  |  |
|  | −2525 | 734 | −274 | −2447 | −2880 | −2171 | −2378 | −1919 | −1233 |
|  | 210 | −466 | −720 | 275 | 394 | 45 | 96 | 359 | 117 |
| * |  |  |  |  |  |  |  |  |  |
|  | −1713 | −2410 | −1660 | −1850 | −2680 | −1637 | 1676 | −1432 | 551 |
|  | 210 | −466 | −720 | 275 | 394 | 45 | 96 | 359 | 117 |
| * |  |  |  |  |  |  |  |  |  |
|  | 2500 | −3828 | −3184 | −2315 | −3640 | 3726 | −379 | −3075 | −2950 |
|  | 210 | −466 | −720 | 275 | 394 | 45 | 96 | 359 | 117 |
| * |  |  |  |  |  |  |  |  |  |
|  | −3430 | 223 | −879 | −3321 | −3670 | −3122 | −3314 | −452 | 114 |
|  | 210 | −466 | −720 | 275 | 394 | 45 | 96 | 359 | 117 |
| * |  |  |  |  |  |  |  |  |  |
|  | 3002 | 1068 | −398 | −3036 | −3519 | −2605 | −2843 | −2673 | −1920 |
|  | 210 | −466 | −720 | 275 | 394 | 45 | 96 | 359 | 117 |
| * |  |  |  |  |  |  |  |  |  |
|  | 2209 | −2532 | −1615 | 617 | −2127 | −214 | 1169 | −956 | 416 |
|  | 210 | −466 | −720 | 275 | 394 | 45 | 96 | 359 | 117 |
| * |  |  |  |  |  |  |  |  |  |
|  | −819 | −2844 | −1946 | 1423 | −2360 | 334 | −1298 | 1120 | 170 |
|  | 210 | −466 | −720 | 275 | 394 | 45 | 96 | 359 | 117 |
| * |  |  |  |  |  |  |  |  |  |
|  | −5449 | 2475 | 2821 | −5714 | −5087 | −4261 | −4955 | −5348 | −3701 |
|  | 210 | −466 | −720 | 275 | 394 | 45 | 96 | 359 | 117 |
| * |  |  |  |  |  |  |  |  |  |
|  | −2514 | −4917 | −4353 | 575 | −3236 | −1786 | −3527 | −2508 | −3007 |
|  | 210 | −466 | −720 | 275 | 394 | 45 | 96 | 359 | 117 |
| * |  |  |  |  |  |  |  |  |  |
|  | −3592 | 1435 | −900 | −3481 | −3802 | −3276 | −3473 | −2983 | −597 |
|  | 210 | −466 | −720 | 275 | 394 | 45 | 96 | 359 | 117 |
| * |  |  |  |  |  |  |  |  |  |
|  | −4085 | −4491 | −3558 | −2925 | −3038 | −3671 | −3948 | 523 | 2255 |
|  | 210 | −466 | −720 | 275 | 394 | 45 | 96 | 359 | 117 |
| * |  |  |  |  |  |  |  |  |  |
|  | 2556 | −1538 | −836 | −1336 | −2470 | −892 | −1164 | −1384 | −1131 |
|  | 210 | −466 | −720 | 275 | 394 | 45 | 96 | 359 | 117 |
| * |  |  |  |  |  |  |  |  |  |
|  | 1335 | −2691 | −1802 | −886 | −2327 | 234 | 1489 | −1200 | −369 |
|  | 210 | −466 | −720 | 275 | 394 | 45 | 96 | 359 | 117 |
| * |  |  |  |  |  |  |  |  |  |
|  | −5446 | 1005 | 1236 | −5724 | −5089 | −4257 | −4949 | −5349 | −3726 |
|  | 210 | −466 | −720 | 275 | 394 | 45 | 96 | 359 | 117 |
| * |  |  |  |  |  |  |  |  |  |
|  | −4127 | −5358 | −4624 | 59 | −3784 | −3697 | −4300 | −2703 | −2949 |
|  | 210 | −466 | −720 | 275 | 394 | 45 | 96 | 359 | 117 |
| * |  |  |  |  |  |  |  |  |  |
|  | −3742 | −4425 | −3503 | −2804 | −3029 | −3419 | −1816 | 1068 | −1817 |
|  | 210 | −466 | −720 | 275 | 394 | 45 | 96 | 359 | 117 |
| * |  |  |  |  |  |  |  |  |  |
|  | −137 | −3947 | −3188 | −1202 | −2990 | −287 | −1831 | −242 | −2356 |
|  | 210 | −466 | −720 | 275 | 394 | 45 | 96 | 359 | 117 |
| * |  |  |  |  |  |  |  |  |  |
|  | −1466 | −2263 | −1508 | 3406 | −2581 | −1353 | −1820 | −247 | 1313 |
|  | 210 | −466 | −720 | 275 | 394 | 45 | 96 | 359 | 117 |
| * |  |  |  |  |  |  |  |  |  |
|  | −5262 | −1015 | −3107 | −3892 | −5106 | −4013 | −4642 | −4501 | −4770 |
|  | 210 | −466 | −720 | 275 | 394 | 45 | 96 | 359 | 117 |
| * |  |  |  |  |  |  |  |  |  |
|  | −5325 | −2915 | −2860 | −4909 | −4787 | −5200 | −5168 | −4266 | −3561 |

-continued

| m ->e | K | L | M | N | P | O | R | S | T |
|---|---|---|---|---|---|---|---|---|---|
| | 210 | −466 | −720 | 275 | 394 | 45 | 96 | 359 | 117 |
| * | | | | | | | | | |
| | −3595 | 1079 | 1156 | −3542 | −3766 | −3052 | −3355 | −3019 | −2168 |
| | 210 | −466 | −720 | 275 | 394 | 45 | 96 | 359 | 117 |
| * | | | | | | | | | |
| | −6203 | −5992 | −6031 | −5971 | −5371 | −6028 | −5699 | −6531 | −6329 |
| | 210 | −466 | −720 | 275 | 394 | 45 | 96 | 359 | 117 |
| * | | | | | | | | | |
| | −5128 | −5785 | −5102 | −4100 | 282 | −4765 | −4941 | −3242 | −3441 |
| | 210 | −466 | −720 | 275 | 394 | 45 | 96 | 359 | 117 |
| * | | | | | | | | | |
| | −6030 | −6539 | −6235 | −5426 | −5034 | −5814 | −5624 | −5041 | −5115 |
| | 210 | −466 | −720 | 275 | 394 | 45 | 96 | 359 | 117 |
| * | | | | | | | | | |
| | −3143 | −5805 | −5439 | −4840 | −4993 | −4014 | 4230 | −5318 | −5151 |
| | 210 | −466 | −720 | 275 | 394 | 45 | 96 | 359 | 117 |
| * | | | | | | | | | |
| | −4583 | −6183 | −5913 | −3747 | −4767 | −4175 | −4884 | −4792 | −5049 |
| | 210 | −466 | −720 | 275 | 394 | 45 | 96 | 359 | 117 |
| * | | | | | | | | | |
| | −6030 | −6539 | −6235 | −5426 | −5034 | −5814 | −5624 | −5041 | −5115 |
| | 210 | −466 | −720 | 275 | 394 | 45 | 96 | 359 | 117 |
| * | | | | | | | | | |
| | −3639 | −3566 | −2927 | −2840 | −3221 | −3299 | −3585 | 346 | −2022 |
| | 210 | −466 | −720 | 275 | 394 | 45 | 96 | 359 | 117 |
| * | | | | | | | | | |
| | −834 | −3054 | 1184 | −859 | −2470 | 595 | −1389 | −1391 | −1518 |
| | 210 | −466 | −720 | 275 | 394 | 45 | 96 | 359 | 117 |
| * | | | | | | | | | |
| | −1798 | −977 | −315 | 492 | −2600 | −1565 | −1879 | 1469 | 2053 |
| | 210 | −466 | −720 | 275 | 394 | 45 | 96 | 359 | 117 |
| * | | | | | | | | | |
| | −2079 | | −3117 | −1233 | −3073 | −1582 | −2813 | −2228 | −2503 |
| | 210 | −466 | −720 | 275 | 394 | 45 | 96 | 359 | 117 |
| * | | | | | | | | | |
| | −1838 | 2157 | −357 | −1927 | −2623 | −1612 | −1910 | 39 | −1078 |
| | 210 | −466 | −720 | 275 | 394 | 45 | 96 | 359 | 117 |
| * | | | | | | | | | |
| | −3254 | −4290 | −3387 | 3818 | −2998 | −2951 | −3423 | −234 | 228 |
| | 210 | −466 | −720 | 275 | 394 | 45 | 96 | 359 | 117 |
| * | | | | | | | | | |
| | 1571 | −3911 | −3113 | −2201 | −3114 | −2006 | −1736 | −1923 | 3444 |
| | 210 | −466 | −720 | 275 | 394 | 45 | 96 | 359 | 117 |
| * | | | | | | | | | |
| | 78 | −4447 | −3759 | 761 | −3106 | 1043 | −2749 | −2297 | −2679 |
| | 210 | −466 | −720 | 275 | 394 | 45 | 96 | 359 | 117 |
| * | | | | | | | | | |
| | −2346 | 1093 | 3659 | −2307 | −2785 | 467 | −2231 | −1817 | −59 |
| | 210 | −466 | −720 | 275 | 394 | 45 | 96 | 359 | 117 |
| * | | | | | | | | | |
| | 2469 | −2522 | −1603 | 266 | −2109 | 522 | 1551 | −254 | −990 |
| | 210 | −466 | −720 | 275 | 394 | 45 | 96 | 359 | 117 |
| * | | | | | | | | | |
| | 338 | −941 | 659 | 291 | −334 | 598 | 147 | −143 | 7 |
| | 210 | −466 | −720 | 275 | 394 | 45 | 96 | 359 | 117 |
| * | | | | | | | | | |
| | 420 | 512 | −1227 | −760 | −2139 | 1266 | 1890 | −975 | −948 |
| | 210 | −466 | −720 | 275 | 394 | 45 | 96 | 359 | 117 |
| * | | | | | | | | | |
| | −1979 | −3329 | −2647 | −1665 | −2946 | −1764 | −2429 | −1806 | −1937 |
| | 210 | −466 | −720 | 275 | 394 | 45 | 96 | 359 | 117 |
| * | | | | | | | | | |
| | 519 | 2067 | 848 | −1624 | −2718 | 1781 | 725 | −1719 | −1418 |
| | 210 | −466 | −720 | 275 | 394 | 45 | 96 | 359 | 117 |
| * | | | | | | | | | |
| | −1204 | −4345 | −3627 | −1146 | −3050 | −1496 | −2798 | −856 | −2573 |
| | 210 | −466 | −720 | 275 | 394 | 45 | 96 | 359 | 117 |
| * | | | | | | | | | |
| | −245 | −2581 | −1678 | 2194 | −2196 | 1039 | 1482 | −1040 | −1092 |
| | 210 | −466 | −720 | 275 | 394 | 45 | 96 | 359 | 117 |
| * | | | | | | | | | |

-continued

| m −>e | K | L | M | N | P | O | R | S | T |
|---|---|---|---|---|---|---|---|---|---|
| | −2791 | 1720 | 3132 | −2694 | −3054 | −2373 | −2581 | −2141 | −1411 |
| | 210 | −466 | −720 | 275 | 394 | 45 | 96 | 359 | 117 |
| * | | | | | | | | | |
| | 508 | −2930 | −2076 | −1300 | −2572 | −823 | 1599 | −500 | −1463 |
| | 210 | −466 | −720 | 275 | 394 | 45 | 96 | 359 | 117 |
| * | | | | | | | | | |
| | 1166 | −2488 | −1564 | 387 | −2070 | 471 | 2128 | −309 | 332 |
| | 210 | −466 | −720 | 275 | 394 | 45 | 96 | 359 | 117 |
| * | | | | | | | | | |
| | −2300 | −901 | 1472 | −2239 | −893 | −1973 | −2197 | −1725 | −1113 |
| | 210 | −466 | −720 | 275 | 394 | 45 | 96 | 359 | 117 |
| * | | | | | | | | | |
| | −3964 | 1977 | 2554 | −3882 | −4056 | −3300 | −3668 | −3416 | −2538 |
| | 210 | −466 | −720 | 275 | 394 | 45 | 96 | 359 | 117 |
| * | | | | | | | | | |
| | 749 | −2502 | −1579 | 918 | −2079 | 1776 | 469 | −899 | 752 |
| | 210 | −466 | −720 | 275 | 394 | 45 | 96 | 359 | 117 |
| * | | | | | | | | | |
| | −3109 | 1631 | 3028 | −3036 | −3351 | −2647 | −2893 | −2497 | −246 |
| | 210 | −466 | −720 | 275 | 394 | 45 | 96 | 359 | 117 |
| * | | | | | | | | | |
| | −2809 | 672 | 1303 | −2705 | −3092 | −2442 | −2643 | −2151 | −1419 |
| | 210 | −466 | −720 | 275 | 394 | 45 | 96 | 359 | 117 |
| * | | | | | | | | | |
| | 958 | −1259 | −562 | −1384 | −2419 | −995 | 817 | −1338 | −1009 |
| | 210 | −466 | −720 | 275 | 394 | 45 | 96 | 359 | 117 |
| * | | | | | | | | | |
| | −924 | −3217 | −2340 | 436 | −2518 | 976 | −1504 | −420 | −1608 |
| | 210 | −466 | −720 | 275 | 394 | 45 | 96 | 359 | 117 |
| * | | | | | | | | | |
| | −4860 | −3314 | −3388 | −3861 | −5053 | −3965 | −4419 | −4476 | −4777 |
| | 210 | −466 | −720 | 275 | 394 | 45 | 96 | 359 | 117 |
| * | | | | | | | | | |
| | 939 | −1605 | −891 | −1427 | −2466 | −1072 | −1499 | −411 | −1115 |
| | 210 | −466 | −720 | 275 | 394 | 45 | 96 | 359 | 117 |
| * | | | | | | | | | |
| | 2054 | −2472 | −1546 | 980 | −2052 | 603 | 1183 | −866 | 205 |
| | 210 | −466 | −720 | 275 | 394 | 45 | 96 | 359 | 117 |
| * | | | | | | | | | |
| | 1371 | −2578 | −1658 | −642 | −2125 | −245 | −31 | 858 | −1025 |
| | 210 | −466 | −720 | 275 | 394 | 45 | 96 | 359 | 117 |
| * | | | | | | | | | |
| | 1262 | −3125 | −2452 | −2120 | −3365 | 1862 | 561 | −2654 | −2443 |
| | 210 | −466 | −720 | 275 | 394 | 45 | 96 | 359 | 117 |
| * | | | | | | | | | |
| | −2776 | −4946 | −4322 | 291 | −3293 | −2075 | −3657 | −2438 | −2858 |
| | 210 | −466 | −720 | 275 | 394 | 45 | 96 | 359 | 117 |
| * | | | | | | | | | |
| | −4913 | −1074 | −2941 | −3762 | −4903 | −3843 | −4408 | −919 | −4284 |
| | 210 | −466 | −720 | 275 | 394 | 45 | 96 | 359 | 117 |
| * | | | | | | | | | |
| | 919 | −1132 | −1553 | 893 | −2056 | 1223 | −713 | −871 | 944 |
| | 210 | −466 | −720 | 275 | 394 | 45 | 96 | 359 | 117 |
| * | | | | | | | | | |
| | −1811 | 555 | −355 | −1900 | 408 | −1582 | −1898 | −1575 | −499 |
| | 210 | −466 | −720 | 275 | 394 | 45 | 96 | 359 | 117 |
| * | | | | | | | | | |
| | 101 | −2489 | −1598 | 278 | −1086 | 2837 | 1581 | −1029 | 1381 |
| | 210 | −466 | −720 | 275 | 394 | 45 | 96 | 359 | 117 |
| * | | | | | | | | | |
| | −5233 | 1117 | 1544 | −5389 | −4953 | −4113 | −4759 | −5019 | −3594 |
| | 210 | −466 | −720 | 275 | 394 | 45 | 96 | 359 | 117 |
| * | | | | | | | | | |
| | −4392 | 2837 | −1006 | −3969 | −4022 | −3904 | −4164 | −3002 | −2754 |
| | 210 | −466 | −720 | 275 | 394 | 45 | 96 | 359 | 117 |
| * | | | | | | | | | |
| | −5239 | 1256 | −646 | −5322 | −5043 | −4488 | −4999 | −4988 | −3295 |
| | 210 | −466 | −720 | 275 | 394 | 45 | 96 | 359 | 117 |
| * | | | | | | | | | |
| | −4583 | −6183 | −5913 | −3747 | −4767 | −4175 | −4884 | −4792 | −5049 |
| | 210 | −466 | −720 | 275 | 394 | 45 | 96 | 359 | 117 |
| * | | | | | | | | | |

-continued

| m −>e | K | L | M | N | P | O | R | S | T |
|---|---|---|---|---|---|---|---|---|---|
| | −6053 | −6538 | −6341 | −5638 | 4316 | −5917 | −5641 | −5486 | −5496 |
| | 210 | −466 | −720 | 275 | 394 | 45 | 96 | 359 | 117 |
| * | | | | | | | | | |
| | 4680 | −5471 | −5024 | −4244 | −4783 | −3408 | −2493 | −4857 | −4726 |
| | 210 | −466 | −720 | 275 | 394 | 45 | 96 | 359 | 117 |
| * | | | | | | | | | |
| | −4533 | −5052 | −4279 | −3436 | 4155 | −4192 | −4369 | −2335 | −2548 |
| | 210 | −466 | −720 | 275 | 394 | 45 | 96 | 359 | 117 |
| * | | | | | | | | | |
| | 2701 | −3003 | 1908 | 2081 | −2743 | 1586 | −404 | −1736 | −1732 |
| | 210 | −466 | −720 | 275 | 394 | 45 | 96 | 359 | 117 |
| * | | | | | | | | | |
| | −4583 | −6183 | −5913 | −3747 | −4767 | −4175 | −4884 | −4792 | −5049 |
| | 210 | −466 | −720 | 275 | 394 | 45 | 96 | 359 | 117 |
| * | | | | | | | | | |
| | −6053 | −6538 | −6341 | −5638 | | −5917 | −5641 | −5486 | −5496 |
| | 210 | −466 | −720 | 275 | 394 | 45 | 96 | 359 | 117 |
| * | | | | | | | | | |
| | −892 | −2555 | 1753 | −2247 | −3160 | −1548 | 2098 | −2129 | 3164 |
| | 210 | −466 | −720 | 275 | 394 | 45 | 96 | 359 | 117 |
| * | | | | | | | | | |
| | 2460 | −2412 | 376 | −776 | −2191 | 560 | −730 | −1027 | 996 |
| | 210 | −466 | −720 | 275 | 394 | 45 | 96 | 359 | 117 |
| * | | | | | | | | | |
| | −2845 | −3764 | −3475 | −1967 | −3709 | −2311 | −3399 | −2927 | −3243 |
| | 210 | −466 | −720 | 275 | 394 | 45 | 96 | 359 | 117 |
| * | | | | | | | | | |
| | −2306 | −2048 | −2010 | −3126 | −4018 | 3975 | −2353 | −3246 | −2972 |
| | 210 | −466 | −720 | 275 | 394 | 45 | 96 | 359 | 117 |
| * | | | | | | | | | |
| | −5204 | 588 | −2693 | −3920 | −5066 | −3993 | −4610 | −4477 | −4604 |
| | 210 | −466 | −720 | 275 | 394 | 45 | 96 | 359 | 117 |
| * | | | | | | | | | |
| | −3417 | 1062 | −1316 | −2809 | −4046 | −2871 | −3673 | −3321 | −3098 |
| | 210 | −466 | −720 | 275 | 394 | 45 | 96 | 359 | 117 |
| * | | | | | | | | | |
| | −2343 | −852 | −208 | −2267 | 1364 | −1992 | −2198 | −1758 | 336 |
| | 210 | −466 | −720 | 275 | 394 | 45 | 96 | 359 | 117 |
| * | | | | | | | | | |
| | −2986 | −4935 | −4319 | −1779 | −3430 | −2333 | −3759 | −2551 | 1960 |
| | 210 | −466 | −720 | 275 | 394 | 45 | 96 | 359 | 117 |
| * | | | | | | | | | |
| | −2859 | −1673 | −1071 | −2602 | −2996 | −2560 | −2812 | 319 | 356 |
| | 210 | −466 | −720 | 275 | 394 | 45 | 96 | 359 | 117 |
| * | | | | | | | | | |
| | −1293 | −3323 | −2474 | −1193 | −2662 | −1815 | 380 | −724 | −1690 |
| | 210 | −466 | −720 | 275 | 394 | 45 | 96 | 359 | 117 |
| * | | | | | | | | | |
| | −1840 | −3474 | −2665 | −42 | −2866 | −1754 | −2195 | −42 | 3311 |
| | 210 | −466 | −720 | 275 | 394 | 45 | 96 | 359 | 117 |
| * | | | | | | | | | |
| | −1803 | −1153 | 1226 | −1896 | −2621 | −1594 | −618 | −1555 | 1741 |
| | 210 | −466 | −720 | 275 | 394 | 45 | 96 | 359 | 117 |
| * | | | | | | | | | |
| | −2590 | 1525 | 1089 | −2484 | −2875 | −2195 | −2387 | −1931 | −1228 |
| | 210 | −466 | −720 | 275 | 394 | 45 | 96 | 359 | 117 |
| * | | | | | | | | | |
| | −3713 | −4492 | −3567 | 555 | −3034 | −3314 | −3765 | −61 | −1848 |
| | 210 | −466 | −720 | 275 | 394 | 45 | 96 | 359 | 117 |
| * | | | | | | | | | |
| | −5257 | −859 | −2061 | −4236 | −5048 | −4187 | −4724 | −4603 | −4458 |
| | 210 | −466 | −720 | 275 | 394 | 45 | 96 | 359 | 117 |
| * | | | | | | | | | |
| | 338 | −941 | 659 | 291 | −334 | 598 | 147 | −143 | 7 |
| | 210 | −466 | −720 | 275 | 394 | 45 | 96 | 359 | 117 |
| * | | | | | | | | | |
| | −5257 | 2650 | 1509 | −5420 | −4986 | −4234 | −4854 | −5036 | −3464 |
| | 210 | −466 | −720 | 275 | 394 | 45 | 96 | 359 | 117 |
| * | | | | | | | | | |

-continued

| m −>e | K | L | M | N | P | O | R | S | T |
|---|---|---|---|---|---|---|---|---|---|
|  | 2005 | −2499 | −1576 | −625 | −2082 | 2156 | 985 | −901 | −958 |
|  | 210 | −466 | −720 | 275 | 394 | 45 | 96 | 359 | 117 |
| * |  |  |  |  |  |  |  |  |  |
|  | 1569 | −2478 | −1554 | −607 | −2064 | 1918 | 125 | −280 | 1845 |
|  | 210 | −466 | −720 | 275 | 394 | 45 | 96 | 359 | 117 |
| * |  |  |  |  |  |  |  |  |  |
|  | −5082 | 1275 | −3001 | −3826 | −4994 | −3925 | −4517 | −4347 | −4486 |
|  | 210 | −466 | −720 | 275 | 394 | 45 | 96 | 359 | 117 |
| * |  |  |  |  |  |  |  |  |  |
|  | −2029 | −4373 | −3659 | 909 | −3058 | −1510 | −2839 | −2220 | −2589 |
|  | 210 | −466 | −720 | 275 | 394 | 45 | 96 | 359 | 117 |
| * |  |  |  |  |  |  |  |  |  |
|  | −656 | 2608 | −1855 | −2584 | −3649 | −1532 | 1920 | −2997 | −2656 |
|  | 210 | −466 | −720 | 275 | 394 | 45 | 96 | 359 | 117 |
| * |  |  |  |  |  |  |  |  |  |
|  | 533 | −2565 | 328 | −642 | 1396 | −249 | −820 | −956 | 36 |
|  | 210 | −466 | −720 | 275 | 394 | 45 | 96 | 359 | 117 |
| * |  |  |  |  |  |  |  |  |  |
|  | 2145 | −3064 | −2175 | 56 | −2431 | 967 | −1320 | −1342 | −1471 |
|  | 210 | −466 | −720 | 275 | 394 | 45 | 96 | 359 | 117 |
| * |  |  |  |  |  |  |  |  |  |
|  | −395 | −182 | 481 | −767 | −2139 | −339 | 266 | −215 | −39 |
|  | 210 | −466 | −720 | 275 | 394 | 45 | 96 | 359 | 117 |
| * |  |  |  |  |  |  |  |  |  |
|  | −4141 | −1500 | −1361 | −3601 | −4252 | −3447 | −3825 | −3494 | −2868 |
|  | 210 | −466 | −720 | 275 | 394 | 45 | 96 | 359 | 117 |
| * |  |  |  |  |  |  |  |  |  |
|  | 3532 | −4797 | −4163 | −3047 | −4026 | −2528 | −1831 | −3329 | −3400 |
|  | 210 | −466 | −720 | 275 | 394 | 45 | 96 | 359 | 117 |
| * |  |  |  |  |  |  |  |  |  |
|  | −4810 | 2411 | −428 | −4847 | −4706 | −4033 | −4515 | −4417 | −3061 |
|  | 210 | −466 | −720 | 275 | 394 | 45 | 96 | 359 | 117 |
| * |  |  |  |  |  |  |  |  |  |
|  | −4850 | −6082 | −5725 | 4411 | −4732 | −4593 | −4904 | −4442 | −4627 |
|  | 210 | −466 | −720 | 275 | 394 | 45 | 96 | 359 | 117 |
| * |  |  |  |  |  |  |  |  |  |
|  | −4159 | 1722 | −717 | −4099 | 1949 | −3712 | 4007 | −3631 | −2464 |
|  | 210 | −466 | −720 | 275 | 394 | 45 | 96 | 359 | 117 |
| * |  |  |  |  |  |  |  |  |  |
|  | −4583 | −6183 | −5913 | −3747 | −4767 | −4175 | −4884 | −4792 | −5049 |
|  | 210 | −466 | −720 | 275 | 394 | 45 | 96 | 359 | 117 |
| * |  |  |  |  |  |  |  |  |  |
|  | −2493 | −1210 | −556 | −2334 | −2768 | −2166 | −2396 | −1684 | 1302 |
|  | 210 | −466 | −720 | 275 | 394 | 45 | 96 | 359 | 117 |
| * |  |  |  |  |  |  |  |  |  |
|  | −3477 | −4658 | −3784 | 3837 | −3115 | −3000 | −3729 | −1807 | −2052 |
|  | 210 | −466 | −720 | 275 | 394 | 45 | 96 | 359 | 117 |
| * |  |  |  |  |  |  |  |  |  |
|  | −5266 | −6082 | −5977 | −5274 | −5186 | −5341 | −5054 | −5722 | −5705 |
|  | 210 | −466 | −720 | 275 | 394 | 45 | 96 | 359 | 117 |
| * |  |  |  |  |  |  |  |  |  |
|  | −2864 | −4585 | −3878 | −2034 | −3343 | −2468 | −3340 | −2287 | −2556 |
|  | 210 | −466 | −720 | 275 | 394 | 45 | 96 | 359 | 117 |
| * |  |  |  |  |  |  |  |  |  |
|  | −693 | −1995 | −1243 | 873 | −2410 | 1832 | −1084 | −1286 | 2408 |
|  | 210 | −466 | −720 | 275 | 394 | 45 | 96 | 359 | 117 |
| * |  |  |  |  |  |  |  |  |  |
|  | −5533 | 2883 | 3237 | −5895 | −5154 | −4292 | −4999 | −5549 | −3886 |
|  | 210 | −466 | −720 | 275 | 394 | 45 | 96 | 359 | 117 |
| * |  |  |  |  |  |  |  |  |  |
|  | −4424 | −4691 | −3755 | −3019 | −3092 | −3936 | −4162 | 1337 | −1879 |
|  | 210 | −466 | −720 | 275 | 394 | 45 | 96 | 359 | 117 |
| * |  |  |  |  |  |  |  |  |  |
|  | −3636 | −4266 | −3635 | −99 | −3416 | −3230 | −3787 | −2185 | −2398 |
|  | 210 | −466 | −720 | 275 | 394 | 45 | 96 | 359 | 117 |
| * |  |  |  |  |  |  |  |  |  |
|  | −3417 | 1381 | −2343 | −3896 | −4606 | −3607 | −3347 | −4116 | −3942 |
|  | 210 | −466 | −720 | 275 | 394 | 45 | 96 | 359 | 117 |
| * |  |  |  |  |  |  |  |  |  |
|  | −1729 | −3753 | −2919 | 2222 | −2829 | −1442 | −2305 | 1194 |  |

-continued

| m ->e | K | L | M | N | P | O | R | S | T |
|---|---|---|---|---|---|---|---|---|---|
|  | 210 | −466 | −720 | 275 | 394 | 45 | 96 | 359 | 117 |
| * |  |  |  |  |  |  |  |  |  |
|  | −5160 | −3061 | −3095 | −3851 | −5019 | −3971 | −4573 | −4367 | −4562 |
|  | 210 | −466 | −720 | 275 | 394 | 45 | 96 | 359 | 117 |
| * |  |  |  |  |  |  |  |  |  |
|  | −241 | −2362 | 390 | −634 | −40 | 1941 | −739 | −894 | 426 |
|  | 210 | −466 | −720 | 275 | 394 | 45 | 96 | 359 | 117 |
| * |  |  |  |  |  |  |  |  |  |
|  | −2082 | −4514 | −4107 | −2763 | −4095 | 92 | −2165 | −3525 | −3677 |
|  | 210 | −466 | −720 | 275 | 394 | 45 | 96 | 359 | 117 |
| * |  |  |  |  |  |  |  |  |  |
|  | −2136 | −4453 | −3755 | −1193 | −3092 | −1590 | −2961 | −2255 | −2635 |
|  | 210 | −466 | −720 | 275 | 394 | 45 | 96 | 359 | 117 |
| * |  |  |  |  |  |  |  |  |  |
|  | −5127 | 2204 | −803 | −5121 | −4973 | −4528 | −4983 | −4783 | −3057 |
|  | 210 | −466 | −720 | 275 | 394 | 45 | 96 | 359 | 117 |
| * |  |  |  |  |  |  |  |  |  |
|  | −337 | −2798 | −1919 | 868 | −2397 | 569 | 2445 | −1288 | −1343 |
|  | 210 | −466 | −720 | 275 | 394 | 45 | 96 | 359 | 117 |
| * |  |  |  |  |  |  |  |  |  |
|  | −2274 | −824 | 1432 | −2219 | −2695 | 2042 | −2148 | −1719 | 1528 |
|  | 210 | −466 | −720 | 275 | 394 | 45 | 96 | 359 | 117 |
| * |  |  |  |  |  |  |  |  |  |
|  | −5094 | −5303 | −4637 | −3980 | −3954 | −4741 | −4797 | −2812 | −3007 |
|  | 210 | −466 | −720 | 275 | 394 | 45 | 96 | 359 | 117 |
| * |  |  |  |  |  |  |  |  |  |
|  | −277 | 1082 | −410 | −1737 | −2569 | −1360 | 2522 | −410 | −1068 |
|  | 210 | −466 | −720 | 275 | 394 | 45 | 96 | 359 | 117 |
| * |  |  |  |  |  |  |  |  |  |
|  | −643 | −920 | −906 | 114 | −2242 | −565 | −1063 | −1106 | 370 |
|  | 210 | −466 | −720 | 275 | 394 | 45 | 96 | 359 | 117 |
| * |  |  |  |  |  |  |  |  |  |
|  | −1207 | 263 | −557 | 1380 | −2458 | −1069 | −1489 | −476 | −1037 |
|  | 210 | −466 | −720 | 275 | 394 | 45 | 96 | 359 | 117 |
| * |  |  |  |  |  |  |  |  |  |
|  | −363 | −4449 | −3755 | 1477 | −3090 | −1551 | −2902 | −2272 | −2659 |
|  | 210 | −466 | −720 | 275 | 394 | 45 | 96 | 359 | 117 |
| * |  |  |  |  |  |  |  |  |  |
|  | 1723 | 1291 | 2513 | −2402 | −2886 | −2100 | −2325 | −1930 | −1249 |
|  | 210 | −466 | −720 | 275 | 394 | 45 | 96 | 359 | 117 |
| * |  |  |  |  |  |  |  |  |  |
|  | −5536 | 3135 | −370 | −5542 | −5143 | −4288 | −4987 | −5397 | −3959 |
|  | 210 | −466 | −720 | 275 | 394 | 45 | 96 | 359 | 117 |
| * |  |  |  |  |  |  |  |  |  |
|  | −4264 | −1129 | −2377 | −3541 | −4076 | −3729 | −4048 | −3027 | −3020 |
|  | 210 | −466 | −720 | 275 | 394 | 45 | 96 | 359 | 117 |
| * |  |  |  |  |  |  |  |  |  |
|  | −2128 | −4093 | −3338 | 332 | −3088 | −1980 | −2503 | 3011 | −2205 |
|  | 210 | −466 | −720 | 275 | 394 | 45 | 96 | 359 | 117 |
| * |  |  |  |  |  |  |  |  |  |
|  | −5067 | 1192 | −1186 | −4980 | −4973 | −4745 | −5079 | −4666 | −2864 |
|  | 210 | −466 | −720 | 275 | 394 | 45 | 96 | 359 | 117 |
| * |  |  |  |  |  |  |  |  |  |
|  | −4787 | −6283 | −6022 | −3676 | −4750 | −4186 | −5191 | −4762 | −5055 |
|  | 210 | −466 | −720 | 275 | 394 | 45 | 96 | 359 | 117 |
| * |  |  |  |  |  |  |  |  |  |
|  | −4125 | 1368 | −1762 | −3486 | −3618 | −3799 | −3953 | −2396 | −2377 |
|  | 210 | −466 | −720 | 275 | 394 | 45 | 96 | 359 | 117 |
| * |  |  |  |  |  |  |  |  |  |
|  | −4850 | −6082 | −5725 | 4411 | −4732 | −4593 | −4904 | −4442 | −4627 |
|  | 210 | −466 | −720 | 275 | 394 | 45 | 96 | 359 | 117 |
| * |  |  |  |  |  |  |  |  |  |
|  | −248 | −2449 | 544 | −670 | −2117 | 2694 | 1514 | −944 | 498 |
|  | 210 | −466 | −720 | 275 | 394 | 45 | 96 | 359 | 117 |
| * |  |  |  |  |  |  |  |  |  |
|  | −3342 | −5272 | −4637 | −3006 | −3958 | 2548 | −3517 | −3070 | −3300 |
|  | 210 | −466 | −720 | 275 | 394 | 45 | 96 | 359 | 117 |
| * |  |  |  |  |  |  |  |  |  |
|  | −946 | −3273 | −2410 | 1223 | −2578 | −803 | 1209 | −403 | −1686 |
|  | 210 | −466 | −720 | 275 | 394 | 45 | 96 | 359 | 117 |

-continued

| m ->e | K | L | M | N | P | O | R | S | T |
|---|---|---|---|---|---|---|---|---|---|
| * | | | | | | | | | |
|  | 950 | 207 | 1982 | −1370 | 1756 | −980 | −1393 | −1333 | −1014 |
|  | 210 | −466 | −720 | 275 | 394 | 45 | 96 | 359 | 117 |
| * | | | | | | | | | |
|  | −1410 | 1858 | −477 | −456 | −570 | 2110 | −1614 | −710 | −1072 |
|  | 210 | −466 | −720 | 275 | 394 | 45 | 96 | 359 | 117 |
| * | | | | | | | | | |
|  | 338 | −941 | 659 | 291 | −334 | 598 | 147 | −143 | 7 |
|  | 210 | −466 | −720 | 275 | 394 | 45 | 96 | 359 | 117 |
| * | | | | | | | | | |
|  | 1258 | 1645 | −580 | 975 | −2451 | −1022 | 117 | −1378 | −44 |
|  | 210 | −466 | −720 | 275 | 394 | 45 | 96 | 359 | 117 |
| * | | | | | | | | | |
|  | −4889 | −3130 | −3107 | −3746 | −4818 | −3883 | −4436 | −4054 | −4213 |
|  | 210 | −466 | −720 | 275 | 394 | 45 | 96 | 359 | 117 |
| * | | | | | | | | | |
|  | −4863 | −5555 | −5403 | −4024 | −4864 | −4404 | −5022 | −4890 | −5088 |
|  | 210 | −466 | −720 | 275 | 394 | 45 | 96 | 359 | 117 |
| * | | | | | | | | | |
|  | −2654 | −5012 | −4468 | −1476 | −3411 | 2464 | −3523 | −2710 | −3180 |
|  | 210 | −466 | −720 | 275 | 394 | 45 | 96 | 359 | 117 |
| * | | | | | | | | | |
|  | −1706 | −1478 | 697 | −1809 | −2839 | −1548 | −2007 | −1775 | 2886 |
|  | 210 | −466 | −720 | 275 | 394 | 45 | 96 | 359 | 117 |
| * | | | | | | | | | |
|  | −3519 | 1330 | −3277 | −2487 | −4027 | −2939 | −4117 | −3445 | −3684 |
|  | 210 | −466 | −720 | 275 | 394 | 45 | 96 | 359 | 117 |
| * | | | | | | | | | |
|  | −303 | −2800 | −1945 | −1024 | −2482 | 2385 | 1159 | −1395 | −1429 |
|  | 210 | −466 | −720 | 275 | 394 | 45 | 96 | 359 | 117 |
| * | | | | | | | | | |
|  | −5109 | −3128 | −3164 | −3822 | −4992 | −3954 | −4550 | −914 | −4537 |
|  | 210 | −466 | −720 | 275 | 394 | 45 | 96 | 359 | 117 |
| * | | | | | | | | | |
|  | −3734 | −780 | −3561 | −3019 | 3618 | −3530 | −3731 | −2122 | −2300 |
|  | 210 | −466 | −720 | 275 | 394 | 45 | 96 | 359 | 117 |
| * | | | | | | | | | |
|  | −526 | −2008 | −1201 | 1155 | −1093 | −465 | −983 | 551 | 2418 |
|  | 210 | −466 | −720 | 275 | 394 | 45 | 96 | 359 | 117 |
| * | | | | | | | | | |
|  | −1177 | −1150 | −2603 | 1047 | −2659 | −937 | −1790 | 212 | −1833 |
|  | 210 | −466 | −720 | 275 | 394 | 45 | 96 | 359 | 117 |
| * | | | | | | | | | |
|  | −1572 | 1200 | −440 | 684 | −2591 | −99 | −1758 | −1555 | −1093 |
|  | 210 | −466 | −720 | 275 | 394 | 45 | 96 | 359 | 117 |
| * | | | | | | | | | |
|  | −1515 | 1083 | −410 | −1730 | −2569 | −1365 | −371 | −327 | −1070 |
|  | 210 | −466 | −720 | 275 | 394 | 45 | 96 | 359 | 117 |
| * | | | | | | | | | |
|  | 514 | −1253 | 320 | −594 | −2050 | −158 | 115 | 620 | 475 |
|  | 210 | −466 | −720 | 275 | 394 | 45 | 96 | 359 | 117 |
| * | | | | | | | | | |
|  | −1291 | −222 | −725 | 1400 | −2485 | −1158 | −1581 | −369 | 2133 |
|  | 210 | −466 | −720 | 275 | 394 | 45 | 96 | 359 | 117 |
| * | | | | | | | | | |
|  | −3763 | −3472 | −2711 | −2860 | −3018 | −3397 | −3649 | −371 | 3024 |
|  | 210 | −466 | −720 | 275 | 394 | 45 | 96 | 359 | 117 |
| * | | | | | | | | | |
|  | −2061 | 2010 | −278 | −2084 | −2676 | 498 | −2047 | −1671 | −171 |
|  | 210 | −466 | −720 | 275 | 394 | 45 | 96 | 359 | 117 |
| * | | | | | | | | | |
|  | −2407 | −373 | −168 | −2310 | −2731 | −2040 | −2226 | −639 | −1077 |
|  | 210 | −466 | −720 | 275 | 394 | 45 | 96 | 359 | 117 |
| * | | | | | | | | | |
|  | −3746 | 1337 | 4541 | −3775 | −3961 | −3190 | −3504 | −3281 | −381 |
|  | 210 | −466 | −720 | 275 | 394 | 45 | 96 | 359 | 117 |
| * | | | | | | | | | |
|  | −2406 | −192 | 1479 | −2312 | −2761 | −2042 | −2240 | −406 | −1123 |
|  | 210 | −466 | −720 | 275 | 394 | 45 | 96 | 359 | 117 |
| * | | | | | | | | | |

-continued

| m −>e | K | L | M | N | P | O | R | S | T |
|---|---|---|---|---|---|---|---|---|---|
| | −1050 | −3330 | −2469 | −915 | −2592 | 1001 | −1642 | −220 | −1723 |
| | 210 | −466 | −720 | 275 | 394 | 45 | 96 | 359 | 117 |
| * | | | | | | | | | |
| | −4753 | 1393 | −861 | −4697 | −4716 | −4269 | −4629 | −4304 | −2798 |
| | 210 | −466 | −720 | 275 | 394 | 45 | 96 | 359 | 117 |
| * | | | | | | | | | |
| | −5234 | 2786 | −540 | −5318 | −5008 | −4398 | −4954 | −4964 | −3282 |
| | 210 | −466 | −720 | 275 | 394 | 45 | 96 | 359 | 117 |
| * | | | | | | | | | |
| | 2204 | −1130 | −1578 | −624 | −2083 | 814 | 944 | −903 | −960 |
| | 210 | −466 | −720 | 275 | 394 | 45 | 96 | 359 | 117 |
| * | | | | | | | | | |
| | −222 | −2394 | 336 | | −2061 | 626 | −263 | 421 | −924 |
| | 210 | −466 | −720 | 275 | 394 | 45 | 96 | 359 | 117 |
| * | | | | | | | | | |
| | −3223 | −4571 | −3714 | −2119 | −3077 | −2685 | −3642 | −14 | −2069 |
| | 210 | −466 | −720 | 275 | 394 | 45 | 96 | 359 | 117 |
| * | | | | | | | | | |
| | −2078 | −3015 | −2271 | −1831 | −2735 | 197 | −2364 | 190 | −1589 |
| | 210 | −466 | −720 | 275 | 394 | 45 | 96 | 359 | 117 |
| * | | | | | | | | | |
| | −3877 | 2085 | −110 | −3854 | 1128 | −3227 | −3601 | −3367 | −2431 |
| | 210 | −466 | −720 | 275 | 394 | 45 | 96 | 359 | 117 |
| * | | | | | | | | | |
| | −438 | −2621 | −1844 | 1572 | −1628 | −64 | −1115 | −688 | −954 |
| | 210 | −466 | −720 | 275 | 394 | 45 | 96 | 359 | 117 |
| * | | | | | | | | | |
| | −1737 | −2659 | −2097 | −1339 | −1786 | −1606 | −1805 | −971 | −1107 |
| | 210 | −466 | −720 | 275 | 394 | 45 | 96 | 359 | 118 |
| * | | | | | | | | | |
| | −1504 | −2284 | −1843 | −1373 | 3767 | −1487 | −1585 | −1143 | −1229 |
| | 210 | −466 | −720 | 275 | 394 | 45 | 96 | 359 | 117 |
| * | | | | | | | | | |
| | 1105 | −1853 | −1038 | −370 | −1543 | −134 | −464 | −352 | −421 |
| | 210 | −466 | −720 | 275 | 394 | 45 | 96 | 359 | 117 |
| * | | | | | | | | | |
| | 123 | −2065 | −1235 | −765 | 927 | −341 | −870 | −977 | 771 |
| | 210 | −466 | −720 | 275 | 394 | 45 | 96 | 359 | 117 |
| * | | | | | | | | | |
| | 1003 | −2470 | −1543 | 140 | 1222 | 782 | 953 | −43 | 1528 |
| | 210 | −466 | −720 | 275 | 394 | 45 | 96 | 359 | 117 |
| * | | | | | | | | | |
| | −6030 | −6539 | −6235 | −5426 | −5034 | −5814 | −5624 | −5041 | −5115 |
| | 210 | −466 | −720 | 275 | 394 | 45 | 96 | 359 | 117 |
| * | | | | | | | | | |
| | −5076 | −5740 | −5043 | −4039 | 2291 | −4709 | −4901 | −3171 | −3373 |
| | 210 | −466 | −720 | 275 | 394 | 45 | 96 | 359 | 117 |
| * | | | | | | | | | |
| | −2752 | 2206 | −223 | −2773 | −3187 | −2399 | 1799 | −2291 | 253 |
| | 210 | −466 | −720 | 275 | 394 | 45 | 96 | 359 | 117 |
| * | | | | | | | | | |
| | −2575 | −4694 | −4212 | 3945 | −3753 | −2478 | −2897 | −2996 | −3298 |
| | 210 | −466 | −720 | 275 | 394 | 45 | 96 | 359 | 117 |
| * | | | | | | | | | |
| | −5852 | −3992 | −4112 | −4995 | −5217 | −5110 | −5315 | −5363 | −5399 |
| | 210 | −466 | −720 | 275 | 394 | 45 | 96 | 359 | 117 |
| * | | | | | | | | | |
| | −3365 | −4864 | −4554 | −2168 | −3906 | −2692 | −4098 | −3307 | −3726 |
| | 210 | −466 | −720 | 275 | 394 | 45 | 96 | 359 | 117 |
| * | | | | | | | | | |
| | −3083 | −2118 | −1567 | −2743 | −3353 | −2703 | −3034 | −485 | −2005 |
| | 210 | −466 | −720 | 275 | 394 | 45 | 96 | 359 | 117 |
| * | | | | | | | | | |
| | 3785 | −3966 | −3350 | −2554 | −3806 | −1483 | −516 | −3312 | −3161 |
| | 210 | −466 | −720 | 275 | 394 | 45 | 96 | 359 | 117 |
| * | | | | | | | | | |
| | −2633 | −346 | −783 | −2500 | 2276 | −2347 | −2594 | −1872 | 715 |
| | 210 | −466 | −720 | 275 | 394 | 45 | 96 | 359 | 117 |
| * | | | | | | | | | |
| | −629 | −715 | −2292 | −1894 | 174 | −1218 | 3533 | 651 | −1925 |
| | 210 | −466 | −720 | 275 | 394 | 45 | 96 | 359 | 117 |

-continued

| m ->e | K | L | M | N | P | O | R | S | T |
|---|---|---|---|---|---|---|---|---|---|
| * | | | | | | | | | |
| | −3143 | −5805 | −5439 | −4840 | −4993 | −4014 | 4330 | −5318 | −5151 |
| | 210 | −466 | −720 | 275 | 394 | 45 | 96 | 359 | 117 |
| * | | | | | | | | | |
| | −232 | −2480 | −1560 | 624 | −666 | 1428 | −740 | 39 | 2295 |
| | 210 | −466 | −720 | 275 | 394 | 45 | 96 | 359 | 117 |
| * | | | | | | | | | |
| | −2280 | −4605 | −3943 | −1231 | −3150 | −1685 | −3140 | 3091 | −2749 |
| | 210 | −466 | −720 | 275 | 394 | 45 | 96 | 359 | 117 |
| * | | | | | | | | | |
| | −2616 | −1518 | −978 | −2397 | −3095 | −2241 | −2563 | −216 | 1898 |
| | 210 | −466 | −720 | 275 | 394 | 45 | 96 | 359 | 117 |
| * | | | | | | | | | |
| | 1205 | −2600 | −1681 | −648 | −2139 | 585 | −841 | −973 | 248 |
| | 210 | −466 | −720 | 275 | 394 | 45 | 96 | 359 | 117 |
| * | | | | | | | | | |
| | 338 | −941 | 659 | 291 | −334 | 598 | 147 | −143 | 7 |
| | 210 | −466 | −720 | 275 | 394 | 45 | 96 | 359 | 117 |
| * | | | | | | | | | |
| | 215 | −426 | 693 | −939 | 1418 | 345 | −227 | −1082 | −961 |
| | 210 | −466 | −720 | 275 | 394 | 45 | 96 | 359 | 117 |
| * | | | | | | | | | |
| | −962 | −3199 | −2337 | −894 | −2544 | 492 | −1537 | −1489 | −1638 |
| | 210 | −466 | −720 | 275 | 394 | 45 | 96 | 359 | 117 |
| * | | | | | | | | | |
| | −3441 | −5486 | −4961 | −2153 | −3821 | −2730 | −4255 | −3154 | −3567 |
| | 210 | −466 | −720 | 275 | 394 | 45 | 96 | 359 | 117 |
| * | | | | | | | | | |
| | −5141 | 2651 | −663 | −5173 | −4965 | −4433 | −4931 | −4819 | −3144 |
| | 210 | −466 | −720 | 275 | 394 | 45 | 96 | 359 | 117 |
| * | | | | | | | | | |
| | −4078 | −1724 | −1536 | −3487 | −1838 | −3365 | −3744 | −3422 | −2946 |
| | 210 | −466 | −720 | 275 | 394 | 45 | 96 | 359 | 117 |
| * | | | | | | | | | |
| | −1057 | 992 | −593 | −1325 | −2393 | −936 | −276 | −1304 | −999 |
| | 210 | −466 | −720 | 275 | 394 | 45 | 96 | 359 | 117 |
| * | | | | | | | | | |
| | −3094 | −3410 | −2609 | −2570 | −2929 | −2839 | −3197 | 1570 | −155 |
| | 210 | −466 | −720 | 275 | 394 | 45 | 96 | 359 | 117 |
| * | | | | | | | | | |
| | −3288 | −4509 | −3848 | −2949 | −3546 | −3299 | −3341 | −2352 | −2548 |
| | 210 | −466 | −720 | 275 | 394 | 45 | 96 | 359 | 117 |
| * | | | | | | | | | |
| | 406 | −1345 | −734 | −2057 | −2878 | −1575 | 172 | −1891 | −1390 |
| | 210 | −466 | −720 | 275 | 394 | 45 | 96 | 359 | 117 |
| * | | | | | | | | | |
| | −4116 | −4288 | −3398 | −2940 | −3040 | −3690 | −3947 | 484 | −1804 |
| | 210 | −466 | −720 | 275 | 394 | 45 | 96 | 359 | 117 |
| * | | | | | | | | | |
| | −4084 | −4444 | −3530 | 1340 | −3050 | −3662 | −3947 | −1624 | −1829 |
| | 210 | −466 | −720 | 275 | 394 | 45 | 96 | 359 | 117 |
| * | | | | | | | | | |
| | −4844 | −362 | 5058 | −5009 | −4816 | −4199 | −4559 | −4488 | −3429 |
| | 210 | −466 | −720 | 275 | 394 | 45 | 96 | 359 | 117 |
| * | | | | | | | | | |
| | −1888 | −4357 | −3653 | −1359 | −3145 | −1638 | 1771 | −503 | −2599 |
| | 210 | −466 | −720 | 275 | 394 | 45 | 96 | 359 | 117 |
| * | | | | | | | | | |
| | −1612 | −2425 | 2062 | 435 | −2620 | −1496 | −1953 | 1109 | 2598 |
| | 210 | −466 | −720 | 275 | 394 | 45 | 96 | 359 | 117 |
| * | | | | | | | | | |
| | −5006 | −1623 | 2952 | −3869 | −4923 | −3893 | −4468 | −4298 | −4237 |
| | 210 | −466 | −720 | 275 | 394 | 45 | 96 | 359 | 117 |
| * | | | | | | | | | |
| | −4125 | 1368 | −1762 | −3486 | −3618 | −3799 | −3953 | −2396 | −2377 |
| | 210 | −466 | −720 | 275 | 394 | 45 | 96 | 359 | 117 |
| * | | | | | | | | | |
| | −567 | 1406 | −311 | −2061 | −2701 | −1716 | 1956 | −1708 | −1121 |
| | 210 | −466 | −720 | 275 | 394 | 45 | 96 | 359 | 117 |
| * | | | | | | | | | |
| | −3626 | 1237 | −2695 | −2780 | −3011 | −3284 | −3555 | −677 | −1747 |

-continued

| m −>e | K | L | M | N | P | O | R | S | T |
|---|---|---|---|---|---|---|---|---|---|
| * | 210 | −466 | −720 | 275 | 394 | 45 | 96 | 359 | 117 |
|  | 1855 | 2371 | −1066 | −2323 | −3278 | −1496 | 360 | −2446 | −2014 |
| * | 210 | −466 | −720 | 275 | 394 | 45 | 96 | 359 | 117 |
|  | 2247 | −1301 | −1757 | −811 | −2263 | 491 | 1587 | −1121 | −1167 |
| * | 210 | −466 | −720 | 275 | 394 | 45 | 96 | 359 | 117 |
|  | −931 | −1546 | −820 | 692 | −2371 | −843 | 1741 | −469 | −1038 |
|  | 210 | −466 | −720 | 275 | 394 | 45 | 96 | 359 | 117 |
| * |  |  |  |  |  |  |  |  |  |
|  | −4402 | −3809 | −3256 | −3167 | −3225 | −3995 | −4150 | −1826 | −1986 |
|  | 210 | −466 | −720 | 275 | 394 | 45 | 96 | 359 | 117 |
| * |  |  |  |  |  |  |  |  |  |
|  | 247 | −1046 | −1336 | 675 | −2101 | −258 | −794 | −334 | −934 |
|  | 210 | −466 | −720 | 275 | 394 | 45 | 96 | 359 | 117 |
| * |  |  |  |  |  |  |  |  |  |
|  | 2511 | −3506 | −2802 | −2133 | −3385 | −1064 | 1852 | −2645 | −2521 |
|  | 210 | −466 | −720 | 275 | 394 | 45 | 96 | 359 | 117 |
| * |  |  |  |  |  |  |  |  |  |
|  | −5358 | 2214 | 3316 | −5599 | −5021 | −4167 | −4850 | −5211 | −3688 |
|  | 210 | −466 | −720 | 275 | 394 | 45 | 96 | 359 | 117 |
| * |  |  |  |  |  |  |  |  |  |
|  | 625 | 584 | −515 | −1883 | −2692 | −1414 | 1794 | −1698 | −1203 |
|  | 210 | −466 | −720 | 275 | 394 | 45 | 96 | 359 | 117 |
| * |  |  |  |  |  |  |  |  |  |
|  | 620 | −2585 | −1665 | 137 | −2128 | 844 | −823 | −959 | −41 |
|  | 210 | −466 | −720 | 275 | 394 | 45 | 96 | 359 | 117 |
| * |  |  |  |  |  |  |  |  |  |
|  | −2532 | −4904 | −4335 | −1252 | −3241 | −1811 | −3527 | −2501 | −2990 |
|  | 210 | −466 | −720 | 275 | 394 | 45 | 96 | 359 | 117 |
| * |  |  |  |  |  |  |  |  |  |
|  | 989 | −2490 | −1565 | 774 | 1615 | 611 | 937 | 553 | −942 |
|  | 210 | −466 | −720 | 275 | 394 | 45 | 96 | 359 | 117 |
| * |  |  |  |  |  |  |  |  |  |
|  | 41 | −1894 | −1096 | −841 | 683 | 68 | −936 | −136 | −956 |
|  | 210 | −466 | −720 | 275 | 394 | 45 | 96 | 359 | 117 |
| * |  |  |  |  |  |  |  |  |  |
|  | −3406 | 1823 | −321 | −3311 | −3599 | −2912 | −3176 | −2794 | −1969 |
|  | 210 | −466 | −720 | 275 | 394 | 45 | 96 | 359 | 117 |
| * |  |  |  |  |  |  |  |  |  |
|  | 514 | −2475 | −1549 | 86 | −2053 | 1563 | 61 | −143 | −197 |
|  | 210 | −466 | −720 | 275 | 394 | 45 | 96 | 359 | 117 |
| * |  |  |  |  |  |  |  |  |  |
|  | 1456 | −2615 | −1696 | 1166 | −2147 | 1657 | −852 | −409 | −1056 |
|  | 210 | −466 | −720 | 275 | 394 | 45 | 96 | 359 | 117 |
| * |  |  |  |  |  |  |  |  |  |
|  | −2431 | 1012 | 1489 | −2324 | −2730 | −2055 | −255 | −1766 | −1074 |
|  | 210 | −466 | −720 | 275 | 394 | 45 | 96 | 359 | 117 |
| * |  |  |  |  |  |  |  |  |  |
|  | −134 | 1151 | 2066 | −2232 | −2720 | −223 | −304 | −1746 | −1089 |
|  | 210 | −466 | −720 | 275 | 394 | 45 | 96 | 359 | 117 |
| * |  |  |  |  |  |  |  |  |  |
|  | 1226 | −2501 | −1576 | −610 | −2073 | 413 | 729 | −291 | −953 |
|  | 210 | −466 | −720 | 275 | 394 | 45 | 96 | 359 | 117 |
| * |  |  |  |  |  |  |  |  |  |
|  | 738 | −2481 | −1555 | 281 | −2057 | 320 | −172 | −872 | −68 |
|  | 210 | −466 | −720 | 275 | 394 | 45 | 96 | 359 | 117 |
| * |  |  |  |  |  |  |  |  |  |
|  | 795 | −2778 | −1964 | −1292 | −2658 | −633 | 3242 | 417 | −1588 |
|  | 210 | −466 | −720 | 275 | 394 | 45 | 96 | 359 | 117 |
| * |  |  |  |  |  |  |  |  |  |
|  | 891 | −3279 | −2619 | −2128 | −3405 | −1166 | 820 | −2667 | −2523 |
|  | 210 | −466 | −720 | 275 | 394 | 45 | 96 | 359 | 117 |
| * |  |  |  |  |  |  |  |  |  |
|  | 605 | −788 | −1475 | −626 | −2069 | 1284 | 427 | 1071 | −929 |
|  | 210 | −466 | −720 | 275 | 394 | 45 | 96 | 359 | 117 |
| * |  |  |  |  |  |  |  |  |  |
|  | −386 | −2470 | −1581 | −713 | −2161 | −325 | −890 | 2478 | −324 |
|  | 210 | −466 | −720 | 275 | 394 | 45 | 96 | 359 | 117 |

-continued

| m −>e | K | L | M | N | P | O | R | S | T |
|---|---|---|---|---|---|---|---|---|---|
| * | | | | | | | | | |
| | −3530 | −2820 | −2586 | −3109 | −4323 | −3009 | −3565 | −3461 | −3428 |
| | 210 | −466 | −720 | 275 | 394 | 45 | 96 | 359 | 117 |
| * | | | | | | | | | |
| | 1161 | 389 | −1533 | 1125 | −131 | −168 | 2 | −164 | 557 |
| | 211 | −466 | −721 | 276 | 393 | 45 | 96 | 359 | 117 |
| * | | | | | | | | | |
| | 254 | −2472 | −1546 | −593 | −2051 | 799 | 115 | 1531 | 906 |
| | 210 | −466 | −720 | 275 | 394 | 45 | 96 | 359 | 117 |
| * | | | | | | | | | |
| | −1035 | −762 | −1957 | −1125 | 1149 | −921 | −1515 | −1387 | −149 |
| | 210 | −466 | −720 | 275 | 394 | 45 | 96 | 359 | 117 |
| * | | | | | | | | | |
| | −778 | 400 | −239 | −2262 | −914 | −1978 | −2197 | −1777 | 1346 |
| | 210 | −466 | −720 | 275 | 394 | 45 | 96 | 359 | 117 |
| * | | | | | | | | | |
| | −3864 | 847 | −2909 | −2938 | −3156 | −3542 | −3752 | −1788 | −1933 |
| | 210 | −466 | −720 | 275 | 394 | 45 | 96 | 359 | 117 |
| * | | | | | | | | | |
| | 1433 | −354 | 117 | 801 | −2020 | 1472 | 466 | −836 | −887 |
| | 210 | −466 | −720 | 275 | 394 | 45 | 96 | 359 | 117 |
| * | | | | | | | | | |
| | 308 | −2493 | −1568 | −601 | 199 | 1422 | −727 | 187 | −166 |
| | 210 | −466 | −720 | 275 | 394 | 45 | 96 | 359 | 117 |
| * | | | | | | | | | |
| | 338 | −941 | 659 | 291 | −334 | 598 | 147 | −143 | 7 |
| | 210 | −466 | −720 | 275 | 394 | 45 | 96 | 359 | 117 |
| * | | | | | | | | | |
| | −2494 | −822 | 1196 | −2403 | −126 | −2131 | −2324 | −1865 | −1168 |
| | 210 | −466 | −720 | 275 | 394 | 45 | 96 | 359 | 117 |
| * | | | | | | | | | |
| | −347 | 105 | −458 | −1568 | −2508 | −1200 | −1588 | −1457 | −1033 |
| | 210 | −466 | −720 | 275 | 394 | 45 | 96 | 359 | 117 |
| * | | | | | | | | | |
| | 240 | −2395 | −1470 | 1122 | −1965 | 522 | −630 | 837 | −34 |
| | 210 | −466 | −720 | 275 | 394 | 45 | 96 | 359 | 117 |
| * | | | | | | | | | |
| | −1831 | −397 | −1274 | −3 | −2773 | −1677 | −2075 | −1633 | −1459 |
| | 210 | −466 | −720 | 275 | 394 | 45 | 96 | 359 | 117 |
| * | | | | | | | | | |
| | 2040 | −2472 | −1546 | 519 | −2052 | 1143 | 415 | 499 | 717 |
| | 210 | −466 | −720 | 275 | 394 | 45 | 96 | 359 | 117 |
| * | | | | | | | | | |
| | −307 | −625 | 696 | −690 | −2100 | −258 | −151 | −93 | 780 |
| | 210 | −466 | −720 | 275 | 394 | 45 | 96 | 359 | 117 |
| * | | | | | | | | | |
| | −455 | 475 | −1718 | 532 | −2218 | −375 | −974 | 1045 | 1564 |
| | 210 | −466 | −720 | 275 | 394 | 45 | 96 | 359 | 117 |
| * | | | | | | | | | |
| | −262 | 2523 | 1205 | −4222 | −4303 | −3468 | −3837 | −3796 | −2830 |
| | 210 | −466 | −720 | 275 | 394 | 45 | 96 | 359 | 117 |
| * | | | | | | | | | |
| | 1493 | −2471 | −1545 | 270 | −1061 | −157 | −422 | −422 | 54 |
| | 210 | −466 | −720 | 275 | 394 | 45 | 96 | 359 | 117 |
| * | | | | | | | | | |
| | 851 | −2570 | −1649 | −635 | −2118 | 444 | −809 | 1514 | −290 |
| | 210 | −466 | −720 | 275 | 394 | 45 | 96 | 359 | 117 |
| * | | | | | | | | | |
| | −1691 | 1129 | −330 | −1845 | −2594 | 221 | 1015 | −484 | −1055 |
| | 210 | −466 | −720 | 275 | 394 | 45 | 96 | 359 | 117 |
| * | | | | | | | | | |
| | −900 | −416 | −704 | −1196 | −2339 | −797 | −1260 | 687 | −49 |
| | 210 | −466 | −720 | 275 | 394 | 45 | 96 | 359 | 117 |
| * | | | | | | | | | |
| | 1572 | −2487 | −1561 | 676 | −2060 | 1100 | −720 | −173 | −45 |
| | 210 | −466 | −720 | 275 | 394 | 45 | 96 | 359 | 117 |
| * | | | | | | | | | |
| | −855 | −2839 | −2606 | −3260 | −4404 | −2976 | 133 | −3614 | −3524 |
| | 210 | −466 | −720 | 275 | 394 | 45 | 96 | 359 | 117 |
| * | | | | | | | | | |
| | −847 | −1803 | −1059 | −1095 | −2363 | −746 | −1268 | −1239 | −1109 |
| | 210 | −466 | −720 | 275 | 394 | 45 | 96 | 359 | 117 |
| * | | | | | | | | | |
| | 575 | 996 | −1351 | −680 | −2095 | 263 | −785 | −91 | −453 |

-continued

| m ->e | K | L | M | N | P | O | R | S | T |
|---|---|---|---|---|---|---|---|---|---|
|  | 210 | −466 | −720 | 275 | 394 | 45 | 96 | 359 | 117 |
| * |  |  |  |  |  |  |  |  |  |
|  | 267 | −897 | −1528 | 1077 | −2052 | 1118 | −708 | 595 | −921 |
|  | 210 | −466 | −720 | 275 | 394 | 45 | 96 | 359 | 117 |
| * |  |  |  |  |  |  |  |  |  |
|  | 1142 | −644 | −1505 | 1346 | 594 | −174 | −432 | −876 | −284 |
|  | 210 | −466 | −720 | 275 | 394 | 45 | 96 | 359 | 117 |
| * |  |  |  |  |  |  |  |  |  |
|  | 586 | −861 | 708 | 808 | 710 | 802 | −666 | 242 | −2 |
|  | 210 | −466 | −720 | 275 | 394 | 45 | 96 | 359 | 117 |
| * |  |  |  |  |  |  |  |  |  |
|  | −111 | −450 | −1423 | −504 | −1958 | 1578 | −617 | −233 | 439 |
|  | 210 | −466 | −720 | 275 | 394 | 45 | 96 | 359 | 117 |
| * |  |  |  |  |  |  |  |  |  |
|  | −295 | −2418 | −1560 | −263 | −1843 | −126 | −852 | 1085 | −887 |
|  | 210 | −466 | −720 | 275 | 394 | 45 | 96 | 359 | 117 |
| * |  |  |  |  |  |  |  |  |  |
|  | 1212 | −1562 | −736 | 96 | −1382 | 470 | 131 | −287 | −318 |
|  | 210 | −466 | −720 | 275 | 394 | 45 | 96 | 359 | 117 |
| * |  |  |  |  |  |  |  |  |  |
|  | −2461 | 2161 | 988 | −2637 | −2874 | −2038 | −2380 | −2319 | −1277 |
|  | 210 | −466 | −720 | 275 | 394 | 45 | 96 | 359 | 117 |
| * |  |  |  |  |  |  |  |  |  |
|  | −239 | −251 | −142 | 675 | −1717 | −142 | −613 | −33 | −383 |
|  | 210 | −466 | −720 | 275 | 394 | 45 | 96 | 359 | 117 |
| * |  |  |  |  |  |  |  |  |  |
|  | −92 | −1018 | −354 | −1776 | 1747 | −1430 | −1772 | −1536 | −1043 |
|  | 210 | −466 | −720 | 275 | 394 | 45 | 96 | 359 | 117 |
| * |  |  |  |  |  |  |  |  |  |
|  | 878 | −2442 | −1522 | 203 | −2052 | 1476 | 325 | −866 | −41 |
|  | 210 | −466 | −720 | 275 | 394 | 45 | 96 | 359 | 117 |
| * |  |  |  |  |  |  |  |  |  |
|  | −198 | −80 | −1537 | 1907 | −2050 | 1346 | −99 | −864 | 569 |
|  | 210 | −466 | −720 | 275 | 394 | 45 | 96 | 359 | 117 |
| * |  |  |  |  |  |  |  |  |  |
|  | 1671 | −360 | −1539 | −594 | −622 | 1599 | 1436 | −865 | 334 |
|  | 210 | −466 | −720 | 275 | 394 | 45 | 96 | 359 | 117 |
| * |  |  |  |  |  |  |  |  |  |
|  | −2704 | −880 | −3001 | 42 | −2954 | −2482 | −2971 | 3040 | −1805 |
|  | 210 | −466 | −720 | 275 | 394 | 45 | 96 | 359 | 117 |
| * |  |  |  |  |  |  |  |  |  |
|  | −1503 | −279 | 1286 | −92 | −2527 | −1318 | −1686 | −1483 | −1029 |
|  | 210 | −466 | −720 | 275 | 394 | 45 | 96 | 359 | 117 |
| * |  |  |  |  |  |  |  |  |  |
|  | 956 | −2556 | −1648 | −726 | −235 | 755 | 1964 | −1012 | −1059 |
|  | 210 | −466 | −720 | 275 | 394 | 45 | 96 | 359 | 117 |
| * |  |  |  |  |  |  |  |  |  |
|  | −2760 | 1475 | −247 | −2787 | −3253 | 2905 | −2674 | −2360 | −1672 |
|  | 210 | −466 | −720 | 275 | 394 | 45 | 96 | 359 | 117 |
| * |  |  |  |  |  |  |  |  |  |
|  | −2488 | −1817 | −1617 | −2456 | −3632 | −2387 | −2824 | −2708 | −2279 |
|  | 210 | −466 | −720 | 275 | 394 | 45 | 96 | 359 | 117 |
| * |  |  |  |  |  |  |  |  |  |
|  | 610 | 446 | −1456 | −633 | −2072 | 1010 | 1766 | −263 | −928 |
|  | 210 | −466 | −720 | 275 | 394 | 45 | 96 | 359 | 117 |
| * |  |  |  |  |  |  |  |  |  |
|  | −3166 | 2331 | −351 | −3080 | −3407 | −2740 | −2969 | −2549 | −1736 |
|  | 210 | −466 | −720 | 275 | 394 | 45 | 96 | 359 | 117 |
| * |  |  |  |  |  |  |  |  |  |
|  | 2410 | −3341 | −2478 | 882 | −2595 | 337 | −1587 | −1558 | −1726 |
|  | 210 | −466 | −720 | 275 | 394 | 45 | 96 | 359 | 117 |
| * |  |  |  |  |  |  |  |  |  |
|  | −231 | −2448 | 681 | 1414 | −2070 | 2317 | −737 | 1098 | −280 |
|  | 210 | −466 | −720 | 275 | 394 | 45 | 96 | 359 | 117 |
| * |  |  |  |  |  |  |  |  |  |
|  | −2938 | 2230 | −330 | −2893 | −3277 | −217 | −2785 | −2389 | 1516 |
|  | 210 | −466 | −720 | 275 | 394 | 45 | 96 | 359 | 117 |
| * |  |  |  |  |  |  |  |  |  |

-continued

| m ->e | K | L | M | N | P | O | R | S | T |
|---|---|---|---|---|---|---|---|---|---|
| | −3436 | 1384 | −620 | −3337 | −3648 | −3052 | −3269 | −2821 | −1888 |
| | 210 | −466 | −720 | 275 | 394 | 45 | 96 | 359 | 117 |
| * | | | | | | | | | |
| | −1486 | −1142 | 1274 | 3200 | −2583 | 280 | −1696 | −1534 | −1102 |
| | 210 | −466 | −720 | 275 | 394 | 45 | 96 | 359 | 117 |
| * | | | | | | | | | |
| | −202 | −2477 | 1021 | 761 | −2054 | 1813 | 414 | 304 | −929 |
| | 210 | −466 | −720 | 275 | 394 | 45 | 96 | 359 | 117 |
| * | | | | | | | | | |
| | −3871 | −3148 | −3048 | −3397 | −4538 | −3440 | −3721 | −3699 | −3833 |
| | 210 | −466 | −720 | 275 | 394 | 45 | 96 | 359 | 117 |
| * | | | | | | | | | |
| | −3586 | 2535 | 1585 | −3549 | −3766 | −365 | −3344 | −3026 | −2171 |
| | 210 | −466 | −720 | 275 | 394 | 45 | 96 | 359 | 117 |
| * | | | | | | | | | |
| | −3142 | 1880 | 1149 | −3061 | −3355 | −2682 | −2926 | −2524 | −64 |
| | 210 | −466 | −720 | 275 | 394 | 45 | 96 | 359 | 117 |
| * | | | | | | | | | |
| | 447 | −2316 | −1391 | 848 | −1885 | 582 | 351 | 31 | −765 |
| | 210 | −466 | −720 | 275 | 394 | 45 | 96 | 359 | 117 |
| * | | | | | | | | | |
| | 456 | −1390 | −635 | −723 | −1980 | −310 | −804 | −19 | 849 |
| | 210 | −466 | −720 | 275 | 394 | 45 | 96 | 359 | 117 |
| * | | | | | | | | | |
| | −1021 | 1151 | −9 | 206 | −2122 | −888 | 2151 | −1078 | −635 |
| | 210 | −466 | −720 | 275 | 394 | 45 | 96 | 359 | 117 |
| * | | | | | | | | | |
| | 94 | −486 | −578 | 661 | −1615 | 151 | 428 | 120 | −400 |
| | 210 | −466 | −720 | 275 | 394 | 45 | 96 | 359 | 117 |
| * | | | | | | | | | |
| | 1558 | −1860 | −953 | 11 | −1461 | 1054 | −76 | 506 | −357 |
| | 210 | −465 | −721 | 275 | 394 | 45 | 96 | 359 | 117 |
| * | | | | | | | | | |
| | 338 | −941 | 659 | 291 | −334 | 598 | 147 | −143 | 7 |
| | 211 | −466 | −721 | 276 | 394 | 45 | 96 | 359 | 118 |
| * | * | * | * | * | * | * | * | * | * |
| | 338 | −941 | 659 | 291 | −334 | 598 | 147 | −143 | 7 |
| | 0 | | | | | | | | |

| V | W | Y | |
|---|---|---|---|
| −471 | 1260 | 199 | 51 |
| −369 | −294 | −249 | |
| 1769 | −2848 | −2496 | 52 |
| −369 | −294 | −249 | |
| −2023 | −2588 | −1891 | 53 |
| −369 | −294 | −249 | |
| −2211 | −2612 | −2088 | 54 |
| −369 | −294 | −249 | |
| 2522 | −4274 | −3775 | 55 |
| −369 | −294 | −249 | |
| −754 | −2421 | −1740 | 56 |
| −369 | −294 | −249 | |
| −3655 | −380 | 4341 | 57 |
| −369 | −294 | −249 | |
| 930 | −3370 | −2737 | 58 |
| −369 | −294 | −249 | |
| −5518 | −4690 | −5554 | 59 |
| −369 | −295 | −250 | |
| −1892 | −2442 | −1783 | 62 |
| −369 | −294 | −249 | |
| −1878 | −2440 | −1756 | 63 |
| −369 | −294 | −249 | |
| −865 | −1771 | −1305 | 64 |
| −369 | −294 | −249 | |
| −1912 | −2474 | −1788 | 65 |
| −369 | −294 | −249 | |
| −2258 | −2837 | −2142 | 66 |

-continued

| V | W | Y | |
|---|---|---|---|
| −369 | −294 | −249 | |
| −1654 | −2530 | −2036 | 67 |
| −369 | −294 | −249 | |
| −703 | −1178 | 1973 | 68 |
| −369 | −294 | −249 | |
| −1168 | −2213 | −1825 | 69 |
| −369 | −294 | −249 | |
| −3156 | −493 | 2114 | 70 |
| −369 | −294 | −249 | |
| −589 | −2767 | −2293 | 71 |
| −369 | −294 | −249 | |
| −132 | 2330 | 3573 | 72 |
| −369 | −294 | −249 | |
| −3890 | −1488 | 4716 | 73 |
| −369 | −294 | −249 | |
| −3961 | −4620 | −3589 | 74 |
| −369 | −294 | −249 | |
| −2866 | −4265 | −3960 | 75 |
| −369 | −294 | −249 | |
| −604 | −2987 | −2252 | 76 |
| −369 | −294 | −249 | |
| −2686 | −3134 | −2484 | 77 |
| −369 | −294 | −249 | |
| 1953 | −1336 | −976 | 78 |
| −369 | −294 | −249 | |
| 2559 | −3880 | −3432 | 79 |

-continued

| V | W | Y | |
|---|---|---|---|
| −369 | −294 | −249 | |
| −1744 | −2394 | −1759 | 80 |
| −369 | −294 | −249 | |
| −2235 | −2897 | −2236 | 81 |
| −369 | −294 | −249 | |
| 269 | −1998 | 1612 | 82 |
| −369 | −294 | −249 | |
| −2128 | −2671 | −2004 | 83 |
| −369 | −294 | −249 | |
| −1168 | −2513 | −2250 | 84 |
| −369 | −294 | −249 | |
| −2163 | −2733 | −2065 | 85 |
| −369 | −294 | −249 | |
| −3563 | −4127 | −3260 | 86 |
| −369 | −294 | −249 | |
| −1820 | 3681 | −1859 | 87 |
| −369 | −294 | −249 | |
| −1696 | −1466 | −539 | 88 |
| −369 | −294 | −249 | |
| −3882 | −3468 | −3430 | 89 |
| −369 | −294 | −249 | |
| −4866 | −2341 | −1279 | 90 |
| −369 | −294 | −249 | |
| −3083 | −4681 | −4554 | 91 |
| −369 | −294 | −249 | |
| 2647 | −2235 | −1917 | 92 |
| −369 | −294 | −249 | |
| −3053 | −4696 | −4614 | 93 |
| −369 | −294 | −249 | |
| −3780 | 3031 | 3651 | 94 |
| −369 | −294 | −249 | |
| −6559 | 6291 | −3733 | 95 |
| −369 | −294 | −249 | |
| −3712 | −3688 | −2968 | 96 |
| −369 | −294 | −249 | |
| −2767 | −4303 | −4118 | 97 |
| −369 | −294 | −249 | |
| 1605 | −2824 | −2691 | 98 |
| −369 | −294 | −249 | |
| −600 | −2527 | −1988 | 99 |
| −369 | −294 | −249 | |
| −1882 | 3639 | −1888 | 100 |
| −369 | −294 | −249 | |
| −426 | −2650 | −1967 | 101 |
| −369 | −294 | −249 | |
| −471 | 1260 | 199 | 102 |
| −369 | −294 | −249 | |
| −2699 | −4191 | −3938 | 103 |
| −369 | −294 | −249 | |
| 603 | −2534 | −1895 | 104 |
| −369 | −294 | −249 | |
| −6188 | −5117 | −5507 | 105 |
| −369 | −294 | −249 | |
| −433 | −2377 | −1966 | 106 |
| −369 | −294 | −249 | |
| −4866 | −2341 | −1279 | 107 |
| −369 | −294 | −249 | |
| −6153 | −5123 | −6096 | 108 |
| −369 | −294 | −249 | |
| 1037 | −2630 | −1963 | 109 |
| −369 | −294 | −249 | |
| −3208 | −4829 | −4747 | 110 |
| −369 | −294 | −249 | |
| 549 | −3668 | −3358 | 111 |
| −369 | −294 | −249 | |
| −1061 | −1945 | 272 | 112 |
| −369 | −294 | −249 | |
| −667 | −2629 | −1949 | 113 |
| −369 | −294 | −249 | |
| −1220 | 1669 | 685 | 114 |
| −369 | −294 | −249 | |
| −2272 | −3163 | −2593 | 115 |
| −369 | −294 | −249 | |

-continued

| V | W | Y | |
|---|---|---|---|
| −5577 | 5797 | −3009 | 116 |
| −369 | −294 | −249 | |
| −671 | −3021 | −2290 | 117 |
| −369 | −294 | −249 | |
| −360 | −175 | 2802 | 118 |
| −369 | −294 | −249 | |
| −1865 | −2426 | −1743 | 120 |
| −369 | −294 | −249 | |
| −1108 | −1927 | 2425 | 121 |
| −369 | −294 | −249 | |
| −1868 | −2484 | −1822 | 122 |
| −369 | −294 | −249 | |
| −2220 | −2788 | −2070 | 123 |
| −369 | −294 | −249 | |
| −1795 | −2431 | −1781 | 124 |
| −369 | −294 | −249 | |
| 239 | −2109 | −1917 | 125 |
| −369 | −294 | −249 | |
| −3108 | −3684 | −2831 | 126 |
| −369 | −294 | −249 | |
| −864 | −1751 | −1277 | 127 |
| −369 | −294 | −249 | |
| −3528 | −4478 | −4636 | 128 |
| −369 | −294 | −249 | |
| −1581 | −2205 | −1638 | 129 |
| −369 | −294 | −249 | |
| −1780 | −2390 | −1815 | 130 |
| −369 | −294 | −249 | |
| −3595 | −3184 | −3156 | 131 |
| −369 | −294 | −249 | |
| 3093 | −2764 | −2407 | 132 |
| −369 | −294 | −249 | |
| 1219 | −3318 | −2582 | 133 |
| −369 | −294 | −249 | |
| 118 | −1822 | 1911 | 134 |
| −369 | −294 | −249 | |
| 393 | −1458 | −1105 | 135 |
| −369 | −294 | −249 | |
| 1653 | −1938 | −991 | 136 |
| −369 | −294 | −249 | |
| −3596 | −3729 | −3191 | 137 |
| −369 | −294 | −249 | |
| −773 | −1748 | −1356 | 138 |
| −369 | −294 | −249 | |
| −505 | −1529 | 755 | 139 |
| −369 | −294 | −249 | |
| −2137 | −2701 | −2014 | 140 |
| −369 | −294 | −249 | |
| −4072 | −3990 | −3669 | 141 |
| −369 | −294 | −249 | |
| −1276 | −3007 | −3044 | 142 |
| −369 | −294 | −249 | |
| −2933 | −3514 | −2754 | 143 |
| −369 | −294 | −249 | |
| 2602 | −2979 | −2593 | 144 |
| −369 | −294 | −249 | |
| −2283 | −2848 | 1814 | 145 |
| −369 | −294 | −249 | |
| −3082 | −832 | 3949 | 146 |
| −369 | −294 | −249 | |
| 919 | 1783 | 2653 | 147 |
| −369 | −294 | −249 | |
| −2856 | −4389 | −4220 | 148 |
| −369 | −294 | −249 | |
| −2825 | −1358 | −250 | 149 |
| −369 | −294 | −249 | |
| −6336 | −4332 | −3976 | 150 |
| −369 | −294 | −249 | |
| −6188 | −5117 | −5507 | 151 |
| −369 | −294 | −249 | |
| 1592 | −2508 | −1898 | 152 |
| −369 | −294 | −249 | |

-continued

| V | W | Y | |
|---|---|---|---|
| −471 | 1260 | 199 | 153 |
| −369 | −294 | −249 | |
| −6188 | −5117 | −5507 | 154 |
| −369 | −294 | −249 | |
| 885 | −3726 | −3666 | 155 |
| −369 | −294 | −249 | |
| 922 | −1580 | −1235 | 156 |
| −369 | −294 | −249 | |
| −3744 | −4510 | −3639 | 157 |
| −369 | −294 | −249 | |
| −2175 | −2752 | −2069 | 158 |
| −369 | −294 | −249 | |
| −3598 | −4890 | −4406 | 159 |
| −369 | −294 | −249 | |
| −2106 | −2669 | −1984 | 160 |
| −369 | −294 | −249 | |
| −2980 | −3986 | −3403 | 161 |
| −369 | −294 | −249 | |
| −579 | −1782 | −1423 | 162 |
| −369 | −294 | −249 | |
| −2087 | −2644 | −1966 | 163 |
| −369 | −294 | −249 | |
| −3990 | −4537 | −3731 | 164 |
| −369 | −294 | −249 | |
| −1088 | −1586 | 2248 | 165 |
| −369 | −294 | −249 | |
| −1371 | −2110 | 963 | 166 |
| −369 | −294 | −249 | |
| −1867 | −2429 | −1749 | 167 |
| −369 | −294 | −249 | |
| −1981 | −1308 | 936 | 168 |
| −369 | −294 | −249 | |
| −1272 | −2805 | −2830 | 169 |
| −369 | −294 | −249 | |
| −2316 | −2873 | −1202 | 170 |
| −369 | −294 | −249 | |
| 224 | −2610 | −1937 | 171 |
| −369 | −294 | −249 | |
| 1751 | −2428 | −2079 | 172 |
| −369 | −294 | −249 | |
| 2933 | −2198 | −1841 | 173 |
| −369 | −294 | −249 | |
| −2171 | −2733 | −2044 | 174 |
| −369 | −294 | −249 | |
| 428 | −1753 | 1366 | 175 |
| −369 | −294 | −249 | |
| −675 | −2502 | −2265 | 176 |
| −369 | −294 | −249 | |
| −384 | −2612 | −1946 | 177 |
| −369 | −294 | −249 | |
| −2191 | −2750 | −2060 | 178 |
| −369 | −294 | −249 | |
| −1692 | −2398 | 1901 | 179 |
| −369 | −294 | −249 | |
| −1481 | −2879 | −2882 | 180 |
| −369 | −294 | −249 | |
| −2089 | −2649 | −1966 | 181 |
| −369 | −294 | −249 | |
| −2122 | −2684 | −1998 | 182 |
| −369 | −294 | −249 | |
| −3122 | −4592 | −4334 | 183 |
| −369 | −294 | −249 | |
| −3491 | −3842 | −3252 | 184 |
| −369 | −294 | −249 | |
| 1830 | −1783 | −1441 | 185 |
| −369 | −294 | −249 | |
| −664 | −3109 | −2822 | 186 |
| −369 | −294 | −249 | |
| 2258 | −3031 | −2851 | 187 |
| −369 | −294 | −249 | |
| −2706 | −3760 | −3674 | 188 |
| −369 | −294 | −249 | |
| −3205 | 5740 | −1122 | 189 |
| −369 | −294 | −249 | |
| 1320 | −3855 | −3498 | 190 |

-continued

| V | W | Y | |
|---|---|---|---|
| −369 | −294 | −249 | |
| −4432 | −4902 | −5198 | 191 |
| −369 | −294 | −249 | |
| −3080 | −4688 | −4571 | 192 |
| −369 | −294 | −249 | |
| −3731 | −4441 | −3700 | 193 |
| −369 | −294 | −249 | |
| 533 | −1764 | −1453 | 194 |
| −369 | −294 | −249 | |
| −4866 | −2341 | −1279 | 195 |
| −369 | −294 | −249 | |
| −2607 | −3929 | −3640 | 196 |
| −369 | −294 | −249 | |
| −4002 | −4523 | −3562 | 197 |
| −369 | −294 | −249 | |
| −3430 | −3945 | −3364 | 198 |
| −369 | −294 | −249 | |
| 1325 | −3074 | −2717 | 199 |
| −369 | −294 | −249 | |
| −4043 | −729 | 3525 | 200 |
| −369 | −294 | −249 | |
| 1944 | −1681 | −1320 | 201 |
| −369 | −294 | −249 | |
| −2836 | −3408 | −2646 | 202 |
| −369 | −294 | −249 | |
| −6153 | −5123 | −6096 | 203 |
| −369 | −294 | −249 | |
| −471 | 1260 | 199 | 204 |
| −369 | −294 | −249 | |
| −409 | −4664 | −4550 | 205 |
| −369 | −294 | −249 | |
| −2566 | −3839 | −3512 | 206 |
| −369 | −294 | −249 | |
| −3205 | −4753 | −4602 | 207 |
| −369 | −294 | −249 | |
| −2953 | −4296 | −3964 | 208 |
| −369 | −294 | −249 | |
| −2541 | −3575 | −3147 | 209 |
| −369 | −294 | −249 | |
| −2126 | −2701 | −334 | 210 |
| −369 | −294 | −249 | |
| 75 | −1934 | −1529 | 211 |
| −369 | −294 | −249 | |
| −2207 | 1553 | −2081 | 212 |
| −369 | −294 | −249 | |
| 3537 | −4643 | −4129 | 213 |
| −369 | −294 | −249 | |
| 767 | −879 | 2654 | 214 |
| −369 | −294 | −249 | |
| −3011 | −4246 | −4000 | 215 |
| −369 | −294 | −249 | |
| −3132 | 2650 | 4319 | 216 |
| −369 | −294 | −249 | |
| −3173 | −4847 | −4779 | 217 |
| −369 | −294 | −249 | |
| −16 | −1624 | −1284 | 218 |
| −369 | −294 | −249 | |
| 718 | −2846 | −2430 | 219 |
| −369 | −294 | −249 | |
| −3942 | −3629 | −3505 | 220 |
| −369 | −294 | −249 | |
| 3027 | −2565 | −2197 | 221 |
| −369 | −294 | −249 | |
| 280 | −2274 | −1989 | 222 |
| −369 | −294 | −249 | |
| −2154 | −2687 | −2028 | 223 |
| −369 | −294 | −249 | |
| −2306 | −3051 | −2433 | 224 |
| −369 | −294 | −249 | |
| −1503 | −3271 | −3471 | 225 |
| −369 | −294 | −249 | |
| −4525 | −5119 | −3978 | 226 |
| −369 | −294 | −249 | |
| 1521 | −2695 | −2335 | 227 |

| V | W | Y | # |
|---|---|---|---|
| −369 | −294 | −249 | |
| −3080 | −4681 | −4557 | 228 |
| −369 | −294 | −249 | |
| 634 | −2040 | −1598 | 229 |
| −369 | −294 | −249 | |
| −2360 | −2812 | 310 | 230 |
| −369 | −294 | −249 | |
| 117 | −3263 | −3460 | 231 |
| −369 | −294 | −249 | |
| −4249 | −4910 | −4848 | 232 |
| −369 | −294 | −249 | |
| −3076 | −4613 | −4438 | 233 |
| −369 | −294 | −249 | |
| −3617 | −4074 | −3314 | 234 |
| −369 | −294 | −249 | |
| −893 | −2696 | −2243 | 235 |
| −369 | −294 | −249 | |
| −3900 | −732 | 4560 | 236 |
| −369 | −294 | −249 | |
| 3821 | −4638 | −4461 | 237 |
| −369 | −294 | −249 | |
| 266 | −2302 | −2075 | 238 |
| −369 | −294 | −249 | |
| −6559 | 6391 | −3733 | 239 |
| −369 | −294 | −249 | |
| −4699 | −5042 | −5532 | 240 |
| −369 | −294 | −249 | |
| −6153 | −5123 | −6096 | 241 |
| −369 | −294 | −249 | |
| −5964 | −4773 | −5292 | 242 |
| −369 | −294 | −249 | |
| −6107 | −5083 | −5486 | 243 |
| −369 | −294 | −249 | |
| −6153 | −5123 | −6096 | 244 |
| −369 | −294 | −249 | |
| −2806 | −2762 | 4321 | 245 |
| −369 | −294 | −249 | |
| −2659 | −3248 | −2518 | 246 |
| −369 | −294 | −249 | |
| 325 | −1553 | 1510 | 247 |
| −369 | −294 | −249 | |
| −3386 | −4143 | −3340 | 248 |
| −369 | −294 | −249 | |
| −582 | 2407 | −1210 | 249 |
| −369 | −294 | −249 | |
| −3062 | −4487 | −4194 | 250 |
| −369 | −294 | −249 | |
| −3160 | −4006 | −3686 | 251 |
| −369 | −294 | −249 | |
| −4074 | −4622 | −3654 | 252 |
| −369 | −294 | −249 | |
| 1113 | −1534 | −1193 | 253 |
| −369 | −294 | −249 | |
| −2140 | −2680 | −2014 | 254 |
| −369 | −294 | −249 | |
| −471 | 1260 | 199 | 255 |
| −369 | −294 | −249 | |
| −993 | −2369 | −1782 | 256 |
| −369 | −294 | −249 | |
| −133 | −3820 | −3246 | 257 |
| −369 | −294 | −249 | |
| −1369 | 1760 | −1802 | 258 |
| −369 | −294 | −249 | |
| −3948 | −4537 | −3568 | 259 |
| −369 | −294 | −249 | |
| −2210 | 1571 | −2082 | 260 |
| −369 | −294 | −249 | |
| 370 | −1706 | 1039 | 261 |
| −369 | −294 | −249 | |
| −2485 | −3089 | −2569 | 262 |
| −369 | −294 | −249 | |
| −2098 | −2652 | −1975 | 263 |
| −369 | −294 | −249 | |
| −475 | −1528 | −1174 | 264 |
| −369 | −294 | −249 | |
| −122 | −2251 | 1119 | 265 |
| −369 | −294 | −249 | |
| −2112 | −2667 | −1988 | 266 |
| −369 | −294 | −249 | |
| −756 | −1968 | −1708 | 267 |
| −369 | −294 | −249 | |
| 1111 | −1853 | −1521 | 268 |
| −369 | −294 | −249 | |
| 1831 | −1782 | −1359 | 269 |
| −369 | −294 | −249 | |
| −2823 | −3391 | −2630 | 270 |
| −369 | −294 | −249 | |
| −4116 | −844 | 4614 | 271 |
| −369 | −294 | −249 | |
| 571 | −2102 | −1665 | 272 |
| −369 | −294 | −249 | |
| −2079 | −2639 | −1958 | 273 |
| −369 | −294 | −249 | |
| −2185 | −2745 | −2056 | 274 |
| −369 | −294 | −249 | |
| −3013 | −3178 | −2982 | 275 |
| −369 | −294 | −249 | |
| −4295 | −5047 | −4127 | 276 |
| −369 | −294 | −249 | |
| −3538 | −732 | 3504 | 277 |
| −369 | −294 | −249 | |
| −2085 | −2647 | −1964 | 278 |
| −369 | −294 | −249 | |
| −578 | −1599 | 672 | 279 |
| −369 | −294 | −249 | |
| −2117 | −2667 | −2040 | 280 |
| −369 | −294 | −249 | |
| −1653 | −3024 | −2977 | 281 |
| −369 | −294 | −249 | |
| −1827 | −3457 | −3347 | 282 |
| −369 | −294 | −249 | |
| −533 | −3603 | −3558 | 283 |
| −369 | −294 | −249 | |
| −6107 | −5083 | −5486 | 284 |
| −369 | −294 | −249 | |
| −6390 | −5102 | −6043 | 285 |
| −369 | −294 | −249 | |
| −5584 | −4639 | −5025 | 286 |
| −369 | −294 | −249 | |
| −3772 | −4881 | −4955 | 287 |
| −369 | −294 | −249 | |
| −2775 | −3062 | −2601 | 288 |
| −369 | −294 | −249 | |
| −6107 | −5083 | −5486 | 289 |
| −369 | −294 | −249 | |
| −6390 | −5102 | −6043 | 290 |
| −369 | −294 | −249 | |
| −2270 | −3058 | −2755 | 291 |
| −369 | −294 | −249 | |
| −2019 | −2628 | −2010 | 292 |
| −369 | −294 | −249 | |
| −3909 | −2018 | −872 | 293 |
| −369 | −294 | −249 | |
| −1751 | −3437 | −2918 | 294 |
| −369 | −294 | −249 | |
| −3605 | −791 | 4567 | 295 |
| −369 | −294 | −249 | |
| −2210 | −2109 | −1168 | 296 |
| −369 | −294 | −249 | |
| 525 | 1608 | 1606 | 297 |
| −369 | −294 | −249 | |
| −4212 | −4943 | −4224 | 298 |
| −369 | −294 | −249 | |
| 2553 | −2416 | −2073 | 299 |
| −369 | −294 | −249 | |
| −2792 | −3540 | −2870 | 300 |

| V | W | Y | |
|---|---|---|---|
| −369 | −294 | −249 | |
| −2773 | −3678 | −3134 | 301 |
| −369 | −294 | −249 | |
| 1404 | −1729 | −1356 | 302 |
| −369 | −294 | −249 | |
| 105 | −1521 | 1527 | 303 |
| −369 | −294 | −249 | |
| −3134 | −4669 | −4455 | 304 |
| −369 | −294 | −249 | |
| −3115 | −1246 | −111 | 305 |
| −369 | −294 | −249 | |
| −471 | 1260 | 199 | 306 |
| −369 | −294 | −249 | |
| −85 | −3297 | −3428 | 307 |
| −369 | −294 | −249 | |
| −2111 | −2661 | −1987 | 308 |
| −369 | −294 | −249 | |
| −2086 | −2645 | −1968 | 309 |
| −369 | −294 | −249 | |
| −3686 | −731 | 3736 | 310 |
| −369 | −294 | −249 | |
| −3973 | −4566 | −3588 | 311 |
| −369 | −294 | −249 | |
| −2597 | −2707 | −2185 | 312 |
| −369 | −294 | −249 | |
| −2170 | −2738 | −2050 | 313 |
| −369 | −294 | −249 | |
| −2672 | −3234 | −2495 | 314 |
| −369 | −294 | −249 | |
| −604 | −2345 | 1579 | 315 |
| −369 | −294 | −249 | |
| 491 | −1216 | 1328 | 316 |
| −369 | −294 | −249 | |
| −4504 | −4387 | −4430 | 317 |
| −369 | −294 | −249 | |
| 1824 | −3171 | −3136 | 318 |
| −369 | −294 | −249 | |
| −5689 | −4872 | −5035 | 319 |
| −369 | −294 | −249 | |
| 904 | −3048 | −2816 | 320 |
| −369 | −294 | −249 | |
| −6107 | −5083 | −5486 | 321 |
| −369 | −294 | −249 | |
| 1028 | −1808 | −1465 | 322 |
| −369 | −294 | −249 | |
| −3368 | −4789 | −4432 | 323 |
| −369 | −294 | −249 | |
| −6336 | −4332 | −3976 | 324 |
| −369 | −294 | −249 | |
| −3712 | −4673 | −4159 | 325 |
| −369 | −294 | −249 | |
| −1615 | 1353 | 355 | 326 |
| −369 | −294 | −249 | |
| −1796 | −3261 | −3457 | 327 |
| −369 | −294 | −249 | |
| −3180 | −4829 | −4744 | 328 |
| −369 | −294 | −249 | |
| −3434 | −3413 | −2529 | 329 |
| −369 | −294 | −249 | |
| −3297 | −2280 | −1292 | 330 |
| −369 | −294 | −249 | |
| −3137 | −3957 | −3248 | 331 |
| −369 | −294 | −249 | |
| −3771 | −742 | 2400 | 332 |
| −369 | −294 | −249 | |
| −384 | −2572 | −1915 | 333 |
| −369 | −294 | −249 | |
| −4578 | −3303 | −2455 | 334 |
| −369 | −294 | −249 | |
| −4020 | −4649 | −3669 | 335 |
| −369 | −294 | −249 | |
| 1096 | −3762 | −3679 | 336 |
| −369 | −294 | −249 | |
| −2456 | −2934 | −2321 | 337 |
| −369 | −294 | −249 | |
| 1807 | −1431 | 1003 | 338 |

| V | W | Y | |
|---|---|---|---|
| −369 | −294 | −249 | |
| −4128 | −4931 | −5200 | 339 |
| −369 | −294 | −249 | |
| 702 | −1647 | −1266 | 340 |
| −369 | −294 | −249 | |
| −499 | 2833 | 79 | 341 |
| −369 | −294 | −249 | |
| −822 | −1723 | 344 | 342 |
| −369 | −294 | −249 | |
| −4058 | −4641 | −3646 | 343 |
| −369 | −294 | −249 | |
| 891 | −1646 | −1308 | 344 |
| −369 | −294 | −249 | |
| −1932 | −2773 | −2309 | 345 |
| −369 | −294 | −249 | |
| −2799 | −1729 | −655 | 346 |
| −369 | −294 | −249 | |
| −3384 | −3901 | −3137 | 347 |
| −369 | −294 | −249 | |
| 1741 | −4142 | −3869 | 348 |
| −369 | −294 | −249 | |
| −6188 | −5117 | −5507 | 349 |
| −369 | −294 | −249 | |
| −2053 | −3726 | −3485 | 350 |
| −369 | −294 | −249 | |
| −5689 | −4872 | −5035 | 351 |
| −369 | −294 | −249 | |
| −2058 | −2641 | −1985 | 352 |
| −369 | −294 | −249 | |
| −4530 | −4778 | −4688 | 353 |
| −369 | −294 | −249 | |
| −2889 | −3440 | −2693 | 354 |
| −369 | −294 | −249 | |
| −854 | −1800 | 1377 | 355 |
| −369 | −294 | −249 | |
| −723 | −1713 | −1319 | 356 |
| −369 | −294 | −249 | |
| −471 | 1260 | 199 | 357 |
| −369 | −294 | −249 | |
| 68 | −1800 | −1383 | 358 |
| −369 | −294 | −249 | |
| −3704 | −843 | 2077 | 359 |
| −369 | −294 | −249 | |
| −5755 | 5837 | −3163 | 360 |
| −369 | −294 | −249 | |
| −4638 | −5009 | −4074 | 361 |
| −369 | −294 | −249 | |
| −761 | −2357 | −1930 | 362 |
| −369 | −294 | −249 | |
| −3809 | −4315 | −3781 | 363 |
| −369 | −294 | −249 | |
| 514 | −2934 | −2364 | 364 |
| −369 | −294 | −249 | |
| −3840 | −745 | 1588 | 365 |
| −369 | −294 | −249 | |
| −3299 | −4374 | −4144 | 366 |
| −369 | −294 | −249 | |
| −1582 | −2356 | −1797 | 367 |
| −369 | −294 | −249 | |
| −3055 | −3636 | −2845 | 368 |
| −369 | −294 | −249 | |
| 1616 | −1703 | −1314 | 369 |
| −369 | −294 | −249 | |
| −653 | −1626 | 3372 | 370 |
| −369 | −294 | −249 | |
| −2062 | −2629 | −1949 | 371 |
| −369 | −294 | −249 | |
| −963 | −1947 | −1528 | 372 |
| −369 | −294 | −249 | |
| 789 | −3927 | −3691 | 373 |
| −369 | −294 | −249 | |
| −506 | −1537 | −1178 | 374 |
| −369 | −294 | −249 | |

| V | W | Y | |
|---|---|---|---|
| 1060 | 1858 | −1084 | 375 |
| −369 | −294 | −249 | |
| −1230 | 1231 | −2166 | 376 |
| −369 | −294 | −249 | |
| 1661 | 1953 | 3240 | 377 |
| −369 | −294 | −249 | |
| −626 | −3510 | −2737 | 378 |
| −369 | −294 | −249 | |
| 2345 | −3556 | −3362 | 379 |
| −369 | −294 | −249 | |
| 734 | −3526 | −3572 | 380 |
| −369 | −294 | −249 | |
| −2112 | −2664 | −1989 | 381 |
| −369 | −294 | −249 | |
| −1997 | −2590 | −1924 | 382 |
| −369 | −294 | −249 | |
| −3384 | −4750 | −4279 | 383 |
| −369 | −294 | −249 | |
| −2329 | −3112 | −2499 | 384 |
| −369 | −294 | −249 | |
| −1024 | −2364 | −2136 | 385 |
| −369 | −294 | −249 | |
| −2173 | −2820 | −1986 | 386 |
| −369 | −294 | −249 | |
| −1936 | −2209 | −2293 | 387 |
| −369 | −294 | −249 | |
| −1796 | −2061 | −2037 | 389 |
| −369 | −294 | −249 | |
| −1271 | −2125 | −1610 | 390 |
| −369 | −294 | −249 | |
| −667 | −2379 | 2237 | 391 |
| −369 | −294 | −249 | |
| −2076 | −2637 | −1955 | 392 |
| −369 | −294 | −249 | |
| −6153 | −5123 | −6096 | 393 |
| −369 | −294 | −249 | |
| −4635 | −5035 | −5498 | 394 |
| −369 | −294 | −249 | |
| −697 | −1864 | −1566 | 395 |
| −369 | −294 | −249 | |
| −4437 | −3600 | −2686 | 396 |
| −369 | −294 | −249 | |
| −4866 | −2341 | −1279 | 397 |
| −369 | −294 | −249 | |
| −4804 | −3495 | 737 | 398 |
| −369 | −294 | −249 | |
| −1776 | −1454 | 1913 | 399 |
| −369 | −294 | −249 | |
| −4115 | −3603 | −3389 | 400 |
| −369 | −294 | −249 | |
| 2313 | −2129 | −1779 | 401 |
| −369 | −294 | −249 | |
| −2662 | −3190 | −2839 | 402 |
| −369 | −294 | −249 | |
| −5964 | −4773 | −5292 | 403 |
| −369 | −294 | −249 | |
| −2083 | −2655 | −1976 | 404 |
| −369 | −294 | −249 | |
| −4162 | −4795 | −3785 | 405 |
| −369 | −294 | −249 | |
| −1228 | −906 | 1070 | 406 |
| −369 | −294 | −249 | |
| −2206 | −2769 | −2076 | 407 |
| −369 | −294 | −249 | |
| −471 | 1360 | 199 | 408 |
| −369 | −294 | −249 | |
| 254 | −2132 | 883 | 409 |
| −369 | −294 | −249 | |
| −1099 | −3379 | 987 | 410 |
| −369 | −294 | −249 | |
| −4971 | −5125 | −4670 | 411 |
| −369 | −294 | −249 | |
| 1908 | −3615 | −3591 | 412 |
| −369 | −294 | −249 | |

| V | W | Y | |
|---|---|---|---|
| −2006 | 4055 | 56 | 413 |
| −369 | −294 | −249 | |
| −869 | −1810 | 2176 | 414 |
| −369 | −294 | −249 | |
| −2497 | −3780 | −3478 | 415 |
| −369 | −294 | −249 | |
| −3629 | −3930 | −3278 | 416 |
| −369 | −294 | −249 | |
| 26 | −2021 | −1655 | 417 |
| −369 | −294 | −249 | |
| −87 | −4541 | −4398 | 418 |
| −369 | −294 | −249 | |
| −3066 | −4648 | −4508 | 419 |
| −369 | −294 | −249 | |
| −1290 | −3293 | −3151 | 420 |
| −369 | −294 | −249 | |
| −3914 | −4464 | −3654 | 421 |
| −369 | −294 | −249 | |
| −1840 | −2841 | −2399 | 422 |
| −369 | −294 | −249 | |
| −3252 | −830 | 3643 | 423 |
| −369 | −294 | −249 | |
| −2053 | −3726 | −3485 | 424 |
| −369 | −294 | −249 | |
| 435 | −1583 | −1225 | 425 |
| −369 | −294 | −249 | |
| −2517 | −3884 | −3627 | 426 |
| −369 | −294 | −249 | |
| −1662 | −2346 | −1935 | 427 |
| −369 | −294 | −249 | |
| −2309 | −2789 | −2166 | 428 |
| −369 | −294 | −249 | |
| 2254 | −2023 | −1565 | 429 |
| −369 | −294 | −249 | |
| −149 | −4587 | −4404 | 430 |
| −369 | −294 | −249 | |
| −427 | −2463 | 1197 | 431 |
| −369 | −294 | −249 | |
| −3495 | −3399 | −3235 | 432 |
| −369 | −294 | −249 | |
| −1727 | −3154 | −3303 | 433 |
| −369 | −294 | −249 | |
| 413 | −1741 | −1377 | 434 |
| −369 | −294 | −249 | |
| −2191 | −2754 | −2062 | 435 |
| −369 | −294 | −249 | |
| −4481 | −5103 | −3988 | 436 |
| −369 | −294 | −249 | |
| −2097 | −2657 | −1975 | 437 |
| −369 | −294 | −249 | |
| 1365 | −2258 | −1704 | 438 |
| −369 | −294 | −249 | |
| 1752 | −2089 | 943 | 439 |
| −369 | −294 | −249 | |
| −2081 | −2643 | −1960 | 440 |
| −369 | −294 | −249 | |
| −2221 | −2783 | −2088 | 441 |
| −369 | −294 | −249 | |
| 894 | 1470 | −1077 | 442 |
| −369 | −294 | −249 | |
| 1184 | −1468 | −1122 | 443 |
| −369 | −294 | −249 | |
| −2108 | −2667 | −1985 | 444 |
| −369 | −294 | −249 | |
| −2087 | −2649 | −1965 | 445 |
| −369 | −294 | −249 | |
| −2495 | −2901 | 541 | 446 |
| −369 | −294 | −249 | |
| −3217 | −2977 | 4298 | 447 |
| −369 | −294 | −249 | |
| 395 | −2580 | −1920 | 448 |
| −369 | −294 | −249 | |
| −2059 | −2688 | −2031 | 449 |

| V | W | Y | |
|---|---|---|---|
| −369 | −294 | −249 | |
| −3094 | 3031 | 2760 | 450 |
| −369 | −294 | −249 | |
| −2059 | −2630 | −1953 | 451 |
| −370 | −295 | −250 | |
| −2078 | −2640 | −1958 | 453 |
| −369 | −294 | −249 | |
| −2292 | −3069 | −2463 | 454 |
| −369 | −294 | −249 | |
| 618 | −1515 | −1165 | 455 |
| −369 | −294 | −249 | |
| −2674 | −4165 | −3918 | 456 |
| −369 | −294 | −249 | |
| −1999 | −2574 | −1903 | 457 |
| −369 | −294 | −249 | |
| −2099 | −2661 | −1976 | 458 |
| −369 | −294 | −249 | |
| −471 | 1260 | 199 | 459 |
| −369 | −294 | −249 | |
| 223 | −1539 | −1195 | 460 |
| −369 | −294 | −249 | |
| 1607 | −1750 | −1344 | 461 |
| −369 | −294 | −249 | |
| −2001 | −2563 | −1878 | 462 |
| −369 | −294 | −249 | |
| −1477 | −2248 | 1794 | 463 |
| −369 | −294 | −249 | |
| −2078 | −2639 | −1958 | 464 |
| −369 | −294 | −249 | |
| −5 | −2460 | −1840 | 465 |
| −369 | −294 | −249 | |
| −2211 | −2813 | −2132 | 466 |
| −369 | −294 | −249 | |
| −1448 | −2581 | −2349 | 467 |
| −369 | −294 | −249 | |
| −2077 | −2639 | −1957 | 468 |
| −369 | −294 | −249 | |
| −2176 | −2739 | −2048 | 469 |
| −369 | −294 | −249 | |
| 439 | −1577 | −1205 | 470 |
| −369 | −294 | −249 | |
| −278 | −1911 | 36 | 471 |
| −369 | −294 | −249 | |
| −2093 | −2654 | −1971 | 472 |
| −369 | −294 | −249 | |
| −3122 | −870 | 4083 | 473 |
| −369 | −294 | −249 | |
| −542 | −2252 | −1747 | 474 |
| −369 | −294 | −249 | |
| −1814 | −2476 | −1850 | 475 |
| −369 | −294 | −249 | |
| −2054 | −2625 | −70 | 476 |
| −369 | −294 | −249 | |
| −2021 | −2605 | −1935 | 477 |
| −369 | −294 | −249 | |
| −673 | −2589 | −1910 | 478 |
| −369 | −294 | −249 | |
| −1945 | −2521 | −1846 | 479 |
| −369 | −294 | −249 | |
| −1985 | −2630 | −1917 | 480 |
| −369 | −294 | −249 | |
| −1195 | −1742 | 1116 | 481 |
| −369 | −294 | −249 | |
| 781 | −1493 | −1288 | 482 |
| −369 | −294 | −249 | |
| 557 | −1348 | −882 | 483 |
| −369 | −294 | −249 | |
| 561 | −1598 | −1219 | 484 |
| −369 | −294 | −249 | |
| −346 | −2620 | 236 | 485 |
| −369 | −294 | −249 | |
| −2067 | −2632 | −1952 | 486 |
| −369 | −294 | −249 | |
| −883 | −2634 | −1953 | 487 |
| −369 | −294 | −249 | |
| −2869 | −4076 | −3665 | 488 |
| −369 | −294 | −249 | |
| −632 | −1617 | 645 | 489 |
| −369 | −294 | −249 | |
| −2189 | −2708 | −2066 | 490 |
| −369 | −294 | −249 | |
| −801 | −1929 | −1608 | 491 |
| −369 | −294 | −249 | |
| 738 | −3560 | −3048 | 492 |
| −369 | −294 | −249 | |
| −735 | −2564 | 773 | 493 |
| −369 | −294 | −249 | |
| 200 | −2069 | 1544 | 494 |
| −369 | −294 | −249 | |
| −2954 | −3510 | −2742 | 495 |
| −369 | −294 | −249 | |
| −2050 | −2632 | −1958 | 496 |
| −369 | −294 | −249 | |
| 294 | −1986 | −1687 | 497 |
| −369 | −294 | −249 | |
| 1594 | −2412 | −2096 | 498 |
| −369 | −294 | −249 | |
| 282 | −1758 | −1363 | 499 |
| −369 | −294 | −249 | |
| −2083 | −2645 | −1962 | 500 |
| −369 | −294 | −249 | |
| −3587 | −932 | 4339 | 501 |
| −369 | −294 | −249 | |
| −949 | −2320 | −2132 | 502 |
| −369 | −294 | −249 | |
| 1400 | −1992 | −1730 | 503 |
| −369 | −294 | −249 | |
| −1922 | −2484 | −1799 | 504 |
| −369 | −294 | −249 | |
| 1219 | −1821 | −1317 | 505 |
| −369 | −294 | −249 | |
| −237 | −1248 | −861 | 506 |
| −369 | −294 | −249 | |
| −968 | −1734 | 343 | 507 |
| −369 | −294 | −249 | |
| −1473 | −2035 | −1367 | 508 |
| −369 | −295 | −250 | |
| −471 | 1260 | 199 | 510 |
| −369 | −295 | −250 | |
| −471 | 1260 | 199 | 518 |
| * | * | * | |

[1]Program name and version

[2]Name of the input sequence alignment file

[3]Length of the alignment: include indels

[4]Type of residues

[5]Map of the match states to the columns of the alignment

[6]Commands used to generate the file: this one means that hmmbuild (default parameters) was applied to the hmm profile

[7]Commands used to generate the file: this one means that hmmcalibrate (default parameters) was applied to the hmm profile

[8]Number of sequences in the alignment

[9]When the file was generated

[10]The trasition probability distribution for the null model (single G state).

[11]The symbol emission probability distribution for the null model (G state); consists of K integers. The null probability used to convert these back to model probabilities is 1/K.

[12]The extreme value distribution parameters μ and lambda respectively, both floating point values. Lambda is positive and nonzero. These values are set when the model is calibrated with hmmcalibrate.

What is claimed is:

1. A recombinant bacterial strain selected from the group consisting of *Zymomonas* and *Zymobacter* comprising a chimeric gene, the chimeric gene comprising:
   a) an isolated nucleic acid molecule comprising a *Z. mobilis* glyceraldehyde-3-phosphate dehydrogenase gene promoter (Pgap) that has a base substitution in
   a position selected from the group consisting of position 116, position 217, and both position 116 and 217; wherein the position numbers are of SEQ ID NO:1; which is an improved Pgap; and
   b) an operably linked isolated nucleic acid molecule encoding a xylose isomerase enzyme.

2. The recombinant strain of claim 1 wherein the base substitution is:
   a) at position 116, a T replacing G; and
   b) at position 217, a T replacing C.

3. The recombinant strain of claim 2 wherein the improved Pgap comprises a sequence selected from the group consisting of SEQ ID NO: 4, 5, 6, 7, 8, 9, 10, 11, and 12.

4. The recombinant strain of claim 1 additionally transformed with genes for expression of xylulokinase, transaldolase and transketolase.

5. The recombinant strain of claim 1 wherein the chimeric gene further comprises an operably linked isolated nucleic acid molecule encoding xylulokinase, forming an operon.

6. The recombinant strain of claim 1 wherein the xylose isomerase enzyme is a protein having an E-value parameter of less than or equal to $3 \times 10^{-10}$ when queried using the Pfam Profile HMM for the xylA family of proteins given in Table 3 and having the four catalytic site residues: histidine 54, aspartic acid 57, glutamic acid 181, and lysine 183, with the position numbers in reference to the *Streptomyces albus* xylose isomerase sequence (SEQ ID NO: 84).

7. A process for engineering a bacterial strain selected from the group consisting of *Zymomonas* and *Zymobacter* comprising:
   transforming with a chimeric gene comprising:
   a) an isolated nucleic acid molecule comprising a *Z. mobilis* glyceraldehyde-3-phosphate dehydrogenase gene promoter that has a base substitution in a position selected from the group consisting of position 116, position 217, and both position 116 and 217; wherein the position numbers are of SEQ ID NO:1; which is an improved Pgap; and
   b) an operably linked isolated nucleic acid molecule encoding a xylose isomerase enzyme.

8. A process for engineering a xylose-utilizing bacterial strain selected from the group consisting of *Zymomonas* and *Zymobacter* comprising in any order the steps of:
   a) transforming with genes or an operon for expression of transaldolase and transketolase; and
   b) transforming with genes or an operon for expression of xylose isomerase and xylulokinase, wherein the xylose isomerase enzyme is expressed from a *Z. mobilis* glyceraldehyde-3-phosphate dehydrogenase gene promoter that has a base substitution in a position selected from the group consisting of position 116, position 217, and both position 116 and 217; wherein the position numbers are of SEQ ID NO:1; which is an improved Pgap.

9. A process for production of ethanol, comprising:
   a) culturing in a medium comprising xylose the recombinant bacterial strain of claim 1; and
   b) maintaining fermentation conditions suitable for ethanol production in any system,
   thereby facilitating the cultured recombinant bacterial strain of claim 1 to convert xylose to ethanol.

* * * * *

SEQUENCE LISTING

<160> NUMBER OF SEQ ID NOS: 141

<210> SEQ ID NO 1
<211> LENGTH: 305
<212> TYPE: DNA
<213> ORGANISM: Zymomonas mobilis

<400> SEQUENCE: 1

```
gttcgatcaa caacccgaat cctatcgtaa tgatgttttg cccgatcagc ctcaatcgac    60
aattttacgc gtttcgatcg aagcagggac gacaattggc tgggaacggt atactggaat   120
aaatggtctt cgttatggta ttgatgtttt tggtgcatcg gccccggcga atgatctata   180
tgctcatttc ggcttgaccg cagtcggcat cacgaacaag gtgttggccg cgatcgccgg   240
taagtcggca cgttaaaaaa tagctatgga atataatagc tacttaataa gttaggagaa   300
taaac                                                               305
```

<210> SEQ ID NO 2
<211> LENGTH: 305
<212> TYPE: DNA
<213> ORGANISM: Zymomonas mobilis

<400> SEQUENCE: 2

```
gttcgatcaa caacccgaat cctatcgtaa tgatgttttg cccgatcagc ctcaatcgac    60
aattttacgc gtttcgatcg aagcagggac gacaattggc tgggaacggt atactggaat   120
aaatggtctt cgttatggta ttgatgtttt tggtgcatcg gccccggcga atgatctata   180
tgctcatttc ggcttgaccg cagtcggcat cacgaacaag gtgttggccg cgatcgccgg   240
taagtcggca cgttaaaaaa tagctatgga atatagtagc tacttaataa gttaggagaa   300
taaac                                                               305
```

<210> SEQ ID NO 3
<211> LENGTH: 304
<212> TYPE: DNA
<213> ORGANISM: artificial sequence
<220> FEATURE:
<223> OTHER INFORMATION: cloned ZmPgap with mutation

<400> SEQUENCE: 3

```
gttcgatcaa caacccgaat cctatcgtaa tgatgttttg cccgatcagc ctcaatcgac    60
aattttacgc gtttcgatcg aagcagggac gacaattggc tgggaacggt atactggaat   120
aaatggtctt cgttatggta ttgatgtttt tggtgcatcg gccccggcga atgatctata   180
tgctcatttc ggcttgaccg cagtcggcat cacgaacaag gtgttggccg cgatcgccgg   240
taagtcggca cgttaaaaaa tagctatgga atataatagc tactaataag ttaggagaat   300
aaac                                                                304
```

<210> SEQ ID NO 4
<211> LENGTH: 304
<212> TYPE: DNA
<213> ORGANISM: artificial sequence
<220> FEATURE:
<223> OTHER INFORMATION: mutated promoter

<400> SEQUENCE: 4

```
gttcgatcaa caacccgaat cctatcgtaa tgatgttttg cccgatcagc ctcaatcgac    60
aattttacgc gtttcgatcg aagcagggac gacaattggc tgggaacggt atacttgaat   120
```

| | |
|---|---|
| aaatggtctt cgttatggta ttgatgttt tggtgcatcg gccccggcga atgatctata | 180 |
| tgctcatttc ggcttgaccg cagtcggcat cacgaacaag gtgttggccg cgatcgccgg | 240 |
| taagtcggca cgttaaaaaa tagctatgga atataatagc tactaataag ttaggagaat | 300 |
| aaac | 304 |

<210> SEQ ID NO 5
<211> LENGTH: 304
<212> TYPE: DNA
<213> ORGANISM: artificial sequence
<220> FEATURE:
<223> OTHER INFORMATION: mutant promoter

<400> SEQUENCE: 5

| | |
|---|---|
| gttcgatcaa caacccgaat cctatcgtaa tgatgttttg cccgatcagc ctcaatcgac | 60 |
| aattttacgc gtttcgatcg aagcagggac gacaattggc tgggaacggt atactggaat | 120 |
| aaatggtctt cgttatggta ttgatgtttt tggtgcatcg gccccggcga atgatctata | 180 |
| tgctcatttc ggcttgaccg cagtcggcat cacgaataag gtgttggccg cgatcgccgg | 240 |
| taagtcggca cgttaaaaaa tagctatgga atataatagc tactaataag ttaggagaat | 300 |
| aaac | 304 |

<210> SEQ ID NO 6
<211> LENGTH: 304
<212> TYPE: DNA
<213> ORGANISM: artificial sequence
<220> FEATURE:
<223> OTHER INFORMATION: double mutation promoter

<400> SEQUENCE: 6

| | |
|---|---|
| gttcgatcaa caacccgaat cctatcgtaa tgatgttttg cccgatcagc ctcaatcgac | 60 |
| aattttacgc gtttcgatcg aagcagggac gacaattggc tgggaacggt atacttgaat | 120 |
| aaatggtctt cgttatggta ttgatgtttt tggtgcatcg gccccggcga atgatctata | 180 |
| tgctcatttc ggcttgaccg cagtcggcat cacgaataag gtgttggccg cgatcgccgg | 240 |
| taagtcggca cgttaaaaaa tagctatgga atataatagc tactaataag ttaggagaat | 300 |
| aaac | 304 |

<210> SEQ ID NO 7
<211> LENGTH: 305
<212> TYPE: DNA
<213> ORGANISM: artificial sequence
<220> FEATURE:
<223> OTHER INFORMATION: promoter with mutation

<400> SEQUENCE: 7

| | |
|---|---|
| gttcgatcaa caacccgaat cctatcgtaa tgatgttttg cccgatcagc ctcaatcgac | 60 |
| aattttacgc gtttcgatcg aagcagggac gacaattggc tgggaacggt atacttgaat | 120 |
| aaatggtctt cgttatggta ttgatgtttt tggtgcatcg gccccggcga atgatctata | 180 |
| tgctcatttc ggcttgaccg cagtcggcat cacgaacaag gtgttggccg cgatcgccgg | 240 |
| taagtcggca cgttaaaaaa tagctatgga atataatagc tacttaataa gttaggagaa | 300 |
| taaac | 305 |

<210> SEQ ID NO 8
<211> LENGTH: 305
<212> TYPE: DNA
<213> ORGANISM: artificial sequence
<220> FEATURE:

<223> OTHER INFORMATION: promoter with mutation

<400> SEQUENCE: 8

```
gttcgatcaa caacccgaat cctatcgtaa tgatgttttg cccgatcagc ctcaatcgac    60
aattttacgc gtttcgatcg aagcagggac gacaattggc tgggaacggt atactggaat   120
aaatggtctt cgttatggta ttgatgtttt tggtgcatcg gccccggcga atgatctata   180
tgctcatttc ggcttgaccg cagtcggcat cacgaataag gtgttggccg cgatcgccgg   240
taagtcggca cgttaaaaaa tagctatgga atataatagc tacttaataa gttaggagaa   300
taaac                                                               305
```

<210> SEQ ID NO 9
<211> LENGTH: 305
<212> TYPE: DNA
<213> ORGANISM: artificial sequence
<220> FEATURE:
<223> OTHER INFORMATION: promoter with mutations

<400> SEQUENCE: 9

```
gttcgatcaa caacccgaat cctatcgtaa tgatgttttg cccgatcagc ctcaatcgac    60
aattttacgc gtttcgatcg aagcagggac gacaattggc tgggaacggt atacttgaat   120
aaatggtctt cgttatggta ttgatgtttt tggtgcatcg gccccggcga atgatctata   180
tgctcatttc ggcttgaccg cagtcggcat cacgaataag gtgttggccg cgatcgccgg   240
taagtcggca cgttaaaaaa tagctatgga atataatagc tacttaataa gttaggagaa   300
taaac                                                               305
```

<210> SEQ ID NO 10
<211> LENGTH: 305
<212> TYPE: DNA
<213> ORGANISM: artificial sequence
<220> FEATURE:
<223> OTHER INFORMATION: promoter with mutation

<400> SEQUENCE: 10

```
gttcgatcaa caacccgaat cctatcgtaa tgatgttttg cccgatcagc ctcaatcgac    60
aattttacgc gtttcgatcg aagcagggac gacaattggc tgggaacggt atacttgaat   120
aaatggtctt cgttatggta ttgatgtttt tggtgcatcg gccccggcga atgatctata   180
tgctcatttc ggcttgaccg cagtcggcat cacgaacaag gtgttggccg cgatcgccgg   240
taagtcggca cgttaaaaaa tagctatgga atatagtagc tacttaataa gttaggagaa   300
taaac                                                               305
```

<210> SEQ ID NO 11
<211> LENGTH: 305
<212> TYPE: DNA
<213> ORGANISM: artificial sequence
<220> FEATURE:
<223> OTHER INFORMATION: promoter with mutation

<400> SEQUENCE: 11

```
gttcgatcaa caacccgaat cctatcgtaa tgatgttttg cccgatcagc ctcaatcgac    60
aattttacgc gtttcgatcg aagcagggac gacaattggc tgggaacggt atactggaat   120
aaatggtctt cgttatggta ttgatgtttt tggtgcatcg gccccggcga atgatctata   180
tgctcatttc ggcttgaccg cagtcggcat cacgaataag gtgttggccg cgatcgccgg   240
taagtcggca cgttaaaaaa tagctatgga atatagtagc tacttaataa gttaggagaa   300
```

```
taaac                                                             305

<210> SEQ ID NO 12
<211> LENGTH: 305
<212> TYPE: DNA
<213> ORGANISM: artificial sequence
<220> FEATURE:
<223> OTHER INFORMATION: promoter with mutations

<400> SEQUENCE: 12
gttcgatcaa cacccgaat cctatcgtaa tgatgttttg cccgatcagc ctcaatcgac     60
aattttacgc gtttcgatcg aagcagggac gacaattggc tgggaacggt atacttgaat  120
aaatggtctt cgttatggta ttgatgtttt tggtgcatcg gccccggcga atgatctata  180
tgctcatttc ggcttgaccg cagtcggcat cacgaataag gtgttggccg cgatcgccgg  240
taagtcggca cgttaaaaaa tagctatgga atatagtagc tacttaataa gttaggagaa  300
taaac                                                             305

<210> SEQ ID NO 13
<211> LENGTH: 24
<212> TYPE: DNA
<213> ORGANISM: artificial sequence
<220> FEATURE:
<223> OTHER INFORMATION: primer

<400> SEQUENCE: 13
cgatcaacaa cccgaatcct atcg                                         24

<210> SEQ ID NO 14
<211> LENGTH: 26
<212> TYPE: DNA
<213> ORGANISM: artificial sequence
<220> FEATURE:
<223> OTHER INFORMATION: primer

<400> SEQUENCE: 14
gccgttattt gtcgaacaga taatgg                                       26

<210> SEQ ID NO 15
<211> LENGTH: 20
<212> TYPE: DNA
<213> ORGANISM: artificial sequence
<220> FEATURE:
<223> OTHER INFORMATION: primer

<400> SEQUENCE: 15
tatgggttca gcggcatgag                                              20

<210> SEQ ID NO 16
<211> LENGTH: 21
<212> TYPE: DNA
<213> ORGANISM: artificial sequence
<220> FEATURE:
<223> OTHER INFORMATION: primer

<400> SEQUENCE: 16
atgggcatga gatccatagc c                                            21

<210> SEQ ID NO 17
<211> LENGTH: 38
<212> TYPE: DNA
<213> ORGANISM: artificial sequence
<220> FEATURE:
<223> OTHER INFORMATION: primer
```

-continued

```
<400> SEQUENCE: 17
ctactcattt cctgcaggtg gtaactcatt gcgcgctc                                    38

<210> SEQ ID NO 18
<211> LENGTH: 38
<212> TYPE: DNA
<213> ORGANISM: artificial sequence
<220> FEATURE:
<223> OTHER INFORMATION: primer

<400> SEQUENCE: 18
catcttactg gcgcgccaaa aatctgcggc tgacatac                                    38

<210> SEQ ID NO 19
<211> LENGTH: 56
<212> TYPE: DNA
<213> ORGANISM: artificial sequence
<220> FEATURE:
<223> OTHER INFORMATION: primer

<400> SEQUENCE: 19
actcatttcc atggcgatcg cactatgcgg ccgcaatgta gcacctgaag tcagcc              56

<210> SEQ ID NO 20
<211> LENGTH: 56
<212> TYPE: DNA
<213> ORGANISM: artificial sequence
<220> FEATURE:
<223> OTHER INFORMATION: primer

<400> SEQUENCE: 20
atctcactcc atggccggcc aactattaat taagaattga ttggctccaa ttcttg              56

<210> SEQ ID NO 21
<211> LENGTH: 39
<212> TYPE: DNA
<213> ORGANISM: artificial sequence
<220> FEATURE:
<223> OTHER INFORMATION: LoxP site oligonucleotide

<400> SEQUENCE: 21
cgcataactt cgtataatgt atgctatacg aagttatgc                                  39

<210> SEQ ID NO 22
<211> LENGTH: 45
<212> TYPE: DNA
<213> ORGANISM: artificial sequence
<220> FEATURE:
<223> OTHER INFORMATION: loxP site oligonucleotide

<400> SEQUENCE: 22
ggccgcataa cttcgtatag catacattat acgaagttat gcgat                           45

<210> SEQ ID NO 23
<211> LENGTH: 43
<212> TYPE: DNA
<213> ORGANISM: artificial sequence
<220> FEATURE:
<223> OTHER INFORMATION: loxP site oligonucleotide

<400> SEQUENCE: 23
taaataactt cgtataatgt atgctatacg aagttatggc cgg                             43

<210> SEQ ID NO 24
<211> LENGTH: 41
<212> TYPE: DNA
```

```
<213> ORGANISM: artificial sequence
<220> FEATURE:
<223> OTHER INFORMATION: loxP site oligonucleotide

<400> SEQUENCE: 24
ccataacttc gtatagcata cattatacga agttatttaa t                    41

<210> SEQ ID NO 25
<211> LENGTH: 26
<212> TYPE: DNA
<213> ORGANISM: artificial sequence
<220> FEATURE:
<223> OTHER INFORMATION: primer

<400> SEQUENCE: 25
ataaaagcgg ccgcagcaca ggatga                                     26

<210> SEQ ID NO 26
<211> LENGTH: 26
<212> TYPE: DNA
<213> ORGANISM: artificial sequence
<220> FEATURE:
<223> OTHER INFORMATION: primer

<400> SEQUENCE: 26
ggcgttaatt aaggcaggtc agcaag                                     26

<210> SEQ ID NO 27
<211> LENGTH: 15
<212> TYPE: DNA
<213> ORGANISM: artificial sequence
<220> FEATURE:
<223> OTHER INFORMATION: primer

<400> SEQUENCE: 27
gcgtcagctg acgcg                                                 15

<210> SEQ ID NO 28
<211> LENGTH: 18
<212> TYPE: DNA
<213> ORGANISM: artificial sequence
<220> FEATURE:
<223> OTHER INFORMATION: primer

<400> SEQUENCE: 28
cacatcgtgg aagcaata                                              18

<210> SEQ ID NO 29
<211> LENGTH: 17
<212> TYPE: DNA
<213> ORGANISM: artificial sequence
<220> FEATURE:
<223> OTHER INFORMATION: primer

<400> SEQUENCE: 29
gccgaaatga gcatata                                               17

<210> SEQ ID NO 30
<211> LENGTH: 15
<212> TYPE: DNA
<213> ORGANISM: artificial sequence
<220> FEATURE:
<223> OTHER INFORMATION: primer

<400> SEQUENCE: 30
gtgccgactt accgg                                                 15
```

<210> SEQ ID NO 31
<211> LENGTH: 16
<212> TYPE: DNA
<213> ORGANISM: artificial sequence
<220> FEATURE:
<223> OTHER INFORMATION: primer

<400> SEQUENCE: 31
tgacggaatg ctaacg                                                      16

<210> SEQ ID NO 32
<211> LENGTH: 35
<212> TYPE: DNA
<213> ORGANISM: artificial sequence
<220> FEATURE:
<223> OTHER INFORMATION: primer

<400> SEQUENCE: 32
ctactcattt atcgatggag cacaggatga cgcct                                 35

<210> SEQ ID NO 33
<211> LENGTH: 34
<212> TYPE: DNA
<213> ORGANISM: artificial sequence
<220> FEATURE:
<223> OTHER INFORMATION: primer

<400> SEQUENCE: 33
catcttacta cgcgttggca ggtcagcaag tgcc                                  34

<210> SEQ ID NO 34
<211> LENGTH: 2013
<212> TYPE: DNA
<213> ORGANISM: artificial sequence
<220> FEATURE:
<223> OTHER INFORMATION: constructed chimeric gene

<400> SEQUENCE: 34
ccatggtgaa acgggggcg aagaagttgt ccatattggc cacgtttaaa tcaaaactgg        60
tgaaactcac ccaggattg gctgagacga aaacatatt ctcaataaac cctttaggga       120
aataggccag gttttcaccg taacacgcca catcttgcga atatatgtgt agaaactgcc      180
ggaaatcgtc gtggtattca ctccagagcg atgaaaacgt ttcagtttgc tcatggaaaa     240
cggtgtaaca agggtgaaca ctatcccata tcaccagctc accgtctttc attgccatac     300
ggaattagcg gccgcgttcg atcaacaacc cgaatcctat cgtaatgatg ttttgcccga     360
tcagcctcaa tcgacaattt tacgcgtttc gatcgaagca gggacgacaa ttggctggga     420
acggtatact ggaataaatg gtcttcgtta tggtattgat gttttggtg catcggcccc       480 ggcgaatgat ctatatgctc atttcggctt gaccgcagtc ggcatcacga caaggtgtt      540 ggccgcgatc gccggtaagt cggcacgtta aaaatagct atggaatata atagctacta      600
ataagttagg agaataaaca tgcaagccta ttttgaccag ctcgatcgcg ttcgttatga     660
aggctcaaaa tcctcaaacc cgttagcatt ccgtcactac aatcccgacg aactggtgtt     720
gggtaagcgt atggaagagc acttgcgttt tgccgcctgc tactggcaca ccttctgctg     780
gaacggggcg gatatgtttg gtgtggggc gtttaatcgt ccgtggcagc agcctggtga     840
ggcactggcg ttggcgaagc gtaaagcaga tgtcgcattt gagttttcc acaagttaca     900 tgtgccattt tattgcttcc acgatgtgga tgtttcccct gagggcgcgt cgttaaaaga     960
gtacatcaat aattttgcgc aaatggttga tgtcctggca ggcaagcaag aagagagcgg    1020

```
cgtgaagctg ctgtggggaa cggccaactg ctttacaaac cctcgctacg gcgcgggtgc      1080
ggcgacgaac ccagatcctg aagtcttcag ctgggcggca acgcaagttg ttacagcgat      1140
ggaagcaacc cataaattgg gcggtgaaaa ctatgtcctg tggggcggtc gtgaaggtta      1200
cgaaacgctg ttaaataccg acttgcgtca ggagcgtgaa caactgggcc gctttatgca      1260
gatggtggtt gagcataaac ataaaatcgg tttccagggc acgttgctta tcgaaccgaa      1320
accgcaagaa ccgaccaaac atcaatatga ttacgatgcc gcgacggtct atggcttcct      1380
gaaacagttt ggtctggaaa aagagattaa actgaacatt gaagctaacc acgcgacgct      1440
ggcaggtcac tctttccatc atgaaatagc caccgccatt gcgcttggcc tgttcggttc      1500
tgtcgacgcc aaccgtggcg atgcgcaact gggctgggac accgaccagt tcccgaacag      1560
tgtggaagag aatgcgctgg tgatgtatga aattctcaaa gcaggcggtt tcaccaccgg      1620
tggtctgaac ttcgatgcca aagtacgtcg tcaaagtact gataaatatg atctgttta      1680 cggtcatatc ggcgcgatgg atacgatggc actggcgctg aaaattgcag cgcgcatgat      1740
tgaagatggc gagctggata acgcatcgc gcagcgttat tccggctgga atagcgaatt      1800
gggccagcaa atcctgaaag gccaaatgtc actggcagat ttagccaaat atgctcagga      1860
acatcatttg tctccggtgc atcagagtgg tcgccaggaa caactggaaa atctggtaaa      1920
ccattatctg ttcgacaaat aacggctaac tgtgcagtcc gttggcccgg ttatcggtag      1980
cgataccggg catttttta aggaacgatc gat                                   2013

<210> SEQ ID NO 35
<211> LENGTH: 40
<212> TYPE: DNA
<213> ORGANISM: artificial sequence
<220> FEATURE:
<223> OTHER INFORMATION: multi-cloning site oligo

<400> SEQUENCE: 35
aattctacct gcaggagtag gccggccatg agcgatcgca                            40

<210> SEQ ID NO 36
<211> LENGTH: 40
<212> TYPE: DNA
<213> ORGANISM: artificial sequence
<220> FEATURE:
<223> OTHER INFORMATION: multi-cloning site oligo

<400> SEQUENCE: 36
agcttgcgat cgctcatggc cggcctactc ctgcaggtag                            40

<210> SEQ ID NO 37
<211> LENGTH: 38
<212> TYPE: DNA
<213> ORGANISM: artificial sequence
<220> FEATURE:
<223> OTHER INFORMATION: primer

<400> SEQUENCE: 37
tcactcatgg ccggccgttc gatcaacaac ccgaatcc                              38

<210> SEQ ID NO 38
<211> LENGTH: 39
<212> TYPE: DNA
<213> ORGANISM: artificial sequence
<220> FEATURE:
<223> OTHER INFORMATION: primer

<400> SEQUENCE: 38
```

```
ctactcatcc tgcaggccga tatacttatc gatcgttcc                              39
```

<210> SEQ ID NO 39
<211> LENGTH: 22
<212> TYPE: DNA
<213> ORGANISM: artificial sequence
<220> FEATURE:
<223> OTHER INFORMATION: primer

<400> SEQUENCE: 39

```
atcaacaacc cgaatcctat cg                                                22
```

<210> SEQ ID NO 40
<211> LENGTH: 20
<212> TYPE: DNA
<213> ORGANISM: artificial sequence
<220> FEATURE:
<223> OTHER INFORMATION: primer

<400> SEQUENCE: 40

```
tatgctcaac caccatctgc                                                   20
```

<210> SEQ ID NO 41
<211> LENGTH: 20
<212> TYPE: DNA
<213> ORGANISM: artificial sequence
<220> FEATURE:
<223> OTHER INFORMATION: primer

<400> SEQUENCE: 41

```
cgacatctgc tttacgcttc                                                   20
```

<210> SEQ ID NO 42
<211> LENGTH: 440
<212> TYPE: PRT
<213> ORGANISM: Escherichia coli

<400> SEQUENCE: 42

```
Met Gln Ala Tyr Phe Asp Gln Leu Asp Arg Val Arg Tyr Glu Gly Ser
1               5                   10                  15

Lys Ser Ser Asn Pro Leu Ala Phe Arg His Tyr Asn Pro Asp Glu Leu
            20                  25                  30

Val Leu Gly Lys Arg Met Glu Glu His Leu Arg Phe Ala Ala Cys Tyr
        35                  40                  45

Trp His Thr Phe Cys Trp Asn Gly Ala Asp Met Phe Gly Val Gly Ala
    50                  55                  60

Phe Asn Arg Pro Trp Gln Gln Pro Gly Glu Ala Leu Ala Leu Ala Lys
65                  70                  75                  80

Arg Lys Ala Asp Val Ala Phe Glu Phe Phe His Lys Leu His Val Pro
                85                  90                  95

Phe Tyr Cys Phe His Asp Val Asp Val Ser Pro Glu Gly Ala Ser Leu
            100                 105                 110

Lys Glu Tyr Ile Asn Asn Phe Ala Gln Met Val Asp Val Leu Ala Gly
        115                 120                 125

Lys Gln Glu Glu Ser Gly Val Lys Leu Leu Trp Gly Thr Ala Asn Cys
    130                 135                 140

Phe Thr Asn Pro Arg Tyr Gly Ala Gly Ala Ala Thr Asn Pro Asp Pro
145                 150                 155                 160

Glu Val Phe Ser Trp Ala Ala Thr Gln Val Val Thr Ala Met Glu Ala
                165                 170                 175

Thr His Lys Leu Gly Gly Glu Asn Tyr Val Leu Trp Gly Gly Arg Glu
```

```
                        180                 185                 190
Gly Tyr Glu Thr Leu Leu Asn Thr Asp Leu Arg Gln Glu Arg Glu Gln
                195                 200                 205
Leu Gly Arg Phe Met Gln Met Val Val Glu His Lys His Lys Ile Gly
            210                 215                 220
Phe Gln Gly Thr Leu Leu Ile Glu Pro Lys Pro Gln Glu Pro Thr Lys
225                 230                 235                 240
His Gln Tyr Asp Tyr Asp Ala Ala Thr Val Tyr Gly Phe Leu Lys Gln
                245                 250                 255
Phe Gly Leu Glu Lys Glu Ile Lys Leu Asn Ile Glu Ala Asn His Ala
            260                 265                 270
Thr Leu Ala Gly His Ser Phe His His Glu Ile Ala Thr Ala Ile Ala
        275                 280                 285
Leu Gly Leu Phe Gly Ser Val Asp Ala Asn Arg Gly Asp Ala Gln Leu
    290                 295                 300
Gly Trp Asp Thr Asp Gln Phe Pro Asn Ser Val Glu Glu Asn Ala Leu
305                 310                 315                 320
Val Met Tyr Glu Ile Leu Lys Ala Gly Gly Phe Thr Thr Gly Gly Leu
                325                 330                 335
Asn Phe Asp Ala Lys Val Arg Arg Gln Ser Thr Asp Lys Tyr Asp Leu
            340                 345                 350
Phe Tyr Gly His Ile Gly Ala Met Asp Thr Met Ala Leu Ala Leu Lys
        355                 360                 365
Ile Ala Ala Arg Met Ile Glu Asp Gly Glu Leu Asp Lys Arg Ile Ala
    370                 375                 380
Gln Arg Tyr Ser Gly Trp Asn Ser Glu Leu Gly Gln Gln Ile Leu Lys
385                 390                 395                 400
Gly Gln Met Ser Leu Ala Asp Leu Ala Lys Tyr Ala Gln Glu His His
                405                 410                 415
Leu Ser Pro Val His Gln Ser Gly Arg Gln Glu Gln Leu Glu Asn Leu
            420                 425                 430
Val Asn His Tyr Leu Phe Asp Lys
        435                 440

<210> SEQ ID NO 43
<211> LENGTH: 1323
<212> TYPE: DNA
<213> ORGANISM: Escherichia coli

<400> SEQUENCE: 43
atgcaagcct attttgacca gctcgatcgc gttcgttatg aaggctcaaa atcctcaaac      60
ccgttagcat tccgtcacta caatcccgac gaactggtgt tgggtaagcg tatggaagag     120
cacttgcgtt ttgccgcctg ctactggcac accttctgct ggaacggggc ggatatgttt     180
ggtgtggggg cgtttaatcg tccgtggcag cagcctggtg aggcactggc gttggcgaag     240
cgtaaagcag atgtcgcatt tgagttttc cacaagttac atgtgccatt ttattgcttc     300
cacgatgtgg atgtttcccc tgagggcgcg tcgttaaaag agtacatcaa taattttgcg     360
caaatggttg atgtcctggc aggcaagcaa gaagagagcg gcgtgaagct gctgtgggga     420
acggccaact gctttacaaa ccctcgctac ggcgcgggtg cggcgacgaa cccagatcct     480
gaagtcttca gctgggcggc aacgcaagtt gttacagcga tggaagcaac ccataaattg     540
ggcggtgaaa actatgtcct gtggggcggt cgtgaaggtt acgaaacgct gttaaatacc     600
gacttgcgtc aggagcgtga acaactgggc cgctttatgc agatggtggt tgagcataaa     660
```

-continued

```
cataaaatcg gtttccaggg cacgttgctt atcgaaccga aaccgcaaga accgaccaaa    720
catcaatatg attacgatgc cgcgacggtc tatggcttcc tgaaacagtt tggtctggaa    780
aaagagatta aactgaacat tgaagctaac cacgcgacgc tggcaggtca ctctttccat    840
catgaaatag ccaccgccat tgcgcttggc ctgttcggtt ctgtcgacgc caaccgtggc    900
gatgcgcaac tgggctggga caccgaccag ttcccgaaca gtgtggaaga gaatgcgctg    960
gtgatgtatg aaattctcaa agcaggcggt ttcaccaccg tggtctgaa cttcgatgcc    1020 aaagtacgtc gtcaaagtac tgataaatat gatctgtttt acggtcatat cggcgcgatg    1080
gatacgatgg cactggcgct gaaaattgca gcgcgcatga ttgaagatgg cgagctggat    1140
aaacgcatcg cgcagcgtta ttccggctgg aatagcgaat tgggccagca aatcctgaaa    1200
ggccaaatgt cactggcaga tttagccaaa tatgctcagg aacatcattt gtctccggtg    1260
catcagagtg gtcgccagga acaactggaa atctggtaa accattatct gttcgacaaa    1320
taa                                                                  1323
```

<210> SEQ ID NO 44
<211> LENGTH: 449
<212> TYPE: PRT
<213> ORGANISM: Lactobacillus brevis

<400> SEQUENCE: 44

```
Met Thr Glu Glu Tyr Trp Lys Gly Val Asp Lys Ile Gln Tyr Val Gly
 1               5                  10                  15

His Gln Asp Lys Lys Ser Gly Leu Gly Phe Gln Tyr Tyr Asn Pro Glu
            20                  25                  30

Glu Glu Ile Met Gly Lys Lys Met Lys Asp Trp Leu Arg Phe Ala Val
        35                  40                  45

Ala Tyr Trp His Thr Phe Asp Gln Arg Leu Val Asp Pro Phe Gly Asp
    50                  55                  60

Gly Thr Ala Gln Arg Pro Tyr Asp Lys Tyr Thr Asp Pro Met Asp Leu
65                  70                  75                  80

Ala Leu Ala Lys Val Asp Ala Ala Phe Glu Phe Tyr Gln Lys Leu Gly
                85                  90                  95

Val Asp Tyr Leu Cys Phe His Asp Arg Asp Leu Ala Pro Glu Gly Asp
            100                 105                 110

Thr Leu Arg Glu Thr Asn Ala Asn Leu Asp Lys Val Val Asp Lys Ile
        115                 120                 125

Val Glu Tyr Gln Lys Thr Ser Gly Met Lys Val Leu Trp Asn Thr Ser
    130                 135                 140

Asn Met Phe Thr Asn Pro Arg Phe Val Glu Gly Ala Ala Thr Ser Pro
145                 150                 155                 160

Tyr Ala Asp Val Phe Ala Tyr Ser Ala Ala Gln Leu Lys His Ser Leu
                165                 170                 175

Glu Ile Gly Lys Arg Val Gly Ser Glu Asn Tyr Val Phe Trp Gly Gly
            180                 185                 190

Arg Glu Gly Tyr Glu Ser Leu Trp Asn Thr Asn Met Lys Gln Glu Gln
        195                 200                 205

Glu His Ala Ala Lys Ile Phe His Met Ala Lys Asp Tyr Ala Asn Glu
    210                 215                 220

Ile Gly Phe Asp Ala Gln Met Leu Leu Glu Pro Lys Pro Lys Glu Pro
225                 230                 235                 240

Thr Thr His Gln Tyr Asp Phe Asp Ala Ala Thr Thr Ile Ala Phe Met
                245                 250                 255
```

```
Lys Glu Tyr Asp Leu Asp Lys Asp Phe Lys Leu Asn Leu Glu Gly Asn
                260                 265                 270

His Ala Asn Leu Ala Gly His Thr Tyr Gln His Glu Ile Arg Val Ala
            275                 280                 285

Arg Glu Ala Gly Leu Leu Gly Ser Leu Asp Ala Asn Gln Gly Asp Lys
        290                 295                 300

Leu Ile Gly Trp Asp Ile Asp Glu Tyr Pro Ser Asn Leu Tyr Glu Thr
305                 310                 315                 320

Thr Ala Ala Met Tyr Glu Val Val Glu Asn Gly Ser Ile Gly Pro Arg
                325                 330                 335

Gly Gly Leu Asn Phe Asp Ala Lys Pro Arg Arg Ser Ser Phe Ala Pro
            340                 345                 350

Glu Asp Leu Phe Leu Gly His Ile Val Gly Met Asp Ser Phe Ala Ala
        355                 360                 365

Gly Leu Arg Val Ala Ala Ala Met Lys Gln Asp Gly Phe Leu Asp Ser
    370                 375                 380

Leu Lys Ala Asp Arg Tyr Ser Ser Tyr Lys Ser Gly Val Gly Ala Asp
385                 390                 395                 400

Ile Glu Ser Gly Lys Ala Asp Leu Lys Ser Leu Glu Ala Tyr Ala Ile
                405                 410                 415

Asp Lys Pro Gln Ser Glu Leu Ile Ala Ala Thr His Ser Asp His Leu
            420                 425                 430

Glu Glu Ile Lys Asp Thr Ile Asn His Tyr Ile Ile Asp Thr Leu Ser
        435                 440                 445

Lys

<210> SEQ ID NO 45
<211> LENGTH: 1350
<212> TYPE: DNA
<213> ORGANISM: Lactobacillus brevis

<400> SEQUENCE: 45
atgactgaag aatactggaa aggcgtcgac aagattcaat acgtcggcca tcaagataag      60
aaatctggtt taggattcca atactacaac ccagaagaag agattatggg taagaaaatg     120
aaggattggt tacggtttgc cgttgcttac tggcacacct ttgaccaacg cctagttgac     180
ccattcggtg acgggaccgc gcaacgtcct tatgacaagt acaccgaccc aatggacttg     240
gctttagcca aggttgatgc tgcctttgaa ttttatcaaa aattaggggt agattacctt     300
tgcttccacg atcgtgactt agctccagaa ggtgatacgt acgcgaaaac gaacgccaac     360
ttggacaaag ttgttgacaa gatcgttgaa taccaaaaga cttctggtat gaaggttctt     420
tggaacacgt caaacatgtt cactaaccct cggttcgttg aagggctgc aacctcacca      480 tacgccgatg tctttgctta cagtgccgca caattgaagc acagtttgga aattggtaag     540
cgggttggct ctgaaaacta tgtcttctgg ggtggccgtg aaggttacga atcactctgg     600
aacaccaaca tgaagcaaga acaagaacac gcagctaaga ttttccatat ggctaaggac     660
tacgctaacg aaatcggctt cgatgctcaa atgttgctgg aaccaaagcc taaggaacca     720
acgactcacc aatatgactt tgatgccgct acgacgattg ccttcatgaa agaatacgac     780
ttggataaag acttcaaatt gaacttggaa ggtaaccacg ctaacttggc aggtcacact     840
taccaacacg aaatccgggt tgctcgtgaa gctggtttgt taggttcatt ggatgctaac     900
caaggtgata agttaattgg ctgggatatc gatgaatacc catcaaactt atacgaaacg     960
accgctgcaa tgtacgaagt tgtcgaaaac ggcagcattg gccctcgcgg tgggttgaac    1020
```

```
tttgatgcta agcctcgtcg ctcctcattt gccccagaag acctcttctt aggccacatt    1080
gttgggatgg atagctttgc tgctggactc cgggttgctg ctgcaatgaa gcaagatggc    1140
ttcttagata gcttgaaggc cgaccgttac agctcataca agtctggtgt tggtgctgat    1200
atcgaaagtg gcaaggctga cttgaagtcc cttgaagctt acgctatcga caagccacaa    1260
tcagaattga tcgcggcaac gcattctgat cacttagaag aaattaagga tacgatcaac    1320
cattacatca tcgatacgtt gagcaagtaa                                      1350
```

<210> SEQ ID NO 46
<211> LENGTH: 439
<212> TYPE: PRT
<213> ORGANISM: Thermoanaerobacterium

<400> SEQUENCE: 46

```
Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Ala Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Lys Thr Asn Lys Asn Leu Asp Thr Ile Val Ala Met Ile Lys Asp
        115                 120                 125

Tyr Leu Lys Thr Ser Lys Thr Lys Val Leu Trp Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Gly Glu Asn Tyr Val Phe Trp Gly Gly Arg Glu
            180                 185                 190

Gly Tyr Glu Thr Leu Leu Asn Thr Asp Met Glu Phe Glu Leu Lys Asn
        195                 200                 205

Phe Ala Arg Phe Leu His Met Ala Ala Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Thr Gly Asp Met Leu Leu
    290                 295                 300

Gly Trp Asp Thr Asp Gln Phe Pro Thr Asp Ile Arg Met Thr Thr Leu
305                 310                 315                 320
```

```
Ala Met Tyr Glu Val Ile Lys Met Gly Gly Phe Asp Lys Gly Gly Leu
            325                 330                 335

Asn Phe Asp Ala Lys Val Arg Arg Ala Ser Phe Glu Pro Glu Asp Leu
        340                 345                 350

Pro Leu Gly His Ile Ala Gly Met Asp Ser Leu Ala Lys Gly Phe Lys
        355                 360                 365

Val Ala Tyr Lys Leu Val Lys Asp Arg Val Phe Asp Lys Phe Ile Glu
    370                 375                 380

Glu Arg Tyr Ala Ser Tyr Lys Asp Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 47
<211> LENGTH: 1320
<212> TYPE: DNA
<213> ORGANISM: Thermoanaerobacterium

<400> SEQUENCE: 47
atgaataaat attttgagaa tgtatctaaa ataaaatatg aagggccaaa atcaaacaat      60
ccctattctt ttaaatttta caatcctgag gaagtaatcg atgccaagac gatggaagag     120
catctccgct tttctatagc ttattggcat acttttactg ctgatggaac agatcaattt     180
ggcaaagcta ccatgcaaag accatggaac cactatacag atcctatgga tatagcaaag     240
gcaagggtag aagcagcatt tgaattttt gataagataa atgcaccttt cttctgcttc      300
catgacaggg atattgcacc tgaaggagac acccttagaa aaacgaacaa aaacttagat     360
acaatagttg ccatgataaa ggactacttg aagaccagca gacgaaagt tttgtggggt      420 actgcaaatc ttttctcaaa tccgagattt gtgcatggtg catcaacatc gtgcaatgct     480
gatgttttcg catattccgc agcgcaagtc aaaaaagccc tcgagattac taaggagctt     540
ggcggcgaaa actacgtatt ctggggtgga agagaaggat atgaaacact tctcaataca     600
gacatggagt ttgagcttaa aaactttgcg agattttgc acatggctgc tgactatgca     660
aaagaaatcg gctttgaagg ccagttcttg attgagccga agccaaagga acctacaaaa     720
caccaatacg actttgatgt ggcaaatgta ttggcattct tgagaaaata cgatcttgac     780
aaatatttca agtgaatat agaggcaaac catgcaacat tggcattcca cgacttccaa     840
catgagctaa gatacgccag aataaacggc gtattaggta caattgacgc aaatacaggt     900
gatatgcttt taggatggga tacagaccag ttccctacag atatacgcat gaccacactt     960
gccatgtatg aagtcataaa gatgggggga tttgacaaag cgggccttaa cttcgatgca    1020
aaagtaagac gtgcttcatt tgagccagaa gatcttccct taggtcacat agctggaatg    1080
gattctcttg caaaaggctt caaggttgct tacaagcttg tgaaagatcg cgttttcgac    1140
aagtttatcg aggaaagata cgcaagctac aaagatggca ttggcgctga tattgtaagt    1200
ggaaaggctg acttcaagag ccttgagaag tatgcattag agcacagcca gattgtcaac    1260
aaatcaggaa gacaagagct attggagtca atcctaaatc agtatttgtt tgcagaatga    1320

<210> SEQ ID NO 48
<211> LENGTH: 439
<212> TYPE: PRT
```

<213> ORGANISM: Clostridium thermosulfurogenes

<400> SEQUENCE: 48

Met Asn Lys Tyr Phe Glu Asn Val Ser

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 49
<211> LENGTH: 1320
<212> TYPE: DNA
<213> ORGANISM: Clostridium thermosulfurogenes

<400> SEQUENCE: 49

```
atgaataaat attttgagaa cgtatctaaa ataaaatatg aaggaccaaa atcaaacaat      60
cctattctt ttaaatttta caatcctgag gaagtaatcg atggtaagac gatggaggag     120
catcttcgct tttctatagc ttattggcac acttttactg ctgatggaac agatcaattt     180
ggcaaagcta ccatgcaaag gccatggaat cactatacag atcctatgga catagctaaa     240
gcaagggtag aggcagcatt tgagttttt gataagataa atgcaccgta tttctgcttc     300
catgatagag atattgcccc tgaaggagac actcttagag agacgaacaa aaatttagat     360
acaatagttg ctatgataaa ggattacttg aagaccagca gacgaaagt tttgtggggt     420
actgcgaatc ttttctccaa tccaagattt gtgcatggtg catcaacgtc ttgcaatgcc     480
gatgttttcg catattctgc agcgcaagtc aaaaaagcac ttgagattac taaggagctt     540
ggtggcgaaa actacgtatt ctggggtgga agagaaggat atgagacact tctcaataca     600
gatatggagt ttgagcttga taattttgca agatttttgc acatggctgt tgattatgca     660
aaggaaatcg gctttgaagg ccagttcttg attgagccga agccaaagga gcctacaaag     720
catcaatacg actttgacgt ggcaaatgta ttggcattct tgagaaaata cgatcttgac     780
aaatatttca agttaatat cgaagcaaat catgcaacat tagcattcca tgatttccag     840
catgagctaa gatacgccag aataaacggt gtattaggat cgattgacgc aaatacgggt     900
gatatgctat taggatggga tacagatcag ttccctacag atatacgcat gacaacactt     960
gctatgtatg aagttataaa gatgggtgga tttgacaaag gcggactcaa cttcgatgcg    1020
aaagtaagac gtgcttcatt tgagccagaa gatcttttct ggggtcacat agcaggaatg    1080
gatgcttttg caaaggctt caaagtggct tacaagcttg taaaagatag ggtatttgac    1140
aagttcatcg aagaaagata tgcaagctac aaagatggca taggtgcaga tattgtaagt    1200
gggaaagctg attttagaag tcttgaaaag tatgcattag agcgcagcca gattgtcaac    1260
aaatcaggaa gacaagagct attagagtca atcctaaatc agtatttgtt tgcagaataa    1320
```

<210> SEQ ID NO 50
<211> LENGTH: 394
<212> TYPE: PRT
<213> ORGANISM: Actinoplanes missouriensis

<400> SEQUENCE: 50

Met Ser Val Gln Ala Thr Arg Glu Asp Lys Phe Ser Phe Gly Leu Trp
1               5                   10                  15

Thr Val Gly Trp Gln Ala Arg Asp Ala Phe Gly Asp Ala Thr Arg Thr
            20                  25                  30

Ala Leu Asp Pro Val Glu Ala Val His Lys Leu Ala Glu Ile Gly Ala
        35                  40                  45

Tyr Gly Ile Thr Phe His Asp Asp Asp Leu Val Pro Phe Gly Ser Asp
    50                  55                  60

```
Ala Gln Thr Arg Asp Gly Ile Ile Ala Gly Phe Lys Lys Ala Leu Asp
 65                  70                  75                  80

Glu Thr Gly Leu Ile Val Pro Met Val Thr Thr Asn Leu Phe Thr His
                 85                  90                  95

Pro Val Phe Lys Asp Gly Gly Phe Thr Ser Asn Asp Arg Ser Val Arg
            100                 105                 110

Arg Tyr Ala Ile Arg Lys Val Leu Arg Gln Met Asp Leu Gly Ala Glu
        115                 120                 125

Leu Gly Ala Lys Thr Leu Val Leu Trp Gly Gly Arg Glu Gly Ala Glu
130                 135                 140

Tyr Asp Ser Ala Lys Asp Val Ser Ala Ala Leu Asp Arg Tyr Arg Glu
145                 150                 155                 160

Ala Leu Asn Leu Leu Ala Gln Tyr Ser Glu Asp Arg Gly Tyr Gly Leu
                165                 170                 175

Arg Phe Ala Ile Glu Pro Lys Pro Asn Glu Pro Arg Gly Asp Ile Leu
            180                 185                 190

Leu Pro Thr Ala Gly His Ala Ile Ala Phe Val Gln Glu Leu Glu Arg
        195                 200                 205

Pro Glu Leu Phe Gly Ile Asn Pro Glu Thr Gly His Glu Gln Met Ser
210                 215                 220

Asn Leu Asn Phe Thr Gln Gly Ile Ala Gln Ala Leu Trp His Lys Lys
225                 230                 235                 240

Leu Phe His Ile Asp Leu Asn Gly Gln His Gly Pro Lys Phe Asp Gln
                245                 250                 255

Asp Leu Val Phe Gly His Gly Asp Leu Leu Asn Ala Phe Ser Leu Val
            260                 265                 270

Asp Leu Leu Glu Asn Gly Pro Asp Gly Ala Pro Ala Tyr Asp Gly Pro
        275                 280                 285

Arg Asn Phe Asp Tyr Lys Pro Ser Arg Thr Glu Asp Tyr Asp Gly Val
290                 295                 300

Trp Glu Ser Ala Lys Ala Asn Ile Arg Met Tyr Leu Leu Leu Lys Glu
305                 310                 315                 320

Arg Ala Lys Ala Phe Arg Ala Asp Pro Glu Val Gln Glu Ala Leu Ala
                325                 330                 335

Ala Ser Lys Val Ala Glu Leu Lys Thr Pro Thr Leu Asn Pro Gly Glu
            340                 345                 350

Gly Tyr Ala Glu Leu Leu Ala Asp Arg Ser Ala Phe Glu Asp Tyr Asp
        355                 360                 365

Ala Asp Ala Val Gly Ala Lys Gly Phe Gly Phe Val Lys Leu Asn Gln
370                 375                 380

Leu Ala Ile Glu His Leu Leu Gly Ala Arg
385                 390

<210> SEQ ID NO 51
<211> LENGTH: 1185
<212> TYPE: DNA
<213> ORGANISM: Actinoplanes missouriensis

<400> SEQUENCE: 51
gtgtctgtcc aggccacacg cgaagacaag ttctccttcg gtctctggac cgttggatgg     60
caggctcgtg acgcgttcgg tgacgccacg cgtacggcac tcgacccggt cgaggccgtg    120
cacaagctcg ctgagatcgg cgcctacggc atcacgttcc acgacgacga cctggtgccc    180
ttcggctcgg acgcccagac ccgcgacggc atcatcgcgg gcttcaagaa ggcgctcgac    240
gagaccggcc tgatcgtccc gatggtgacc accaacctct tcacccaccc ggtgttcaag    300
```

```
gacggcggct tcaccagcaa cgaccgttcc gtgcggcgct acgcgatccg caaggtgctg      360
cgccagatgg acctcggcgc cgagctgggc gcgaagacgc tcgtcctctg gggcggccgc      420
gagggcgccg agtacgactc ggccaaggac gtcagcgccg ccctcgaccg ctaccgcgag      480
gcgctcaacc tgctcgcgca gtactccgag gaccgcggtt acggcctgcg cttcgccatc      540
gagccgaagc cgaacgagcc ccgcggcgac atcctgctcc cgaccgccgg ccacgccatc      600
gcgttcgtgc aggagctgga gcgtcccgag ctcttcggca tcaacccgga gaccgggcac      660
gagcagatgt cgaaccctca cttcacccag ggcatcgccc aggcgctgtg cacaagaag       720 ctgttccaca tcgacctgaa cggtcagcac ggcccgaagt cgaccagga cctggtcttc       780 ggccacggtg acctgctcaa cgcgttctcg ctggtcgacc tcctggagaa cggtccggac      840
ggcgccccgg cgtacgacgg accccgtcac ttcgactaca agccgtcccg taccgaggac      900
tacgacggcg tctgggagtc ggcgaaggcc aacatccgga tgtacctgct gctcaaggag      960
cgggccaagg cgttccgcgc cgaccccgag gtgcaggagg cgctcgccgc cagcaaggtc      1020
gcggagctga agaccccgac cctgaacccg ggcgagggat acgccgagct gctcgccgac      1080
cgcagcgcgt tcgaggacta cgacgccgac gccgtgggcg ccaagggctt cggcttcgtc      1140
aagctgaacc agctcgcgat cgagcacctg ctcggagccc gctga                     1185

<210> SEQ ID NO 52
<211> LENGTH: 395
<212> TYPE: PRT
<213> ORGANISM: Arthrobacter strain B3728

<400> SEQUENCE: 52

Met Ser Val Gln Pro Thr Pro Ala Asp His Phe Thr Phe Gly Leu Trp
1               5                   10                  15

Thr Val Gly Trp Thr Gly Ala Asp Pro Phe Gly Val Ala Thr Arg Ala
            20                  25                  30

Asn Leu Asp Pro Val Glu Ala Val His Lys Leu Ala Glu Leu Gly Ala
        35                  40                  45

Tyr Gly Ile Thr Phe His Asp Asn Asp Leu Ile Pro Phe Asp Ala Thr
    50                  55                  60

Ala Ala Glu Arg Glu Lys Ile Leu Gly Asp Phe Asn Gln Ala Leu Ala
65                  70                  75                  80

Asp Thr Gly Leu Lys Val Pro Met Val Thr Thr Asn Leu Phe Ser His
                85                  90                  95

Pro Val Phe Lys Asp Gly Gly Phe Thr Ser Asn Asp Arg Ser Ile Arg
            100                 105                 110

Arg Phe Ala Leu Ala Lys Val Leu His Asn Ile Asp Leu Ala Ala Glu
        115                 120                 125

Met Gly Ala Glu Thr Phe Val Met Trp Gly Gly Arg Glu Gly Ser Glu
    130                 135                 140

Tyr Asp Gly Ser Lys Asp Leu Ala Ala Ala Leu Asp Arg Met Arg Glu
145                 150                 155                 160

Gly Val Asp Thr Ala Ala Gly Tyr Ile Lys Asp Lys Gly Tyr Asn Leu
                165                 170                 175

Arg Ile Ala Leu Glu Pro Lys Pro Asn Glu Pro Arg Gly Asp Ile Phe
            180                 185                 190

Leu Pro Thr Val Gly His Gly Leu Ala Phe Ile Glu Gln Leu Glu His
        195                 200                 205

Gly Asp Ile Val Gly Leu Asn Pro Glu Thr Gly His Glu Gln Met Ala
    210                 215                 220
```

```
Gly Leu Asn Phe Thr His Gly Ile Ala Gln Ala Leu Trp Ala Glu Lys
225                 230                 235                 240

Leu Phe His Ile Asp Leu Asn Gly Gln Arg Gly Ile Lys Tyr Asp Gln
            245                 250                 255

Asp Leu Val Phe Gly His Gly Asp Leu Thr Ser Ala Phe Phe Thr Val
        260                 265                 270

Asp Leu Leu Glu Asn Gly Phe Pro Asn Gly Gly Pro Lys Tyr Thr Gly
    275                 280                 285

Pro Arg His Phe Asp Tyr Lys Pro Ser Arg Thr Asp Gly Tyr Asp Gly
290                 295                 300

Val Trp Asp Ser Ala Lys Ala Asn Met Ser Met Tyr Leu Leu Leu Lys
305                 310                 315                 320

Glu Arg Ala Leu Ala Phe Arg Ala Asp Pro Glu Val Gln Glu Ala Met
                325                 330                 335

Lys Thr Ser Gly Val Phe Glu Leu Gly Glu Thr Thr Leu Asn Ala Gly
            340                 345                 350

Glu Ser Ala Ala Asp Leu Met Asn Asp Ser Ala Ser Phe Ala Gly Phe
        355                 360                 365

Asp Ala Glu Ala Ala Ala Glu Arg Asn Phe Ala Phe Ile Arg Leu Asn
    370                 375                 380

Gln Leu Ala Ile Glu His Leu Leu Gly Ser Arg
385                 390                 395

<210> SEQ ID NO 53
<211> LENGTH: 1188
<212> TYPE: DNA
<213> ORGANISM: Arthrobacter strain B3728

<400> SEQUENCE: 53
atgagcgttc agccgacccc tgcagaccac ttcacctttg gcctctggac cgtaggatgg      60
accggcgccg acccattcgg tgtcgccacc cgcaagaacc tggacccggt agaagccgtc     120
cacaagctgg ccgagctcgg cgcctacggc atcaccttcc acgacaatga cctgattcct     180
tttgacgcca ccgaggcaga gcgcgaaaag atccttggtg acttcaacca ggcgctgaag     240
gacaccggcc tgaaggtccc aatggtgacc accaacctgt tcagccaccc ggtcttcaag     300
gacggcggct tcacctctaa cgaccgctcg atccgtcgtt ttgcactggc taaggtcctg     360
cacaacatcg acttggcagc cgagatgggc gccgaaacct tcgtcatgtg ggcggcgc      420
gaaggcagcg aatacgacgg ttccaaggac ctggccgcag cacttgatcg catgcgcgaa     480
ggcgtggaca cggcagctgg ctacatcaag gacaagggtt acaacctgcg catcgcgctg     540
gagccaaagc caaatgaacc acgcggcgac atcttcctgc ctaccgtcgg ccacggcctg     600
gccttcatcg agcagctgga gcacggcgac atcgtcggcc tgaacccaga aaccggccac     660
gagcagatgg ccggcctgaa cttcacccac ggcatcgctc aggcactgtg ggccgagaag     720
ctgttccaca ttgacctcaa cggccagcgc ggcatcaagt acgaccagga cctggtcttc     780
ggccacggcg atctgaccag cgcgttcttc accgtagacc tgctggaaaa cggcttccct     840
aacggcggac aaagtacac cggcccacgc cacttcgact acaagccatc gcgcaccgac     900
ggctacgacg gcgtgtggga ctcggccaag gccaacatgt ccatgtacct gctgctcaag     960
gaacgtgccc tggccttccg tgcggatcca gaggtacagg aagccatgaa gacctcgggc    1020
gtcttcgaac tgggcgaaac cacccctgaac gccggggaaa gcgcagcgga tctgatgaat    1080
gattccgcga gcttcgcagg ctttgacgcc gaggccgccg cagagcgcaa cttcgcgttc    1140
```
atccgcctga accagctggc catcgagcac ctgctcggct cccgctaa         1188

<210> SEQ ID NO 54
<211> LENGTH: 448
<212> TYPE: PRT
<213> ORGANISM: Bacillus licheniformis

<400> SEQUENCE: 54

```
Met Phe Phe Arg Asn Ile Gly Met Ile Glu Tyr Glu Gly Ala Asp Ser
1               5                   10                  15

Glu Asn Pro Tyr Ala Phe Lys Tyr Tyr Asn Pro Asp Glu Phe Val Gly
            20                  25                  30

Gly Lys Thr Met Lys Glu His Leu Arg Phe Ala Val Ala Tyr Trp His
        35                  40                  45

Thr Phe Asp Ala Asp Gly Lys Asp Pro Phe Gly Asp Gly Thr Met Phe
    50                  55                  60

Arg Ala Trp Asn Arg Leu Thr His Pro Leu Asp Lys Ala Lys Ala Arg
65                  70                  75                  80

Ala Glu Ala Ala Phe Glu Phe Glu Lys Leu Gly Val Pro Tyr Phe
                85                  90                  95

Cys Phe His Asp Val Asp Ile Val Asp Glu Gly Ala Thr Leu Arg Glu
            100                 105                 110

Thr Phe Thr Tyr Leu Asp Gln Met Ser Ser Phe Leu Lys Glu Met Met
        115                 120                 125

Glu Thr Ser His Val Gln Leu Leu Trp Asn Thr Ala Asn Met Phe Thr
    130                 135                 140

His Pro Arg Tyr Val His Gly Ala Ala Thr Ser Cys Asn Ala Asp Val
145                 150                 155                 160

Tyr Ala Tyr Ala Ala Lys Val Lys Lys Gly Leu Asp Ile Ala Lys
                165                 170                 175

Glu Leu Gly Ala Glu Asn Tyr Val Phe Trp Gly Gly Arg Glu Gly Tyr
            180                 185                 190

Glu Thr Leu Leu Asn Thr Asp Met Lys Leu Glu Leu Glu Asn Leu Ser
        195                 200                 205

Ser Phe Tyr Arg Met Ala Val Glu Tyr Ala Arg Glu Ile Gly Phe Asp
    210                 215                 220

Gly Gln Phe Leu Ile Glu Pro Lys Pro Lys Glu Pro Thr Lys His Gln
225                 230                 235                 240

Tyr Asp Phe Asp Ala Ala Thr Thr Ile Ala Phe Leu Glu Thr Tyr Gly
                245                 250                 255

Leu Lys Asp His Phe Lys Leu Asn Leu Glu Ala Asn His Ala Thr Leu
            260                 265                 270

Ala Gly His Thr Phe Glu His Glu Leu Arg Val Ala Ala Leu His Asp
        275                 280                 285

Met Leu Gly Ser Ile Asp Ala Asn Gln Gly Asp Leu Leu Leu Gly Trp
    290                 295                 300

Asp Thr Asp Glu Phe Pro Thr Asp Leu Tyr Ser Ala Val Leu Ala Met
305                 310                 315                 320

Tyr Glu Ile Leu Lys Ala Gly Gly Phe Lys Thr Gly Gly Ile Asn Phe
                325                 330                 335

Asp Ala Lys Val Arg Arg Pro Ser Phe Ala Glu Asp Leu Phe His
            340                 345                 350

Ala His Ile Ala Gly Met Asp Thr Tyr Ala Val Gly Leu Lys Val Ala
        355                 360                 365

Ser Arg Leu Leu Glu Asp Lys Ala Leu Asp Gln Val Ile Glu Glu Arg
```

```
           370              375                 380
Tyr Glu Ser Tyr Thr Lys Gly Ile Gly Leu Glu Ile Lys Glu Gly Arg
385                 390                 395                 400

Thr Asp Leu Lys Lys Leu Ala Ala Tyr Ala Leu Glu Asn Asp His Ile
                405                 410                 415

Glu Asn Gln Ser Gly Arg Gln Glu Arg Leu Lys Ala Thr Val Asn Arg
            420                 425                 430

Tyr Leu Leu Asn Ala Leu Arg Glu Ala Pro Ala Gly Lys Glu Thr His
        435                 440                 445

<210> SEQ ID NO 55
<211> LENGTH: 1347
<212> TYPE: DNA
<213> ORGANISM: Bacillus licheniformis

<400> SEQUENCE: 55 atgttttta gaaatatcgg aatgattgag tatgaagggg ccgattcgga aaatccttac      60
gcatttaaat attacaaccc tgatgaattt gtcggcggca aaacgatgaa ggaacacctt     120
cgcttcgctg ttgcgtattg cataccttt gatgcgacg ggaaagaccc tttcggcgac      180
gggacgatgt tccgggcgtg gaaccggctg acacatcctt tggataaagc gaaagccagg    240
gcggaagcgg cttttgaatt ttttgaaaag ctcggcgtgc cctatttctg ttttcatgat    300
gttgatattg tcgatgaagg agcaacattg cgtgaaactt tcacgtattt ggatcaaatg    360
tcgtcttttc tcaaagaaat gatggagaca agccatgttc agctgctttg gaatacagcc    420
aatatgttta cgcatccgag atatgtccac ggggccgcaa cttcttgcaa tgcagacgtc    480
tatgcctatg cagctgcaaa agtgaaaaaa ggcctggaca tcgccaaaga gcttggagcg    540
gaaaactatg tgttctgggg cggaagagaa ggttatgaaa cattgctgaa tacagatatg    600
aagcttgagc tcgaaaactt gtcttcattt tatagaatgg cagttgagta tgcgcgtgaa    660
atcggttttg acggccaatt tttaatcgag ccgaagccga aggagccgac gaagcaccaa    720
tacgattttg atgcagccac aacgatcgct tttttagaaa cttacggttt aaaagaccat    780
tttaaactta atcttgaggc gaaccatgcg acattgccg gcatacatt tgagcatgaa      840 ctaagggtgg ctgccttgca cgatatgctg ggttccattg atgccaacca gggcgatttg    900
ctcttgggct gggataccga tgagtttccg accgatctgt attctgcggt tctggcgatg    960
tatgaaattt tgaaagcagg cgggtttaaa accggcggca tcaacttcga tgctaaagta   1020
aggcgcccgt catttgccga tgaggacttg tttcacgctc atatcgcagg aatggatacg   1080
tatgcagtcg gcttgaaagt cgcctcccgt ctgcttgaag ataaagcgct cgatcaggtt   1140
atcgaagaac gttatgagag ctatacgaaa ggcatcgggc ttgaaatcaa agaaggccgc   1200
accgatctga aaaagctcgc cgcttacgct cttgaaaacg accatattga aaatcagtca   1260
ggccgccaag aacggctgaa ggcgaccgtt aaccgttact tattgaacgc tttgcgcgaa   1320
gcgccggcag gaaaggagac acactag                                       1347

<210> SEQ ID NO 56
<211> LENGTH: 441
<212> TYPE: PRT
<213> ORGANISM: Geobacillus sterothermophilus

<400> SEQUENCE: 56

Met Pro Tyr Phe Asp Asn Ile Ser Thr Ile Ala Tyr Glu Gly Pro Ala
1               5                   10                  15

Ser Lys Asn Pro Leu Ala Phe Lys Phe Tyr Asn Pro Glu Glu Lys Val
```

-continued

```
                    20                  25                  30
Gly Asp Lys Thr Met Glu Glu His Leu Arg Phe Ser Val Ala Tyr Trp
                35                  40                  45
His Thr Phe Thr Gly Asp Gly Ser Asp Pro Phe Gly Ala Gly Asn Met
                50                  55                  60
Ile Arg Pro Trp Asn Lys Tyr Ser Gly Met Asp Leu Ala Lys Ala Arg
 65                  70                  75                  80
Val Glu Ala Ala Phe Glu Phe Phe Glu Lys Leu Asn Ile Pro Phe Phe
                    85                  90                  95
Cys Phe His Asp Val Asp Ile Ala Pro Glu Gly Glu Thr Leu Lys Glu
                100                 105                 110
Thr Tyr Lys Asn Leu Asp Ile Ile Val Asp Met Ile Glu Glu Tyr Met
                115                 120                 125
Lys Thr Ser Lys Thr Lys Leu Leu Trp Asn Thr Ala Asn Leu Phe Thr
                130                 135                 140
His Pro Arg Phe Val His Gly Ala Ala Thr Ser Cys Asn Ala Asp Val
145                 150                 155                 160
Phe Ala Tyr Ala Ala Lys Val Lys Lys Gly Leu Glu Ile Ala Lys
                165                 170                 175
Arg Leu Gly Ala Glu Asn Tyr Val Phe Trp Gly Gly Arg Glu Gly Tyr
                180                 185                 190
Glu Thr Leu Leu Asn Thr Asp Met Lys Leu Glu Leu Asp Asn Leu Ala
                195                 200                 205
Arg Phe Leu His Met Ala Val Asp Tyr Ala Lys Glu Ile Gly Phe Asp
                210                 215                 220
Gly Gln Phe Leu Ile Glu Pro Lys Pro Lys Glu Pro Thr Lys His Gln
225                 230                 235                 240
Tyr Asp Phe Asp Val Ala Thr Arg Leu Ala Phe Leu Gln Thr Tyr Gly
                245                 250                 255
Leu Lys Asp Tyr Phe Lys Phe Asn Ile Glu Ala Asn His Ala Thr Leu
                260                 265                 270
Ala Gly His Thr Phe Glu His Glu Leu Arg Val Ala Arg Ile His Gly
                275                 280                 285
Met Leu Gly Ser Val Asp Ala Asn Gln Gly Asp Met Leu Leu Gly Trp
                290                 295                 300
Asp Thr Asp Glu Phe Pro Thr Asp Leu Tyr Ser Thr Thr Leu Ala Met
305                 310                 315                 320
Tyr Glu Ile Leu Lys Asn Gly Gly Leu Gly Arg Gly Gly Leu Asn Phe
                325                 330                 335
Asp Ala Lys Val Arg Arg Gly Ser Phe Glu Pro Glu Asp Leu Phe Tyr
                340                 345                 350
Ala His Ile Ala Gly Met Asp Ser Phe Ala Val Gly Leu Lys Val Ala
                355                 360                 365
His Arg Leu Ile Glu Asp Arg Val Phe Asp Phe Ile Glu Glu Arg
                370                 375                 380
Tyr Lys Ser Tyr Thr Glu Gly Ile Gly Arg Glu Ile Val Glu Gly Thr
385                 390                 395                 400
Ala Asp Phe His Lys Leu Glu Ala His Ala Leu Gln Leu Gly Glu Ile
                405                 410                 415
Gln Asn Gln Ser Gly Arg Gln Glu Arg Leu Lys Thr Leu Leu Asn Gln
                420                 425                 430
Tyr Leu Leu Glu Val Cys Ala Ala Arg
                435                 440
```

<210> SEQ ID NO 57
<211> LENGTH: 1326
<212> TYPE: DNA
<213> ORGANISM: Geobacillus stearothermophilus

<400> SEQUENCE: 57

```
atgccttatt ttgacaacat cagcaccatc gcctatgaag gaccggcgtc taaaaatccg      60
cttgcgttta gtttttacaa tccggaagaa aaagtcggcg ataaaacaat ggaagagcat     120
ttgcgttttt cggttgcgta ttggcatacg tttacaggag atggatcaga tccgtttggg     180
gctggcaata tgatccgtcc atggaacaaa tacagcggaa tggatttggc caaagcgcgt     240
gttgaagctg cttttgagtt ttttgaaaaa ttaaatattc cattttctg tttccatgat      300
gtggatattg ccccagaagg agaaacatta aagaaacat ataaaaattt agatattatc      360
gtagacatga ttgaggaata tgaaaaaca agcaaaacga agctgctttg aatacggcg       420
aacttattta cccatcctcg cttttgtccat ggcgccgcca cttcttgcaa cgccgatgtt     480
tttgcctatg cagcggccaa agtaaaaaaa gggttggaaa ttgcgaagcg gctaggagcg     540
gaaaactacg tattttgggg cggacgagaa gggtatgaaa cactattaaa taccgatatg     600
aaacttgagc tggacaactt ggcccgcttc ttgcatatgg cggtggatta tgcgaaagaa     660
atcgggtttg acgggcaatt tttaattgag ccgaagccga aagagccgac gaaacaccaa     720
tatgactttg atgttgcgac acgattggca tttttgcaaa catacggact gaaagattac     780
tttaagttca atattgaagc gaaccatgca acgctggcgg acatacgtt tgaacatgaa      840
ttgcgggtag cgcgcattca tggcatgtta ggctctgttg acgcaaacca aggagatatg     900
ttgttaggat gggatacgga cgaattcccg acagacttat attctacgac tttggcaatg     960
tatgaaattt tgaaaaacgg cggccttggc cgtggcggtt tgaattttga tgcgaaagta    1020
agaagaggat cgtttgagcc ggaagatttg ttctatgccc atatcgccgg aatggacagt    1080
tttgcggttg gattaaaagt agcccatcgg ttaatagaag accgcgtttt tgatgagttt    1140
attgaagaac ggtacaaaag ttatacagaa ggaattggcc gggaaatcgt cgaaggaacg    1200
gcagatttcc acaaattaga agcacatgct ttacaactag gggaaatcca aaatcaatcg    1260
ggcagacaag aacggctgaa acattgctt aaccaatatt tgcttgaagt ttgcgcagcc    1320
cgttaa                                                               1326
```

<210> SEQ ID NO 58
<211> LENGTH: 445
<212> TYPE: PRT
<213> ORGANISM: Bacillus coagulans

<400> SEQUENCE: 58

```
Met Met Ala Tyr Phe Pro Asn Val Ser Lys Ile Thr Tyr Ser Gly Lys
1               5                   10                  15
Gln Leu Lys Ser Gly Leu Ser Phe Asn His Tyr Asn Pro Lys Glu Leu
            20                  25                  30
Val Gly Gly Lys Thr Met Glu Glu Gln Leu Arg Phe Ser Val Ala Phe
        35                  40                  45
Trp His Thr Phe Thr Glu Ser Gly Thr Asp Pro Phe Gly Ala Gly Ser
    50                  55                  60
Lys Ile Arg Pro Trp Asp Arg Phe Thr Gly Met Asp Leu Ala Lys Ala
65                  70                  75                  80
Arg Val Glu Ala Ala Phe Glu Phe Phe Glu Lys Leu Gly Asn Pro Tyr
                85                  90                  95
```

```
Phe Cys Phe His Asp Arg Asp Ile Ala Pro Glu Gly Asp Thr Leu Arg
            100                 105                 110

Glu Thr Asn Lys Asn Leu Asp Val Ile Val Ala Met Ile Lys Asp Tyr
        115                 120                 125

Met Lys Thr Ser Lys Val Lys Leu Leu Trp Asn Thr Ala Asn Met Phe
130                 135                 140

Thr Asn Pro Arg Phe Val His Gly Ala Ala Ser Ser Cys Asn Ala Asp
145                 150                 155                 160

Val Phe Ala Tyr Ala Ala Ala Gln Val Lys Lys Gly Leu Glu Val Gly
                165                 170                 175

Lys Glu Leu Gly Ala Glu Asn Tyr Val Phe Trp Gly Arg Glu Gly
            180                 185                 190

Tyr Glu Thr Leu Leu Asn Thr Asp Leu Lys Leu Glu Gln Asp Asn Leu
        195                 200                 205

Ala Arg Phe Phe His Met Ala Val Asp Tyr Ala Lys Glu Ile Gly Phe
    210                 215                 220

Asp Ala Gln Phe Leu Leu Glu Pro Lys Pro Lys Glu Pro Thr Lys His
225                 230                 235                 240

Gln Tyr Asp Phe Asp Ala Ala Thr Thr Ile Ala Phe Leu Lys Thr Tyr
                245                 250                 255

Asp Leu Asp Gln His Phe Lys Leu Asn Leu Glu Ala Asn His Ala Thr
            260                 265                 270

Leu Ala Gly His Thr Phe Glu His Glu Ile Arg Val Ala Arg Thr His
        275                 280                 285

Gly Leu Leu Gly Ser Leu Asp Ala Asn Gln Gly Asp Pro Leu Leu Gly
    290                 295                 300

Trp Asp Thr Asp Glu Phe Pro Thr Asp Leu Tyr Ser Thr Thr Leu Ala
305                 310                 315                 320

Met Tyr Glu Val Leu Lys Asn Gly Gly Leu Gly Arg Gly Gly Leu Asn
                325                 330                 335

Phe Asp Ala Lys Thr Arg Arg Ala Ser Phe Thr Asp Glu Asp Leu Phe
            340                 345                 350

Tyr Ala His Ile Ala Gly Met Asp Ser Phe Ala Leu Gly Leu Lys Val
        355                 360                 365

Ala Asn Arg Leu Ile Glu Asp Arg Val Phe Asp Ala Phe Ile Glu Glu
    370                 375                 380

Arg Tyr Ser Ser Tyr Lys Glu Gly Ile Gly Ala Asp Ile Val Ser Gly
385                 390                 395                 400

Lys Ala Asp Phe Lys Ser Leu Glu Asn Tyr Ile Leu Asp Lys Lys Glu
                405                 410                 415

Ile Ile Asn Gln Ser Gly Arg Leu Glu Gln Leu Lys Asn Thr Leu Asn
            420                 425                 430

His Tyr Ile Val Gln Glu Ala Tyr Gln Ser Val Asn Ala
        435                 440                 445

<210> SEQ ID NO 59
<211> LENGTH: 1338
<212> TYPE: DNA
<213> ORGANISM: Bacillus coagulans

<400> SEQUENCE: 59
atgatggcat attttccaaa tgtcagcaaa atcacttatt ctggcaaaca attgaaaagc      60
ggtctttcat ttaatcatta caatccgaaa gaactcgttg gtggaaaaac gatggaagaa     120
cagcttcgat tctcagtcgc attctggcac acctttactg aaagcggtac cgatccgttt     180
```

```
ggcgcaggct ccaagatccg cccgtgggat cgcttcacag gcatggatct tgccaaagca    240
agagtagaag cagcatttga atttttgaa aaactaggta acccttattt ctgctttcat    300
gaccgcgata ttgctcctga aggcgataca ttaagggaaa caaataaaaa tctggacgtc    360
atcgttgcca tgattaaaga ttatatgaaa acaagcaaag taaaactctt atggaataca    420
gccaatatgt tcacaaatcc acgttttgtc cacggtgcag ctagctcttg caacgcagat    480
gttttcgcgt acgcagccgc ccaagtgaaa aagggcttg aagtcgggaa agaactgggc    540
gctgaaaact atgtattttg gggcggccgg gaaggctatg aaactttgtt aaatacagat    600
ttgaagctgg aacaggacaa cctggcacgg ttcttccata tggccgttga ttacgcgaaa    660
gaaatcggat ttgatgctca gttcttgctt gagccgaaac cgaagaacc gacaaaacat    720
caatatgatt ttgatgctgc tacgactatt gcattcttaa aaacttacga tttggatcaa    780
cacttcaagc tgaatcttga agcaaatcat gccactttgg ccggccatac gtttgaacat    840
gaaatccggg ttgcgcgtac ccacggcttg cttggctctt tggatgcgaa ccagggtgat    900
ccgctgctcg gctgggatac agatgaattc ccgacagatc tctattccac cacgcttgcg    960
atgtatgaag tattgaaaaa cggcggcctt ggcaggggcg gattgaactt tgatgcgaaa   1020
acacgccgcg cctcgttcac agatgaagat ctgtttatg cccatattgc cggtatggac   1080
agctttgccc ttggattaaa agtagcgaac cggctgattg aagaccgggt atttgatgcc   1140
tttatcgaag aacggtacag cagttataaa gaaggcatcg gcgccgatat cgtttccggc   1200
aaagctgatt ttaaatcact tgaaaattat attcttgata aaaagaaat tataaaccaa   1260
tctggccgcc tggaacaact gaaaaatacg ctgaaccatt atattgtgca agaagcctat   1320
caaagtgtaa atgcataa                                                1338

<210> SEQ ID NO 60
<211> LENGTH: 445
<212> TYPE: PRT
<213> ORGANISM: Bacillus subtilis

<400> SEQUENCE: 60

Met Ala Gln Ser His Ser Ser Ser Ile Asn Tyr Phe Gly Ser Ala Asn
1               5                   10                  15

Lys Val Val Tyr Glu Gly Lys Asp Ser Thr Asn Pro Leu Ala Phe Lys
            20                  25                  30

Tyr Tyr Asn Pro Gln Glu Val Ile Gly Gly Lys Thr Leu Lys Glu His
        35                  40                  45

Leu Arg Phe Ser Ile Ala Tyr Trp His Thr Phe Thr Ala Asp Gly Thr
    50                  55                  60

Asp Val Phe Gly Ala Ala Thr Met Gln Arg Pro Trp Asp His Tyr Lys
65                  70                  75                  80

Gly Met Asp Leu Ala Lys Met Arg Val Glu Ala Ala Phe Glu Met Phe
                85                  90                  95

Glu Lys Leu Asp Ala Pro Phe Phe Ala Phe His Asp Arg Asp Ile Ala
            100                 105                 110

Pro Glu Gly Ser Thr Leu Lys Glu Thr Asn Gln Asn Leu Asp Met Ile
        115                 120                 125

Met Gly Met Ile Lys Asp Tyr Met Arg Asn Ser Gly Val Lys Leu Leu
    130                 135                 140

Trp Asn Thr Ala Asn Met Phe Thr Asn Pro Arg Phe Val His Gly Ala
145                 150                 155                 160

Ala Thr Ser Cys Asn Ala Asp Val Phe Ala Tyr Ala Ala Ala Gln Val
                165                 170                 175
```

```
Lys Lys Gly Leu Glu Thr Ala Lys Glu Leu Gly Ala Glu Asn Tyr Val
            180                 185                 190
Phe Trp Gly Gly Arg Glu Gly Tyr Glu Thr Leu Leu Asn Thr Asp Leu
            195                 200                 205
Lys Phe Glu Leu Asp Asp Leu Ala Arg Phe Met His Met Ala Val Asp
210                 215                 220
Tyr Ala Lys Glu Ile Gly Tyr Thr Gly Gln Phe Leu Ile Glu Pro Lys
225                 230                 235                 240
Pro Lys Glu Pro Thr Ala His Gln Tyr Asp Thr Asp Ala Ala Thr Thr
            245                 250                 255
Ile Ala Phe Leu Lys Gln Tyr Gly Leu Asp Asn His Phe Lys Leu Asn
            260                 265                 270
Leu Glu Ala Asn His Ala Thr Leu Ala Gly His Thr Phe Glu His Glu
            275                 280                 285
Leu Arg Met Ala Arg Val His Gly Leu Leu Gly Ser Val Asp Ala Asn
            290                 295                 300
Gln Gly His Pro Leu Leu Gly Trp Asp Thr Asp Glu Phe Pro Thr Asp
305                 310                 315                 320
Leu Tyr Ser Thr Thr Leu Ala Met Tyr Glu Ile Leu Gln Asn Gly Gly
            325                 330                 335
Leu Gly Ser Gly Gly Leu Asn Phe Asp Ala Lys Val Arg Arg Ser Ser
            340                 345                 350
Phe Glu Pro Asp Asp Leu Ile Tyr Ala His Ile Ala Gly Met Asp Ala
            355                 360                 365
Phe Ala Arg Gly Leu Lys Val Ala His Lys Leu Ile Glu Asp Arg Val
            370                 375                 380
Phe Glu Asp Val Ile Gln His Arg Tyr Arg Ser Phe Thr Glu Gly Ile
385                 390                 395                 400
Gly Leu Glu Ile Ile Glu Gly Arg Ala Asn Phe His Thr Leu Glu Gln
            405                 410                 415
Tyr Ala Leu Asn His Lys Ser Ile Lys Asn Glu Ser Gly Arg Gln Glu
            420                 425                 430
Lys Leu Lys Ala Ile Leu Asn Gln Tyr Ile Leu Glu Val
            435                 440                 445

<210> SEQ ID NO 61
<211> LENGTH: 1338
<212> TYPE: DNA
<213> ORGANISM: Bacillus subtilis

<400> SEQUENCE: 61
atggctcaat ctcattccag ttcaatcaac tattttggaa gcgcaaacaa agtggtttac      60
gaagggaaag attcgactaa tcctttagca tttaaatatt ataatcctca agaagtaatc     120
ggcggaaaaa cgctgaaaga gcatttgcga ttttctattg cctattgca  tacatttact     180 gctgatggta cagacgtttt tggagcagct acgatgcaaa gaccatggga tcactataaa     240
ggcatggatc tagcgaagat gagagtagaa gcagcatttg agatgtttga aaaactagat     300
gcaccattct ttgcttttca tgaccgggat attgcaccag aaggcagtac gctaaaagag     360
acaaaccaaa atttagatat gatcatgggc atgattaaag attacatgag aaatagcggc     420
gttaagctat tatggaatac agcaaacatg tttacgaatc cccgtttcgt ccatggtgcc     480
gcgacttctt gcaatgcaga gtgtttgcg tatgctgcag cacaagtgaa aaagggtta      540 gaaacagcaa aagagcttgg cgctgagaac tatgtatttt ggggcggccg tgaaggatat     600
```

-continued

```
gaaacattgt taaataccga tttaaaattt gagcttgatg atttggctag atttatgcat    660
atggcagtgg attatgcgaa ggaaatcggg tacacagggc agtttttgat tgagccaaaa    720
ccaaaagagc cgaccgccca tcaatacgat acagatgcag caacaaccat tgccttttg     780 aagcaatatg gcttagacaa tcattttaaa ttaaatcttg aagccaatca tgccacatta    840
gccgggcata cattcgaaca tgaattacgc atggcaagag tacatggtct gcttggctct    900
gttgacgcaa accagggtca tcctctttta ggctgggaca cggatgaatt ccgacggat     960 ttatattcta cgacattagc aatgtacgaa atcctgcaaa atggcggcct tggaagcggc   1020
ggattaaact tgacgcgaa ggtcagaaga tcttctttcg agcctgatga tctaatatat    1080
gcccatattg cagggatgga tgcatttgca agaggattga agttgccca caaattaatc    1140 gaagatcgtg tgtttgaaga tgtgattcaa catcgttacc gcagctttac tgaagggatt   1200
ggtcttgaaa ttatagaagg aagagctaat ttccacacac ttgagcaata tgcgctaaat   1260
cataaatcaa ttaaaaacga atctggaaga caggagaaat aaaagcgat attgaaccaa    1320 tacattttag aagtataa                                                 1338
```

```
<210> SEQ ID NO 62
<211> LENGTH: 438
<212> TYPE: PRT
<213> ORGANISM: Bacteroides vulgatus

<400> SEQUENCE: 62
```

| Met | Ala | Thr | Lys | Glu | Tyr | Phe | Pro | Gly | Ile | Gly | Lys | Ile | Lys | Phe | Glu |
|---|---|---|---|---|---|---|---|---|---|---|---|---|---|---|---|
| 1 | | | | 5 | | | | | 10 | | | | | 15 | |

| Gly | Lys | Glu | Ser | Lys | Asn | Pro | Met | Ala | Phe | Arg | Tyr | Tyr | Asp | Ala | Glu |
| | | | 20 | | | | | 25 | | | | | 30 | | |

| Lys | Val | Ile | Asn | Gly | Lys | Lys | Met | Lys | Asp | Trp | Leu | Lys | Phe | Ala | Met |
| | | 35 | | | | | 40 | | | | | 45 | | | |

| Ala | Trp | Trp | His | Thr | Leu | Cys | Ala | Glu | Gly | Gly | Asp | Gln | Phe | Gly | Gly |
| | 50 | | | | | 55 | | | | | 60 | | | | |

| Gly | Thr | Lys | Lys | Phe | Pro | Trp | Asn | Gly | Asp | Ala | Asp | Lys | Val | Gln | Ala |
| 65 | | | | | 70 | | | | | 75 | | | | | 80 |

| Ala | Lys | Asn | Lys | Met | Asp | Ala | Gly | Phe | Glu | Phe | Met | Gln | Lys | Met | Gly |
| | | | | 85 | | | | | 90 | | | | | 95 | |

| Ile | Glu | Tyr | Tyr | Cys | Phe | His | Asp | Val | Asp | Leu | Cys | Glu | Glu | Ala | Asp |
| | | | 100 | | | | | 105 | | | | | 110 | | |

| Thr | Ile | Glu | Glu | Tyr | Glu | Ala | Asn | Leu | Lys | Glu | Ile | Val | Ala | Tyr | Ala |
| | | 115 | | | | | 120 | | | | | 125 | | | |

| Lys | Gln | Lys | Gln | Ala | Glu | Thr | Gly | Ile | Lys | Leu | Leu | Trp | Gly | Thr | Ala |
| | 130 | | | | | 135 | | | | | 140 | | | | |

| Asn | Val | Phe | Gly | His | Ala | Arg | Tyr | Met | Asn | Gly | Ala | Ala | Thr | Asn | Pro |
| 145 | | | | | 150 | | | | | 155 | | | | | 160 |

| Glu | Phe | Asp | Val | Val | Ala | Arg | Ala | Ala | Val | Gln | Ile | Lys | Asn | Ala | Ile |
| | | | | 165 | | | | | 170 | | | | | 175 | |

| Asp | Ala | Thr | Ile | Glu | Leu | Gly | Gly | Ser | Asn | Tyr | Val | Phe | Trp | Gly | Gly |
| | | | 180 | | | | | 185 | | | | | 190 | | |

| Arg | Glu | Gly | Tyr | Met | Ser | Leu | Leu | Asn | Thr | Asp | Gln | Lys | Arg | Glu | Lys |
| | | 195 | | | | | 200 | | | | | 205 | | | |

| Glu | His | Leu | Ala | Gln | Met | Leu | Thr | Ile | Ala | Arg | Asp | Tyr | Ala | Arg | Ser |
| | 210 | | | | | 215 | | | | | 220 | | | | |

| Lys | Gly | Phe | Thr | Gly | Thr | Phe | Leu | Ile | Glu | Pro | Lys | Pro | Met | Glu | Pro |
| 225 | | | | | 230 | | | | | 235 | | | | | 240 |

| Thr | Lys | His | Gln | Tyr | Asp | Val | Asp | Thr | Glu | Thr | Val | Val | Gly | Phe | Leu |

```
                 245                 250                 255
Lys Thr His Gly Leu Asp Lys Asp Phe Lys Val Asn Ile Glu Val Asn
            260                 265                 270

His Ala Thr Leu Ala Gly His Thr Phe Glu His Glu Leu Ala Val Ala
        275                 280                 285

Val Asp Asn Gly Met Leu Gly Ser Ile Asp Ala Asn Arg Gly Asp Tyr
    290                 295                 300

Gln Asn Gly Trp Asp Thr Asp Gln Phe Pro Ile Asp Asn Tyr Glu Leu
305                 310                 315                 320

Thr Gln Ala Met Met Gln Ile Ile Arg Asn Gly Gly Leu Gly Asn Gly
                325                 330                 335

Gly Thr Asn Phe Asp Ala Lys Thr Arg Arg Asn Ser Thr Asp Leu Glu
            340                 345                 350

Asp Ile Phe Ile Ala His Ile Ala Gly Met Asp Ala Met Ala Arg Ala
        355                 360                 365

Leu Glu Ser Ala Ala Ala Leu Leu Asn Glu Ser Pro Tyr Cys Lys Met
    370                 375                 380

Leu Ser Asp Arg Tyr Ala Ser Phe Asp Ser Gly Lys Gly Lys Glu Phe
385                 390                 395                 400

Glu Glu Gly Lys Leu Thr Leu Glu Asp Val Val Ala Tyr Ala Lys Gln
                405                 410                 415

Asn Gly Glu Pro Lys Gln Val Ser Gly Lys Gln Glu Leu Tyr Glu Ala
            420                 425                 430

Ile Val Asn Met Tyr Cys
        435

<210> SEQ ID NO 63
<211> LENGTH: 1317
<212> TYPE: DNA
<213> ORGANISM: Bacteroides vulgatus

<400> SEQUENCE: 63
atggctacaa aagagtattt tcccggtata ggaaagatta aatttgaagg taaggaaagt      60
aagaacccga tggcgttccg ttattatgat gctgaaaagg taattaacgg caagaagatg     120
aaagactggt tgaagtttgc tatggcatgg tggcatacgt tgtgtgccga gggcggtgac     180
cagtttggcg gcggaacaaa gaaattccct tggaacggtg atgccgataa ggtgcaggct     240
gccaagaata gatggatgc cggctttgaa ttcatgcaga aaatgggaat cgaatattat     300
tgtttccatg atgtggactt gtgtgaggaa gccgatacaa tcgaggaata tgaagcgaat     360
ctgaaagaga tagttgctta tgccaaacag aaacaggctg aaaccggaat caaattgtta     420
tggggtacgg caaatgtttt tggtcatgca cgctatatga acggggctgc tacaaacccc     480
gaatttgatg tggttgcccg cgctgctgtc cagataaaga acgctattga cgctaccatc     540
gaactgggtg gctccaatta cgtgttctgg ggtggacgtg aagggtatat gtctttattg     600
aatacagatc agaagcgtga gaaagaacat ctggctcaga tgttgaccat tgcccgcgat     660
tatgcccgga gcaaagggtt tacaggtact ttcctgattg aacccaaacc gatggagccg     720
actaagcatc aatatgatgt ggataccgaa actgtggtag ggttcttgaa aactcacgga     780
ctggacaagg atttcaaggt gaacattgaa gtgaatcatg ctacgttggc tggtcataca     840
tttgaacatg aactggctgt tgcggtagat aacggaatgt gggatctat tgacgctaac      900 cgtggcgatt atcagaacgg atgggataca gaccagttcc ctatcgacaa ttacgaactg     960
acccaggcca tgatgcagat tatccgcaat ggcggtttgg gtaatggcgg taccaacttt    1020
```

-continued

```
gatgccaaga cacgtcgtaa ctctactgat ctggaagata tctttatcgc ccatattgca    1080
ggtatggacg ctatggcgcg tgcattggaa agtgctgctg ctttgcttaa tgaatctcct    1140
tactgcaaga tgttgtcaga ccgctatgct tcattcgaca gtggcaaagg caaagaattt    1200
gaagaaggca agctgacact ggaagacgta gtggcttatg ctaagcagaa tggtgagccc    1260
aagcaagtaa gcggtaagca ggaattgtac gaagccatcg taaatatgta ttgctga       1317
```

<210> SEQ ID NO 64
<211> LENGTH: 449
<212> TYPE: PRT
<213> ORGANISM: Bifidobacterium adolescentis

<400> SEQUENCE: 64

```
Met Gly Leu Trp Asp Ile Asp Lys Ile Pro Tyr Val Gly Arg Glu Lys
1               5                   10                  15

Gly Pro Gln Glu Gly Leu Ala Phe His Tyr Tyr Asp Ala Asp Lys Val
                20                  25                  30

Val Ala Gly Lys Lys Met Lys Asp Trp Leu Arg Phe Gly Val Ala Trp
            35                  40                  45

Trp His Thr Phe Asp Gln Gln Leu Val Asp Pro Phe Gly Thr Gly Thr
        50                  55                  60

Ala Gln Arg Pro Trp Tyr Gly Lys Tyr Ser Asp Pro Glu Asp Glu Ala
65                  70                  75                  80

Leu Ala Lys Val Asp Tyr Ala Phe Glu Phe Gln Lys Leu Gly Val
                85                  90                  95

Glu Tyr Phe Cys Phe His Asp Arg Asp Ile Ala Pro Glu Gly Asp Thr
            100                 105                 110

Leu Arg Glu Thr Asp Lys Asn Leu Asp Lys Val Val Asp Lys Ile Glu
        115                 120                 125

Glu Asn Met Lys Ser Thr Gly Ile Lys Leu Leu Trp Asn Thr Ser Ser
130                 135                 140

Leu Phe Thr Asn Pro Arg Phe Val Ser Gly Ala Ser Thr Ser Pro Phe
145                 150                 155                 160

Ala Asp Ile Tyr Ala Tyr Ala Gly Gly Gln Leu Lys His Ser Leu Glu
                165                 170                 175

Ile Ala Lys Arg Leu Gly Ala Glu Asn Tyr Val Phe Trp Gly Gly Arg
            180                 185                 190

Glu Gly Tyr Glu Asn Leu Trp Asn Thr Gln Met Lys Arg Glu Gln Glu
        195                 200                 205

His Met Ala Lys Phe Phe His Met Cys His Asp Tyr Ala Lys Glu Ile
210                 215                 220

Gly Leu Asp Ala Gln Phe Leu Ile Glu Pro Lys Ala Lys Glu Pro Thr
225                 230                 235                 240

Met Phe Gln Tyr Asp Phe Asp Ala Ala Thr Ala Ile Asn Phe Leu Arg
                245                 250                 255

Thr Tyr Asp Leu Met Asp Val Phe Lys Leu Asn Leu Glu Gly Asn His
            260                 265                 270

Ala Asn Leu Ala Gly His Thr Tyr Gln His Glu Ile Arg Thr Ala Arg
        275                 280                 285

Glu Ala Gly Val Leu Gly Ser Leu Asp Ala Asn Gln Gly Asp Lys Leu
290                 295                 300

Ile Gly Trp Asp Met Asp Glu Phe Pro Thr Asp Leu Tyr Glu Thr Ser
305                 310                 315                 320

Thr Val Met Trp Glu Val Leu Ala Glu Gly Gln Ile Gly Pro His Gly
                325                 330                 335
```

```
Gly Leu Asn Phe Asp Ala Lys Pro Arg Arg Thr Ser Phe Thr Ala Glu
                340                 345                 350
Asp Leu Phe Arg Ser His Ile Ala Gly Met Asp Ser Phe Ala Ala Gly
            355                 360                 365
Leu Leu Val Ala Ala Lys Met His Glu Asp Lys Val Ile Glu Asn Leu
    370                 375                 380
Gln Ala Glu Arg Tyr Ser Ser Phe Asp Ser Gly Ile Gly Ala Thr Val
385                 390                 395                 400
Glu Asn Gly Thr Ala Ser Leu Ala Ser Leu Glu Glu Tyr Ala Leu Asp
                405                 410                 415
Ile Pro Gln Ser Lys Leu Ile Glu Ala Thr Lys Ser Asp His Leu Glu
            420                 425                 430
Ser Val Lys Ala Thr Ile Asn Asn Tyr Met Ile Asp Ala Leu Ala Glu
    435                 440                 445
Ala
```

<210> SEQ ID NO 65
<211> LENGTH: 1350
<212> TYPE: DNA
<213> ORGANISM: Bifidobacterium adolescentis

<400> SEQUENCE: 65

```
atgggtctgt gggatatcga taagattccg tacgtcggtc gcgaaaaggg gccgcaggag      60
ggtcttgctt tccattacta cgatgccgac aaggtcgttg ccggcaagaa gatgaaggac     120
tggctgcgtt tcggcgtcgc atggtggcac accttcgacc agcagctcgt cgatccgttc     180
ggcaccggca ccgcccagcg tccgtggtac ggcaagtatt ccgatccgga ggacgaggcc     240
ctggccaagg tcgactacgc cttcgagttc ttccagaagc tcggcgtcga gtacttctgc     300
ttccatgatc gcgacatcgc tccggaaggc gacaccctgc gcgagaccga caagaacctg     360
gacaaggtcg tcgacaagat cgaagagaac atgaagtcca ccggcatcaa gctgctgtgg     420
aacacctcct ccctgttcac caacccgcgc ttcgtctccg gcgcctccac ctccccgttc     480
gccgacatct acgcgtacgc cggcggccag ctgaagcact ccctggagat cgccaagcgc     540
cttggtgccg agaactacgt gttctggggc ggccgtgaag gctacgagaa cctgtggaac     600
acccagatga agcgcgagca ggagcacatg gccaagttct ccacatgtg ccatgactac      660
gcgaaggaaa tcggcctgga cgcccagttc ctgatcgagc cgaaggccaa ggaaccgacg     720
atgttccagt acgacttcga tgccgccacc gccatcaact tcctgcgcac ctatgatctg     780
atggacgtct tcaagctgaa cctggaaggc aaccacgcca acctggccgg ccacacctac     840
cagcacgaga tccgcaccgc ccgcgaggcc ggcgtgctcg gctccttgga cgccaaccag     900
ggcgacaagc tcatcggctg ggatatggat gagttcccga ccgacctgta cgagacctcc     960
accgttatgt gggaagtcct cgccgaaggc cagatcggcc tcacggtgg tctgaacttc     1020
gacgccaagc cgcgtcgtac ctccttcacc gccgaggatc tgttccgttc ccacatcgca    1080
ggcatggatt ccttcgcagc aggcctcctg gtcgccgcca agatgcacga ggacaaggtc    1140
atcgagaacc tgcaggccga gcgctacagc tccttcgatt ccggcatcgg cgcaaccgtc    1200
gagaacggca ccgcctccct ggcttccctc gaggagtacg ctctggatat cccgcagtcc    1260
aagctcatcg aagccaccaa gtccgatcac ctcgagtccg tcaaggccac gatcaacaac    1320
tacatgatcg acgccctggc cgaggcgtga                                     1350
```

<210> SEQ ID NO 66

```
<211> LENGTH: 439
<212> TYPE: PRT
<213> ORGANISM: Erwinia carotovora

<400> SEQUENCE: 66
```

| | | | | | | | | | | | | | | |
|---|---|---|---|---|---|---|---|---|---|---|---|---|---|---|
| Met | Gln | Ala | Tyr | Phe | Glu | Gln | Ile | Glu | Lys | Val | Arg | Tyr | Gly | Ser |
| 1 | | | | 5 | | | | | 10 | | | | | 15 |
| Gln | Ser | Ser | Asn | Pro | Phe | Ala | Phe | Arg | His | Tyr | Asn | Pro | Asp | Gln | Glu |
| | | | 20 | | | | | 25 | | | | | 30 | | |
| Ile | Leu | Gly | Lys | Arg | Met | Ala | Asp | His | Leu | Arg | Phe | Ala | Val | Ala | Tyr |
| | | | 35 | | | | | 40 | | | | | 45 | | |
| Trp | His | Thr | Phe | Cys | Trp | Asn | Gly | Ser | Asp | Met | Phe | Gly | Val | Gly | Ser |
| 50 | | | | | 55 | | | | | 60 | | | | | |
| Phe | Ala | Arg | Pro | Trp | Gln | Gln | Ser | Gly | Asp | Ala | Leu | Glu | Leu | Ala | Lys |
| 65 | | | | | 70 | | | | | 75 | | | | | 80 |
| Arg | Lys | Ala | Asp | Ile | Ala | Phe | Glu | Phe | Phe | Gln | Lys | Leu | Ser | Val | Pro |
| | | | | 85 | | | | | 90 | | | | | 95 | |
| Tyr | Tyr | Cys | Phe | His | Asp | Val | Asp | Val | Ala | Pro | Glu | Gly | Asn | Ser | Leu |
| | | | 100 | | | | | 105 | | | | | 110 | | |
| Lys | Glu | Tyr | Leu | His | Asn | Ile | Ala | Val | Ile | Thr | Asp | Val | Leu | Ala | Glu |
| | | | 115 | | | | | 120 | | | | | 125 | | |
| Lys | Gln | Gln | Asp | Ser | Gly | Val | Lys | Leu | Leu | Trp | Gly | Thr | Ala | Asn | Cys |
| | 130 | | | | | 135 | | | | | 140 | | | | |
| Phe | Thr | Asn | Pro | Arg | Tyr | Gly | Ala | Gly | Ala | Ala | Thr | Asn | Pro | Asp | Pro |
| 145 | | | | | 150 | | | | | 155 | | | | | 160 |
| Asp | Val | Phe | Ala | Trp | Ala | Ala | Thr | Gln | Val | Phe | Thr | Ala | Met | Asn | Ala |
| | | | | 165 | | | | | 170 | | | | | 175 | |
| Thr | Lys | Thr | Leu | Gly | Gly | Glu | Asn | Tyr | Val | Leu | Trp | Gly | Gly | Arg | Glu |
| | | | 180 | | | | | 185 | | | | | 190 | | |
| Gly | Tyr | Glu | Thr | Leu | Leu | Asn | Thr | Asp | Leu | Arg | Gln | Glu | Arg | Glu | Gln |
| | | | 195 | | | | | 200 | | | | | 205 | | |
| Ile | Gly | Arg | Phe | Met | Gln | Met | Val | Val | Glu | His | Lys | His | Lys | Ile | Gly |
| | 210 | | | | | 215 | | | | | 220 | | | | |
| Phe | Gln | Gly | Thr | Leu | Leu | Ile | Glu | Pro | Lys | Pro | Gln | Glu | Pro | Thr | Lys |
| 225 | | | | | 230 | | | | | 235 | | | | | 240 |
| His | Gln | Tyr | Asp | Tyr | Asp | Val | Ala | Thr | Val | Tyr | Gly | Phe | Leu | Lys | Gln |
| | | | | 245 | | | | | 250 | | | | | 255 | |
| Phe | Gly | Leu | Glu | Lys | Glu | Ile | Lys | Val | Asn | Val | Glu | Ala | Asn | His | Ala |
| | | | 260 | | | | | 265 | | | | | 270 | | |
| Thr | Leu | Ala | Gly | His | Ser | Phe | His | His | Glu | Ile | Ala | Thr | Ala | Val | Ala |
| | | | 275 | | | | | 280 | | | | | 285 | | |
| Leu | Gly | Val | Phe | Gly | Ser | Val | Asp | Ala | Asn | Arg | Gly | Asp | Pro | Gln | Leu |
| | 290 | | | | | 295 | | | | | 300 | | | | |
| Gly | Trp | Asp | Thr | Asp | Gln | Phe | Pro | Asn | Ser | Val | Glu | Glu | Asn | Thr | Leu |
| 305 | | | | | 310 | | | | | 315 | | | | | 320 |
| Ile | Met | Tyr | Glu | Ile | Leu | Lys | Ala | Gly | Gly | Phe | Thr | Thr | Gly | Gly | Leu |
| | | | | 325 | | | | | 330 | | | | | 335 | |
| Asn | Phe | Asp | Ala | Lys | Val | Arg | Arg | Gln | Ser | Thr | Asp | Tyr | Asp | Leu |
| | | | 340 | | | | | 345 | | | | | 350 | | |
| Phe | His | Ala | His | Ile | Gly | Ala | Met | Asp | Thr | Met | Ala | Leu | Ala | Leu | Lys |
| | | | 355 | | | | | 360 | | | | | 365 | | |
| Ala | Ala | Ala | Arg | Met | Ile | Glu | Asp | Asp | Lys | Leu | Asn | Gln | Leu | Val | Ala |
| | 370 | | | | | 375 | | | | | 380 | | | | |
| Lys | Arg | Tyr | Ala | Gly | Trp | Asn | Gly | Glu | Leu | Gly | Gln | Gln | Ile | Leu | Gln |
| 385 | | | | | 390 | | | | | 395 | | | | | 400 |

Gly Asn Ala Ser Leu Glu Ser Leu Ala Gln Tyr Ala Glu Ser His Gln
                405                 410                 415

Leu Ala Pro Gln His Gln Ser Gly Gln Gln Glu Leu Leu Glu Asn Leu
            420                 425                 430

Val Asn Arg His Leu Phe Gly
        435

<210> SEQ ID NO 67
<211> LENGTH: 1320
<212> TYPE: DNA
<213> ORGANISM: Erwinia carotovora

<400> SEQUENCE: 67

```
atgcaagcct attttgaaca gatcgaaaaa gttcgttatg aaggtagcca aagcagtaat     60
cccttcgcct ttcgtcacta caatcccgat caggaaattc tcggtaaacg tatggcggac    120
catttgcgtt ttgccgtcgc ttattggcac acgttctgct ggaacggctc ggatatgttc    180
ggcgtcggat cctttgcccg gccgtggcag cagtcgggcg atgcgctgga actggcgaag    240
cgcaaagcgg atatcgcatt cgaattcttt caaaaactaa gcgtgcctta ctactgcttt    300
catgacgtcg atgtcgcgcc ggaagggaac tcgctgaaag aatatctgca taacattgcg    360
gtgatcaccg atgtgctggc ggaaaagcag caggatagcg gcgtgaagct gctgtggggc    420
accgctaact gcttcaccaa tccccgctat ggcgcaggcg cggccaccaa tcctgatcca    480
gatgtgtttg cctgggctgc tacgcaggtg ttcacggcaa tgaacgcgac caaaacactg    540
ggcggtgaaa actatgtgct gtgggcgggg cgcgaagggt atgaaactct gctcaatacc    600
gacctgcgtc aggagcgtga gcaaattggc cgctttatgc aaatggttgt cgagcataaa    660
cacaaaatcg gttttcaggg cacactgctc attgaaccga accgcaggaa accgactaaa    720
catcagtacg attacgatgt cgccactgtt tatggcttcc tgaaacagtt ggggctggaa    780
aaagagatta agtcaacgt ggaagccaac cacgcgacgc ttgctgggca ttcattccac    840
catgagatcg ccaccgctgt cgcgctgggc gttttcggat cggtcgatgc caatcgcggc    900
gaccctcagc ttggctggga caccgatcag ttccctaaca gcgtggaaga aaacacgctg    960
atcatgtatg aaattctcaa ggcaggcggc ttcacgacag gtgggctgaa ctttgatgcc   1020
aaagttcgtc gccagagcac cgatcgctat gaccttttcc atgcgcatat cggcgcgatg   1080
gatacaatgg cactggcgct caaggctgct gccagaatga ttgaagatga taagctcaat   1140
caattggtcg ccaagcgcta tgcgggctgg aacggtgaac taggtcagca aattctgcaa   1200
ggcaacgcgt cgctggaatc gctggctcag tatgcggaaa gccatcaact ggcaccacag   1260
caccagagcg gccagcagga actgctggaa aatctggtta accgccatct atttggctag   1320
```

<210> SEQ ID NO 68
<211> LENGTH: 479
<212> TYPE: PRT
<213> ORGANISM: Hordeum vulgare

<400> SEQUENCE: 68

Met Lys Gly Gly Glu Leu Leu Val Leu Leu Ala Ser Ser Leu Cys
1               5                   10                  15

Leu Ser Ala Ala Val Ala Ala Gln Glu Thr Cys Pro Ala Asp Ile Gly
                20                  25                  30

Ala Lys Cys Thr Asp Ala Ala Ser Asp Asp Trp Glu Gly Glu Phe Phe
            35                  40                  45

Pro Gly Ile Asp Lys Ile Asn Tyr Glu Gly Pro Thr Ser Lys Lys Pro

```
              50                  55                  60
Leu Ser Tyr Lys Trp Tyr Asn Ala Glu Glu Val Ile Leu Gly Lys Lys
 65                  70                  75                  80

Met Lys Asp Trp Phe Arg Phe Ser Val Ala Phe Trp His Thr Phe Arg
                     85                  90                  95

Gly Thr Gly Gly Asp Pro Phe Gly Ala Pro Thr Lys Asn Trp Pro Trp
                100                 105                 110

Glu Asp Gly Thr Asn Ser Leu Ala Met Ala Lys Arg Arg Met Lys Ala
                115                 120                 125

His Phe Glu Phe Met Glu Lys Leu Gly Val Glu Arg Trp Cys Phe His
                130                 135                 140

Asp Arg Asp Ile Ala Pro Asp Gly Lys Thr Leu Ala Glu Thr Asn Ala
145                 150                 155                 160

Asn Leu Asp Glu Ile Val Glu Leu Ala Lys Gln Leu Gln Ser Glu Thr
                165                 170                 175

Asn Ile Lys Pro Leu Trp Gly Thr Ala Gln Leu Phe Met His Pro Arg
                180                 185                 190

Tyr Met His Gly Ala Ala Thr Ser Pro Glu Val Lys Val Tyr Ala Tyr
                195                 200                 205

Ala Ala Ala Gln Val Lys Lys Ala Leu Glu Val Thr His Tyr Leu Gly
210                 215                 220

Gly Glu Asn Tyr Val Phe Trp Gly Gly Arg Glu Gly Tyr Gln Thr Leu
225                 230                 235                 240

Leu Asn Thr Asp Met Lys Arg Glu Leu Glu His Leu Ala Asn Phe Leu
                245                 250                 255

Gln Ala Ala Val Asn His Lys Lys Lys Ile Gly Phe Asn Gly Thr Leu
                260                 265                 270

Leu Ile Glu Pro Lys Pro Gln Glu Pro Thr Lys His Gln Tyr Asp Trp
                275                 280                 285

Asp Val Ala Thr Thr Phe Ser Phe Leu Gln Lys Phe Gly Leu Thr Gly
                290                 295                 300

Glu Phe Lys Ile Asn Val Glu Cys Asn His Ala Thr Leu Ser Gly His
305                 310                 315                 320

Ser Cys His His Glu Leu Glu Thr Ala Arg Ile Asn Asp Ile Leu Gly
                325                 330                 335

Asn Ile Asp Ala Asn Thr Gly Asp Pro Gln Val Gly Trp Asp Thr Asp
                340                 345                 350

Glu Phe Leu Thr Asp Ile Ser Glu Ala Thr Leu Ile Met Ser Ser Val
                355                 360                 365

Val Lys Asn Asp Gly Leu Ala Pro Gly Gly Phe Asn Phe Tyr Ala Lys
                370                 375                 380

Leu Arg Arg Glu Ser Thr Asp Val Glu Asp Leu Phe Ile Ala His Ile
385                 390                 395                 400

Ser Gly Met Asp Thr Met Ala Arg Gly Arg Arg Asn Val Val Lys Leu
                405                 410                 415

Ile Glu Asp Gly Ser Leu Asp Glu Leu Val Arg Lys Arg Tyr Gln Ser
                420                 425                 430

Phe Asp Thr Glu Ile Gly Ala Met Ile Glu Gly Ser Ser Ser Phe Thr
                435                 440                 445

Ala Gln Cys Lys Tyr Ile Ser Ala Pro Met Ile Val Pro Tyr Asp Leu
                450                 455                 460

Leu Leu Pro Ala Glu Leu Ala Glu Met Leu Phe Gln Ser Ala Leu
465                 470                 475
```

<210> SEQ ID NO 69
<211> LENGTH: 1440
<212> TYPE: DNA
<213> ORGANISM: Hordeum vulgare

<400> SEQUENCE: 69

| | | | | | |
|---|---|---|---|---|---|
| atgaagggcg | gggagctcct | ggtcctgctg | ctggcctcgt | ccctctgcct | gtccgccgcg | 60 |
| gttgccgcgc | aggaaacctg | cccggccgac | atcggcgcca | agtgcaccga | tgccgcctcc | 120 |
| gatgattggg | agggcgagtt | cttccccggc | attgacaaga | tcaactatga | gggtcctacc | 180 |
| agcaagaagc | cgctttctta | caagtggtat | aacgcggagg | aagtgatcct | cggaaagaaa | 240 |
| atgaaggatt | ggtttcggtt | cagcgtggcg | ttttggcata | cgttccgggg | tactggagga | 300 |
| gatccctttg | gtgcacctac | gaagaactgg | ccttgggagg | atggcaccaa | ttccttggcc | 360 |
| atggctaaga | agaatgaa | agctcacttc | gagttcatgg | agaagcttgg | agttgaaagg | 420 |
| tggtgcttcc | atgacaggga | catcgcccct | gatggcaaaa | cactcgcgga | aacaaatgct | 480 |
| aacttggatg | agatagttga | gctggcaaag | caactccaga | gtgagaccaa | tataaagcca | 540 |
| ttatggggaa | ctgcacaact | tttcatgcat | ccacgttaca | tgcacggagc | tgctactagc | 600 |
| ccagaggtca | aggtgtatgc | ttatgctgct | gctcaagtga | agaaagcttt | ggaggttact | 660 |
| cactacctag | gcggtgagaa | ctacgtattc | tggggtggaa | gagagggtta | ccaaactctt | 720 |
| ctcaataccg | atatgaagag | ggaacttgaa | catttggcta | actttcttca | agctgctgtt | 780 |
| aaccacaaga | agaagatcgg | ctttaacgga | acattgttga | tagagcctaa | gccacaagaa | 840 |
| ccaacaaagc | atcagtatga | ctgggatgtt | gcaactacat | tctctttcct | acagaagttt | 900 |
| ggtcttacag | gggaattcaa | gataaatgtt | gagtgcaacc | atgctactct | ctctggacat | 960 |
| agctgccatc | acgagcttga | gactgcacgc | attaatgaca | ttcttggaaa | cattgatgca | 1020 |
| aacactggtg | atccacaggt | tggttgggac | acgatgagt | tccttacaga | catttcagaa | 1080 |
| gctaccttga | ttatgtcaag | tgtagttaag | aatgatggac | ttgcgcctgg | tggcttcaac | 1140 |
| ttttacgcca | aattgcggag | ggagagtact | gatgttgagg | acctgtttat | tgcccatatc | 1200 |
| tctgggatgg | acaccatggc | ccgcggccgc | cgcaatgttg | tcaagctgat | tgaggatggt | 1260 |
| tccctggacg | agcttgtacg | caaacgctac | cagagctttg | acactgagat | tggtgccatg | 1320 |
| atcgagggca | gctcgtcttt | cacagcacaa | tgcaaatata | tttctgcgcc | gatgattgtt | 1380 |
| ccttacgacc | ttttgttgcc | cgctgaattg | gctgagatgc | tgttccaatc | cgctctgtag | 1440 |

<210> SEQ ID NO 70
<211> LENGTH: 444
<212> TYPE: PRT
<213> ORGANISM: Klebsiella pneumoniae

<400> SEQUENCE: 70

Met Glu Phe Ser Met Gln Thr Tyr Phe Asp Gln Leu Asp Arg Val Arg
1               5                   10                  15

Tyr Glu Gly Pro Lys Ser Thr Asn Pro Leu Ala Phe Arg His Tyr Asn
            20                  25                  30

Pro Asp Glu Leu Val Leu Gly Lys Arg Met Glu Asp His Leu Arg Phe
        35                  40                  45

Ala Ala Cys Tyr Trp His Thr Phe Cys Trp Asn Gly Ala Asp Met Phe
    50                  55                  60

Gly Val Gly Ser Phe Asp Arg Pro Trp Gln Gln Pro Gly Asp Ala Leu
65                  70                  75                  80

Glu Met Ala Lys Arg Lys Ala Asp Val Ala Phe Glu Phe Phe His Lys

```
              85                  90                  95
Leu Asn Val Pro Tyr Tyr Cys Phe His Asp Val Asp Val Ser Pro Glu
            100                 105                 110
Gly Ala Ser Leu Lys Glu Tyr Ser Asn Asn Phe Ala Arg Met Val Glu
            115                 120                 125
Val Leu Ala Glu Lys Gln Gln Gln Ser Gly Val Lys Leu Leu Trp Gly
            130                 135                 140
Thr Ala Asn Cys Phe Thr Asn Pro Arg Tyr Gly Ala Gly Ala Ala Thr
145                 150                 155                 160
Asn Pro Asp Pro Glu Val Phe Ser Trp Ala Ala Thr Gln Val Val Thr
                165                 170                 175
Ala Met Asn Ala Thr His Gln Leu Gly Gly Glu Asn Tyr Val Leu Trp
            180                 185                 190
Gly Gly Arg Glu Gly Tyr Glu Thr Leu Leu Asn Thr Asp Leu Arg Gln
            195                 200                 205
Glu Arg Glu Gln Ile Gly Arg Phe Met Gln Leu Val Val Glu His Lys
            210                 215                 220
His Lys Ile Gly Phe Lys Gly Thr Leu Leu Ile Glu Pro Lys Pro Gln
225                 230                 235                 240
Glu Pro Thr Lys His Gln Tyr Asp Tyr Asp Ala Ser Thr Val Tyr Gly
                245                 250                 255
Phe Leu Lys Gln Phe Gly Leu Glu Lys Glu Ile Lys Leu Asn Ile Glu
            260                 265                 270
Ala Asn His Ala Thr Leu Ala Gly His Ser Phe His His Glu Ile Ala
            275                 280                 285
Thr Ala Ile Ala Leu Gly Leu Phe Gly Ser Val Asp Ala Asn Arg Gly
            290                 295                 300
Asp Pro Gln Leu Gly Trp Asp Thr Asp Gln Phe Pro Asn Ser Val Glu
305                 310                 315                 320
Glu Asn Ala Leu Val Met Tyr Glu Ile Leu Lys Ala Gly Gly Phe Thr
                325                 330                 335
Thr Gly Gly Leu Asn Phe Asp Ala Lys Val Arg Arg Gln Ser Thr Asp
            340                 345                 350
Lys Tyr Asp Leu Phe Tyr Gly His Ile Gly Ala Met Asp Thr Met Ala
            355                 360                 365
Leu Ser Leu Lys Val Ala Ala Arg Met Ile Glu Asp Gly Glu Leu Asp
            370                 375                 380
Lys Arg Val Ala Arg Tyr Ala Gly Trp Asn Gly Glu Leu Gly Gln
385                 390                 395                 400
Gln Ile Leu Asn Gly Gln Met Thr Leu Ser Asp Ile Ala Gln Tyr Ala
            405                 410                 415
Ala Gln His Gln Leu Ala Pro Gln His Arg Ser Gly Gln Gln Glu Gln
            420                 425                 430
Leu Glu Asn Leu Val Asn His Tyr Leu Phe Asp Lys
            435                 440

<210> SEQ ID NO 71
<211> LENGTH: 1335
<212> TYPE: DNA
<213> ORGANISM: Klebsiella pneumoniae

<400> SEQUENCE: 71
atggagttct ctatgcagac ctatttcgat caactcgatc gcgttcgtta cgaaggcccg      60
aaatccacta accgctggc tttccgtcat tacaacccgg atgaactggt gctgggcaaa     120
```

```
cggatggaag atcatctgcg ttttgcggcc tgttactggc acaccttctg ctggaatggc    180
gccgatatgt ttggcgtggg ctcctttgat cgtcccctggc agcagcctgg cgacgccctg   240
gagatggcca aacgcaaagc cgatgtggcg ttcgaattct tccataaact caacgtgcct    300
tactactgct tccacgacgt tgacgtctcg ccggaaggcg cttcgctcaa ggagtacagc    360
aataacttcg cccggatggt cgaggtgctg gctgagaaac agcagcagag cggcgtgaag    420
cttctgtggg ggaccgcaaa ctgctttacc aacccgcgct acggcgccgg cgcggccacc    480
aacccggatc cggaagtatt tagctgggcg gccacccagg tggtcaccgc catgaatgcc    540
acccatcaac tggcggtga  aaactatgtg ctgtggggcg tcgcgaggg  ctatgaaacc    600
ctgctgaata ccgacctgcg ccaggagcgt gagcagattg ccgctttat  gcagctggtg    660
gtggagcata agcataaaat cggctttaaa ggcacgctgc tgattgagcc caaaccgcag    720
gagccgacca agcatcagta tgactatgat gcctctaccg tttacggctt cctcaaacag    780
tttggtctgg aaaagagat  taaactgaat attgaagcta accatgccac gctcgccggc    840
cattcgttcc atcatgaaat tgcgacggcc attgcgctgg ggctgttcgg ctccgttgac    900
gccaaccgcg gcgatccgca gctgggctgg gataccgacc agttcccgaa cagcgtcgaa    960
gagaacgcgc tggtgatgta tgaaatcctc aaagcgggcg gcttcaccac cggcgggctc   1020
aactttgatg cgaaagtgcg ccggcagagc accgacaaat acgatctgtt ctatggtcat   1080
attggcgcga tggataccat ggcgctgtcg ctgaaggtcg cggcgcggat gatcgaggac   1140
ggcgaactgg ataagcgcgt ggccagacgc tacgccggct ggaacggtga gctggggcag   1200
cagatcctta acgggcagat gaccctgagc gatattgccc agtatgccgc tcagcatcag   1260
ctggcgccgc agcatcgcag cggccagcag gaacaactgg aaaacctggt caaccattat   1320
ctgtttgaca agtaa                                                    1335
```

<210> SEQ ID NO 72
<211> LENGTH: 439
<212> TYPE: PRT
<213> ORGANISM: Lactococcus lactis

<400> SEQUENCE: 72

```
Met Ala Tyr Phe Asn Asp Ile Ala Pro Ile Lys Tyr Glu Gly Thr Lys
1               5                   10                  15

Thr Lys Asn Met Phe Ala Phe Arg His Tyr Asn Pro Glu Glu Val Val
            20                  25                  30

Ala Gly Lys Thr Met Glu Glu Gln Leu His Phe Ala Leu Ala Phe Trp
        35                  40                  45

His Thr Ile Thr Met Asp Gly Ser Asp Pro Phe Gly Gly Ala Thr Met
    50                  55                  60

Glu Arg Pro Trp Asp Leu Glu Gly Gly Ser Glu Leu Asp Arg Ala His
65                  70                  75                  80

Arg Arg Val Asp Ala Phe Phe Glu Ile Ala Glu Lys Leu Gly Val Lys
                85                  90                  95

Tyr Tyr Cys Phe His Asp Ile Asp Ile Ala Pro Thr Gly Asn Ser Leu
            100                 105                 110

Lys Glu Phe Tyr Ala Asn Leu Asp Glu Ile Thr Asp His Leu Leu Glu
        115                 120                 125

Lys Gln Lys Ala Thr Gly Ile Lys Leu Leu Trp Asn Thr Ala Asn Met
    130                 135                 140

Phe Ser Asn Pro Arg Tyr Met Asn Gly Val Ser Thr Ser Asn Arg Ala
145                 150                 155                 160
```

```
Glu Val Phe Ala Tyr Gly Ala Ala Gln Val Lys Lys Gly Leu Glu Leu
                165                 170                 175

Ser Lys Lys Leu Gly Gly Glu Asn Tyr Val Phe Trp Gly Gly Arg Glu
            180                 185                 190

Gly Tyr Glu Ser Leu Leu Asn Thr Asp Met Gly Leu Glu Met Asp His
        195                 200                 205

Met Ala Lys Phe Phe His Leu Ala Ile Asp Tyr Ala Lys Ser Ile Asn
    210                 215                 220

His Leu Pro Ile Phe Leu Ile Glu Pro Lys Pro Lys Glu Pro Met Thr
225                 230                 235                 240

His Gln Tyr Asp Phe Asp Ser Ala Thr Ala Leu Ala Phe Leu Gln Lys
                245                 250                 255

Tyr Asp Leu Asp Lys Tyr Phe Lys Leu Asn Leu Glu Thr Asn His Ala
            260                 265                 270

Trp Leu Ala Gly His Thr Phe Glu His Glu Leu Asn Thr Ala Arg Thr
        275                 280                 285

Phe Asn Ala Leu Gly Ser Ile Asp Ala Asn Gln Gly Asn Tyr Leu Leu
    290                 295                 300

Gly Trp Asp Thr Asp Glu Phe Pro Thr Leu Val Ile Asp Ile Thr Leu
305                 310                 315                 320

Ala Met His Gln Ile Leu Leu Asn Gly Gly Leu Gly Lys Gly Gly Ile
                325                 330                 335

Asn Phe Asp Ala Lys Val Arg Arg Thr Ser Phe Lys Ala Glu Asp Leu
            340                 345                 350

Ile Leu Ala His Ile Ala Gly Met Asp Thr Tyr Ala Arg Ala Leu Lys
        355                 360                 365

Gly Ala Ala Ile Ile Glu Asp Lys Phe Leu Ser Asp Ile Val Asp
    370                 375                 380

Glu Arg Tyr Ser Ser Tyr Lys Asn Thr Glu Val Gly Gln Ser Ile Glu
385                 390                 395                 400

Asn Gly Thr Ala Thr Phe Glu Ser Leu Ala Ala Phe Ala Leu Glu His
                405                 410                 415

Gly Asp Asp Ile Glu Leu Asp Ser Asn His Leu Glu Tyr Ile Lys Ser
            420                 425                 430

Val Leu Asn Asp Tyr Leu Val
        435

<210> SEQ ID NO 73
<211> LENGTH: 1320
<212> TYPE: DNA
<213> ORGANISM: Lactococcus lactis

<400> SEQUENCE: 73
atggcttact ttaacgacat cgcacctatc aaatacgaag gtacaaaaac taaaaatatg      60
tttgcctttc gtcattataa tccagaagaa gtagttgctg gtaaaacaat ggaagaacaa     120
cttcattttg cccttgcatt ttggcataca attacgatgg atgggtcaga tccctttggg     180
ggagcaacaa tggaacgtcc ttgggatttg aaggtggtt ctgaacttga ccgtgctcac      240
cgtcgagtag atgctttctt tgaaattgct gaaaaattag gtgttaaata ttattgtttc     300
catgatattg atattgcacc tactggaaat tctttgaaag aatttttatgc taatttggac    360 gaaattactg accaccttct tgaaaaacaa aaagcaacag gcattaaatt actttggaat    420
acagcaaaca tgttttcaaa tccccgctat atgaatggtg tttcaacttc taatcgtgct    480
gaagtctttg cttatggtgc tgcacaagtt aaaaaaggtc ttgaacttc taaaaaactc     540
```

-continued

```
ggtggtgaaa attatgtctt ctggggtggt cgtgaaggtt atgaatcact tttgaataca    600
gatatgggtc ttgaaatgga tcatatggca aaattcttcc atttggcaat tgattatgca    660
aaatcaatca accacttgcc tatttcttg attgaaccaa aaccaaaaga accaatgact     720
caccaatatg attttgactc agcaacagct cttgctttct tgcaaaaata tgacttggac    780
aaatacttca aactcaatct tgaaacaaat catgcttggt tggctgggca cacttttgaa    840
cacgaattaa atactgcacg tactttcaat gctttgggtt ctattgatgc caatcaagga    900
aattacttgc ttggttggga tacagatgaa ttcccaacac ttgttattga tatcacactt    960
gcgatgcacc aaattctttt gaacggtgga cttggcaaag gtggaattaa ctttgatgcg   1020
aaagtacgtc gtacaagttt caaagcagaa gatttaattc ttgctcatat tgcagggatg   1080
gatacttatg cgcgtgcttt gaaaggtgca gcagcaatca ttgaagataa attcttgtct   1140
gatattgttg acgaacgtta tagttcatac aaaaatacag aagttggtca atccattgaa   1200
aatggaacag caacttttga agtcttgct gcatttgcac ttgaacatgg tgacgatatt    1260
gaacttgatt ctaatcactt ggaatacatc aaatcagtat tgaatgacta tcttgtttaa   1320
```

<210> SEQ ID NO 74
<211> LENGTH: 449
<212> TYPE: PRT
<213> ORGANISM: Lactobacillus reuteri

<400> SEQUENCE: 74

```
Met Ala Asp Leu Trp Asn Asn Ile Asp Lys Ile Glu Tyr Glu Gly Pro
1               5                   10                  15

His Lys Ser Ile Lys Ser Gly Leu Phe Tyr Gln Tyr Tyr Asn Pro Asp
                20                  25                  30

Glu Val Ile Leu Gly Lys Lys Met Lys Asp Trp Leu Arg Phe Ser Val
            35                  40                  45

Ala Tyr Trp His Thr Phe Asp Gln Arg Leu Val Asp Pro Phe Gly Asp
        50                  55                  60

Gly Thr Ala Gln Arg Pro Tyr Asp Lys Tyr Ser Asp Pro Met Asp Cys
65                  70                  75                  80

Ala Leu Ala Lys Val Asp Tyr Ala Phe Glu Phe Tyr Asn Lys Leu Gly
                85                  90                  95

Val Asp Phe Leu Cys Phe His Asp Arg Asp Leu Ala Pro Glu Gly Asp
            100                 105                 110

Thr Leu Arg Glu Thr Asn Lys Asn Leu Asp Arg Val Val Asp Lys Ile
        115                 120                 125

Val Glu Tyr Gln Lys Ala Thr Gly Met Lys Val Leu Trp Asn Thr Ser
    130                 135                 140

Asn Leu Phe Thr Asn Pro Arg Phe Leu Glu Gly Ala Gly Thr Ala Pro
145                 150                 155                 160

Ser Ala Glu Ile Tyr Ala Tyr Ala Ala Ala Gln Leu Lys His Ser Leu
                165                 170                 175

Glu Val Gly Lys Arg Val Gly Ser Glu Asn Tyr Val Phe Trp Gly Gly
            180                 185                 190

Arg Glu Gly Tyr Glu Ser Leu Trp Asn Thr Asp Met Lys Arg Glu Gln
        195                 200                 205

Ser His Ile Ala Lys Phe Phe His Met Ala Lys Asp Tyr Ala Asn Glu
    210                 215                 220

Ile Gly Phe Asp Ala Gln Met Leu Leu Glu Pro Lys Pro Lys Glu Pro
225                 230                 235                 240

Thr Thr His Gln Tyr Asp Phe Asp Ala Ala Thr Thr Ile Asn Phe Met
```

```
                    245                 250                 255
Cys Glu Tyr Gly Leu Asp Lys Asp Phe Lys Leu Asn Leu Glu Gly Asn
            260                 265                 270

His Ala Asn Leu Ala Gly His Thr Tyr Gln His Glu Ile Arg Val Ala
        275                 280                 285

Arg Glu Ala Gly Leu Leu Gly Ser Leu Asp Ala Asn Gln Gly Asp Lys
        290                 295                 300

Leu Ile Gly Trp Asp Ile Asp Glu Tyr Pro Ser Asn Leu Tyr Glu Thr
305                 310                 315                 320

Thr Ala Ala Met Trp Glu Val Ile Gln Asn Gly Ser Ile Gly Pro Arg
                325                 330                 335

Gly Gly Leu Asn Phe Asp Ala Lys Pro Arg Arg Thr Ser Phe Lys Pro
            340                 345                 350

Val Asp Leu Phe Tyr Gly His Ile Val Gly Met Asp Ser Phe Ala Ala
        355                 360                 365

Gly Leu Arg Val Ala Ala Ala Met Lys Glu Asp Gly Phe Leu Asp Asp
        370                 375                 380

Ile Ile Lys Glu Arg Tyr Ser Thr Trp Asp Glu Gly Leu Gly Lys Ser
385                 390                 395                 400

Ile Glu Asp Gly Asn Glu Asn Phe Ala Ser Leu Glu Glu Lys Val Ile
                405                 410                 415

Asp Thr Pro Gln Ser Glu Leu Leu Ala Ala Thr His Ser Asp His Leu
            420                 425                 430

Glu Glu Ile Lys Asp Thr Ile Asn His Tyr Met Ile Glu Thr Leu Ala
        435                 440                 445

Lys

<210> SEQ ID NO 75
<211> LENGTH: 1350
<212> TYPE: DNA
<213> ORGANISM: Lactobacillus reuteri

<400> SEQUENCE: 75
atggctgatt tatggaataa tattgataaa attgaatacg agggaccaca taaaagtatt      60
aagtctggtt tgttctacca atactacaac ccggatgaag taattttagg taagaaaatg     120
aaggattggc ttcgtttctc agttgcatat tggcacacat tcgatcaacg gttagttgac     180
ccattcggtg atggaactgc tcaacgtcca tatgataaat acagtgaccc aatggattgc     240
gctttagcaa aggttgatta tgcattcgaa ttttataaca aattaggtgt tgatttcctt     300
tgtttccacg atcgtgattt agctccagaa ggtgacacac ttcgcgaaac aaacaagaat     360
ttggatcgag tagttgataa gattgttgaa tatcaaaaag ctaccggcat gaaagttctt     420
tggaatactt caaacctctt tacaaatcca cgattcttag aaggtgctgg tactgctcct     480
tcagcagaaa tttacgctta tgctgctgct caattaaagc acagtcttga agttggtaag     540
cgcgttggtt cagagaacta tgtcttctgg ggtggacgtg aaggatatga atcactttgg     600
aacacagata tgaagcgtga acaatctcat attgctaagt tcttccacat ggctaaagat     660
tacgctaatg aaattggttt tgacgctcaa atgcttcttg aaccaaagcc aaaggaacca     720
actactcacc aatatgactt tgatgctgca acaacaatca acttcatgtg tgaatatggt     780
cttgataagg actttaagct taaccttgaa ggtaaccatg ctaatttagc tggtcacacg     840
taccaacatg aaattcgggt tgctcgtgaa gccggattac ttggttctct tgatgctaac     900
caaggtgata agttaattgg ttgggatatt gatgaatatc catctaacct ttatgaaact     960
```

```
actgctgcta tgtgggaagt tattcaaaac ggtagcatcg gacctcgtgg tggattaaac    1020
tttgatgcaa aaccacgtcg gacatcgttt aagcctgtag atcttttcta tggtcacatt    1080
gttgggatgg atagctttgc tgctggctta cgggttgctg ctgctatgaa ggaagacggt    1140
ttcttagatg atattattaa agaacgttac tccacatggg atgaaggctt aggtaagagt    1200
attgaagacg gtaatgaaaa ctttgctagt cttgaagaaa aagtaattga tactccacaa    1260
agcgaattgt tagcagccac acattcagac catcttgaag aaattaagga cacaattaac    1320
cactacatga ttgaaacgct tgctaagtaa                                      1350
```

```
<210> SEQ ID NO 76
<211> LENGTH: 448
<212> TYPE: PRT
<213> ORGANISM: Leuconostoc mesenteroides

<400> SEQUENCE: 76
```

| | | | | | | | | | | | | | | |
|---|---|---|---|---|---|---|---|---|---|---|---|---|---|---|
| Met | Ala | Glu | Leu | Phe | Asp | Phe | Pro | Gln | Val | Thr | Phe | Val | Gly | Ile | Gln |
| 1 | | | | 5 | | | | | 10 | | | | | 15 | |
| Ser | Leu | Gln | Ala | Gly | Asp | Gly | Phe | His | Tyr | Tyr | Asn | Pro | Asp | Glu | Ile |
| | | | 20 | | | | | 25 | | | | | 30 | | |
| Val | Lys | Gly | Lys | Lys | Met | Ser | Asp | Trp | Leu | Lys | Phe | Ser | Val | Thr | Tyr |
| | | 35 | | | | | 40 | | | | | 45 | | | |
| Trp | His | Thr | Met | Asp | Gln | Arg | Leu | Val | Asp | Pro | Phe | Gly | Glu | Gly | Thr |
| | 50 | | | | | 55 | | | | | 60 | | | | |
| Ala | Val | Arg | Pro | Trp | Asp | Asn | Gln | Gly | Lys | Pro | Asp | Ser | Met | Glu | Gln |
| 65 | | | | | 70 | | | | | 75 | | | | | 80 |
| Ala | Leu | Ala | Lys | Val | Asp | Tyr | Leu | Phe | Glu | Phe | Leu | Lys | Thr | Asp | |
| | | | | 85 | | | | | 90 | | | | | 95 | |
| Val | Asn | Tyr | Phe | Ala | Phe | His | Asp | Arg | Asp | Leu | Ala | Pro | Glu | Gly | His |
| | | | 100 | | | | | 105 | | | | | 110 | | |
| Thr | Leu | Ala | Glu | Thr | Asn | Lys | Asn | Leu | Asp | Gln | Val | Ile | Asp | Lys | Ile |
| | | | 115 | | | | | 120 | | | | | 125 | | |
| Glu | Gln | Lys | Ile | His | Glu | Thr | Gly | Lys | Lys | Leu | Leu | Trp | Asn | Thr | Ser |
| | 130 | | | | | 135 | | | | | 140 | | | | |
| Ser | Leu | Phe | Thr | Asn | Lys | Arg | Phe | Leu | Ala | Gly | Gly | Ala | Thr | Thr | Pro |
| 145 | | | | | 150 | | | | | 155 | | | | | 160 |
| Phe | Ala | Glu | Val | Phe | Ala | Tyr | Ala | Ala | Gly | Gln | Ile | Lys | His | Ser | Leu |
| | | | | 165 | | | | | 170 | | | | | 175 | |
| Asp | Ile | Ala | Lys | Arg | Leu | Gly | Ser | Glu | Ser | Tyr | Val | Phe | Trp | Gly | Gly |
| | | | 180 | | | | | 185 | | | | | 190 | | |
| Arg | Glu | Gly | Tyr | Asp | Phe | Leu | Leu | Asn | Thr | Asp | Thr | Lys | Arg | Glu | Leu |
| | | 195 | | | | | 200 | | | | | 205 | | | |
| Asp | His | Ile | Ala | Ala | Phe | Phe | Lys | Leu | Ala | Lys | Asp | Tyr | Ala | Asn | Glu |
| | 210 | | | | | 215 | | | | | 220 | | | | |
| Ile | Gly | Tyr | Gln | Gly | Gln | Phe | Leu | Ile | Glu | Pro | Lys | Pro | Lys | Glu | Pro |
| 225 | | | | | 230 | | | | | 235 | | | | | 240 |
| Thr | Gln | His | Gln | Tyr | Asp | Phe | Asp | Val | Gln | Thr | Thr | Ile | Ala | Phe | Leu |
| | | | | 245 | | | | | 250 | | | | | 255 | |
| Lys | Thr | Tyr | Gly | Leu | Glu | Asp | Thr | Phe | Lys | Leu | Asn | Leu | Glu | Gly | Asn |
| | | | 260 | | | | | 265 | | | | | 270 | | |
| His | Ala | Tyr | Leu | Ala | Gly | His | Thr | Tyr | Glu | His | Glu | Val | Arg | Phe | Ala |
| | | 275 | | | | | 280 | | | | | 285 | | | |
| Arg | Glu | Ala | Gly | Leu | Leu | Gly | Ser | Leu | Asp | Ala | Asn | Met | Gly | Asp | Lys |
| | 290 | | | | | 295 | | | | | 300 | | | | |
| Leu | Thr | Gly | Trp | Asp | Ile | Asp | Glu | Phe | Pro | Asn | Asp | Val | Tyr | Glu | Ala |

```
                    305                 310                 315                 320
Thr Leu Val Met Tyr Glu Phe Leu Lys Asn Gly Gly Leu Pro Thr Gly
                325                 330                 335

Gly Leu Asn Phe Asp Ser Lys Ala Arg Arg Gln Ser Phe Gln Ala Asp
            340                 345                 350

Asp Leu Phe Tyr Ala His Ile Ala Gly Met Asp Thr Tyr Ala Ala Gly
        355                 360                 365

Leu Lys Val Ala Ala Lys Leu Ile Asp Asp Gln Val Ile Glu Asn Val
    370                 375                 380

Leu Lys Glu Arg Tyr Ala Ser Phe Asp Ser Gly Ile Gly Ala Asp Phe
385                 390                 395                 400

Glu Ala Gly Lys Val Thr Leu Lys Glu Leu Ala Thr Tyr Ile Glu Asn
                405                 410                 415

Lys Thr Asp Glu Glu Ile Asn Ala Thr Leu Lys Ser Gly Arg Gln Glu
            420                 425                 430

Arg Ile Lys Gln Thr Leu Asn Asn Tyr Ile Phe Ser Val Leu Gly Ser
        435                 440                 445
```

<210> SEQ ID NO 77
<211> LENGTH: 1347
<212> TYPE: DNA
<213> ORGANISM: Leuconostoc mesenteroides

<400> SEQUENCE: 77

```
atggcagaac ttttgatt tccccaagta acatttgtag aatacaatc attacaagcg    60
ggtgatggat ttcattatta taatccagat gaaatagtta aaggtaagaa atgagtgac  120
tggctaaagt tttcagtgac ttattggcat acaatggacc aacgcttagt agacccattt  180
ggtgaaggaa cagcagtccg gccgtgggac aatcaaggta aaccagattc aatggagcaa  240
gcattagcga aggttgatta tttgtttgag ttttggaaa aaactgacgt taattacttt  300
gccttttcatg atcgtgatct tgcacctgaa ggtcatacac ttgccgaaac aaataaaaat  360
ttagatcaag ttattgacaa aattgaacaa aaaatacatg aaacaggtaa aaaacttttta  420
tggaatactt catcactatt tacgaataaa cgttttttgg ctggtggcgc aactacacca  480
tttgctgagg tatttgctta tgcagctgga caaattaagc attcattaga tattgccaag  540
cgcttaggat cagaatcata tgtttttctgg ggcggacgag aaggctacga cttttctatta  600
aatactgaca ccaaacgtga attagaccat attgcagcat tcttaagct agctaaggat  660
tatgcaaatg aaattggtta tcagggacaa ttcttgattg aacccaagcc caagaaccaa  720
acacagcatc aatatgattt tgatgtgcaa acaacaattg ctttctgaa aacttatgga  780
ttagaggata cattcaagtt gaacttggaa ggcaatcacg cctacttagc tggtcacacg  840
tatgagcatg aagtgagatt tgcgcgagag gctggttttgt tagggtcatt agatgctaac  900
atgggtgata gctcactgg ttgggacatt gatgaatttc aaatgatgt ttatgaggcg  960
accttagtaa tgtatgaatt cttgaaaaac gggggtctac caactggtgg tttgaatttt  1020
gattcgaaag cacgccgtca agttttccaa gctgacgatt tgttctacgc gcatattgct  1080
ggtatggata cttatgctgc tggcttgaaa gttgctgcta agctaattga tgaccaagtg  1140
attgaaaatg ttctgaaaga gcggtatgct tcattttgatt cgggtattgg cgctgatttt  1200
gaagctggga agttaccttt aaaagaattg gccaccttata ttgaaaaata aacagatgaa  1260
gaaatcaacg caaccctcaa gtcaggtcgc aagaacgaa tcaaacaaac attgaataat  1320
tacattttt ctgtacttgg atcttaa                                        1347
```

```
<210> SEQ ID NO 78
<211> LENGTH: 439
<212> TYPE: PRT
<213> ORGANISM: Thermoanaerobacterium thermosulfurigenes

<400> SEQUENCE: 78

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Arg Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Trp Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Arg Glu Asn Tyr Val Phe Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Thr Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380
```

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 79
<211> LENGTH: 1320
<212> TYPE: DNA
<213> ORGANISM: Thermoanaerobacterium Thermosulfurigenes

<400> SEQUENCE: 79

| | |
|---|---:|
| atgaataaat attttgagaa cgtatctaaa ataaaatatg aaggaccaaa atcaaacaat | 60 |
| ccttattctt ttaaatttta caatcctgag gaagtaatcg atggtaagac gatggaggag | 120 |
| catcttcgct tttctatagc ttattggcac acttttactg ctgatggaac agatcaattt | 180 |
| ggcaaagcta ccatgcaaag gccatggaat cactatacag atcctatgga catagctaaa | 240 |
| gcaagggtag aggcagcatt tgagtttttt gataagataa atgcaccgta tttctgcttc | 300 |
| catgatagat atattgcccc tgaaggagac actcttagag agacgaacaa aaatttagat | 360 |
| acaatagttg ctatgataaa ggattacttg aagaccagca gacgaaagt tttgtggggt | 420 |
| actgcgaatc ttttctccaa tccaagattt gtgcatggtg catcaacgtc ttgcaatgcc | 480 |
| gatgttttcg catattctgc agcgcaagtc aaaaaagcac ttgagattac taaggagctt | 540 |
| ggtggcgaaa actacgtatt ctggggtgga agagaaggat atgagacact tctcaataca | 600 |
| gatatggagt ttgagcttga taattttgca agatttttgc acatggctgt tgattatgca | 660 |
| aaggaaatcg gctttgaagg ccagttcttg attgagccga agccaaagga gcctacaaag | 720 |
| catcaatacg actttgacgt ggcaaatgta ttggcattct tgagaaaata cgatcttgac | 780 |
| aaatatttca agttaatat cgaagcaaat catgcaacat tagcattcca tgatttccag | 840 |
| catgagctaa gatacgccag aataaacggt gtattaggat cgattgacgc aaatacgggt | 900 |
| gatatgctat taggatggga tacagatcag ttccctacag atatacgcat gacaacactt | 960 |
| gctatgtatg aagttataaa gatgggtgga tttgacaaag gcggactcaa cttcgatgcg | 1020 |
| aaagtaagac gtgcttcatt tgagccagaa gatcttttct tgggtcacat agcaggaatg | 1080 |
| gatgcttttg caaaaggctt caaagtggct tacaagcttg taaagatag ggtatttgac | 1140 |
| aagttcatcg aagaaagata tgcaagctac aaagatggca taggtgcaga tattgtaagt | 1200 |
| gggaaagctg attttagaag tcttgaaaag tatgcattag agcgcagcca gattgtcaac | 1260 |
| aaatcaggaa gacaagagct attagagtca atcctaaatc agtatttgtt tgcagaataa | 1320 |

<210> SEQ ID NO 80
<211> LENGTH: 444
<212> TYPE: PRT
<213> ORGANISM: Thermotoga neapolitana

<400> SEQUENCE: 80

Met Ala Glu Phe Phe Pro Glu Ile Pro Lys Val Gln Phe Glu Gly Lys
1               5                   10                  15

Glu Ser Thr Asn Pro Leu Ala Phe Lys Phe Tyr Asp Pro Glu Glu Ile
                20                  25                  30

Ile Asp Gly Lys Pro Leu Lys Asp His Leu Lys Phe Ser Val Ala Phe
            35                  40                  45

-continued

Trp His Thr Phe Val Asn Glu Gly Arg Asp Pro Phe Gly Asp Pro Thr
    50                  55                  60

Ala Asp Arg Pro Trp Asn Arg Tyr Thr Asp Pro Met Asp Lys Ala Phe
65                  70                  75                  80

Ala Arg Val Asp Ala Leu Phe Glu Phe Cys Glu Lys Leu Asn Ile Glu
                85                  90                  95

Tyr Phe Cys Phe His Asp Arg Asp Ile Ala Pro Glu Gly Lys Thr Leu
            100                 105                 110

Arg Glu Thr Asn Lys Ile Leu Asp Lys Val Val Glu Arg Ile Lys Glu
        115                 120                 125

Arg Met Lys Asp Ser Asn Val Lys Leu Leu Trp Gly Thr Ala Asn Leu
    130                 135                 140

Phe Ser His Pro Arg Tyr Met His Gly Ala Ala Thr Thr Cys Ser Ala
145                 150                 155                 160

Asp Val Phe Ala Tyr Ala Ala Ala Gln Val Lys Lys Ala Leu Glu Ile
                165                 170                 175

Thr Lys Glu Leu Gly Gly Glu Gly Tyr Val Phe Trp Gly Gly Arg Glu
            180                 185                 190

Gly Tyr Glu Thr Leu Leu Asn Thr Asp Leu Gly Phe Glu Leu Glu Asn
        195                 200                 205

Leu Ala Arg Phe Leu Arg Met Ala Val Asp Tyr Ala Lys Arg Ile Gly
    210                 215                 220

Phe Thr Gly Gln Phe Leu Ile Glu Pro Lys Pro Lys Glu Pro Thr Lys
225                 230                 235                 240

His Gln Tyr Asp Phe Asp Val Ala Thr Ala Tyr Ala Phe Leu Lys Ser
                245                 250                 255

His Gly Leu Asp Glu Tyr Phe Lys Phe Asn Ile Glu Ala Asn His Ala
            260                 265                 270

Thr Leu Ala Gly His Thr Phe Gln His Glu Leu Arg Met Ala Arg Ile
        275                 280                 285

Leu Gly Lys Leu Gly Ser Ile Asp Ala Asn Gln Gly Asp Leu Leu Leu
    290                 295                 300

Gly Trp Asp Thr Asp Gln Phe Pro Thr Asn Val Tyr Asp Thr Thr Leu
305                 310                 315                 320

Ala Met Tyr Glu Val Ile Lys Ala Gly Gly Phe Thr Lys Gly Gly Leu
                325                 330                 335

Asn Phe Asp Ala Lys Val Arg Arg Ala Ser Tyr Lys Val Glu Asp Leu
            340                 345                 350

Phe Ile Gly His Ile Ala Gly Met Asp Thr Phe Ala Leu Gly Phe Lys
        355                 360                 365

Val Ala Tyr Lys Leu Val Lys Asp Gly Val Leu Asp Lys Phe Ile Glu
    370                 375                 380

Glu Lys Tyr Arg Ser Phe Arg Glu Gly Ile Gly Arg Asp Ile Val Glu
385                 390                 395                 400

Gly Lys Val Asp Phe Glu Lys Leu Glu Glu Tyr Ile Ile Asp Lys Glu
                405                 410                 415

Thr Ile Glu Leu Pro Ser Gly Lys Gln Glu Tyr Leu Glu Ser Leu Ile
            420                 425                 430

Asn Ser Tyr Ile Val Lys Thr Ile Leu Glu Leu Arg
        435                 440

<210> SEQ ID NO 81
<211> LENGTH: 1335
<212> TYPE: DNA

<213> ORGANISM: Thermotoga neapolitana

<400> SEQUENCE: 81

```
atggctgaat ctttccaga atcccgaaa gtgcagttcg aaggcaaaga agcacaaat      60
ccacttgcgt tcaagttcta cgatccagaa gagatcatcg acggcaaacc cctcaaggac    120
catctgaagt ctccgttgc cttctggcac accttcgtga acgagggaag ggatcccttc     180
ggagacccaa cggccgatcg tccctggaac aggtacaccg atcccatgga caaggctttt    240
gcaagggtgg acgcccttt tgaattctgc gaaaaactca acatcgagta cttctgcttc    300
cacgacagag acatcgctcc cgagggaaaa acgctgaggg agacaaacaa aattttggac    360
aaagtagtgg agagaatcaa agagagaatg aaagacagca acgtgaagct cctctggggt    420
actgcaaacc tcttttccca cccaaggtac atgcatggtg cagcgacaac ctgcagtgct    480
gatgttttg cgtacgcggc cgcccaggtg aaaaagccc ttgagatcac caaagaactt     540
ggaggagaag ggtacgtctt ctggggtgga agagaaggat acgaaacact cctcaacacg    600
gaccttggat tcgaacttga aacctcgcc cgcttcctca gaatggctgt ggattatgca    660
aaaaggatcg gtttcaccgg acagttcctc atcgaaccaa aaccgaaaga cccaccaaa    720
caccagtacg acttcgacgt tgcaaccgcc tatgccttcc tgaagagcca cggtctcgat    780
gaatacttca aattcaacat cgaggcaaac acgccacac tcgccggtca caccttccag     840
cacgaactga aatggcaag gatccttgga aaactcggaa gcatcgatgc aaaccaggga    900
gaccttcttc ttggatggga caccgatcag ttcccaacaa acgtctacga tacaaccctt    960
gcaatgtacg aagtgataaa agcgggaggc ttcacaaaag gtgggctcaa cttcgatgcg   1020
aaggtgagga gggcttctta caaagtggag gacctcttca tagggcacat agcgggaatg   1080
gacacctttg cactcggttt caaggtggca tacaaactcg tgaaggatgg tgttctggac   1140
aaattcatcg aagaaaagta cagaagtttc agggagggca ttggaaggga catcgtcgaa   1200
ggtaaagtgg attttgaaaa acttgaagag tatataatag acaaagaaac gatagaactt   1260
ccatctggaa agcaagaata cctggaaagc ctcatcaaca gttacatagt gaagaccatt   1320
ctggaactga ggtga                                                    1335
```

<210> SEQ ID NO 82
<211> LENGTH: 388
<212> TYPE: PRT
<213> ORGANISM: Streptomyces rubiginosus

<400> SEQUENCE: 82

```
Met Asn Tyr Gln Pro Thr Pro Glu Asp Arg Phe Thr Phe Gly Leu Trp
  1               5                  10                  15

Thr Val Gly Trp Glu Gly Arg Asp Pro Phe Gly Asp Ala Thr Arg Arg
             20                  25                  30

Ala Leu Asp Pro Val Glu Ser Val Arg Arg Leu Ala Glu Leu Gly Ala
         35                  40                  45

His Gly Val Thr Phe His Asp Asp Leu Ile Pro Phe Gly Ser Ser
     50                  55                  60

Asp Ser Glu Arg Glu Glu His Val Lys Arg Phe Arg Gln Ala Leu Asp
 65                  70                  75                  80

Asp Thr Gly Met Lys Val Pro Met Ala Thr Thr Asn Leu Phe Thr His
                 85                  90                  95

Pro Val Phe Lys Asp Gly Gly Phe Thr Ala Asn Asp Arg Asp Val Arg
            100                 105                 110

Arg Tyr Ala Leu Arg Lys Thr Ile Arg Asn Ile Asp Leu Ala Val Glu
```

```
                    115                 120                 125
Leu Gly Ala Glu Thr Tyr Val Ala Trp Gly Arg Glu Gly Ala Glu
    130                 135                 140

Ser Gly Gly Ala Lys Asp Val Arg Asp Ala Leu Asp Arg Met Lys Glu
145                 150                 155                 160

Ala Phe Asp Leu Leu Gly Glu Tyr Val Thr Ser Gln Gly Tyr Asp Ile
                165                 170                 175

Arg Phe Ala Ile Glu Pro Lys Pro Asn Glu Pro Arg Gly Asp Ile Leu
            180                 185                 190

Leu Pro Thr Val Gly His Ala Leu Ala Phe Ile Glu Arg Leu Glu Arg
        195                 200                 205

Pro Glu Leu Tyr Gly Val Asn Pro Glu Val Gly His Glu Gln Met Ala
    210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Asn Gly Ile Lys Tyr Asp Gln
                245                 250                 255

Asp Leu Arg Phe Gly Ala Gly Asp Leu Arg Ala Ala Phe Trp Leu Val
            260                 265                 270

Asp Leu Leu Glu Ser Ala Gly Tyr Ser Gly Pro Arg His Phe Asp Phe
        275                 280                 285

Lys Pro Pro Arg Thr Glu Asp Phe Asp Gly Val Trp Ala Ser Ala Ala
    290                 295                 300

Gly Cys Met Arg Asn Tyr Leu Ile Leu Lys Glu Arg Ala Ala Ala Phe
305                 310                 315                 320

Arg Ala Asp Pro Glu Val Gln Glu Ala Leu Arg Ala Ser Arg Leu Asp
                325                 330                 335

Glu Leu Ala Arg Pro Thr Ala Ala Asp Gly Leu Gln Ala Leu Leu Asp
            340                 345                 350

Asp Arg Ser Ala Phe Glu Glu Phe Asp Val Asp Ala Ala Ala Ala Arg
        355                 360                 365

Gly Met Ala Phe Glu Arg Leu Asp Gln Leu Ala Met Asp His Leu Leu
    370                 375                 380

Gly Ala Arg Gly
385

<210> SEQ ID NO 83
<211> LENGTH: 1167
<212> TYPE: DNA
<213> ORGANISM: Streptomyces rubiginosus

<400> SEQUENCE: 83
atgaactacc agcccacccc cgaggacagg ttcaccttcg actgtggac cgtcggctgg     60 cagggacggg acccccttcgg tgacgccacg cggcgcgccc tcgacccggt cgagtcggtg    120
cggcggctgg ccgagctggg cgcccacggc gtcacgttcc acgacgacga cctcatcccc    180
ttcggctcca gcgacagcga gcgcgaggag cacgtcaagc ggttccggca ggcgctggac    240
gacaccggca tgaaggtgcc gatggccacc accaacctgt tcacccaccc ggtgttcaag    300
gacggcggct tcaccgccaa cgaccgcgac gtgcgccgct acgccctgcg caagaccatc    360
cgcaacatcg acctcgcggt cgagctcggc gccgagacct atgtggcctg ggcggccgc    420 gagggtgccg agtcgggtgg cgccaaggac gtgcgggacg ccctcgaccg catgaaggag    480
gccttcgacc tgctcggcga gtacgtcacc tcccagggct acgacatccg cttcgccatc    540
gagcccaagc cgaacgagcc gcgcggcgac atcctgctcc ccaccgtcgg ccacgccctg    600
```

```
gcgttcatcg agcgcctgga gcgaccggag ctgtacggcg tgaacccgga ggtcggccac    660
gagcagatgg ccgggctgaa cttcccgcac ggcatcgcgc aggcgctgtg ggcgggcaag    720
ctgttccaca tcgacctcaa cggccagaac ggcatcaagt acgaccagga cctccgcttc    780
ggcgcgggcg acctgcgggc cgcgttctgg ctggtggacc tgctggagtc ggccggctac    840
agcggcccgc ggcacttcga cttcaagccg ccgcggaccg aggacttcga cggggtgtgg    900
gcctcggcgg ccggctgcat gcgcaactac ctgatcctca aggagcgtgc ggcggccttc    960
cgcgccgacc ccgaggtgca ggaggcgctg cgcgcgtccc gtctggacga gctggcccgg   1020
cccacggcgg ccgacggtct gcaggccctg ctcgacgacc ggtccgcctt cgaggagttc   1080
gacgtcgacg cggcggcggc ccgtgggatg gccttcgagc gcctggacca gctggcgatg   1140
gaccacctgc tgggcgcccg gggctga                                       1167
```

<210> SEQ ID NO 84
<211> LENGTH: 391
<212> TYPE: PRT
<213> ORGANISM: Streptomyces albus

<400> SEQUENCE: 84

```
Met Asn Tyr Gln Pro Thr Pro Glu Asp Arg Phe Thr Phe Gly Leu Trp
1               5                   10                  15

Thr Val Gly Trp Glu Gly Arg Asp Pro Phe Gly Asp Ala Thr Arg Thr
            20                  25                  30

Ala Leu Asp Pro Val Glu Ser Val Arg Arg Leu Ala Glu Leu Gly Ala
        35                  40                  45

His Gly Val Thr Phe His Asp Asp Leu Ile Pro Phe Gly Ser Ser
    50                  55                  60

Asp Ser Glu Arg Tyr Glu His Val Lys Arg Phe Arg Gln Ala Leu Asp
65                  70                  75                  80

Asp Thr Gly Met Lys Val Pro Met Ala Thr Thr Asn Leu Phe Thr His
                85                  90                  95

Pro Val Phe Lys Asp Gly Gly Phe Thr Ala Asn Asp Arg Asp Val Arg
            100                 105                 110

Arg Tyr Ala Leu Arg Lys Thr Ile Arg Asn Ile Asp Leu Ala Val Glu
        115                 120                 125

Leu Gly Ala Glu Thr Tyr Val Ala Trp Gly Gly Arg Glu Gly Ala Glu
    130                 135                 140

Ser Gly Gly Ala Lys Asp Val Arg Asp Ala Leu Asp Arg Met Lys Glu
145                 150                 155                 160

Ala Phe Asp Leu Leu Gly Glu Tyr Val Thr Ser Gln Gly Tyr Asp Ile
                165                 170                 175

Arg Phe Ala Ile Glu Pro Lys Pro Asn Glu Pro Arg Gly Asp Ile Leu
            180                 185                 190

Leu Pro Thr Val Gly His Ala Leu Ala Phe Ile Glu Arg Leu Glu Arg
        195                 200                 205

Pro Glu Leu Tyr Gly Val Asn Pro Glu Val Gly His Glu Gln Met Ala
    210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Asn Gly Ile Lys Tyr Asp Gln
                245                 250                 255

Asp Leu Arg Phe Gly Ala Gly Asp Leu Arg Ala Ala Phe Trp Leu Val
            260                 265                 270
```

-continued

Asp Leu Leu Glu Ser Ala Gly Tyr Ser Gly Pro Arg His Phe Asp Phe
            275                 280                 285

Lys Pro Pro Arg Thr Glu Asp Phe Asp Gly Val Trp Ala Ser Ala Ala
        290                 295                 300

Gly Cys Met Arg Asn Tyr Leu Ile Leu Lys Glu Arg Ala Ala Ala Phe
305                 310                 315                 320

Arg Ala Asp Pro Glu Val Gln Glu Ala Leu Arg Ala Ser Arg Leu Asp
                325                 330                 335

Glu Leu Ala Arg Pro Thr Ala Ala Asp Gly Leu Gln Ala Leu Leu Asp
            340                 345                 350

Asp Arg Ser Ala Phe Glu Glu Phe Asp Val Asp Ala Ala Ala Ala Arg
        355                 360                 365

Gly Met Ala Phe Glu Arg Leu Asp Gln Leu Ala Met Asp His Leu Leu
    370                 375                 380

Gly Ala Arg Gly Ala Ala Ala
385                 390

<210> SEQ ID NO 85
<211> LENGTH: 1167
<212> TYPE: DNA
<213> ORGANISM: artificial sequence
<220> FEATURE:
<223> OTHER INFORMATION: designed coding sequence

<400> SEQUENCE: 85
atgaactacc agcccacccc cgaggacagg ttcaccttcg gactgtggac cgtcggctgg      60
gagggacggg accccttcgg tgacgccacg cggagcgccc tcgacccggt cgagtcggtg     120
cggcggctgg ccgagctggg cgcccacggc gtcacgttcc acgacgacga cctcatcccc     180
ttcggctcca gcgacagcga cgctacgag cacgtcaagc ggttccggca ggcgctggac     240
gacaccggca tgaaggtgcc gatggccacc accaacctgt tcacccaccc ggtgttcaag     300
gacggcggct tcaccgccaa cgaccgcgac gtgcgccgct acgccctgcg caagaccatc     360
cgcaacatcg acctcgcggt cgagctcggc gccgagacct atgtggcctg ggcggccgc     420 gagggtgccg agtcgggtgg cgccaaggac gtgcgggacg ccctcgaccg catgaaggag     480
gccttcgacc tgctcggcga gtacgtcacc tcccagggct acgacatccg cttcgccatc     540
gagcccaagc gaacgagcc gcggcgac atcctgctcc ccaccgtcgg ccacgccctg     600
gcgttcatcg agcgcctgga cgaccggag ctgtacggcg tgaaccccga ggtcggccac     660
gagcagatgg ccgggctgaa cttcccgcac ggcatcgcgc aggcgctgtg ggcgggcaag     720
ctgttccaca tcgacctcaa cggccagaac ggcatcaagt acgaccagga cctccgcttc     780
ggcgcgggcg acctgcgggc cgcgttctgg ctggtggacc tgctggagtc ggccggctac     840 agcggccgc ggcacttcga cttcaagccg ccgcggaccg aggacttcga cggggtgtgg     900
gcctcggcgg ccggctgcat gcgcaactac ctgatcctca aggagcgtgc ggcggccttc     960
cgcgccgacc ccgaggtgca ggaggcgctg cgcgcgtccc gtctggacga gctggcccgg    1020
cccacggcgg ccgacggtct gcaggccctg ctcgacgacc ggtccgcctt cgaggagttc    1080
gacgtcgacg cggcggcggc ccgtgggatg gccttcgagc gctggaccag ctggcgatg    1140 gaccaccctgc tgggcgcccg gggctga                                       1167

<210> SEQ ID NO 86
<211> LENGTH: 387
<212> TYPE: PRT
<213> ORGANISM: Thermus thermophilus

<400> SEQUENCE: 86

```
Met Tyr Glu Pro Lys Pro Glu His Arg Phe Thr Phe Gly Leu Trp Thr
1               5                   10                  15
Val Gly Asn Val Gly Arg Asp Pro Phe Gly Asp Ala Val Arg Glu Arg
                20                  25                  30
Leu Asp Pro Val Tyr Val Val His Lys Leu Ala Glu Leu Gly Ala Tyr
            35                  40                  45
Gly Val Asn Leu His Asp Glu Asp Leu Ile Pro Arg Gly Thr Pro Pro
        50                  55                  60
Gln Glu Arg Asp Gln Ile Val Arg Arg Phe Lys Lys Ala Leu Asp Glu
65                  70                  75                  80
Thr Gly Leu Lys Val Pro Met Val Thr Ala Asn Leu Phe Ser Asp Pro
                85                  90                  95
Ala Phe Lys Asp Gly Ala Phe Thr Ser Pro Asp Pro Trp Val Arg Ala
                100                 105                 110
Tyr Ala Leu Arg Lys Ser Leu Glu Thr Met Asp Leu Gly Ala Glu Leu
            115                 120                 125
Gly Ala Glu Ile Tyr Val Val Trp Pro Gly Arg Glu Gly Ala Glu Val
        130                 135                 140
Glu Ala Thr Gly Lys Ala Arg Lys Val Trp Asp Trp Val Arg Glu Ala
145                 150                 155                 160
Leu Asn Phe Met Ala Ala Tyr Ala Glu Asp Gln Gly Tyr Gly Tyr Arg
                165                 170                 175
Phe Ala Leu Glu Pro Lys Pro Asn Glu Pro Arg Gly Asp Ile Tyr Phe
                180                 185                 190
Ala Thr Val Gly Ser Met Leu Ala Phe Ile His Thr Leu Asp Arg Pro
            195                 200                 205
Glu Arg Phe Gly Leu Asn Pro Glu Phe Ala His Glu Thr Met Ala Gly
        210                 215                 220
Leu Asn Phe Val His Ala Val Ala Gln Ala Leu Asp Ala Gly Lys Leu
225                 230                 235                 240
Phe His Ile Asp Leu Asn Asp Gln Arg Met Ser Arg Phe Asp Gln Asp
                245                 250                 255
Leu Arg Phe Gly Ser Glu Asn Leu Lys Ala Ala Phe Phe Leu Val Asp
                260                 265                 270
Leu Leu Glu Ser Ser Gly Tyr Gln Gly Pro Arg His Phe Asp Ala His
            275                 280                 285
Ala Leu Arg Thr Glu Asp Glu Gly Val Trp Ala Phe Ala Arg Gly
        290                 295                 300
Cys Met Arg Thr Tyr Leu Ile Leu Lys Glu Arg Ala Glu Ala Phe Arg
305                 310                 315                 320
Glu Asp Pro Glu Val Lys Glu Leu Leu Ala Ala Tyr Tyr Gln Glu Asp
                325                 330                 335
Pro Ala Ala Leu Ala Leu Leu Gly Pro Tyr Ser Arg Glu Lys Ala Glu
                340                 345                 350
Ala Leu Lys Arg Ala Glu Leu Pro Leu Glu Ala Lys Arg Arg Arg Gly
            355                 360                 365
Tyr Ala Leu Glu Arg Leu Asp Gln Leu Ala Val Glu Tyr Leu Leu Gly
        370                 375                 380
Val Arg Gly
385
```

<210> SEQ ID NO 87
<211> LENGTH: 1164

<212> TYPE: DNA
<213> ORGANISM: Thermus thermophilus

<400> SEQUENCE: 87

```
gtgtacgagc ccaaaccgga gcacaggttt acctttggcc tttggactgt gggcaatgtg      60
ggccgtgatc ccttcgggga cgcggttcgg gagaggctgg acccggttta cgtggttcat     120
aagctggcgg agcttggggc ctacggggta accttcacg acgaggacct gatcccgcgg      180
ggcacgcctc ctcaggagcg ggaccagatc gtgaggcgct caagaaggc tctcgatgaa      240
accggcctca aggtcccat ggtcaccgcc aacctcttct ccgaccctgc tttcaaggac      300
ggggccttca cgagcccga cccttgggtt cgggcctatg ccttgcggaa gagcctggag      360
accatggacc tgggggcaga gcttggggcc gagatctacg tggtctggcc gggccgggag      420
ggagctgagg tggaggccac gggcaaggcc cggaaggtct gggactgggt gcgggaggcg      480
ctgaacttca tggccgccta cgccgaggac cagggatacg ggtaccggtt gccctcgag      540
cccaagccta cgagccccg gggggacatt tacttcgcca ccgtggggag catgctcgcc      600
tttattcata ccctggaccg gcccgagcgc ttcggcctga ccccgagtt cgcccacgag      660
accatggccg ggcttaactt tgtccacgcc gtggcccagg ctctcgacgc cgggaagctt      720
ttccacattg acctcaacga ccaacggatg agccggtttg accaggacct ccgcttcggc      780
tcggagaacc tcaaggcggc cttttttcctg gtggacctcc tggaaagctc cggctaccag      840
ggcccccgcc actttgacgc ccacgccctg cgtaccgagg acgaagaagg ggtttgggcc      900
ttcgcccgag gctgcatgcg tacctacctg atcttaaagg aaagggctga agccttccgc      960
gaggatcccg aggtcaagga gcttcttgcc gcttactatc aagaagatcc tgcggccttg     1020
gccctttgg gccctactc ccgcgagaag gccgaagccc tcaagcgggc ggagcttccc      1080
ctcgaggcca gcggcgccg gggttatgcc ctggaacgcc tggaccagct ggcggtggag     1140
tacctcctgg gggtgcgggg gtga                                           1164
```

<210> SEQ ID NO 88
<211> LENGTH: 388
<212> TYPE: PRT
<213> ORGANISM: Streptomyces diastaticus

<400> SEQUENCE: 88

```
Met Ser Tyr Gln Pro Thr Pro Glu Asp Lys Phe Thr Phe Gly Leu Trp
  1               5                  10                  15

Thr Val Gly Trp Gln Gly Arg Asp Pro Phe Gly Asp Ala Thr Arg Gly
         20                  25                  30

Ala Leu Asp Pro Ala Glu Ser Val Arg Arg Leu Ala Glu Leu Gly Ala
     35                  40                  45

His Gly Val Thr Phe His Asp Asp Leu Ile Pro Phe Gly Ala Thr
     50                  55                  60

Asp Ser Glu Arg Ala Glu His Ile Lys Arg Phe Arg Gln Gly Leu Asp
 65                  70                  75                  80

Glu Thr Gly Met Lys Val Pro Met Ala Thr Thr Asn Leu Phe Thr His
                 85                  90                  95

Pro Val Phe Lys Asp Gly Gly Phe Thr Ala Asn Asp Arg Asp Val Arg
            100                 105                 110

Arg Tyr Ala Val Arg Lys Thr Ile Arg Asn Ile Asp Leu Ala Val Glu
        115                 120                 125

Leu Gly Ala Gln Thr Tyr Val Ala Trp Gly Gly Arg Glu Gly Ala Glu
    130                 135                 140
```

```
Ser Gly Ala Ala Lys Asp Val Arg Val Ala Leu Asp Arg Met Lys Glu
145                 150                 155                 160

Ala Phe Asp Leu Leu Gly Glu Tyr Val Thr Ser Gln Gly Tyr Asp Thr
            165                 170                 175

Pro Phe Ala Ile Glu Pro Lys Pro Asn Glu Pro Arg Gly Asp Ile Leu
            180                 185                 190

Leu Pro Thr Ile Gly His Ala Leu Ala Phe Ile Asp Gly Leu Glu Arg
            195                 200                 205

Pro Glu Leu Tyr Gly Val Asn Pro Glu Val Gly His Glu Gln Met Ala
210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Ser Gly Ile Lys Tyr Asp Gln
            245                 250                 255

Asp Leu Arg Phe Gly Pro Gly Asp Leu Ala Ala Ala Phe Trp Leu Val
            260                 265                 270

Asp Leu Leu Glu Ser Ala Gly Tyr Glu Gly Pro Arg His Phe Asp Phe
            275                 280                 285

Lys Pro Pro Arg Thr Glu Asp Phe Asp Gly Val Trp Ala Ser Ala Ala
290                 295                 300

Gly Cys Met Arg Asn Tyr Leu Ile Leu Lys Glu Arg Ala Ala Ala Phe
305                 310                 315                 320

Arg Ala Asp Pro Glu Val Gln Glu Ala Leu Arg Ala Arg Leu Asp
            325                 330                 335

Glu Leu Ala Gln Pro Thr Ala Gly Asp Gly Leu Gln Ala Leu Leu Pro
            340                 345                 350

Asp Arg Ser Ala Phe Glu Asp Phe Asp Pro Ala Ala Ala Ala Arg
            355                 360                 365

Gly Met Ala Phe Glu Arg Leu Asp Gln Leu Ala Met Asp His Leu Leu
            370                 375                 380

Gly Ala Arg Gly
385

<210> SEQ ID NO 89
<211> LENGTH: 1167
<212> TYPE: DNA
<213> ORGANISM: Streptomyces diastaticus

<400> SEQUENCE: 89
atgagctacc agcccacccc cgaggacaag ttcacgttcg gcctgtggac cgtcggctgg      60
cagggacggg acccttcgg cgacgccacc cgcggcgccc tcgacccggc cgagtccgtc     120
cgccgcctcg ccgagctcgg cgcccacggc gtgacgttcc acgacgacga cctcatcccc     180
ttcggcgcga cggacagcga gcgcgccgag cacatcaagc ggttccgcca ggggctggac     240
gagaccggca tgaaggtccc gatggcgacc accaacctgt tcacccaccc ggtgttttaag     300 gacggcggct tcaccgcgaa cgaccgtgac gtgcgccgtt acgccgtgcg caagaccatc     360
cgcaacatcg acctcgcggt cgagctcggc gcgcagacct acgtcgcctg ggcggccgc     420 gagggcgccg agtccggcgc cgccaaggac gtccgggtcg ccctcgaccg catgaaggag     480
gctttcgacc tcctcggcga gtacgtcacc tcccagggct acgacactcc gttcgccatc     540
gagcccaagc cgaacgagcc ccgcggcgac atcctcctgc cgacgatcgg ccacgccctc     600
gccttcatcg acggcctcga gcgcccggag ctgtacggcg tcaacccgga ggtcggccac     660
gagcagatgg ccgggctcaa cttccccgcac ggcatcgccc aggccctgtg ggcgggcaag     720
```

-continued

```
ctgttccaca tcgacctcaa cggccagtcc ggcatcaagt acgaccagga cctccgcttc    780
gggccgggcg acctggccgc cgcgttctgg ctggtggacc tgctggagtc ggccggctac    840
gagggcccgc gccacttcga cttcaagccg ccgcggaccg aggacttcga cggcgtctgg    900
gcctccgcgg ccggctgcat gcgcaactac ctgatcctca aggagcgcgc ggccgccttc    960
cgtgcggacc cggaggtgca ggaggcgctg cgcgcggccc ggctggacga gctcgcccag   1020
ccgacggcgg cgacggcct ccaggccctg ctgcccgacc gctcggcgtt cgaggacttc   1080
gacccggacg cggcggcggc ccgtggcatg gccttcgagc ggctggacca gctggcgatg   1140
gaccacctgc tgggcgcgcg gggctag                                      1167
```

<210> SEQ ID NO 90
<211> LENGTH: 387
<212> TYPE: PRT
<213> ORGANISM: Streptomyces coelicolor

<400> SEQUENCE: 90

```
Met Asn Tyr Gln Pro Thr Pro Glu Asp Arg Phe Thr Phe Gly Leu Trp
  1               5                  10                  15

Thr Val Gly Trp Gln Gly Arg Asp Pro Phe Gly Asp Ala Thr Arg Gln
             20                  25                  30

Ala Leu Asp Pro Ala Glu Ser Val Arg Arg Leu Ser Glu Leu Gly Ala
         35                  40                  45

Tyr Gly Val Thr Phe His Asp Asp Leu Ile Pro Phe Gly Ser Ser
     50                  55                  60

Asp Thr Glu Arg Glu Ser His Ile Lys Arg Phe Arg Gln Ala Leu Asp
 65                  70                  75                  80

Ala Thr Gly Met Lys Val Pro Met Ala Thr Thr Asn Leu Phe Thr His
                 85                  90                  95

Pro Val Phe Lys Asp Gly Ala Phe Thr Ala Asn Asp Arg Asp Val Arg
            100                 105                 110

Arg Tyr Ala Leu Arg Lys Thr Ile Arg Asn Ile Asp Leu Ala Val Glu
        115                 120                 125

Leu Gly Ala Ser Val Tyr Val Ala Trp Gly Gly Arg Glu Gly Ala Glu
    130                 135                 140

Ser Gly Ala Ala Lys Asp Val Arg Asp Ala Leu Asp Arg Met Lys Glu
145                 150                 155                 160

Ala Phe Asp Leu Leu Gly Glu Tyr Val Thr Glu Gln Gly Tyr Asp Leu
                165                 170                 175

Lys Phe Ala Ile Glu Pro Lys Pro Asn Glu Pro Arg Gly Asp Ile Leu
            180                 185                 190

Leu Pro Thr Val Gly His Ala Leu Ala Phe Ile Glu Arg Leu Glu Arg
        195                 200                 205

Pro Glu Leu Tyr Gly Val Asn Pro Glu Val Gly His Glu Gln Met Ala
    210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Ser Gly Ile Lys Tyr Asp Gln
                245                 250                 255

Asp Leu Arg Phe Gly Ala Gly Asp Leu Arg Ala Ala Phe Trp Leu Val
            260                 265                 270

Asp Leu Leu Glu Arg Ala Gly Tyr Ala Gly Pro Arg His Phe Asp Phe
        275                 280                 285

Lys Pro Pro Arg Thr Glu Asp Phe Asp Gly Val Trp Ala Ser Ala Ala
    290                 295                 300
```

```
Gly Cys Met Arg Asn Tyr Leu Ile Leu Lys Asp Arg Ala Ala Ala Phe
305                 310                 315                 320

Arg Ala Asp Pro Gln Val Gln Glu Ala Leu Ala Ala Ala Arg Leu Asp
            325                 330                 335

Glu Leu Ala Arg Pro Thr Ala Glu Asp Gly Leu Ala Ala Leu Leu Ala
            340                 345                 350

Asp Arg Ser Ala Tyr Asp Thr Phe Asp Val Asp Ala Ala Ala Ala Arg
        355                 360                 365

Gly Met Ala Phe Glu His Leu Asp Gln Leu Ala Met Asp His Leu Leu
    370                 375                 380

Gly Ala Arg
385

<210> SEQ ID NO 91
<211> LENGTH: 1164
<212> TYPE: DNA
<213> ORGANISM: Streptomyces coelicolor

<400> SEQUENCE: 91
atgaactacc agcccactcc cgaggacagg ttcacgttcg gtttgtggac ggtcggctgg      60
cagggccgtg acccgttcgg tgacgccacc aggcaggccc tggaccccgc cgagtcggta     120
cggcgtctgt ccgagctggg tgcgtacggc gtcacgttcc acgacgacga cctgatcccc     180
ttcgggtcga gcgacacgga gcgggagtcg cacatcaagc ggttccggca ggcgctggac     240
gcgaccggca tgaaggtgcc gatggcgacg acgaacctgt tcacgcaccc ggtgttcaaa     300
gacggcgcct tcacggcgaa cgaccgggac gtgcggcggt acgcgctgcg caagacgatc     360
cgcaacatcg acctcgcggt cgagctgggc gcgagcgtct acgtggcctg ggcggccgg      420 gagggtgcgg agtccggcgc ggccaaggac gtgcgggacg cgctcgaccg gatgaaggag     480
gccttcgacc tgctgggcga gtacgtcacc gagcagggct acgacctgaa gttcgcgatc     540
gagccgaagc ccaacgagcc gcgcggtgac atcctgctcc cgacggtcgg ccacgccctc     600
gccttcatcg agcgcctcga gcggccgag ctgtacggcg tgaacccgga ggtcggccac      660
gagcagatgg ccggcctgaa cttcccccac ggcatcgccc aggcgctgtg gcggggcaag     720
ctcttccaca tcgacctcaa cggccagtcg ggcatcaagt acgaccagga cctgaggttc     780
ggcgcgggcg acctgcgggc gcgttctgg ctcgtcgacc tgctggagcg ggccgggtac      840
gcgggtccgc ggcacttcga cttcaagccc ccgcggaccg aggacttcga cggcgtgtgg     900
gcgtcggccg ccggctgcat gcgcaactac ctgatcctca aggaccgggc ggcggcattc     960
cgcgccgacc cgcaggtgca ggaggcgctg gccgcggccc ggctggacga actggcccgc    1020
ccgaccgccg aggacggtct cgccgccctg ctggccgacc ggagcgccta cgacaccttc    1080
gacgtggacg cggccgccgc gcgaggcatg gcgttcgagc acctcgacca gctcgccatg    1140
gaccacctcc tcggcgcccg ctga                                           1164

<210> SEQ ID NO 92
<211> LENGTH: 387
<212> TYPE: PRT
<213> ORGANISM: Thermus Caldophilus

<400> SEQUENCE: 92

Met Tyr Glu Pro Lys Pro Glu His Arg Phe Thr Phe Gly Leu Trp Thr
1               5                   10                  15

Val Gly Asn Val Gly Arg Asp Pro Phe Gly Asp Ala Val Arg Glu Arg
            20                  25                  30
```

Leu Asp Pro Val Tyr Val Gly His Lys Leu Ala Glu Leu Gly Val His
            35                  40                  45

Gly Val Asn Leu His Asp Glu Asp Leu Ile Pro Arg Gly Thr Pro Pro
 50                  55                  60

Gln Glu Arg Asp Gln Ile Val Arg Arg Phe Lys Ala Leu Asp Glu
 65                  70                  75                  80

Thr Gly Leu Lys Val Pro Met Val Thr Gly Asn Leu Phe Ser Asp Pro
                85                  90                  95

Gly Phe Lys Asp Gly Phe Thr Ser Arg Asp Pro Trp Val Arg Ala
                100                 105                 110

Tyr Ala Phe Arg Lys Ser Leu Glu Thr Met Asp Leu Gly Ala Glu Leu
            115                 120                 125

Gly Ala Glu Ile Tyr Val Val Trp Pro Gly Arg Glu Gly Ala Glu Val
            130                 135                 140

Glu Ala Thr Gly Lys Ala Arg Lys Val Trp Asp Trp Val Arg Glu Pro
145                 150                 155                 160

Leu Asn Phe Met Ala Ala Tyr Ala Glu Asp Gln Gly Tyr Gly Tyr Arg
                165                 170                 175

Phe Ala Leu Glu Pro Lys Pro Asn Glu Pro Arg Gly Asp Ile Tyr Phe
            180                 185                 190

Ala Thr Val Gly Ser Met Leu Ala Leu Ile His Thr Leu Glu Arg Pro
            195                 200                 205

Glu Arg Phe Gly Leu Asn Pro Glu Phe Ala His Glu Thr Met Ala Gly
            210                 215                 220

Leu Asn Phe Val His Ala Val Ala Gln Ala Leu Asp Ala Gly Lys Leu
225                 230                 235                 240

Leu His Ile Asp Leu Asn Gly Gln Arg Met Asn Arg Phe Asp Gln Asp
                245                 250                 255

Leu Arg Phe Gly Ser Glu Asn Leu Lys Ala Ala Phe Leu Leu Val Asp
            260                 265                 270

Leu Leu Glu Ser Ser Gly Tyr Gln Gly Pro Arg His Phe Asp Ala His
            275                 280                 285

Ala Leu Arg Thr Glu Asp Glu Gly Val Trp Ala Phe Ala Arg Gly
            290                 295                 300

Cys Met Arg Thr Tyr Leu Ile Leu Lys Glu Arg Ala Glu Ala Phe Arg
305                 310                 315                 320

Glu Asp Pro Glu Val Lys Glu Leu Leu Ala Ala Tyr Tyr Gln Glu Asp
                325                 330                 335

Pro Ala Ala Leu Pro Leu Met Asp Pro Tyr Ser His Glu Lys Ala Glu
            340                 345                 350

Ala Leu Lys Arg Ala Glu Leu Pro Leu Glu Ala Lys Arg His Arg Gly
            355                 360                 365

Tyr Ala Leu Glu Arg Leu Asp Gln Leu Ala Val Glu Tyr Leu Leu Gly
            370                 375                 380

Val Arg Gly
385

<210> SEQ ID NO 93
<211> LENGTH: 1164
<212> TYPE: DNA
<213> ORGANISM: artificial sequence
<220> FEATURE:
<223> OTHER INFORMATION: designed coding sequence

<400> SEQUENCE: 93

-continued

```
atgtacgagc ctaaaccgga gcacaggttt acctttggcc tttggactgt gggcaatgtg      60
ggccgtgatc ccttcgggga cgcggttcgg gagaggctgg acccggttta cgtggttcat     120
aagctggcgg agcttggggt ccacggggta aaccttcacg acgaggacct gatcccgcgg     180
ggcacgcctc ctcaggagcg ggaccagatc gtgaggcgct tcaagagggc tctcgatgaa     240
accggcctca aggtccccat ggtcaccggc aacctcttct ccgaccctgg tttcaaggac     300
gggggcttca cgagccggga cccttgggtt cgggcctatg cctttcggaa gagcctggag     360
accatggacc tgggggcaga gcttggggcc gagatctacg tggtctggcc gggccgggag     420
ggagctgagg tggaggccac gggcaaggcc cggaaggtct gggactgggt gcgggagccg     480
ctgaacttca tggccgccta cgccgaggac cagggatacg ggtaccggtt tgccctcgag     540
cccaagccta acgagccccg gggggacatt tacttcgcca ccgtggggag catgctcgcc     600
ttaattcata ccctggagcg gcccgagcgc ttcggcctga accccgagtt cgcccacgag     660
accatggccg ggcttaactt tgtccacgcc gtggcccagg ctctcgacgc cgggaagctt     720
ttgcacattg acctcaacgg ccaacggatg aaccggtttg accaggacct ccgcttcggc     780
tcggagaacc tcaaggcggc ctttctcctg gtggacctcc tggaaagctc cggctaccag     840
ggcccccgcc actttgacgc ccacgccctg cgtaccgagg acgaagaagg ggtttgggcc     900
ttcgcccgag gctgcatgcg tacctacctg atcttaaagg aaagggctga agccttccgc     960
gaggatcccg aggtcaagga gcttcttgcc gcttactatc aagaagatcc tgcggccttg    1020
cccettatgg acccctactc ccacgagaag gccgaagccc tcaagcgggc ggagcttccc    1080
ctcgaggcca agcggcaccg ggttatgccc ctggaacgcc tggaccagct ggcggtggag    1140
tacctcctgg gggtgcgggg gtga                                           1164
```

<210> SEQ ID NO 94
<211> LENGTH: 445
<212> TYPE: PRT
<213> ORGANISM: Xanthomonas campestris

<400> SEQUENCE: 94

```
Met Ser Asn Thr Val Tyr Ile Gly Ala Lys Glu Tyr Phe Pro Gly Ile
1               5                   10                  15

Gly Lys Ile Gly Phe Glu Gly Arg Asp Ser Asp Asn Pro Leu Ala Phe
            20                  25                  30

Lys Val Tyr Asp Ala Asn Lys Thr Ile Gly Asp Lys Thr Met Ala Glu
        35                  40                  45

His Leu Arg Phe Ala Val Ala Tyr Trp His Ser Phe Cys Gly Asn Gly
    50                  55                  60

Ala Asp Pro Phe Gly Pro Gly Thr Arg Ala Tyr Pro Trp Asp Ala Gly
65                  70                  75                  80

Thr Thr Ala Leu Asn Arg Ala Glu Ala Lys Ala Asp Ala Ala Phe Glu
                85                  90                  95

Phe Phe Thr Lys Leu Gly Val Pro Tyr Tyr Cys Phe His Asp Ile Asp
            100                 105                 110

Leu Ala Pro Asp Ala Asp Asp Ile Gly Glu Tyr Glu Lys Asn Leu Lys
        115                 120                 125

His Met Val Gly Ile Ala Lys Gln Arg Gln Ala Asp Thr Gly Ile Lys
    130                 135                 140

Leu Leu Trp Gly Thr Ala Asn Leu Phe Ser His Pro Arg Tyr Met Asn
145                 150                 155                 160

Gly Ala Ser Thr Asn Pro Asp Phe Asn Val Val Ala Arg Ala Ala Val
                165                 170                 175
```

```
Gln Val Lys Ala Ala Ile Asp Ala Thr Val Glu Leu Gly Gly Glu Asn
            180                 185                 190

Tyr Val Phe Trp Gly Arg Glu Gly Tyr Ala Cys Leu His Asn Thr
        195                 200                 205

Gln Met Lys Arg Glu Gln Asp Asn Met Ala Arg Phe Leu Thr Leu Ala
    210                 215                 220

Arg Asp Tyr Gly Arg Ala Ile Gly Phe Lys Gly Asn Phe Leu Ile Glu
225                 230                 235                 240

Pro Lys Pro Met Glu Pro Met Lys His Gln Tyr Asp Phe Asp Ser Ala
                245                 250                 255

Thr Val Ile Gly Phe Leu Arg Gln His Gly Leu Asp Gln Asp Phe Lys
            260                 265                 270

Leu Asn Ile Glu Ala Asn His Ala Thr Leu Ser Gly His Ser Phe Glu
        275                 280                 285

His Asp Leu Gln Val Ala Ser Asp Ala Gly Leu Leu Gly Ser Ile Asp
    290                 295                 300

Ala Asn Arg Gly Asn Pro Gln Asn Gly Trp Asp Thr Asp Gln Phe Pro
305                 310                 315                 320

Thr Asp Leu Tyr Asp Thr Val Gly Ala Met Leu Val Val Leu Arg Gln
                325                 330                 335

Gly Gly Leu Ala Pro Gly Gly Leu Asn Phe Asp Ala Lys Val Arg Arg
            340                 345                 350

Glu Ser Ser Asp Pro Gln Asp Leu Phe Leu Ala His Ile Gly Gly Met
        355                 360                 365

Asp Ala Phe Ala Arg Gly Leu Glu Val Ala Asn Ala Leu Leu Thr Ala
    370                 375                 380

Ser Pro Leu Glu Gln Trp Arg Ala Glu Arg Tyr Ala Ser Phe Asp Ser
385                 390                 395                 400

Gly Ala Gly Ala Asp Phe Ala Ala Gly Lys Thr Thr Leu Ala Asp Leu
                405                 410                 415

Ala Lys His Ala Ala Ser Asn Ala Pro Gln Gln Leu Ser Gly Arg Gln
            420                 425                 430

Glu Ala Tyr Glu Asn Leu Ile Asn Gln Tyr Leu Thr Arg
        435                 440                 445

<210> SEQ ID NO 95
<211> LENGTH: 1338
<212> TYPE: DNA
<213> ORGANISM: Xanthomonas campestris

<400> SEQUENCE: 95
atgagcaaca ccgtgtacat cggcgcgaaa gaatatttcc ccggcatcgg caagatcggc        60
ttcgaaggcc gcgattcgga caacccgctc gcgttcaagg tctacgacgc caacaaaacc       120
atcggcgaca agaccatggc cgagcatctg cgctttgccg tggcctactg cacagcttc        180 tgcggcaatg gcgccgaccc gttcggcccg ggcacgcggg cgtatccgtg ggatgcgggc       240
actaccgcgt tgaaccgtgc cgaagccaag gccgatgcgg cgttcgagtt cttcaccaag       300
ctcggcgtgc cgtactactg cttccacgat atcgacctgg caccggatgc cgacgacatc       360
ggcgagtacg aaaagaatct caaacacatg gtgggcatcg ccaagcagcg ccaggccgac       420
accggcatca agctgttgtg gggcacggcc aacctgttct cgcacccgcg ctacatgaat       480
ggcgcatcga ccaaccccgga cttcaatgtc gtggcgcgcg ccgccgtgca ggtcaaggcc       540
gcgatcgatg ccaccgttga attgggcggc gaaaactacg tgttctgggg cggccgcgaa       600
```

```
                                                -continued ggctacgcct gcctgcacaa cacgcagatg aagcgcgagc aggacaacat ggcgcgcttc     660
ctcaccctgg cgcgcgacta cggccgcgcg attggcttca agggcaattt cctgatcgag     720
cccaagccca tggagccgat gaagcaccag tacgatttcg acagcgccac ggtgatcggc     780
ttcctgcgcc agcatggcct ggaccaggat ttcaagctca acatcgaggc caatcacgcc     840
accttgtccg gccatagctt cgagcatgac ctgcaggtgg catccgatgc cggcctgctc     900
ggcagcatcg atgccaaccg cggcaacccg cagaacggct gggacaccga ccagttcccg     960
accgacctgt acgacaccgt cggcgccatg ctggtggtgc tgcggcaggg cgggctggca    1020
ccgggcggct tgaacttcga tgccaaggtg cgtcgcgaat cgtccgaccc gcaggacctg    1080
ttcctggccc acatcggcgg catggacgcg ttcgcacgcg ggctggaagt ggccaacgcg    1140
ctgctgaccg cctcgccgct ggaacagtgg cgcgccgagc gttacgccag cttcgacagc    1200
ggcgccggcg cggactttgc cgcaggcaag accacgctgg ccgatctggc caagcacgcg    1260
gccagcaatg cgccccagca actcagcggc cgccaggaag cgtatgaaaa cctgatcaat    1320
cagtatctga cgcgttga                                                  1338
```

<210> SEQ ID NO 96
<211> LENGTH: 387
<212> TYPE: PRT
<213> ORGANISM: Thermus aquaticus

<400> SEQUENCE: 96

```
Met Tyr Glu Pro Lys Pro Glu His Arg Phe Thr Phe Gly Leu Trp Thr
1               5                   10                  15

Val Gly Asn Val Gly Arg Asp Pro Phe Gly Asp Ala Val Arg Glu Arg
            20                  25                  30

Leu Asp Pro Val Tyr Val Val His Lys Leu Ala Glu Leu Gly Ala Tyr
        35                  40                  45

Gly Val Asn Leu His Asp Glu Asp Leu Ile Pro Arg Gly Thr Pro Pro
    50                  55                  60

Gln Glu Arg Asp Gln Ile Val Arg Arg Phe Lys Lys Ala Leu Asp Glu
65                  70                  75                  80

Thr Gly Leu Lys Val Pro Met Val Thr Ala Asn Leu Phe Ser Asp Pro
                85                  90                  95

Ala Phe Lys Asp Gly Ala Phe Thr Ser Pro Asp Pro Trp Val Arg Ala
            100                 105                 110

Tyr Ala Leu Arg Lys Ser Leu Glu Thr Met Asp Leu Gly Ala Glu Leu
        115                 120                 125

Gly Ala Glu Ile Tyr Val Val Trp Pro Gly Arg Glu Gly Ala Glu Val
    130                 135                 140

Glu Ala Thr Gly Lys Ala Arg Lys Val Trp Asp Trp Val Arg Glu Ala
145                 150                 155                 160

Leu Asn Phe Met Ala Ala Tyr Ala Glu Asp Gln Gly Tyr Gly Tyr Arg
                165                 170                 175

Phe Ala Leu Glu Pro Lys Pro Asn Glu Pro Arg Gly Asp Ile Tyr Phe
            180                 185                 190

Ala Thr Val Gly Ser Met Leu Ala Phe Ile His Thr Leu Asp Arg Pro
        195                 200                 205

Glu Arg Phe Gly Leu Asn Pro Glu Phe Ala His Glu Thr Met Ala Gly
    210                 215                 220

Leu Asn Phe Val His Ala Val Ala Gln Ala Leu Asp Ala Gly Lys Leu
225                 230                 235                 240

Phe His Ile Asp Leu Asn Asp Gln Arg Met Ser Arg Phe Asp Gln Asp
```

```
                    245                 250                 255
Leu Arg Phe Gly Ser Glu Asn Leu Lys Ala Ala Phe Phe Leu Val Asp
            260                 265                 270

Leu Leu Glu Ser Ser Gly Tyr Gln Gly Pro Arg His Phe Asp Ala His
        275                 280                 285

Ala Leu Arg Thr Glu Asp Glu Gly Val Trp Ala Phe Ala Arg Gly
    290                 295                 300

Cys Met Arg Thr Tyr Leu Ile Leu Lys Glu Arg Ala Glu Ala Phe Arg
305                 310                 315                 320

Glu Asp Pro Glu Val Lys Glu Leu Leu Ala Ala Tyr Tyr Gln Glu Asp
                325                 330                 335

Pro Ala Ala Leu Ala Leu Leu Gly Pro Tyr Ser Arg Glu Lys Ala Glu
            340                 345                 350

Ala Leu Lys Arg Ala Glu Leu Pro Leu Glu Ala Lys Arg Arg Arg Gly
        355                 360                 365

Tyr Ala Leu Glu Arg Leu Asp Gln Leu Ala Val Glu Tyr Leu Leu Gly
    370                 375                 380

Val Arg Gly
385

<210> SEQ ID NO 97
<211> LENGTH: 1164
<212> TYPE: DNA
<213> ORGANISM: Thermus thermophilus

<400> SEQUENCE: 97
atgtacgagc ctaaaccgga gcacaggttt acctttggcc tttggactgt gggcaatgtg      60
ggccgtgatc ccttcgggga cgcggttcgg gagaggctgg acccggttta cgtggttcat     120
aagctggcgg agcttggggc ctacggggta aaccttcacg acgaggacct gatcccgcgg     180
ggcacgcctc ctcaggagcg ggaccagatc gtgaggcgct tcaagaaggc tctcgatgaa     240
accggcctca aggtccccat ggtcaccgcc aacctcttct ccgaccctgc tttcaaggac     300
ggggccttca cgagcccgga ccctggggtt cgggcctatg ccttgcggaa gagcctggag     360
accatggacc tggggggcaga gcttggggcc gagatctacg tggtctggcc gggccgggag     420
ggagctgagg tggaggccac gggcaaggcc cggaaggtct gggactgggt gcgggaggcg     480
ctgaacttca tggccgccta cgccgaggac cagggatacg ggtaccggtt tgccctcgag     540
cccaagccta cgagcccccg gggggacatt tacttcgcca ccgtggggag catgctcgcc     600
tttattcata ccctggaccg gcccgagcgc ttcggcctga ccccgagtt cgcccacgag     660
accatggccg gcttaacctt tgtccacgcc gtggcccagg ctctcgacgc cgggaagctt     720
ttccacattg acctcaacga ccaacggatg agccggtttg accaggacct ccgcttcggc     780
tcggagaacc tcaaggcggc cttttttcctg gtggacctcc tggaaagctc cggctaccag     840
ggcccccgcc actttgacgc ccacgccctg cgtaccgagg acgaagaagg ggtttgggcc     900
ttcgcccgag gctgcatgcg ctactactg atcttaaagg aaagggctga agccttccgc     960
gaggatcccg aggtcaagga gcttcttgcc gcttactatc aagaagatcc tgcggccttg    1020
gcccttttgg gcccctactc ccgcgagaag gccgaagccc tcaagcgggc ggagcttccc    1080
ctcgaggcca agcggcgccg gggttatgcc ctgaacgcc tggaccagct ggcggtggag    1140
tacctcctgg gggtgcgggg gtga                                          1164

<210> SEQ ID NO 98
<211> LENGTH: 435
```

```
<212> TYPE: PRT
<213> ORGANISM: Tetragenococcus halophilus

<400> SEQUENCE: 98

Met Asp Tyr Phe Glu Asn Val Pro Lys Val Gln Tyr Glu Gly Lys Asn
1               5                   10                  15

Ala Lys Ser Lys Tyr Ala Phe Arg His Tyr Asn Pro Glu Glu Ile Ile
            20                  25                  30

Met Gly Lys Pro Met Lys Asp His Leu Arg Phe Ser Val Ala Phe Trp
        35                  40                  45

His Thr Met Thr Glu Asp Gly Ser Asp Pro Phe Gly Asp Gly Thr Tyr
    50                  55                  60

Gln Arg Asn Trp Glu Gly Ser Thr Pro Met Glu Thr Ala Lys Asn Arg
65                  70                  75                  80

Val Asp Ala Phe Phe Glu Ile Leu Glu Lys Leu Gly Ala Glu Tyr Phe
                85                  90                  95

Cys Phe His Asp Val Asp Ile Ala Pro Gln Gly Asp Ser Leu Lys Glu
            100                 105                 110

Phe Leu Glu Asn Ile Asp Val Met Thr Asp Tyr Ile Lys Gly Lys Met
        115                 120                 125

Asp Lys Thr Gly Val Lys Leu Leu Trp Asn Thr Ala Asn Met Phe Thr
130                 135                 140

His Pro Thr Phe Val Asn Gly Ala Ala Thr Thr Asn Asn Ala Asp Val
145                 150                 155                 160

Tyr Ser Met Ala Ala Ala Gln Val Lys Lys Gly Leu Asp Val Ser Lys
                165                 170                 175

Lys Leu Asn Gly Glu Asn Tyr Val Phe Trp Gly Gly Arg Glu Gly Tyr
            180                 185                 190

Glu Asn Leu Leu Asn Thr Asp Met Asn Phe Glu Leu Asp Asn Leu Ala
        195                 200                 205

Arg Phe Tyr Gln Met Val Ile Asp Tyr Ala Gln Lys Ile Asp Tyr His
    210                 215                 220

Pro Gln Phe Leu Ile Glu Pro Lys Pro Lys Glu Pro Thr Lys His Gln
225                 230                 235                 240

Tyr Asp Tyr Asp Ala Ala Thr Ala Met Ala Phe Ile Gln Lys Tyr Asn
                245                 250                 255

Leu Glu Asp Ser Phe Lys Leu Asn Leu Glu Ala Asn His Ala Thr Leu
            260                 265                 270

Ala Gly His Thr Phe Glu His Glu Leu Asn Val Ala Lys Asn Tyr Asn
        275                 280                 285

Ala Leu Gly Ser Leu Asp Ala Asn Gln Gly Asp Leu Leu Leu Gly Trp
    290                 295                 300

Asp Thr Asp Glu Phe Pro Thr Asp Ile Tyr Thr Ala Thr Leu Ala Met
305                 310                 315                 320

Tyr Glu Val Leu Asp Phe Gly Gly Ile Ala Pro Gly Gly Leu Asn Phe
                325                 330                 335

Asp Ala Lys Val Arg Arg Thr Ser Phe Ala Met Asp Asp Leu Ile Leu
            340                 345                 350

Ala His Ile Ala Gly Met Asp Thr Tyr Ala Arg Gly Leu Arg Ala Ala
        355                 360                 365

Ala Lys Met Lys Asp Asp Asn Phe Glu Gln Ile Ile Ala Asn Arg
    370                 375                 380

Tyr Glu Ser Phe Ser Ser Gly Ile Gly Lys Gln Ile Val Glu Asn Lys
385                 390                 395                 400
```

```
Glu Asp Leu Glu Ser Leu Thr Asn Tyr Ala Leu Ser Leu Asn Gly Val
            405                 410                 415

Glu Asn Lys Ser Gly His Ile Glu His Leu Lys Ser Leu Leu Asn Asp
            420                 425                 430

Tyr Leu Val
        435

<210> SEQ ID NO 99
<211> LENGTH: 1308
<212> TYPE: DNA
<213> ORGANISM: Tetragenococcus halophilus

<400> SEQUENCE: 99
atggactatt tgaaaacgt tccaaaagtg cagtatgaag ggaagaatgc caaaagtaaa      60
tatgcgtttc ggcactataa ccccgaagaa attatcatgg ggaagccgat gaaagaccat    120
ttacgttttt cagtcgcttt ttggcatacg atgacagaag atggatccga tccatttgga    180
gatgggactt accaaagaaa ttgggaagga agcacaccaa tggaaacggc taaaaatcgt    240
gtagatgctt ttttgaaat attagaaaaa ttaggagccg agtattttg tttccatgat      300 gttgatatag ctcctcaagg cgattcttta aaagaatttt tggaaaatat tgatgttatg    360
acggactata ttaaaggaaa atggataaaa acaggagtca agctgttatg aacacagca     420 aatatgttta ctcatccaac atttgttaat ggggccgcaa caacaaataa tgcagatgtt    480
tattctatgg cagcagccca ggttaagaaa ggcttagacg ttagcaaaaa attaaatggc    540
gaaaattatg ttttttgggg cggaagagaa ggatatgaaa acctgttgaa tacagatatg    600
aattttgaac ttgacaactt agcccgtttt tatcaaatgg tgattgacta tgctcaaaaa    660
atcgattatc accctcagtt tttaatcgaa ccaaaaccta agaaccaac aaagcaccaa     720 tacgattacg acgcagctac tgcaatggca tttatccaaa aatataactt agaagatagc    780
tttaaattaa atctggaagc caatcatgca actcttgctg acatacgtt gaacatgag      840 ttaaacgttg caaaaatta taatgctcta ggttcactag acgccaatca aggtgattta    900
cttctgggat gggatactga tgaattccct actgatatat atacggcgac gttagccatg   960
tatgaagtcc tagattttgg tggcatagcg ccaggaggcc tcaattttga tgcgaaagtt   1020
cgaaggactt catttgcaat ggacgatttg attctagccc atattgccgg tatggatacg   1080
tatgccagag gattacgtgc ggcagctaaa atgaaagatg ataacttttt tgaacaaatt   1140
attgctaata gatacgaaag cttttcctct ggtattggca aacagattgt ggaaaataag   1200
gaagatctcg aatccttaac gaactacgca ttatcactta tggagtaga aaataaatca    1260 ggacatattg aacatcttaa atcgcttctt aatgactatt tggtatag             1308

<210> SEQ ID NO 100
<211> LENGTH: 439
<212> TYPE: PRT
<213> ORGANISM: Staphylococcus xylosus

<400> SEQUENCE: 100

Met Ser Tyr Phe Asp Ile Asn Lys Val Asn Tyr Glu Gly Pro Lys Ser
1               5                   10                  15

Asn Asn Ala Phe Ser Phe Lys Tyr Tyr Asn Pro Glu Glu Lys Leu Gly
            20                  25                  30

Asn His Ser Met Ser Glu Leu Leu Arg Phe Ser Val Ala Tyr Trp His
        35                  40                  45

Thr Phe Thr Ala Asp Leu Ser Asp Pro Phe Gly Val Gly Val Ala Glu
    50                  55                  60
```

Arg Asp Trp Asp Ser Leu Asp Glu Met Glu Lys Ala Lys Ala Arg Val
65                  70                  75                  80

Glu Ala Ile Phe Glu Phe Met Glu Lys Thr Arg Ile Asp Tyr Phe Cys
            85                  90                  95

Phe His Asp Val Asp Ile Ser Pro Glu Gly Ala Ser Leu Lys Glu Ser
                100                 105                 110

Asn Glu Asn Leu Asp Ile Ile Val Glu Leu Ile Lys Glu Lys Met Asp
            115                 120                 125

Gln Thr Gly Lys Lys Leu Leu Trp Asn Thr Thr Asn Asn Phe Thr His
        130                 135                 140

Glu Arg Phe Val His Gly Ala Ala Thr Ser Ser Asn Ala Glu Val Phe
145                 150                 155                 160

Ala Tyr Ala Ala Lys Val Lys Lys Ser Leu Glu Ile Ala Lys Lys
                165                 170                 175

Leu Gly Ser Glu Asn Phe Val Phe Trp Gly Arg Glu Gly Tyr Glu
            180                 185                 190

Ser Leu Leu Asn Thr Asn Met Lys Leu Glu Leu Asp Asn Leu Ala Thr
        195                 200                 205

Phe Phe Lys Met Ala Lys Ser Tyr Ala Asp Glu Ile Gly Tyr Thr Gly
        210                 215                 220

Gln Phe Leu Ile Glu Pro Lys Pro Lys Glu Pro Thr Thr His Gln Tyr
225                 230                 235                 240

Asp Thr Asp Val Ala Thr Ala His Ala Phe Leu Gln Lys Tyr Asp Leu
                245                 250                 255

Asp Lys Asp Phe Lys Phe Asn Ile Glu Ala Asn His Ala Thr Leu Ala
                260                 265                 270

Gly His Thr Phe Gln His Glu Leu Arg Tyr Ala Arg Asp Asn Met
        275                 280                 285

Leu Gly Ser Val Asp Ala Asn Gln Gly His Pro Leu Leu Gly Trp Asp
        290                 295                 300

Thr Asp Glu Ser Thr Asp Val Tyr Asp Thr Thr Leu Ala Met Tyr Glu
305                 310                 315                 320

Ile Leu Lys Asn Gly Gly Leu Ala Pro Gly Gly Leu Asn Phe Asp Ala
                325                 330                 335

Lys Pro Arg Thr Ser Phe Lys Gln Glu Asp Leu Ile Leu Thr His
                340                 345                 350

Ile Ala Gly Met Asp Thr Phe Ala Leu Gly Leu Arg Val Ala Tyr Lys
        355                 360                 365

Met Ile Glu Asp Asn Phe Phe Glu Asn Ile Met Asp Glu Lys Tyr Lys
370                 375                 380

Ser Phe Asn Glu Gly Ile Gly Lys Lys Ile Val Glu Gly Glu Thr Ser
385                 390                 395                 400

Leu Lys Glu Leu Glu Asp Tyr Ala Phe Asn Ile Asn Thr Ile Asn Asn
                405                 410                 415

Thr Ser Asp His Leu Glu Val Ile Lys Ser Gln Ile Asn Gln Tyr Ile
                420                 425                 430

Leu Asn Ile Asn Asn Lys Asp
        435

<210> SEQ ID NO 101
<211> LENGTH: 1320
<212> TYPE: DNA
<213> ORGANISM: Staphylococcus xylosus

<400> SEQUENCE: 101

-continued

```
atgtcttatt tgatatcaa taaagtaaat tacgaaggtc ctaagtcaaa taacgctttt      60
agttttaagt attacaatcc tgaagaaaaa cttggtaatc actccatgtc agaacttta     120 agattcagtg tcgcttattg gcacactttt actgctgacc tttccgatcc attcggtgtg    180
ggtgttgcgg aacgtgattg ggattcatta gacgagatgg aaaaagcaaa agcaagagta    240
gaagcaattt ttgaatttat ggaaaaaaca cgtattgatt actttgtttt tcacgatgta    300
gacatttctc cagaaggcgc atctttaaaa gaatctaatg aaaatttaga tatcattgta    360
gaacttatta agaaaaaat ggatcaaact ggtaagaaat actttggaa tacaaccaac     420 aactttactc acgagcgttt tgttcatggt gcagccacgt cttcaaatgc tgaagtattt    480
gcatatgcag ctgcaaaagt aaaaaaatca ttagaaattg ctaaaaaact tggttctgaa    540
aactttgttt tttggggcgg tcgtgaaggc tatgaaagtt tattaaatac taatatgaaa    600
ttagagttag ataacttagc tactttcttt aaaatggcaa aaagttacgc agatgaaatt    660
ggctatacgg gtcaattttt aatagaacca aaacctaaag aacctaccac acatcaatat    720
gatactgatg ttgcaactgc acacgctttc ttacaaaaat atgatttaga taaagacttt    780
aaatttaata ttgaagctaa ccacgcgacg ctggctggcc acacattcca acatgaatta    840
agatatgcac gtgataacaa tatgttgggt tcagtagatg ctaaccaagg acatcccctt    900
ttaggatggg atacagatga atcaactgat gtatacgata ctacgttagc aatgtacgaa    960
atacttaaaa atggcgggtt ggctccaggg ggattaaact tgatgctaa acctagaaga   1020 acatcattta aacaagagga tttaatttta actcacattg cgggtatgga tactttcgca   1080
ttaggcctac gagttgctta aagatgatt gaagataatt tctttgaaaa tattatggat    1140
gaaaaataca atcatttaa tgaaggcatt ggtaagaaaa tagttgaagg agagacttca    1200
ttgaaagaat tagaagatta tgctttcaat attaatacaa ttaataatac ctctgatcat   1260
ttagaagtta ttaaatcaca aattaatcaa tatatcttaa atattaataa taaggattga   1320
```

<210> SEQ ID NO 102
<211> LENGTH: 407
<212> TYPE: PRT
<213> ORGANISM: Mycobacterium smegmatis str. MC2 155]

<400> SEQUENCE: 102

```
Met Thr Val Leu Glu Ser Asn Val Ser Thr Thr Glu Pro Leu Thr Pro
1               5                   10                  15

Lys Arg Glu Asp Arg Phe Ser Phe Gly Leu Trp Thr Ile Gly Trp Asn
            20                  25                  30

Gly Asn Asp Pro Phe Gly Val Ala Thr Arg Pro Ala Leu Asp Val Val
        35                  40                  45

Glu Ala Val Glu Lys Leu Ala Glu Leu Gly Ala Tyr Gly Leu Thr Phe
    50                  55                  60

His Asp Asp Leu Phe Ala Phe Gly Ser Ser Asp Thr Glu Arg Arg
65                  70                  75                  80

Arg Met Val Asp Arg Leu Thr Ser Ala Leu Ser Ala Asn Gly Met Val
                85                  90                  95

Val Pro Met Val Thr Thr Asn Leu Phe Thr Gln Pro Val Phe Lys Asp
            100                 105                 110

Gly Gly Phe Thr Ser Asn Asp Arg Thr Val Arg Arg Phe Ala Leu Arg
        115                 120                 125

Lys Val Leu Arg Asn Ile Asp Leu Ala Ile Glu Leu Gly Ala Glu Thr
    130                 135                 140
```

```
Phe Val Leu Trp Gly Gly Arg Glu Gly Ser Glu Tyr Asp Ser Ala Lys
145                 150                 155                 160

Asp Val Gln Ala Ala Leu Ala Arg Tyr Arg Glu Ala Met Asp Leu Leu
                165                 170                 175

Cys Gln Tyr Val Ile Asp Gln Gly Ser Gly Leu Arg Phe Ala Ile Glu
            180                 185                 190

Pro Lys Pro Asn Glu Pro Arg Gly Asp Ile Leu Leu Pro Thr Val Gly
        195                 200                 205

His Ala Leu Ala Phe Ile Asp Thr Leu Ala Arg Pro Glu Met Val Gly
210                 215                 220

Val Asn Pro Glu Thr Gly His Glu Gln Met Ser Gly Leu Asn Phe Met
225                 230                 235                 240

His Gly Ile Ala Gln Ala Leu Tyr Ser Gly Lys Leu Phe His Ile Asp
                245                 250                 255

Leu Asn Gly Gln Arg Gly Ile Lys Phe Asp Gln Asp Leu Val Phe Gly
            260                 265                 270

His Gly Asp Leu Ala Asn Ala Phe Ala Leu Val Asp Leu Leu Glu His
        275                 280                 285

Gly Gly Pro Asp Gly Thr Pro Ala Tyr Glu Gly Pro Arg His Phe Asp
290                 295                 300

Tyr Lys Pro Ser Arg Thr Glu Asp Ile Asp Gly Val Trp Ala Ser Ala
305                 310                 315                 320

Ala Ala Asn Met Arg Met Tyr Leu Leu Leu Lys Gln Arg Ala Glu Ala
                325                 330                 335

Phe Arg Ala Asp Pro Ala Val Arg Glu Ala Met Ala Ala Ala Lys Val
            340                 345                 350

Ala Glu Leu Arg Gln Pro Thr Leu Ala Pro Gly Glu Thr Tyr His Asp
        355                 360                 365

Leu Leu Ala Asp Arg Ser Ala Phe Glu Glu Phe Asp Ser Glu Ala Tyr
370                 375                 380

Phe Gly Gly Lys Gly Cys Gly Phe Val Ala Leu Gln Gln Leu Ala Ile
385                 390                 395                 400

Glu His Leu Met Gly Ala Arg
                405

<210> SEQ ID NO 103
<211> LENGTH: 1224
<212> TYPE: DNA
<213> ORGANISM: Mycobacterium smegmatis

<400> SEQUENCE: 103
atgaccgtgt tggagtcgaa cgtctccaca accgaaccgc tcaccccgaa gcgagaggac      60
cgtttctcgt tcggcctctg gaccatcggc tggaacggaa cgatccgtt cggcgtcgcc     120 acccgcccgg cgctcgacgt cgtggaggcc gtcgagaaac tggccgaact cggcgcgtac     180
gggctgacgt tccacgatga cgacctgttc gcgttcggca gttccgacac cgagcggcgg     240
cggatggtcg accggttgac gtcggcgttg tcggccaacg gcatggtggt cccgatggtg     300
acgaccaacc tgttcaccca gcccgtcttc aaggacggcg gtttcaccag caacgaccgc     360
acggtgcggc gtttcgcgct cgcaaggtg ctgcgcaaca tcgatttggc catcgaactc     420
ggcgccgaga ccttcgtgtt gtgggcggc cgtgagggca cgaatacga ctcggccaag     480 gacgtgcagg ccgcgctggc ggcgtaccgc gaagcgatgg atctgttgtg ccagtacgtg     540
atcgaccagg gcagcgggtt gcgcttcgcg atcgaaccca aacccaacga gccgcgcggc     600
gacatcctgc tgcccacggt ggggcacgcg ctggcattca tcgacaccct ggcccgcccg     660
```

```
gagatggtcg gggtgaaccc cgagaccggc cacgagcaga tgtccggcct gaacttcatg      720
cacggcatcg cacaggccct gtacagcggc aagctcttcc acatcgacct caacggtcag      780
cggggcatca agttcgacca ggacctcgtg ttcgggcacg gcgacctggc caatgccttc      840
gcgctcgtgg atctgctcga acacggtggt cccgacggca ccccggcgta cgagggtcct      900
cggcacttcg actacaagcc cagccgcacc gaggacatcg acggtgtgtg ggcctcggcg      960
gccgcgaaca tgcggatgta cctgctgctc aagcagcgcg ccgaggcgtt ccgcgccgat     1020
cccgcggtgc gtgaggcgat ggcggcggcc aaggtggccg aattgcggca gccgacgctc     1080
gcgccgggcg agacgtacca cgacctgttg gccgaccgct cggccttcga ggagttcgac     1140
agtgaggcct atttcggcgg caagggttgc ggtttcgtcg cattgcagca gttggccatc     1200
gaacacctga tgggcgcgcg atga                                            1224
```

<210> SEQ ID NO 104
<211> LENGTH: 437
<212> TYPE: PRT
<213> ORGANISM: Piromyces sp. E2

<400> SEQUENCE: 104

```
Met Ala Lys Glu Tyr Phe Pro Gln Ile Gln Lys Ile Lys Phe Glu Gly
1               5                   10                  15

Lys Asp Ser Lys Asn Pro Leu Ala Phe His Tyr Tyr Asp Ala Glu Lys
                20                  25                  30

Glu Val Met Gly Lys Lys Met Lys Asp Trp Leu Arg Phe Ala Met Ala
            35                  40                  45

Trp Trp His Thr Leu Cys Ala Glu Gly Ala Asp Gln Phe Gly Gly Gly
        50                  55                  60

Thr Lys Ser Phe Pro Trp Asn Glu Gly Thr Asp Ala Ile Glu Ile Ala
65                  70                  75                  80

Lys Gln Lys Val Asp Ala Gly Phe Glu Ile Met Gln Lys Leu Gly Ile
                85                  90                  95

Pro Tyr Tyr Cys Phe His Asp Val Asp Leu Val Ser Glu Gly Asn Ser
            100                 105                 110

Ile Glu Glu Tyr Glu Ser Asn Leu Lys Ala Val Val Ala Tyr Leu Lys
        115                 120                 125

Glu Lys Gln Lys Glu Thr Gly Ile Lys Leu Leu Trp Ser Thr Ala Asn
    130                 135                 140

Val Phe Gly His Lys Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Glu Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Ala Ile Gly Phe Leu Lys
                245                 250                 255

Ala His Asn Leu Asp Lys Asp Phe Lys Val Asn Ile Glu Val Asn His
            260                 265                 270
```

```
Ala Thr Leu Ala Gly His Thr Phe Glu His Glu Leu Ala Cys Ala Val
        275                 280                 285
Asp Ala Gly Met Leu Gly Ser Ile Asp Ala Asn Arg Gly Asp Tyr Gln
    290                 295                 300
Asn Gly Trp Asp Thr Asp Gln Phe Pro Ile Asp Gln Tyr Glu Leu Val
305                 310                 315                 320
Gln Ala Trp Met Glu Ile Ile Arg Gly Gly Phe Val Thr Gly Gly
            325                 330                 335
Thr Asn Phe Asp Ala Lys Thr Arg Arg Asn Ser Thr Asp Leu Glu Asp
                340                 345                 350
Ile Ile Ile Ala His Val Ser Gly Met Asp Ala Met Ala Arg Ala Leu
                355                 360                 365
Glu Asn Ala Ala Lys Leu Leu Gln Glu Ser Pro Tyr Thr Lys Met Lys
    370                 375                 380
Lys Glu Arg Tyr Ala Ser Phe Asp Ser Gly Ile Gly Lys Asp Phe Glu
385                 390                 395                 400
Asp Gly Lys Leu Thr Leu Glu Gln Val Tyr Glu Tyr Gly Lys Lys Asn
            405                 410                 415
Gly Glu Pro Lys Gln Thr Ser Gly Lys Gln Glu Leu Tyr Glu Ala Ile
        420                 425                 430
Val Ala Met Tyr Gln
        435

<210> SEQ ID NO 105
<211> LENGTH: 1314
<212> TYPE: DNA
<213> ORGANISM: Piromyces sp. E2

<400> SEQUENCE: 105
atggctaagg aatatttccc acaaattcaa aagattaagt tcgaaggtaa ggattctaag      60
aatccattag ccttccacta ctacgatgct gaaaaggaag tcatgggtaa gaaaatgaag     120
gattggttac gtttcgccat ggcctggtgg cacactcttt gcgccgaagg tgctgaccaa     180
ttcggtggag gtacaaagtc tttcccatgg aacgaaggta ctgatgctat gaaaattgcc     240
aagcaaaagg ttgatgctgg tttcgaaatc atgcaaaagc ttggtattcc atactactgt     300
ttccacgatg ttgatcttgt ttccgaaggt aactctattg aagaatacga atccaacctt     360
aaggctgtcg ttgcttacct caaggaaaag caaaaggaaa ccggtattaa gcttctctgg     420
agtactgcta acgtcttcgg tcacaagcgt tacatgaacg gtgcctccac taacccagac     480
tttgatgttg tcgcccgtgc tattgttcaa attaagaacg ccatagacgc cggtattgaa     540
cttggtgctg aaaactacgt cttctggggt ggtcgtgaag gttacatgag tctccttaac     600
actgaccaaa agcgtgaaaa ggaacacatg gccactatgc ttaccatggc tcgtgactac     660
gctcgttcca aggattcaa gggtactttc tcattgaac caaagccaat ggaaccaacc     720
aagcaccaat acgatgttga cactgaaacc gctattggtt ccttaaggc ccacaactta     780 gacaaggact tcaaggtcaa cattgaagtt aaccacgcta ctcttgctgg tcacactttc     840
gaacacgaac ttgcctgtgc tgttgatgct ggtatgctcg gttccattga tgctaaccgt     900
ggtgactacc aaaacggttg ggatactgat caattcccaa ttgatcaata cgaactcgtc     960
caagcttgga tggaaatcat ccgtggtggt ggtttcgtta ctggtggtac aaacttcgat    1020
gccaagactc gtcgtaactc tactgacctc gaagacatca tcattgccca cgtttctggt    1080
atggatgcta tggctcgtgc tcttgaaaac gctgccaagc tcctccaaga atctccatac    1140
accaagatga agaaggaacg ttacgcttcc ttcgacagtg gtattggtaa ggactttgaa    1200
```

```
gatggtaagc tcaccctcga acaagtttac gaatacggta agaagaacgg tgaaccaaag    1260
caaacttctg gtaagcaaga actctacgaa gctattgttg ccatgtacca ataa          1314
```

<210> SEQ ID NO 106
<211> LENGTH: 484
<212> TYPE: PRT
<213> ORGANISM: Escherichia coli

<400> SEQUENCE: 106

```
Met Tyr Ile Gly Ile Asp Leu Gly Thr Ser Gly Val Lys Val Ile Leu
1               5                   10                  15

Leu Asn Glu Gln Gly Glu Val Val Ala Ala Gln Thr Glu Lys Leu Thr
            20                  25                  30

Val Ser Arg Pro His Pro Leu Trp Ser Glu Gln Asp Pro Glu Gln Trp
        35                  40                  45

Trp Gln Ala Thr Asp Arg Ala Met Lys Ala Leu Gly Asp Gln His Ser
    50                  55                  60

Leu Gln Asp Val Lys Ala Leu Gly Ile Ala Gly Gln Met His Gly Ala
65                  70                  75                  80

Thr Leu Leu Asp Ala Gln Gln Arg Val Leu Arg Pro Ala Ile Leu Trp
                85                  90                  95

Asn Asp Gly Arg Cys Ala Gln Glu Cys Thr Leu Leu Glu Ala Arg Val
            100                 105                 110

Pro Gln Ser Arg Val Ile Thr Gly Asn Leu Met Met Pro Gly Phe Thr
        115                 120                 125

Ala Pro Lys Leu Leu Trp Val Gln Arg His Glu Pro Glu Ile Phe Arg
    130                 135                 140

Gln Ile Asp Lys Val Leu Leu Pro Lys Asp Tyr Leu Arg Leu Arg Met
145                 150                 155                 160

Thr Gly Glu Phe Ala Ser Asp Met Ser Asp Ala Ala Gly Thr Met Trp
                165                 170                 175

Leu Asp Val Ala Lys Arg Asp Trp Ser Asp Val Met Leu Gln Ala Cys
            180                 185                 190

Asp Leu Ser Arg Asp Gln Met Pro Ala Leu Tyr Glu Gly Ser Glu Ile
        195                 200                 205

Thr Gly Ala Leu Leu Pro Glu Val Ala Lys Ala Trp Gly Met Ala Thr
    210                 215                 220

Val Pro Val Val Ala Gly Gly Asp Asn Ala Ala Gly Ala Val Gly
225                 230                 235                 240

Val Gly Met Val Asp Ala Asn Gln Ala Met Leu Ser Leu Gly Thr Ser
                245                 250                 255

Gly Val Tyr Phe Ala Val Ser Glu Gly Phe Leu Ser Lys Pro Glu Ser
            260                 265                 270

Ala Val His Ser Phe Cys His Ala Leu Pro Gln Arg Trp His Leu Met
        275                 280                 285

Ser Val Met Leu Ser Ala Ser Cys Leu Asp Trp Ala Ala Lys Leu
    290                 295                 300

Thr Gly Leu Ser Asn Val Pro Ala Leu Ile Ala Ala Gln Gln Ala
305                 310                 315                 320

Asp Glu Ser Ala Glu Pro Val Trp Phe Leu Pro Tyr Leu Ser Gly Glu
                325                 330                 335

Arg Thr Pro His Asn Asn Pro Gln Ala Lys Gly Val Phe Phe Gly Leu
            340                 345                 350

Thr His Gln His Gly Pro Asn Glu Leu Ala Arg Ala Val Leu Glu Gly
```

|     |     |     | 355 |     |     |     | 360 |     |     |     | 365 |
| --- | --- | --- | --- | --- | --- | --- | --- | --- | --- | --- | --- |

Val Gly Tyr Ala Leu Ala Asp Gly Met Asp Val His Ala Cys Gly
        370                 375                 380

Ile Lys Pro Gln Ser Val Thr Leu Ile Gly Gly Ala Arg Ser Glu
385                 390                 395                 400

Tyr Trp Arg Gln Met Leu Ala Asp Ile Ser Gly Gln Leu Asp Tyr
                405                 410                 415

Arg Thr Gly Gly Asp Val Gly Pro Ala Leu Gly Ala Ala Arg Leu Ala
            420                 425                 430

Gln Ile Ala Ala Asn Pro Glu Lys Ser Leu Ile Glu Leu Leu Pro Gln
                435                 440                 445

Leu Pro Leu Glu Gln Ser His Leu Pro Asp Ala Gln Arg Tyr Ala Ala
        450                 455                 460

Tyr Gln Pro Arg Arg Glu Thr Phe Arg Arg Leu Tyr Gln Gln Leu Leu
465                 470                 475                 480

Pro Leu Met Ala

<210> SEQ ID NO 107
<211> LENGTH: 1455
<212> TYPE: DNA
<213> ORGANISM: Escherichia coli

<400> SEQUENCE: 107

```
atgtatatcg ggatagatct tggcacctcg gcgtaaaag ttatttttgct caacgagcag      60
ggtgaggtgg ttgctgcgca acggaaaag ctgaccgttt cgcgcccgca tccactctgg     120
tcggaacaag acccggaaca gtggtggcag gcaactgatc gcgcaatgaa agctctgggc     180
gatcagcatt ctctgcagga cgttaaagca ttgggtattg ccggccagat gcacggagca     240
accttgctgg atgctcagca acgggtgtta cgccctgcca ttttgtggaa cgacgggcgc     300
tgtgcgcaag agtgcacttt gctggaagcg cgagttccgc aatcgcgggt gattaccggc     360
aacctgatga tgcccggatt tactgcgcct aaattgctat gggttcagcg gcatgagccg     420
gagatattcc gtcaaatcga caaagtatta ttaccgaaag attacttgcg tctgcgtatg     480
acgggggagt ttgccagcga tatgtctgac gcagctggca ccatgtggct ggatgtcgca     540
aagcgtgact ggagtgacgt catgctgcag gcttgcgact tatctcgtga ccagatgccc     600
gcattatacg aaggcagcga attactggt gctttgttac ctgaagttgc gaaagcgtgg     660
ggtatggcga cggtgccagt tgtcgcaggc ggtggcgaca atgcagctgg tgcagttggt     720
gtgggaatgg ttgatgctaa tcaggcaatg ttatcgctgg gacgtcgggg ggtctatttt     780
gctgtcagcg aagggttctt aagcaagcca gaaagcgccg tacatagctt ttgccatgcg     840
ctaccgcaac gttggcattt aatgtctgtg atgctgagtg cagcgtcgtg tctggattgg     900
gccgcgaaat taaccggcct gagcaatgtc ccagctttaa tcgctgcagc tcaacaggct     960
gatgaaagtg ccgagccagt ttggtttctg ccttatcttt ccggcgagcg tacgccacac    1020
aataatcccc aggcgaaggg ggttttcttt ggtttgactc atcaacatgg ccccaatgaa    1080
ctggcgcgag cagtgctgga aggcgtgggt tatgcgctgg cagatggcat ggatgtcgtg    1140
catgcctgcg gtattaaacc gcaaagtgtt acgttgattg ggggcggggc gcgtagtgag    1200
tactggcgtc agatgctggc ggatatcagc ggtcagcagc tcgattaccg tacggggggg    1260
gatgtggggc cagcactggg cgcagcaagg ctggcgcaga tcgcggcgaa tccagagaaa    1320
tcgctcattg aattgttgcc gcaactaccg ttagaacagt cgcatctacc agatgcgcag    1380
cgttatgccg cttatcagcc acgacgagaa acgttccgtc gcctctatca gcaacttctg    1440
```

```
ccattaatgg cgtaa                                                    1455
```

<210> SEQ ID NO 108
<211> LENGTH: 496
<212> TYPE: PRT
<213> ORGANISM: Pseudomonas putida

<400> SEQUENCE: 108

| | | | | | | | | | | | | | | |
|---|---|---|---|---|---|---|---|---|---|---|---|---|---|---|
| Met | Glu | Gly | Leu | Phe | Leu | Gly | Ile | Asp | Cys | Gly | Thr | Gln | Gly | Thr | Lys |
| 1 | | | | 5 | | | | | 10 | | | | | 15 | |
| Ala | Leu | Val | Leu | Asp | Ala | Gly | Ser | Gly | Arg | Val | Leu | Gly | Leu | Gly | Ser |
| | | | 20 | | | | | 25 | | | | | 30 | | |
| Ala | Ala | His | Ala | Pro | Ala | Arg | Gly | Arg | Asp | Gly | Arg | Arg | Glu | Gln | Asp |
| | | | 35 | | | | | 40 | | | | | 45 | | |
| Pro | Ala | Asp | Trp | Leu | Ala | Ala | Leu | His | Thr | Ala | Val | Ala | Gly | Ala | Leu |
| | | 50 | | | | | 55 | | | | | 60 | | | |
| His | Gly | Ala | Gly | Val | Asn | Gly | Gln | Ala | Ile | Arg | Ala | Leu | Ala | Val | Ser |
| 65 | | | | | 70 | | | | | 75 | | | | | 80 |
| Gly | Gln | Gln | His | Gly | Leu | Val | Met | Leu | Asp | Ala | Gln | Gly | Gln | Val | Leu |
| | | | | 85 | | | | | 90 | | | | | 95 | |
| Arg | Pro | Ala | Lys | Leu | Trp | Cys | Asp | Thr | Glu | Thr | Ala | Glu | Asn | Gln |
| | | | 100 | | | | | 105 | | | | | 110 | | |
| Lys | Leu | Leu | Asn | Val | Leu | Gly | Gly | Pro | Gln | Gly | Ser | Ile | Glu | Arg | Leu |
| | | | 115 | | | | | 120 | | | | | 125 | | |
| Gly | Leu | Val | Ile | Ala | Pro | Gly | Tyr | Thr | Val | Ser | Lys | Leu | Leu | Trp | Ser |
| | | | 130 | | | | | 135 | | | | | 140 | | |
| Lys | Arg | Ser | Phe | Pro | Asp | Leu | Phe | Ala | Arg | Leu | Ala | His | Val | Leu | Leu |
| 145 | | | | | 150 | | | | | 155 | | | | | 160 |
| Pro | His | Asp | Tyr | Leu | Asn | Tyr | Trp | Leu | Thr | Gly | Arg | Ala | Cys | Ser | Glu |
| | | | | 165 | | | | | 170 | | | | | 175 | |
| Pro | Gly | Asp | Ala | Ser | Gly | Thr | Gly | Tyr | Tyr | Asn | Val | His | His | Asn | Thr |
| | | | 180 | | | | | 185 | | | | | 190 | | |
| Trp | Ala | Thr | Asp | Val | Leu | Gln | His | Ile | Glu | Pro | Gly | Glu | Arg | Leu | Leu |
| | | | 195 | | | | | 200 | | | | | 205 | | |
| Ala | Ala | Leu | Pro | Glu | Leu | Leu | Ala | Pro | Gly | Asp | Cys | Val | Gly | Pro | Leu |
| | | 210 | | | | | 215 | | | | | 220 | | | |
| Arg | Glu | Gln | Ala | Ala | Ala | Gly | Leu | Gly | Leu | Asn | Pro | His | Ala | Trp | Val |
| 225 | | | | | 230 | | | | | 235 | | | | | 240 |
| Ala | Thr | Gly | Gly | Gly | Asp | Asn | Met | Leu | Ser | Ala | Ile | Gly | Thr | Gly | Asn |
| | | | | 245 | | | | | 250 | | | | | 255 | |
| Ile | Ser | Pro | Gly | Met | Ile | Thr | Leu | Ser | Leu | Gly | Thr | Ser | Gly | Thr | Leu |
| | | | 260 | | | | | 265 | | | | | 270 | | |
| Ala | Ala | Tyr | Ala | Asp | His | Ala | Gln | Phe | Asn | Pro | Lys | Gly | Glu | Val | Ala |
| | | | 275 | | | | | 280 | | | | | 285 | | |
| Asn | Phe | Cys | Ala | Ser | Ser | Gly | Gly | Trp | Leu | Pro | Leu | Val | Cys | Thr | Met |
| | | 290 | | | | | 295 | | | | | 300 | | | |
| Asn | Leu | Thr | Asn | Ala | Cys | Ala | Leu | Val | Arg | Asp | Leu | Leu | Glu | Leu | Asp |
| 305 | | | | | 310 | | | | | 315 | | | | | 320 |
| Leu | Thr | Arg | Phe | Thr | Ala | Leu | Ala | Ala | Gln | Ala | Pro | Val | Gly | Ala | Glu |
| | | | | 325 | | | | | 330 | | | | | 335 | |
| Gly | Leu | Leu | Met | Leu | Pro | Phe | Phe | Asp | Gly | Glu | Arg | Val | Pro | Ala | Leu |
| | | | 340 | | | | | 345 | | | | | 350 | | |
| Pro | Thr | Ala | Ser | Ala | Ser | Leu | His | Gly | Met | Thr | Ser | Ala | Asn | Leu | Thr |
| | | | 355 | | | | | 360 | | | | | 365 | | |

```
Arg Ala Asn Leu Cys Arg Ala Val Leu Glu Gly Thr Cys Phe Ser Leu
        370                 375                 380

Arg Tyr Gly Leu Asp Leu Leu His Ala Ser Gly Leu Gln Gly Ser Glu
385                 390                 395                 400

Ile Arg Leu Val Gly Gly Ala Ala Lys Ser Glu Leu Trp Arg Gln Val
                405                 410                 415

Leu Ala Asn Leu Leu Gly Leu Pro Val Val Cys Pro Arg Gln Thr Glu
            420                 425                 430

Ala Ala Ala Leu Gly Ala Ala Ile Gln Ala Ala Trp Ser Leu Gly Arg
        435                 440                 445

Gln Leu Gly His Gly Asp Ser Leu Gln Ala Leu Cys Glu Arg Cys Val
    450                 455                 460

Glu Leu Asp Glu Ser Thr Arg Thr Leu Pro Arg Leu Ala Gln Gln Ala
465                 470                 475                 480

Ala Tyr Gly Val Ala Tyr Arg Arg Tyr Leu Asp His Leu Pro Ala His
                485                 490                 495

<210> SEQ ID NO 109
<211> LENGTH: 1491
<212> TYPE: DNA
<213> ORGANISM: Pseudomonas putida

<400> SEQUENCE: 109
atggaaggac tgtttctcgg cattgattgc ggcacccagg caccaaggc gctggtgctg      60 gacgctggca gtggccgggt gctgggcctt ggtagtgccg cgcacgcgcc tgcacggggc    120
cgcgacgggc gccgcgagca agacccggcc gactggctcg ccgccctgca cacggcagtc    180
gctggcgcgc tgcatggggc cggcgtcaat ggccaggcca tccgtgcgct ggcggtatcc    240
ggccagcagc atggcctggt gatgctggac gcccaaggcc aggtactgcg cccggccaag    300
ctctggtgcg acaccgaaac cacggcagaa aaccagaagc tgctgaacgt gctcggcggc    360
ccgcagggct cgatcgaacg cctggggctg gtgattgcgc cgggctatac cgtgtccaaa    420
ctgctgtgga gcaaacgcag cttccccgac ctgttcgccc gcctggccca tgtgctgctg    480
ccccacgatt acctcaatta ctggctgaca ggccgcgcct gcagcgagcc gggcgatgcg    540
tctggcaccg ttactacaa cgtgcaccac aacacctggg caaccgatgt gctgcaacac    600
atcgaaccgg cgagcgcct gctggcggca ctgcccgagc tgctcgcacc cggcgactgc    660
gtcggtccgc tgcgcgagca ggccgccgca ggcctggggc tgaaccctca cgcctgggtg    720
gccaccggcg cggcgacaa catgctcagc gccatcggta ccggcaatat cagccctggc    780
atgattaccc tcagcctggg cacctcgggt accctggcag cttacgccga ccatgcccag    840 ttcaaccccca agggcgaggt ggcgaacttc tgcgcctcca gcgtggctg gttgcccttg    900 gtctgcacga tgaacctgac caacgcctgc gcgctggtac gtgacctgct tgagctggac    960
ctcacccgct tcacagccct cgccgcccaa gcccgtcg gtgccgaagg cctgttgatg   1020
ctgccattct tcgatggcga acgggtaccc gcgctgccta ctgccagcgc cagcctgcat   1080
ggtatgacca cgccaacct gacacgcgcc aacctgtgcc gggccgtgct cgaaggcact   1140
tgcttcagcc tgcgctatgg cctggacctg ctgcacgcca gcggcctgca gggcagcgaa   1200
atccgcctgg tggcggggc ggcaaaaagc gagctgtggc gccaggtact ggccaatctg   1260
ctcggcctgc cagtggtgtg cccgcgccag accgaagccg ccgcgctggg gcggcaatt   1320 caggctgcct ggagccttgg ccgccaactg ggccacggcg acagcctcca ggccctgtgc   1380
gagcgctgcg tcgagctgga cgaaagcacc cgcaccctgc cacgtctggc gcagcaggcc   1440
```

```
gcctatggtg tggcctacag acgctacctg gatcacctgc ctgcgcactg a            1491
```

<210> SEQ ID NO 110
<211> LENGTH: 484
<212> TYPE: PRT
<213> ORGANISM: Rhizobium leguminosarum

<400> SEQUENCE: 110

| | | | | | | | | | | | | | | |
|---|---|---|---|---|---|---|---|---|---|---|---|---|---|---|
| Met | Tyr | Leu | Gly | Leu | Asp | Leu | Gly | Thr | Ser | Gly | Val | Lys | Ala | Met | Leu |
| 1 | | | | 5 | | | | | 10 | | | | | 15 | |
| Ile | Asp | Gly | Asp | Gln | Lys | Ile | Val | Gly | Ser | Ala | Asn | Gly | Ser | Leu | Asp |
| | | 20 | | | | | 25 | | | | | 30 | | | |
| Val | Ser | Arg | Pro | His | Ser | Gly | Trp | Ser | Glu | Gln | Glu | Pro | Ala | His | Trp |
| | 35 | | | | | 40 | | | | | 45 | | | | |
| Val | Arg | Ala | Thr | Glu | Glu | Ala | Val | Ala | Gly | Leu | Lys | Ala | Lys | His | Pro |
| 50 | | | | | 55 | | | | | 60 | | | | | |
| Lys | Glu | Leu | Ala | Ala | Val | Lys | Gly | Ile | Gly | Leu | Ser | Gly | Gln | Met | His |
| 65 | | | | | 70 | | | | | 75 | | | | | 80 |
| Gly | Ala | Thr | Leu | Ile | Asp | Ala | Ala | Asp | Lys | Ala | Leu | Arg | Pro | Cys | Ile |
| | | | | 85 | | | | | 90 | | | | | 95 | |
| Leu | Trp | Asn | Asp | Thr | Arg | Ser | His | Val | Glu | Ala | Ala | Ala | Leu | Asp | Ala |
| | | | 100 | | | | | 105 | | | | | 110 | | |
| Asp | Pro | Arg | Phe | Arg | Ala | Leu | Thr | Gly | Asn | Ile | Val | Phe | Pro | Gly | Phe |
| | | 115 | | | | | 120 | | | | | 125 | | | |
| Thr | Ala | Pro | Lys | Leu | Ala | Trp | Val | Glu | Lys | His | Glu | Arg | Asp | Val | Phe |
| | 130 | | | | | 135 | | | | | 140 | | | | |
| Ala | Lys | Ile | Ala | Lys | Val | Leu | Leu | Pro | Lys | Asp | Tyr | Leu | Arg | Leu | Trp |
| 145 | | | | | 150 | | | | | 155 | | | | | 160 |
| Leu | Thr | Gly | Asp | His | Ile | Ser | Glu | Met | Ser | Asp | Ser | Ala | Gly | Thr | Ser |
| | | | | 165 | | | | | 170 | | | | | 175 | |
| Trp | Leu | Asp | Thr | Gly | Lys | Arg | Ala | Trp | Ser | Ser | Glu | Leu | Leu | Ala | Ala |
| | | | 180 | | | | | 185 | | | | | 190 | | |
| Thr | Asn | Leu | Ser | Glu | Glu | Gln | Met | Pro | Ala | Leu | Val | Glu | Gly | Thr | Ala |
| | | 195 | | | | | 200 | | | | | 205 | | | |
| Gln | Ala | Gly | Gln | Leu | Arg | Ala | Glu | Leu | Val | Ala | Gln | Trp | Gly | Ile | Ser |
| | 210 | | | | | 215 | | | | | 220 | | | | |
| Gly | Asn | Val | Val | Ala | Gly | Gly | Ala | Gly | Asp | Asn | Ala | Ala | Ser | Ala |
| 225 | | | | | 230 | | | | | 235 | | | | | 240 |
| Cys | Gly | Met | Gly | Thr | Val | Ser | Asp | Gly | Ala | Ala | Phe | Val | Ser | Leu | Gly |
| | | | | 245 | | | | | 250 | | | | | 255 | |
| Thr | Ser | Gly | Val | Leu | Phe | Ala | Ala | Asn | Gly | Ser | Tyr | Leu | Pro | Lys | Pro |
| | | | 260 | | | | | 265 | | | | | 270 | | |
| Glu | Ser | Ala | Val | His | Ala | Phe | Cys | His | Ala | Leu | Pro | Asn | Thr | Trp | His |
| | | 275 | | | | | 280 | | | | | 285 | | | |
| Gln | Met | Gly | Val | Ile | Leu | Ser | Ala | Thr | Asp | Ala | Leu | Asn | Trp | His | Ser |
| | 290 | | | | | 295 | | | | | 300 | | | | |
| Gly | Val | Thr | Gly | Lys | Ser | Ala | Ala | Asp | Leu | Thr | Gly | Glu | Leu | Gly | Glu |
| 305 | | | | | 310 | | | | | 315 | | | | | 320 |
| Thr | Leu | Lys | Ala | Pro | Thr | Gly | Val | Thr | Phe | Leu | Pro | Tyr | Leu | Ser | Gly |
| | | | | 325 | | | | | 330 | | | | | 335 | |
| Glu | Arg | Thr | Pro | His | Asn | Asp | Ala | Val | Ile | Arg | Gly | Ala | Phe | Ile | Gly |
| | | | 340 | | | | | 345 | | | | | 350 | | |
| Leu | Glu | His | Glu | Ser | Ser | Arg | Ala | Val | Leu | Thr | Gln | Ala | Val | Leu | Glu |
| | | 355 | | | | | 360 | | | | | 365 | | | |
| Gly | Val | Ala | Phe | Ala | Ile | Arg | Asp | Asn | Leu | Glu | Ala | Leu | Arg | Ser | Ala |

```
                370            375            380
Gly Thr Gly Ile Ser Arg Val Thr Ala Ile Gly Gly Ser Arg Ser
385            390            395            400

His Tyr Trp Leu Ala Ser Ile Ala Thr Ala Leu Gly Val Pro Val Asp
           405            410            415

Leu Pro Ala Asp Gly Asp Phe Gly Ala Ala Phe Gly Ala Ala Arg Leu
            420            425            430

Gly Leu Ile Ala Ala Thr Gly Ala Asp Pro Ile Ala Val Cys Thr Pro
            435            440            445

Pro Val Thr Ser Gly Thr Ile Glu Pro Val Ser Ala Leu Ser Gly Ala
        450            455            460

Tyr Glu Asp Ala Tyr Thr Arg Tyr Arg Ala Val Tyr Pro Ala Val Lys
465            470            475            480

Ser Leu Ala His

<210> SEQ ID NO 111
<211> LENGTH: 1455
<212> TYPE: DNA
<213> ORGANISM: Rhizobium leguminosarum

<400> SEQUENCE: 111
atgtatctcg gtctcgatct cggaacctcc ggcgtcaagg cgatgctgat cgacggcgat    60
cagaagatcg tcggctcggc caatggttcg ctcgacgtct cgcgtccgca ttccggctgg   120
tcggagcagg agccggccca ctgggtgcgt gccaccgaag aggccgttgc cggcctgaag   180
gcaaaacatc cgaaagagct tgccgcggtc aagggcatcg cctttccgg ccagatgcac    240 ggcgcgacgc tgatcgatgc cgccgacaag gcgctgcgcc cctgcatcct ctggaacgac   300
acgcgcagcc acgtcgaggc tgcagccctc gatgccgacc gcgcttccg cgcgctcacc    360 ggcaacatcg tcttcccgg cttcacggcg ccgaagctcg cctgggtcga agcacgag     420 cgcgatgttt tcgccaagat cgccaaggtg ctgctgccga aggactatct gcgtctgtgg   480
ctgaccggcg accatatctc cgaaatgtcg gattcggccg gcacctcctg gctcgacacc   540
ggcaagcgcg cctggtcgtc cgaactgctc gccgccacca tctttccga ggagcagatg    600 ccggcgcttg tcgagggcac cgcgcaggct ggtcagctgc gggcagaact tgtggcgcaa   660
tgggggatct ccggcaatgt cgtcgtcgcc ggcggggccg cgacaatgc cgcctcggcc    720 tgcggcatgg gcacggtcag cgatggcgcc gccttcgtct cgctcggcac gtcgggcgtg   780 cttttttgccg ccaatggctc ctatctgccg aagccggaaa gtgccgtgca tgccttctgc   840
cacgcgctgc cgaacaccctg gcatcagatg ggcgtcatcc tctcggccac cgatgcgctc   900
aactggcatt caggggtgac cggcaagtcg cggccgatc tcaccggcga actcggcgag    960
acgttgaagg cgccgaccgg cgtcaccttc ctgccctatc tttccggcga gcgcacgccg   1020
cacaatgatg ccgtcatccg cggcgccttc atcggcctcg aacatgaaag cagccgtgcc   1080
gtgctcaccc aggcggtgct cgaaggtgtg gcctttgcca tccgcgacaa tctcgaagcg   1140
ctgcgttcgg ccggcaccgg tatctcccgc gtcacggcga tcggcggcgg ttcgcgctcg   1200
cattactggc tggcgtcgat cgcgaccgcg ctcggcgttc cggtcgacct gcccgccgac   1260
ggcgatttcg gcgcggcctt cggcgccgcc cgctcggcc tgattgctgc gacgggtgcc   1320
gatccgattg ccgtctgcac gccgccggtg acatcaggca cgatcgagcc ggtgtcggcg   1380
ctgagcggcg cttacgagga tgcctatacg cgctaccgcg cagtttatcc ggcggtcaaa   1440
tcgctggcgc attga                                                    1455
```

```
<210> SEQ ID NO 112
<211> LENGTH: 483
<212> TYPE: PRT
<213> ORGANISM: Klebsiella pneumoniae

<400> SEQUENCE: 112

Met Tyr Ile Gly Ile Asp Leu Gly Thr Ser Gly Val Lys Ala Ile Leu
1               5                   10                  15

Leu Asn Glu Gln Gly Glu Val Val Ala Ser His Thr Glu Lys Leu Thr
            20                  25                  30

Val Ser Arg Pro His Pro Leu Trp Ser Glu Gln Asp Pro Glu Gln Trp
        35                  40                  45

Trp Leu Ala Thr Asp Thr Ala Met Lys Ala Leu Gly Ala His Asp Ser
    50                  55                  60

Leu Arg His Val Lys Gly Leu Gly Ile Ala Gly Gln Met His Gly Ala
65                  70                  75                  80

Thr Leu Leu Asp Lys Ser Leu Gln Val Leu Arg Pro Ala Ile Leu Trp
                85                  90                  95

Asn Asp Gly Arg Cys Ala Glu Glu Cys Gln Leu Leu Glu Asp Lys Val
            100                 105                 110

Ser Ala Ser Arg Gln Ile Thr Gly Asn Leu Met Met Pro Gly Phe Thr
        115                 120                 125

Ala Pro Lys Leu Leu Trp Val Gln Arg His Glu Ala Ala Val Phe Ser
    130                 135                 140

Gln Val Asp Lys Val Leu Leu Pro Lys Asp Tyr Leu Arg Leu Arg Met
145                 150                 155                 160

Thr Gly Glu Leu Ala Ser Asp Met Ser Asp Ala Ala Gly Thr Met Trp
                165                 170                 175

Leu Asp Val Ala Arg Arg Asp Trp Ser Asp Glu Met Leu Ala Ala Cys
            180                 185                 190

Asp Leu Ser Arg Asp Ala Met Pro Ala Leu Phe Glu Gly Ser Asp Val
        195                 200                 205

Thr Gly Gln Leu Arg Pro Glu Val Ala Gln Ala Trp Asn Met Pro Pro
    210                 215                 220

Ala Leu Val Val Gly Gly Gly Asp Asn Ala Ala Gly Ala Val Gly Ile
225                 230                 235                 240

Ile Gly Met Ala Asp Ala Gly Gln Ala Met Leu Ser Leu Gly Thr Ser
                245                 250                 255

Gly Val Tyr Phe Ala Val Ser Glu Gly Phe Leu Ser Lys Pro Glu Ser
            260                 265                 270

Ala Val His Ser Phe Cys His Ala Cys Arg Gly Arg Trp His Leu Met
        275                 280                 285

Ser Val Met Leu Ser Ala Ala Ser Cys Leu Asp Trp Ala Ala Lys Leu
    290                 295                 300

Thr Gly Leu Ala Ser Val Pro Ala Leu Ile Ala Ala Gln Thr Ala
305                 310                 315                 320

Asp Glu Ser Ala Gly Pro Val Trp Phe Leu Pro Tyr Leu Ser Gly Glu
                325                 330                 335

Arg Thr Pro His Asn Asn Pro Gln Ala Lys Gly Val Phe Phe Gly Leu
            340                 345                 350

Thr His Gln His Gly Pro Ala Glu Leu Ala Arg Ala Val Leu Glu Gly
        355                 360                 365

Val Gly Tyr Ala Leu Ala Asp Gly Met Asp Val Val His Ala Cys Ala
    370                 375                 380
```

```
Ile Lys Pro Glu Ala Ile Thr Leu Ile Gly Gly Arg Ala Arg Tyr
385                 390                 395                 400

Trp Arg Gln Met Leu Ala Asp Ile Ser Gly Leu Gln Leu Asp Tyr Arg
                405                 410                 415

Thr Gly Gly Asp Val Gly Pro Ala Leu Gly Ala Ala Arg Leu Ala His
                420                 425                 430

Val Ala Val His Asp Glu Ala Asp Arg Pro Gly Leu Leu Lys Pro Leu
            435                 440                 445

Pro Leu Glu Gln Ala His Arg Pro Asp Asp Arg Arg Val Ala His Tyr
                450                 455                 460

Ala Pro Gln Arg Glu Ile Phe Ala Arg Ile Phe Ser Lys Leu Lys Pro
465                 470                 475                 480

Leu Met Ser
```

```
<210> SEQ ID NO 113
<211> LENGTH: 1452
<212> TYPE: DNA
<213> ORGANISM: Klebsiella pneumoniae

<400> SEQUENCE: 113
atgtatatcg gcatcgatct ggggacgtcg ggcgtcaaag ccattctgct caatgagcag      60
ggtgaggtag tggcatcgca taccgaaaaa ctcaccgtct cgcgtccgca tccgctgtgg     120
tcggagcaag atcccgaaca gtggtggctg gcgacggaca cggcgatgaa agccctgggc     180
gcgcacgata gcctgcgcca cgtgaagggc ctgggcattg ccgggcagat gcacggcgcc     240
accctactgg ataaatcgtt acaggtgttg cgtccggcca ttttatggaa tgacggccgc     300
tgcgccgaag agtgccagct gctggaagac aaagtcagcg cttcccggca gatcaccggc     360
aaccttatga tgccgggctt tacggcgccg aagctcttat gggtacagcg ccacgaggcg     420
gcagtgttca gccaggtcga taaagtgctg ctgcccaagg attatctgcg cctgcgcatg     480
accggcgagc ttgccagcga tatgtctgac gccgccggca cgatgtggct ggacgtcgcc     540
cggcgcgact ggagcgacga gatgctcgcc gcctgcgatc tcagtcggga tgcgatgccg     600
gcgctgttcg aaggcagcga tgtcaccggg caactgcgac ctgaggtggc gcaggcgtgg     660
aatatgccgc cggcgctggt ggtgggcggc ggggcgaca acgccgccgg ggccgtcggg     720
atcggcatgg ccgatgccgg tcaggcgatg ctgtcgctgg gtacgtcagg cgtctacttc     780
gccgtcagtg aagggttcct tagcaaaccc gaaagcgcgg tgcacagctt ctgccatgcc     840
tgccgcggcc gctggcattt gatgtcggtg atgctcagcg cggcctcctg tctggactgg     900
gcggcaaaat taaccggtct cgccagcgtg ccggcgctga tcgcggcggc gcagacggcg     960
gatgaaagcg ccggtccggt gtggttcctg ccctatctgt ctggcgaacg cacgccgcac    1020
aacaacccgc aggctaaggg cgtctttttt ggcctgacgc atcagcatgg gccggcagag    1080
ctggcgcggg cggtgctgga aggggtgggc tatgcgctgg cggatggtat ggacgtggtg    1140
cacgcctgcg ccatcaagcc ggaagcaatc acgcttatcg gcggcggacg cgcacgttac    1200
tggcggcaaa tgctggcgga tatcagcggc ctgcagctcg attaccgtac cgggggcgat    1260
gtcggcccgg cgctgggggc ggccaggctg gcgcacgtgg cggttcacga cgaggcagac    1320
cgccccgggc tgctgaagcc gctgccgctt gaacaagccc atcgcccgga cgatcgccgt    1380
gtggcccact atgcgccgca gcgggaaatc ttcgccagaa ttttcagcaa actgaaaccg    1440
ctgatgtctt ag                                                        1452

<210> SEQ ID NO 114
```

<211> LENGTH: 484
<212> TYPE: PRT
<213> ORGANISM: Salmonella typhimurium

<400> SEQUENCE: 114

```
Met Tyr Ile Gly Ile Asp Leu Gly Thr Ser Gly Val Lys Ala Ile Leu
1               5                   10                  15

Leu Asn Glu Gln Gly Asp Val Leu Ala Thr His Thr Glu Lys Leu Thr
            20                  25                  30

Val Ser Arg Pro His Pro Leu Trp Ser Glu Gln Pro Glu Gln Trp
        35                  40                  45

Trp Gln Ala Thr Asp Arg Ala Val Lys Gly Leu Gly Arg Gln Gln Ser
    50                  55                  60

Leu Ser Gly Val Arg Ala Leu Gly Ile Ala Gly Gln Met His Gly Ala
65                  70                  75                  80

Thr Leu Leu Asp Ser Arg Gln Gln Val Leu Arg Pro Ala Ile Leu Trp
                85                  90                  95

Asn Asp Gly Arg Cys Ser Glu Glu Cys Ala Trp Leu Glu Lys Gln Val
            100                 105                 110

Pro Gln Ser Arg Ala Ile Thr Gly Asn Leu Met Met Pro Gly Phe Thr
        115                 120                 125

Ala Pro Lys Leu Val Trp Val Gln Arg His Glu Pro Asp Ile Phe Tyr
    130                 135                 140

Gln Ile Asp Lys Val Leu Leu Pro Lys Asp Phe Leu Arg Leu Arg Met
145                 150                 155                 160

Thr Gly Val Phe Ala Ser Asp Met Ser Asp Ala Ala Gly Thr Met Trp
                165                 170                 175

Leu Asp Val Lys Lys Arg Asp Trp Ser Asp Val Met Leu Asn Ala Cys
            180                 185                 190

His Leu Thr Arg Gln Gln Met Pro Ala Leu Phe Glu Gly Ser Asp Ile
        195                 200                 205

Thr Gly Thr Leu Leu Pro Glu Val Ala Ser Ala Trp Gly Met Pro Ala
    210                 215                 220

Val Pro Val Val Ala Gly Gly Asp Asn Ala Ala Gly Ala Val Gly
225                 230                 235                 240

Val Gly Met Ile Asp Ala Gly Gln Ala Met Leu Ser Leu Gly Thr Ser
                245                 250                 255

Gly Val Tyr Phe Ala Val Ser Asp Gly Phe Leu Ser Lys Pro Glu Ser
            260                 265                 270

Ala Val His Ser Phe Cys His Ala Leu Pro Glu Arg Trp His Leu Met
        275                 280                 285

Ser Val Met Leu Ser Ala Ala Ser Cys Leu Asp Trp Ala Ala Lys Leu
    290                 295                 300

Thr Gly Gln Glu Asn Val Pro Ala Leu Ile Ala Ala Gln Gln Ala
305                 310                 315                 320

Asp Glu His Ala Asp Ser Ile Trp Phe Leu Pro Tyr Leu Ser Gly Glu
                325                 330                 335

Arg Thr Pro His Asn Asn Pro Gln Ala Lys Gly Val Phe Phe Gly Leu
            340                 345                 350

Thr His Gln His Gly Pro Ala Glu Leu Ala Arg Ala Val Leu Glu Gly
        355                 360                 365

Val Gly Tyr Ala Leu Ala Asp Gly Met Asp Val Val His Ala Cys Gly
    370                 375                 380

Val Lys Pro Ala Ser Val Thr Leu Ile Gly Gly Gly Ala Arg Ser Glu
385                 390                 395                 400
```

```
Tyr Trp Arg Gln Met Leu Ser Asp Ile Ser Gly Leu Gln Leu Asp Tyr
            405                 410                 415
Arg Thr Gly Gly Asp Val Gly Pro Ala Leu Gly Ala Ala Arg Leu Ala
        420                 425                 430
Gln Ile Ala Val Asn Lys Gln Thr Pro Leu Ala Asp Val Leu Pro Gln
                435                 440                 445
Leu Pro Leu Glu Gln Ala His Tyr Pro Asp Ala Gln Arg His Ala Val
    450                 455                 460
Tyr Gln Gln Arg Arg Glu Thr Phe Arg Arg Leu Tyr Gln Gln Leu Leu
465                 470                 475                 480
Pro Leu Met Ser

<210> SEQ ID NO 115
<211> LENGTH: 1455
<212> TYPE: DNA
<213> ORGANISM: Salmonella typhimurium

<400> SEQUENCE: 115
atgtatatcg ggatcgatct tggtacatcg ggtgtaaaag ctatcctgtt gaatgagcag     60
ggcgatgtgc tggctacgca tactgaaaaa ctgaccgtat cgcgtccgca tcccttatgg    120
tcggaacagg aaccagagca gtggtggcag gcgacggatc gtgcggttaa aggtttaggt    180
cggcaacagt cgttaagtgg cgtccgggcg ttgggcatcg ccggacaaat gcatggcgcg    240
acattgcttg atagccgtca gcaggttctg cgaccagcga tttttatggaa tgacggacgc    300
tgtagcgaag agtgcgcctg gctggaaaaa caggtgccgc agtcgcgtgc gataaccggt    360
aatctgatga tgcccggttt taccgcgccc aaattagtct gggtgcagcg ccacgaaccg    420
gatatttctt accagataga caaggttctg ctgccgaaag attttctgcg gctgcgaatg    480
acaggcgtct ttgccagcga tatgtcggat gcggcgggaa cgatgtggct ggacgtgaaa    540
aagcgcgact ggagcgacgt tatgctcaac gcctgtcatt taacccgaca gcagatgcca    600
gcgttatttg aaggtagtga cattaccgga acgttgctgc ggaggtggc cagcgcatgg    660
ggaatgccag cagtacctgt ggtggcgggc ggcggcgaca atgcggctgg cgcggtcggc    720
gtaggaatga tcgatgccgg acaggcgatg ctctcactcg gaacatcggg cgtctatttt    780
gccgtcagcg acggctttct gagtaaaccg gagagcgcag tacacagttt ttgccatgcg    840
ctgccggaac gctggcattt aatgtctgtg atgttgagcg ccgcctcttg tctggactgg    900
gcggctaaac tcaccgggca ggagaacgtc cggcgctga ttgccgccgc acagcaggcg    960
gatgagcatg ccgattcgat ctggttttg ccgtacctgt ccggcgagcg cacgccgcat   1020
aataatccgc aggcaaaagg cgttttcttt ggtttaaccc atcagcatgg cccggcggaa   1080
ctggcgcggg cggtactgga gggcgtggga tatgctttgg cggacggtat ggatgtggtt   1140
cacgcctgcg gcgtcaaacc cgccagcgtg acgcttatcg gcggcgggc gcgcagcgaa   1200
tactggcgtc agatgctatc tgatattagc gggctacagc ttgattatcg tactggcggc   1260
gatgtagggc cagcgctggg cgcggcgcgt ctggcgcaaa ttgcggtgaa taaacagacc   1320
ccgctcgccg atgtattgcc gcagttgccg ctggagcagg cgcattatcc tgatgcgcag   1380
cgtcatgcgg tttatcaaca acgtcgtgaa accttccgtc gactttatca gcagctgttg   1440
ccgttgatgt cataa                                                    1455

<210> SEQ ID NO 116
<211> LENGTH: 478
<212> TYPE: PRT
```

<213> ORGANISM: Rhodobacter sphaeroides

<400> SEQUENCE: 116

```
Met Tyr Ile Gly Leu Asp Leu Gly Thr Ser Gly Leu Lys Gly Ile Leu
1               5                   10                  15

Ile Asp Glu Gly Gln Arg Val Leu Ala Glu Ala Ser Ala Pro Leu Thr
            20                  25                  30

Val Ser Arg Pro His Glu Gly Trp Ser Glu Gln Ser Pro Ala Asp Trp
        35                  40                  45

Ile Ala Ala Glu Ala Val Met Asp Gln Leu Ala Ala Gln Gly Leu
    50                  55                  60

Ala Gly Val Lys Gly Ile Gly Leu Ser Gly Gln Met His Gly Ala Thr
65                  70                  75                  80

Leu Leu Asp Ala Ser Asp Glu Val Leu Arg Pro Cys Ile Leu Trp Asn
                85                  90                  95

Asp Thr Arg Ser His Ala Glu Ala Thr Glu Leu Asp Ala Asp Pro Arg
            100                 105                 110

Phe Arg Ala Ile Thr Gly Asn Ile Val Phe Pro Gly Phe Thr Ala Pro
        115                 120                 125

Lys Leu Ala Trp Val Ala Arg His Glu Pro Ala Ile Arg Ala Arg Val
    130                 135                 140

Ala Arg Val Leu Leu Pro Lys Asp Tyr Leu Arg Leu Trp Leu Thr Gly
145                 150                 155                 160

Glu His Val Ala Glu Met Ser Asp Ala Ala Gly Thr Ser Trp Leu Asp
                165                 170                 175

Val Gly Ala Arg Asp Trp Ser Asp Glu Leu Leu Ala Ala Thr Asp Leu
            180                 185                 190

Ser Arg Glu Ala Met Pro Arg Leu Val Glu Gly Ser Ala Val Ser Gly
        195                 200                 205

Glu Leu Arg Pro Ala Leu Ala Ala Arg Trp Gly Leu Pro Gln Arg Val
    210                 215                 220

Val Val Ala Gly Gly Gly Gly Asp Asn Ala Ala Ser Ala Val Gly Val
225                 230                 235                 240

Gly Val Val Arg Ala Gly Glu Ala Phe Val Ser Leu Gly Thr Ser Gly
                245                 250                 255

Val Leu Phe Ala Ala Thr Asp Gly Tyr Gln Pro Ala Pro Glu Thr Ala
            260                 265                 270

Val His Thr Phe Cys His Ala Leu Pro Glu Ala Trp His Gln Met Gly
        275                 280                 285

Val Ile Leu Ala Ala Thr Asp Ala Leu Asn Trp Tyr Ala Arg Leu Val
    290                 295                 300

Gly Gln Glu Ala Arg Val Leu Thr Gly Asp Leu Gly Ala Leu Gln Ala
305                 310                 315                 320

Pro Gly Arg Ala Leu Phe Leu Pro Tyr Leu Gly Gly Glu Arg Thr Pro
                325                 330                 335

Leu Asn Asp Ala Ala Ile Arg Gly Ala Phe Thr Gly Leu Glu His Ala
            340                 345                 350

Thr Asp Arg Ala Ala Gly Thr Arg Ala Val Leu Glu Gly Val Thr Phe
        355                 360                 365

Ala Ile Arg Asp Cys Arg Asp Ala Leu Ala Ala Thr Gly Thr Arg Leu
    370                 375                 380

Glu Ser Leu Leu Ala Val Gly Gly Gly Ser Arg Ser Asp Tyr Trp Leu
385                 390                 395                 400

Ser Ala Ile Ala Thr Ala Leu Asp Val Pro Val Leu Leu Pro Ala Ala
```

```
                           405                 410                 415
Gly Asp Phe Gly Gly Ala Phe Gly Ala Ala Arg Leu Ala Leu Met Ala
            420                 425                 430

Ala Thr Gly Ala Gly Ala Glu Ile Ala Thr Leu Pro Pro Ile Ala Arg
            435                 440                 445

Thr Ile Pro Pro Glu Arg Gly Leu Thr Ser Ala Phe Asp Asp Ala His
            450                 455                 460

Ala Arg Tyr Arg Ala Ala Gln Thr Ala Ile Arg Ser Leu Thr
465                 470                 475

<210> SEQ ID NO 117
<211> LENGTH: 1437
<212> TYPE: DNA
<213> ORGANISM: Rhodobacter sphaeroides

<400> SEQUENCE: 117
atgtacatcg gtctcgatct cgggacgtcc gggctcaagg gcatcctgat cgacgaaggc      60
cagcgcgtgc tggccgaggc gagcgcgcct ctcactgtca gccgtccgca cgaggggtgg     120
tccgaacagt cgccggccga ctggatcgcg cggccgaggc cggtgatgga ccagcttgcg     180
gcgcaggggc ttgcgggcgt gaagggcatc gggctctcgg ccagatgca cggcgcgacg      240 ctgctggatg cctcggacga ggtgctgcgg ccctgcatcc tgtggaacga cacccgcagc     300
catgccgagg cgacggaact ggatgccgat ccgcggtttc gggccatcac cggcaacatc     360
gtctttccgg gcttcaccgc gcccaagctg gctgggtcg cgcggcacga gccggcgatc      420
cgggcgcggg tggcgcgggt tctgctgccc aaggattacc tgcggctctg gctgacgggc     480
gagcatgtcg ccgagatgtc ggacgccgcc gggacgagct ggctggatgt cggcgcgcgc     540
gactggtcgg acgaacttct ggccgcgacc gacctctcgc gcgaggcgat gccgcggctg     600
gtcgagggtt cggccgtgtc gggtgagttg cgcccggcgc tggccgcccg ctggggcttg     660
ccccaaaggg tggtcgtggc gggcggaggc ggcgacaacg ccgcctcggc cgtgggggtg     720
ggcgtggtcc cgcgcaggcg aggccttcgt cagccttggca cctccggggt gctgtttgcc     780
gccaccgacg gctaccagcc ggcgccggag acggccgttc ataccttctg ccacgccctg     840
cccgaggcgt ggcaccagat gggcgtgatc ctcgccgcga ccgacgcgct gaactggtat     900
gcgcggctgg tggggcagga ggcgcgggtg ctgaccggcg accttggcgc gcttcaggcg     960
ccggggcgtg cgttgttcct gccctatctc gggggcgagc ggacgccgct gaacgacgcg    1020
gcgatccgcg gcgccttcac cgggctcgaa catgcgaccg accgcgccgc cggaacgcgg    1080
gccgttctgg aaggcgtgac cttcgccatc cgcgactgcc gcgacgcgct ggccgcgacg    1140
ggaacccggc tggagagcct tctggccgtc ggcggcggct cgcgctcgga ctactggctg    1200
tcggccatcg cgacggcgct ggacgtgccg gtgctgctgc ctgcggcggg cgacttcggc    1260
ggcgccttcg gggccgcgcg ccttgcgctg atggccgcga ccggggccgg ggccgagatc    1320
gcgaccctgc cgcccatcgc ccgcaccatc ccgcccgagc gcggcctcac gtccgccttc    1380
gacgacgcac acgcgcgcta tcgcgccgcc cagacagcca tcaggagcct cacatga      1437

<210> SEQ ID NO 118
<211> LENGTH: 317
<212> TYPE: PRT
<213> ORGANISM: Escherichia coli

<400> SEQUENCE: 118

Met Thr Asp Lys Leu Thr Ser Leu Arg Gln Tyr Thr Thr Val Val Ala
1               5                   10                  15
```

Asp Thr Gly Asp Ile Ala Ala Met Lys Leu Tyr Gln Pro Gln Asp Ala
            20                  25                  30

Thr Thr Asn Pro Ser Leu Ile Leu Asn Ala Ala Gln Ile Pro Glu Tyr
        35                  40                  45

Arg Lys Leu Ile Asp Asp Ala Val Ala Trp Ala Lys Gln Gln Ser Asn
50                  55                  60

Asp Arg Ala Gln Gln Ile Val Asp Ala Thr Asp Lys Leu Ala Val Asn
65                  70                  75                  80

Ile Gly Leu Glu Ile Leu Lys Leu Val Pro Gly Arg Ile Ser Thr Glu
                85                  90                  95

Val Asp Ala Arg Leu Ser Tyr Asp Thr Glu Ala Ser Ile Ala Lys Ala
            100                 105                 110

Lys Arg Leu Ile Lys Leu Tyr Asn Asp Ala Gly Ile Ser Asn Asp Arg
        115                 120                 125

Ile Leu Ile Lys Leu Ala Ser Thr Trp Gln Gly Ile Arg Ala Ala Glu
130                 135                 140

Gln Leu Glu Lys Glu Gly Ile Asn Cys Asn Leu Thr Leu Leu Phe Ser
145                 150                 155                 160

Phe Ala Gln Ala Arg Ala Cys Ala Glu Ala Gly Val Phe Leu Ile Ser
                165                 170                 175

Pro Phe Val Gly Arg Ile Leu Asp Trp Tyr Lys Ala Asn Thr Asp Lys
            180                 185                 190

Lys Glu Tyr Ala Pro Ala Glu Asp Pro Gly Val Val Ser Val Ser Glu
        195                 200                 205

Ile Tyr Gln Tyr Tyr Lys Glu His Gly Tyr Glu Thr Val Val Met Gly
210                 215                 220

Ala Ser Phe Arg Asn Ile Gly Glu Ile Leu Glu Leu Ala Gly Cys Asp
225                 230                 235                 240

Arg Leu Thr Ile Ala Pro Ala Leu Leu Lys Glu Leu Ala Glu Ser Glu
                245                 250                 255

Gly Ala Ile Glu Arg Lys Leu Ser Tyr Thr Gly Glu Val Lys Ala Arg
            260                 265                 270

Pro Ala Arg Ile Thr Glu Ser Glu Phe Leu Trp Gln His Asn Gln Asp
        275                 280                 285

Pro Met Ala Val Asp Lys Leu Ala Glu Gly Ile Arg Lys Phe Ala Ile
290                 295                 300

Asp Gln Glu Lys Leu Glu Lys Met Ile Gly Asp Leu Leu
305                 310                 315

<210> SEQ ID NO 119
<211> LENGTH: 954
<212> TYPE: DNA
<213> ORGANISM: Escherichia coli

<400> SEQUENCE: 119
atgacggaca aattgaccctc ccttcgtcag tacaccaccg tagtggccga cactggggac      60
atcgcggcaa tgaagctgta tcaaccgcag gatgccacaa ccaacccttc tctcattctt     120
aacgcagcgc agattccgga ataccgtaag ttgattgatg atgctgtcgc ctgggcgaaa     180
cagcagagca acgatcgcgc gcagcagatc gtggacgcga ccgacaaact ggcagtaaat     240
attggtctgg aaatcctgaa actggttccg ggccgtatct caactgaagt tgatgcgcgt     300
ctttcctatg acaccgaagc gtcaattgcg aaagcaaaac gcctgatcaa actctacaac     360
gatgctggta ttagcaacga tcgtattctg atcaaactgg cttctacctg gcagggtatc     420

```
cgtgctgcag aacagctgga aaaagaaggc atcaactgta acctgaccct gctgttctcc    480
ttcgctcagg ctcgtgcttg tgcggaagcg ggcgtgttcc tgatctcgcc gtttgttggc    540
cgtattcttg actggtacaa agcgaatacc gataagaaag agtacgctcc ggcagaagat    600
ccgggcgtgg tttctgtatc tgaaatctac cagtactaca agagcacgg ttatgaaacc     660 gtggttatgg gcgcaagctt ccgtaacatc ggcgaaattc tggaactggc aggctgcgac    720
cgtctgacca tcgcaccggc actgctgaaa gagctggcgg agagcgaagg ggctatcgaa    780
cgtaaactgt cttacaccgg cgaagtgaaa gcgcgtccgg cgcgtatcac tgagtccgag    840
ttcctgtggc agcacaacca ggatccaatg gcagtagata aactggcgga aggtatccgt    900
aagtttgcta ttgaccagga aaaactggaa aaaatgatcg gcgatctgct gtaa          954
```

```
<210> SEQ ID NO 120
<211> LENGTH: 308
<212> TYPE: PRT
<213> ORGANISM: Pseudomonas putida

<400> SEQUENCE: 120

Met Thr Ser Lys Leu Glu Gln Leu Lys Gln Phe Thr Thr Val Val Ala
1               5                   10                  15

Asp Thr Gly Asp Leu Asp Ala Ile Thr Arg Leu Lys Pro Val Asp Ala
            20                  25                  30

Thr Thr Asn Pro Ser Leu Leu Leu Lys Ala Ala Ala Ile Pro Gly Tyr
        35                  40                  45

Ala Asp Leu Leu Lys Gln Val Lys Ser Asp Ala Lys Gly Asn Val Asp
    50                  55                  60

Leu Ala Cys Asp Lys Phe Ala Val Ala Val Gly Ala Gly Ile Leu Lys
65                  70                  75                  80

Val Ile Pro Gly Arg Ile Ser Thr Glu Val Asp Ala Arg Leu Ser Phe
                85                  90                  95

Asp Glu Pro Ala Leu Leu Ser Lys Ala Arg Gln Leu Ile Glu Leu Tyr
            100                 105                 110

Gln Ala Ala Gly Ile Pro Lys Asp Arg Val Leu Ile Lys Leu Ala Ser
        115                 120                 125

Thr Trp Glu Gly Ile Arg Ala Ala Glu Gln Leu Glu Lys Glu Gly Ile
    130                 135                 140

Gln Thr Asn Leu Thr Leu Leu Phe Ser Phe Ala Gln Ala Gln Ala Cys
145                 150                 155                 160

Ala Asp Ala Gly Val Phe Leu Ile Ser Pro Phe Val Gly Arg Ile Tyr
                165                 170                 175

Asp Trp Tyr Lys Lys Ser Thr Gly Gln Glu Tyr Val Gly Ala Asn Asp
            180                 185                 190

Pro Gly Val Gln Ser Val Thr Arg Ile Tyr Asn Tyr Tyr Lys Ala Asn
        195                 200                 205

Gly Tyr Asn Thr Val Val Met Gly Ala Ser Phe Arg Asn Ile Gly Gln
    210                 215                 220

Ile Glu Gln Leu Ala Gly Cys Asp Arg Leu Thr Ile Ser Pro Glu Leu
225                 230                 235                 240

Leu Gln Gln Leu Ser Asp Asp Gln Gly Glu Leu Pro Gln Val Leu Lys
                245                 250                 255

Pro Gly Asp Ala Gly Glu Ala Lys Gln Val Leu Ser Glu Ser Gln Phe
            260                 265                 270

Arg Trp Ala Met Asn Glu Asp Ala Met Gly Thr Glu Lys Leu Ala Glu
        275                 280                 285
```

Gly Ile Arg Gln Phe Ala Arg Asp Gln Glu Lys Leu Glu Lys Leu Met
            290                 295                 300

Ala Asp Lys Ala
305

<210> SEQ ID NO 121
<211> LENGTH: 927
<212> TYPE: DNA
<213> ORGANISM: Pseudomonas putida

<400> SEQUENCE: 121

| | | |
|---|---|---|
| atgacttcca agctggaaca actcaagcag ttcaccaccg tggtcgccga caccggggat | 60 |
| ctggacgcca tcacccgcct caagccggtc gatgccacca ccaaccccctc gttgctgcta | 120 |
| aaggctgccg ctatcccggg ttatgccgac ctgctcaagc aggtaaaaag cgatgccaag | 180 |
| ggcaatgtcg acctggcgtg cgacaagttc gcggtggcgg tgggcgctgg cattctgaaa | 240 |
| gtgatccctg gcgcatctc caccgaagtg gatgcgcgcc tgtcgttcga cgaaccggca | 300 |
| ctgctgagca aggcccgcca gctgatcgag ctttaccagg ccgccgggat cccaaagac | 360 |
| cgcgtgctga tcaagctggc ctccacctgg gaaggcatcc gcgccgccga gcagttggag | 420 |
| aaggaaggca tccagaccaa cctgaccctg ctgttctcct tcgcccaggc ccaggcctgc | 480 |
| gccgatgccg gtgtgttcct gatttcgccg ttcgtgggcc ggatctacga ttggtacaag | 540 |
| aaaagcaccg gccaggagta cgtgggtgcc aatgacccgg gcgtacagtc ggtcacacgc | 600 |
| atctacaact actacaaggc caacggctac aacaccgtgg tcatgggcgc cagcttccgc | 660 |
| aacattggcc agatcgaaca actggctggc tgcgatcgcc tgaccatcag cccggagctg | 720 |
| ctgcagcaac tgagcgatga ccagggcgag ctgccgcagg tgctaaagcc gggcgatgcc | 780 |
| ggcgaggcca agcaggtgct cagcgaaagc cagttccgct gggccatgaa cgaagacgcc | 840 |
| atgggcaccg agaactggcc gagggcatt cgccagttcg cccgtgacca ggagaagctg | 900 |
| gaaaagctga tggctgacaa agcctga | 927 |

<210> SEQ ID NO 122
<211> LENGTH: 321
<212> TYPE: PRT
<213> ORGANISM: Rhizobium leguminosarum

<400> SEQUENCE: 122

Met Thr Ser Lys Leu Asp Gln Leu Arg Glu Ile Thr Thr Val Val Ala
1               5                   10                  15

Asp Thr Gly Asp Ile Glu Ala Val Ala Arg Leu Lys Pro Val Asp Cys
            20                  25                  30

Thr Thr Asn Pro Ser Ile Val Leu Lys Ala Leu Gly Thr Pro Met Phe
        35                  40                  45

Ala Asp Ala Ile Lys Glu Ala Val Ala Trp Gly Lys Lys Gln Gly Gly
    50                  55                  60

Asn Pro Asp Ala Val Ser Ser Ala Val Ala Asp Arg Leu Ala Ile Ser
65                  70                  75                  80

Val Gly Ala Ala Leu Val Lys Leu Val Pro Gly Arg Val Ser Thr Glu
                85                  90                  95

Val Asp Ala Asp Leu Ser Phe Asp Thr Glu Ala Ser Leu Ala Lys Ala
            100                 105                 110

Arg Ser Ile Ile Ala Ala Tyr Lys Asp Arg Gly Ile Asp Gln Asp Arg
        115                 120                 125

Ile Leu Ile Lys Leu Ala Ser Thr Trp Glu Gly Ile Arg Ala Ala Glu
    130                 135                 140

```
Val Leu Gln Lys Glu Gly Ile Asp Cys Asn Leu Thr Leu Leu Phe Ser
145                 150                 155                 160

Lys Ala Gln Ala Ile Ala Cys Ala Asp Ala Lys Val Phe Leu Ile Ser
            165                 170                 175

Pro Phe Val Gly Arg Ile Leu Asp Trp Tyr Lys Ser Thr Gly Lys
        180                 185                 190

Asp Tyr Thr Ala Glu Glu Asp Pro Gly Val Ile Ser Val Arg Glu Ile
            195                 200                 205

Tyr Asn Tyr Tyr Lys Ala Asn Asp Ile Lys Thr Ile Val Met Gly Ala
    210                 215                 220

Ser Phe Arg Ser Ala Gly Glu Ile Glu Ala Leu Ala Gly Cys Asp Arg
225                 230                 235                 240

Leu Thr Ile Ser Pro Asn Leu Leu Asp Glu Leu Ala Lys Asp Glu Gly
            245                 250                 255

Lys Leu Glu Arg Lys Leu Ser Pro Gly Arg Lys Pro Asp Pro Lys
        260                 265                 270

Val Ser Val Asp Glu Lys Thr Phe Arg Trp Met Met Asn Glu Asp Ala
    275                 280                 285

Met Ala Thr Glu Lys Leu Ala Glu Gly Ile Arg Ala Phe Ala Lys Asp
    290                 295                 300

Leu Gly Thr Leu Arg Thr Met Val Gln Lys Glu Leu Gln Leu Ala Ala
305                 310                 315                 320

Ala
```

<210> SEQ ID NO 123
<211> LENGTH: 966
<212> TYPE: DNA
<213> ORGANISM: Rhizobium leguminosarum

<400> SEQUENCE: 123

```
atgacatcca agcttgacca actccgcgag attaccaccg tcgtcgccga caccggcgat      60
atcgaagccg tcgcccgcct gaagcctgtg gattgcacga cgaacccgag catcgtgctg     120
aaggccctcg gcacgccgat gtttgccgac gccatcaagg aagccgttgc ctggggcaag     180
aagcagggcg gcaatcctga cgccgtttcg tcggccgttg ccgaccgtct cgccatctcc     240
gtcggcgcag ccctggtgaa gctcgttccg ggccgtgtct cgaccgaagt cgacgccgat     300
ctttccttcg atacggaggc ttcgcttgcc aaggcgcggt cgatcatcgc cgcctataag     360
gatcgcggca tcgatcagga ccgcatcctc atcaagctcg cttccacctg ggaaggcatc     420
cgcgctgcgg aagtgctgca gaaggaaggc atcgactgca atctgacact gctcttcagc     480
aaggcccagg caatcgcctg cgcggacgcc aaggtgttcc tgatctcgcc cttcgtcggc     540
cgcatcctcg actggtacaa gaatcgacc ggcaaggact acaccgccga ggaagatccg     600
ggcgtcatct ccgtccgtga aatctacaac tactacaagg cgaacgatat caagacgatc     660
gtcatgggcg cctccttccg cagcgccggc gaaattgaag cgcttgccgg ctgcgaccgc     720
ctgaccatca gcccgaacct gctcgacgaa ctcgccaagg atgaaggcaa gctggagcgc     780
aagctttcgc cggaaggccg caagccggat ccgaaggtgt ctgtcgacga agaccttc      840
cgctggatga tgaacgaaga tgcgatggcg acggaaaaac tcgccgaagg catccgcgct     900
ttcgccaagg atttgggaac gttgcgcacc atggtgcaga aggaactgca gctcgccgcc     960
gcctga                                                                966
```

<210> SEQ ID NO 124

<211> LENGTH: 318
<212> TYPE: PRT
<213> ORGANISM: Klebsiella pneumoniae

<400> SEQUENCE: 124

Met Asn Gln Leu Asp Ser Ile Lys Gln Phe Thr Thr Val Val Ala Asp
1               5                   10                  15

Ser Gly Asp Ile Glu Ser Ile Arg His Tyr His Pro Glu Asp Ala Thr
            20                  25                  30

Thr Asn Pro Ser Leu Leu Leu Lys Ala Ala Gly Leu Ala Ser Tyr Ser
        35                  40                  45

Gly Leu Ile Asp Asp Ala Ile Ala Trp Ala Lys Lys Gln Gly Gly Gly
    50                  55                  60

Arg Glu Ala Gln Val Ala His Ala Cys Asp Lys Leu Ala Val Asn Phe
65                  70                  75                  80

Gly Ala Glu Ile Leu Lys Ser Ile Pro Gly Arg Val Ser Thr Glu Val
                85                  90                  95

Asp Ala Arg Leu Ser Phe Asn Arg Glu Lys Ser Ile Glu Lys Ala Arg
            100                 105                 110

His Leu Val Ala Leu Tyr Gln Glu Met Gly Ile Asp Lys Ser Arg Ile
        115                 120                 125

Leu Ile Lys Leu Ala Ser Thr Trp Glu Gly Ile Arg Ala Ala Glu Val
    130                 135                 140

Leu Glu Lys Glu Gly Ile His Cys Asn Leu Thr Leu Leu Phe Ser Phe
145                 150                 155                 160

Ala Gln Ala Arg Ala Cys Ala Glu Ala Gly Val Tyr Leu Ile Ser Pro
                165                 170                 175

Phe Val Gly Arg Ile Tyr Asp Trp Tyr Gln Ala Arg Lys Pro Leu Glu
            180                 185                 190

Pro Tyr Val Val Glu Glu Asp Pro Gly Val Lys Ser Val Arg Asn Ile
        195                 200                 205

Tyr Asp Tyr Phe Lys Gln His Lys Tyr Asn Thr Ile Val Met Gly Ala
    210                 215                 220

Ser Phe Arg Arg Thr Glu Gln Ile Leu Ala Leu Val Gly Cys Asp Arg
225                 230                 235                 240

Leu Thr Ile Ala Pro Pro Leu Leu Lys Glu Leu Gln Ala Ser Asp Thr
                245                 250                 255

Pro Val Val Arg Lys Leu Ile Pro Ala Ser Gln Ile Leu Pro Arg Pro
            260                 265                 270

Val Pro Leu Ser Glu Ala Glu Phe Arg Trp Glu His Asn Gln Asp Pro
        275                 280                 285

Met Ala Val Glu Lys Leu Ala Glu Gly Ile Arg Leu Phe Ala Val Asp
    290                 295                 300

Gln Arg Lys Leu Glu Asp Leu Leu Ala Ala Lys Leu Ser Leu
305                 310                 315

<210> SEQ ID NO 125
<211> LENGTH: 957
<212> TYPE: DNA
<213> ORGANISM: Klebsiella pneumoniae

<400> SEQUENCE: 125
atgaatcagt tagacagcat caagcagttc accacggtgg tcgccgacag cggagacatc    60
gaatccatcc gccactacca tccggaagac gccaccacca cccctctct gctgctgaag    120 gccgccggcc tggcgtccta tagcggcctc atcgacgacg ctatcgcctg gccaaaaaa    180

```
cagggtggcg gccgcgaagc gcaggtggct cacgcctgcg ataagctggc ggtcaatttt    240
ggcgcggaga tcctcaaaag cattcccggg cgggtctcca ccgaggtgga cgcccggctc    300
tccttcaacc gcgagaaaag tatcgagaag gctcgccacc tggtggcgct gtatcaggag    360
atgggcattg ataagtcgcg gatcctgatc aagctggcat ccacctggga ggggatccgc    420
gccgcggagg tgctggagaa agaggggatc cactgcaacc tgacgctgct gttttccttc    480
gcccaggccc gggcctgcgc cgaggccggg gtttatctca tctccccgtt cgttgggcgt    540
atttatgact ggtatcaggc gcgcaaaccg ctggagcctt acgtggtgga ggaagatccg    600
ggggtgaaat cggtgcgcaa tatctatgac tatttcaaac agcataaata caacaccatc    660
gtgatgggcg ccagcttccg ccgcaccgag cagatcctgg cgctggtcgg ttgcgaccgg    720
ttgaccatcg ccccgccttt attaaaagag ctgcaggcca gcgataccccc ggtggtgcgc    780 aaactgatcc ctgccagcca gatcctgccg cgtccggtgc cgctcagtga agcggagttc    840
cgctgggaac ataatcagga tccgatggcg gtcgaaaagc tagcggaggg gatccgcctg    900
ttcgccgtcg atcagcgcaa actggaagat ctgcttgccg ccaaactgtc actttag     957
```

<210> SEQ ID NO 126
<211> LENGTH: 316
<212> TYPE: PRT
<213> ORGANISM: Salmonella typhimurium

<400> SEQUENCE: 126

```
Met Asn Gln Leu Asp Gly Ile Lys Gln Phe Thr Thr Val Val Ala Asp
1               5                   10                  15

Ser Gly Asp Ile Glu Ser Ile Arg His Tyr Gln Pro Gln Asp Ala Thr
            20                  25                  30

Thr Asn Pro Ser Leu Leu Leu Lys Ala Ala Gly Leu Glu Gln Tyr Gly
        35                  40                  45

His Leu Ile Glu Asp Ala Ile Ala Trp Gly Lys Lys His Gly Gly Thr
    50                  55                  60

Gln Glu Gln Gln Val Ala Ala Ser Asp Lys Leu Ala Val Asn Phe
65                  70                  75                  80

Gly Ala Glu Ile Leu Lys Ser Ile Pro Gly Arg Val Ser Thr Glu Val
                85                  90                  95

Asp Ala Arg Leu Ser Phe Asp Lys Glu Lys Ser Ile Glu Lys Ala Arg
            100                 105                 110

His Leu Val Asp Leu Tyr Gln Gln Gly Val Asp Lys Ser Arg Ile
        115                 120                 125

Leu Ile Lys Leu Ala Ala Thr Trp Glu Gly Ile Arg Ala Ala Gly Gln
130                 135                 140

Leu Glu Lys Glu Gly Ile Asn Cys Asn Leu Thr Leu Leu Phe Ser Phe
145                 150                 155                 160

Ala Gln Ala Arg Ala Cys Ala Glu Ala Gly Val Tyr Leu Ile Ser Pro
                165                 170                 175

Phe Val Gly Arg Ile Tyr Asp Trp Tyr Gln Ala Arg Ser Pro Leu Glu
            180                 185                 190

Pro Tyr Val Val Glu Glu Asp Pro Gly Val Lys Ser Val Arg Asn Ile
        195                 200                 205

Tyr Asp Tyr Phe Lys Gln His Arg Tyr Glu Thr Ile Val Met Gly Ala
    210                 215                 220

Ser Phe Arg Arg Thr Glu Gln Ile Leu Ala Leu Thr Gly Cys Asp Arg
225                 230                 235                 240

Leu Thr Ile Ser Pro Asn Leu Leu Lys Glu Leu Lys Glu Lys Glu Glu
```

245                 250                 255
Pro Val Ile Arg Lys Leu Val Pro Ser Ser Gln Met Phe His Arg Pro
                260                 265                 270

Thr Pro Met Thr Glu Ala Glu Phe Arg Trp Glu His Asn Gln Asp Ala
            275                 280                 285

Met Ala Val Glu Lys Leu Ser Glu Gly Ile Arg Leu Phe Ala Val Asp
        290                 295                 300

Gln Arg Lys Leu Glu Asp Leu Leu Ala Ala Lys Leu
305                 310                 315

<210> SEQ ID NO 127
<211> LENGTH: 951
<212> TYPE: DNA
<213> ORGANISM: Salmonella typhimurium

<400> SEQUENCE: 127
atgaaccagc tagacggcat caaacaattc actaccgtcg tcgccgatag cggcgacatc      60
gagtccatcc gccactacca gccgcaggat gccacgacaa atccctcttt actgttaaaa     120
gccgccgggc ttgagcagta tggtcatttg attgaggatg cgattgcctg ggggaaaaaa     180
cacggcggta cgcaggaaca gcaggttgcg gcagccagcg ataaactggc ggttaatttt     240
ggcgcggaaa tactgaaaag tattcccggt cgcgtctcca ctgaagtcga cgcgcggtta     300
tcgttcgata agaaaaaag tatcgagaaa gcgcgccatc tggtggatct ctaccagcag     360
cagggtgttg ataaatcacg cattctgatc aagctcgccg cgacctggga aggtatccgc     420
gccgccgggc agctcgaaaa agagggtatt aattgcaacc tgacgttgtt gttctctttt     480
gcccaggcgc gcgcctgcgc cgaagcgggc gtctatttga tctctccgtt cgtgggccga     540
atttacgact ggtatcaggc gcgtagtccg ctggagccgt atgtcgtgga ggaagatccc     600
ggcgtgaaat cggtacgcaa tatctacgat tactttaaac agcatcgcta tgaaaccatc     660
gtgatggggg caagtttccg ccgtactgag caaatcctcg cgctaaccgg ctgcgatcga     720
ctgactatct cccctaacct gcttaaagag ctgaaagaaa agaagaaacc ggtgatccgt     780
aaactggtgc cttcctcgca gatgttccac cgtcctacgc caatgacgga agcggagttc     840
cgctgggaac ataatcagga cgcgatggcc gtagagaagc tgtcggaagg tatccgtctt     900
tttgccgttg accagcgcaa actggaagac ctgcttgccg ccaaactata a              951

<210> SEQ ID NO 128
<211> LENGTH: 219
<212> TYPE: PRT
<213> ORGANISM: Rhodobacter sphaeroides

<400> SEQUENCE: 128

Met Lys Phe Phe Val Asp Ser Ala Asp Val Ala Ala Ile Ala Glu Leu
1               5                   10                  15

Asn Ala Leu Gly Met Val Asp Gly Val Thr Thr Asn Pro Ser Leu Ile
            20                  25                  30

Leu Lys Ser Gly Arg Asn Ile Leu Glu Val Thr Arg Glu Ile Cys Asp
        35                  40                  45

Leu Val Ala Gly Pro Val Ser Ala Glu Val Val Ala Ala Lys Ala Asp
    50                  55                  60

Asp Met Ile Glu Glu Gly Arg Lys Leu Ala Glu Ile Ala Pro Asn Ile
65                  70                  75                  80

Thr Val Lys Val Pro Leu Thr Trp Asp Gly Leu Lys Ala Cys Lys Val
                85                  90                  95

```
Leu Thr Asp Glu Gly Arg Met Val Asn Val Thr Leu Cys Phe Ser Val
                100                 105                 110

Asn Gln Ala Leu Leu Ala Ala Lys Ala Gly Ala Thr Phe Ile Ser Pro
            115                 120                 125

Phe Ile Gly Arg Leu Asp Asp Ile Asn Leu Asp Gly Leu Glu Leu Ile
        130                 135                 140

Ala Asp Ile Arg Gln Val Tyr Asp Asn Tyr Asp Phe Gln Thr Glu Val
145                 150                 155                 160

Leu Ala Ala Ser Ile Arg Thr Pro Asn His Val Ala Gln Cys Ala Arg
                165                 170                 175

Ile Gly Ala Asp Val Ile Thr Ala Pro Pro Ala Val Ile Lys Gly Leu
            180                 185                 190

Ala Asn His Val Leu Thr Asp Lys Gly Leu Glu Met Phe Asp Ala Asp
        195                 200                 205

Trp Ala Lys Thr Gly Gln Thr Ile Leu Ser Leu
        210                 215

<210> SEQ ID NO 129
<211> LENGTH: 660
<212> TYPE: DNA
<213> ORGANISM: Rhodobacter sphaeroides

<400> SEQUENCE: 129
atgaaattct tcgtcgactc cgccgacgtc gcggcgattg ccgaactcaa tgccctcggc      60
atggtggacg gtgtcacgac gaacccgtcg ctgatcctga agtcggggcg caacatcctc     120
gaggtgacgc gcgagatctg tgacctcgtc gcgggcccgg tctcggccga ggtcgtggcc     180
gccaaggcgg acgacatgat cgaggaaggc cgcaagctgg ccgagatcgc gccgaacatc     240
accgtcaagg tgccgctgac ctgggacggg ctgaaggcct gcaaggtgct gacggacgaa     300
ggccgcatgg tcaatgtgac gctctgcttc tcggtcaacc aggcgctgct ggccgccaag     360
gcgggcgcga ccttcatctc gcccttcatc gggcggctgg acgatatcaa cctcgacggg     420
ctcgagctga tcgccgacat ccgtcaggtc tatgacaact acgacttcca gaccgaggtg     480
ctggccgcct cgatccgcac gccgaaccat gtcgcgcaat gcgcccgcat cggcgccgac     540
gtgatcaccg cgccgcccgc ggtcatcaag ggcctcgcca accatgtcct gaccgacaag     600
ggtctcgaga tgttcgacgc cgactgggcc aagaccgggc agaccatcct gtccctgtga     660

<210> SEQ ID NO 130
<211> LENGTH: 663
<212> TYPE: PRT
<213> ORGANISM: Escherichia coli

<400> SEQUENCE: 130

Met Ser Ser Arg Lys Glu Leu Ala Asn Ala Ile Arg Ala Leu Ser Met
1               5                   10                  15

Asp Ala Val Gln Lys Ala Lys Ser Gly His Pro Gly Ala Pro Met Gly
            20                  25                  30

Met Ala Asp Ile Ala Glu Val Leu Trp Arg Asp Phe Leu Lys His Asn
        35                  40                  45

Pro Gln Asn Pro Ser Trp Ala Asp Arg Asp Arg Phe Val Leu Ser Asn
    50                  55                  60

Gly His Gly Ser Met Leu Ile Tyr Ser Leu Leu His Leu Thr Gly Tyr
65                  70                  75                  80

Asp Leu Pro Met Glu Glu Leu Lys Asn Phe Arg Gln Leu His Ser Lys
                85                  90                  95
```

-continued

```
Thr Pro Gly His Pro Glu Val Gly Tyr Thr Ala Gly Val Glu Thr Thr
            100                 105                 110
Thr Gly Pro Leu Gly Gln Gly Ile Ala Asn Ala Val Gly Met Ala Ile
        115                 120                 125
Ala Glu Lys Thr Leu Ala Ala Gln Phe Asn Arg Pro Gly His Asp Ile
130                 135                 140
Val Asp His Tyr Thr Tyr Ala Phe Met Gly Asp Gly Cys Met Met Glu
145                 150                 155                 160
Gly Ile Ser His Glu Val Cys Ser Leu Ala Gly Thr Leu Lys Leu Gly
                165                 170                 175
Lys Leu Ile Ala Phe Tyr Asp Asp Asn Gly Ile Ser Ile Asp Gly His
            180                 185                 190
Val Glu Gly Trp Phe Thr Asp Asp Thr Ala Met Arg Phe Glu Ala Tyr
        195                 200                 205
Gly Trp His Val Ile Arg Asp Ile Asp Gly His Asp Ala Ala Ser Ile
    210                 215                 220
Lys Arg Ala Val Glu Glu Ala Arg Ala Val Thr Asp Lys Pro Ser Leu
225                 230                 235                 240
Leu Met Cys Lys Thr Ile Ile Gly Phe Gly Ser Pro Asn Lys Ala Gly
                245                 250                 255
Thr His Asp Ser His Gly Ala Pro Leu Gly Asp Ala Glu Ile Ala Leu
            260                 265                 270
Thr Arg Glu Gln Leu Gly Trp Lys Tyr Ala Pro Phe Glu Ile Pro Ser
        275                 280                 285
Glu Ile Tyr Ala Gln Trp Asp Ala Lys Glu Ala Gly Gln Ala Lys Glu
    290                 295                 300
Ser Ala Trp Asn Glu Lys Phe Ala Ala Tyr Ala Lys Ala Tyr Pro Gln
305                 310                 315                 320
Glu Ala Ala Glu Phe Thr Arg Arg Met Lys Gly Glu Met Pro Ser Asp
                325                 330                 335
Phe Asp Ala Lys Ala Lys Glu Phe Ile Ala Lys Leu Gln Ala Asn Pro
            340                 345                 350
Ala Lys Ile Ala Ser Arg Lys Ala Ser Gln Asn Ala Ile Glu Ala Phe
        355                 360                 365
Gly Pro Leu Leu Pro Glu Phe Leu Gly Gly Ser Ala Asp Leu Ala Pro
    370                 375                 380
Ser Asn Leu Thr Leu Trp Ser Gly Ser Lys Ala Ile Asn Glu Asp Ala
385                 390                 395                 400
Ala Gly Asn Tyr Ile His Tyr Gly Val Arg Glu Phe Gly Met Thr Ala
                405                 410                 415
Ile Ala Asn Gly Ile Ser Leu His Gly Gly Phe Leu Pro Tyr Thr Ser
            420                 425                 430
Thr Phe Leu Met Phe Val Glu Tyr Ala Arg Asn Ala Val Arg Met Ala
        435                 440                 445
Ala Leu Met Lys Gln Arg Gln Val Met Val Tyr Thr His Asp Ser Ile
    450                 455                 460
Gly Leu Gly Glu Asp Gly Pro Thr His Gln Pro Val Glu Gln Val Ala
465                 470                 475                 480
Ser Leu Arg Val Thr Pro Asn Met Ser Thr Trp Arg Pro Cys Asp Gln
                485                 490                 495
Val Glu Ser Ala Val Ala Trp Lys Tyr Gly Val Glu Arg Gln Asp Gly
            500                 505                 510
Pro Thr Ala Leu Ile Leu Ser Arg Gln Asn Leu Ala Gln Gln Glu Arg
        515                 520                 525
```

```
Thr Glu Glu Gln Leu Ala Asn Ile Ala Arg Gly Gly Tyr Val Leu Lys
        530                 535                 540

Asp Cys Ala Gly Gln Pro Glu Leu Ile Phe Ile Ala Thr Gly Ser Glu
545                 550                 555                 560

Val Glu Leu Ala Val Ala Ala Tyr Glu Lys Leu Thr Ala Glu Gly Val
                565                 570                 575

Lys Ala Arg Val Val Ser Met Pro Ser Thr Asp Ala Phe Asp Lys Gln
        580                 585                 590

Asp Ala Ala Tyr Arg Glu Ser Val Leu Pro Lys Ala Val Thr Ala Arg
            595                 600                 605

Val Ala Val Glu Ala Gly Ile Ala Asp Tyr Trp Tyr Lys Tyr Val Gly
        610                 615                 620

Leu Asn Gly Ala Ile Val Gly Met Thr Thr Phe Gly Glu Ser Ala Pro
625                 630                 635                 640

Ala Glu Leu Leu Phe Glu Glu Phe Gly Phe Thr Val Asp Asn Val Val
                645                 650                 655

Ala Lys Ala Lys Glu Leu Leu
        660
```

<210> SEQ ID NO 131
<211> LENGTH: 1992
<212> TYPE: DNA
<213> ORGANISM: Escherichia coli

<400> SEQUENCE: 131

| | | | | | |
|---|---|---|---|---|---|
| atgtcctcac | gtaaagagct | tgccaatgct | attcgtgcgc | tgagcatgga | cgcagtacag | 60 |
| aaagccaaat | ccggtcaccc | gggtgcccct | atgggtatgg | ctgacattgc | cgaagtcctg | 120 |
| tggcgtgatt | tcctgaaaca | caacccgcag | aatccgtcct | gggctgaccg | tgaccgcttc | 180 |
| gtgctgtcca | cggccacgg | ctccatgctg | atctacagcc | tgctgcacct | caccggttac | 240 |
| gatctgccga | tggaagaact | gaaaaacttc | cgtcagctgc | actctaaaac | tccgggtcac | 300 |
| ccggaagtgg | gttacaccgc | tggtgtggaa | accaccaccg | gtccgctggg | tcagggtatt | 360 |
| gccaacgcag | tcggtatggc | gattgcagaa | aaaacgctgg | cggcgcagtt | aaccgtccg | 420 |
| ggccacgaca | ttgtcgacca | ctacacctac | gccttcatgg | gcgacggctg | catgatggaa | 480 |
| ggcatctccc | acgaagtttg | ctctctggcg | gtacgctga | gctgggtaa | actgattgca | 540 |
| ttctacgatg | acaacggtat | ttctatcgat | ggtcacgttg | aaggctggtt | caccgacgac | 600 |
| accgcaatgc | gtttcgaagc | ttacggctgg | cacgttattc | gcgacatcga | cggtcatgac | 660 |
| gcggcatcta | tcaaacgcgc | agtagaagaa | gcgcgcgcag | tgactgacaa | accttccctg | 720 |
| ctgatgtgca | aaaccatcat | cggtttcggt | tccccgaaca | aagccggtac | ccacgactcc | 780 |
| cacggtgcgc | cgctgggcga | cgctgaaatt | gccctgaccc | gcaacaact | gggctggaaa | 840 |
| tatgcgccgt | tcgaaatccc | gtctgaaatc | tatgctcagt | gggatgcgaa | agaagcaggc | 900 |
| caggcgaaag | aatccgcatg | gaacgagaaa | ttcgctgctt | acgcgaaagc | ttatccgcag | 960 |
| gaagccgctg | aatttacccg | ccgtatgaaa | ggcgaaatgc | cgtctgactt | cgacgctaaa | 1020 |
| gcgaaagagt | tcatcgctaa | actgcaggct | aatccggcga | aaatcgccag | ccgtaaagcg | 1080 |
| tctcagaatg | ctatcgaagc | gttcggtccg | ctgttgccgg | aattcctcgg | cggttctgct | 1140 |
| gacctggcgc | cgtctaacct | gaccctgtgg | tctggttcta | aagcaatcaa | cgaagatgct | 1200 |
| gcgggtaact | acatccacta | cggtgttcgc | gagttcggta | tgaccgcgat | tgctaacggt | 1260 |
| atctccctgc | acggtggctt | cctgccgtac | acctccacct | tcctgatgtt | cgtggaatac | 1320 |

-continued

```
gcacgtaacg ccgtacgtat ggctgcgctg atgaaacagc gtcaggtgat ggtttacacc    1380
cacgactcca tcggtctggg cgaagacggc ccgactcacc agccggttga gcaggtcgct    1440
tctctgcgcg taaccccgaa catgtctaca tggcgtccgt gtgaccaggt tgaatccgcg    1500
gtcgcgtgga atacggtgt tgagcgtcag gacggcccga ccgcactgat cctctcccgt    1560
cagaacctgg cgcagcagga acgaactgaa gagcaactgg caaacatcgc gcgcggtggt    1620
tatgtgctga agactgcgc cggtcagccg gaactgattt tcatcgctac cggttcagaa    1680
gttgaactgg ctgttgctgc ctacgaaaaa ctgactgccg aaggcgtgaa agcgcgcgtg    1740
gtgtccatgc cgtctaccga cgcatttgac aagcaggatg ctgcttaccg tgaatccgta    1800
ctgccgaaag cggttactgc acgcgttgct gtagaagcgg gtattgctga ctactggtac    1860
aagtatgttg gcctgaacgg tgctatcgtc ggtatgacca ccttcggtga atctgctccg    1920
gcagagctgc tgtttgaaga gttcggcttc actgttgata cgttgttgc gaaagcaaaa    1980 gaactgctgt aa                                                        1992
```

<210> SEQ ID NO 132
<211> LENGTH: 665
<212> TYPE: PRT
<213> ORGANISM: Pseudomonas putida

<400> SEQUENCE: 132

```
Met Pro Ser Arg Arg Glu Arg Ala Asn Ala Ile Arg Ala Leu Ser Met
1               5                   10                  15

Asp Ala Val Gln Lys Ala Asn Ser Gly His Pro Gly Ala Pro Met Gly
            20                  25                  30

Met Ala Asp Ile Ala Glu Val Leu Trp Arg Asp Tyr Leu Lys His Asn
        35                  40                  45

Pro Ser Asn Pro Ser Phe Ala Asp Arg Asp Arg Phe Val Leu Ser Asn
    50                  55                  60

Gly His Gly Ser Met Leu Ile Tyr Ser Leu Leu His Leu Thr Gly Tyr
65                  70                  75                  80

Asp Val Thr Ile Asp Asp Leu Lys Ser Phe Arg Gln Leu His Ser Arg
                85                  90                  95

Thr Pro Gly His Pro Glu Phe Gly Tyr Thr Pro Gly Val Glu Thr Thr
            100                 105                 110

Thr Gly Pro Leu Gly Gln Gly Leu Ala Asn Ala Val Gly Phe Ala Leu
        115                 120                 125

Ala Glu Lys Val Leu Gly Ala Gln Phe Asn Arg Glu Gly His Asn Ile
    130                 135                 140

Val Asp His Asn Thr Tyr Val Phe Leu Gly Asp Gly Cys Met Met Glu
145                 150                 155                 160

Gly Ile Ser His Glu Val Ala Ser Leu Ala Gly Thr Leu Gly Leu Asn
                165                 170                 175

Lys Leu Val Ala Phe Tyr Asp Asp Asn Gly Ile Ser Ile Asp Gly Glu
            180                 185                 190

Val Glu Gly Trp Phe Thr Asp Thr Pro Lys Arg Phe Glu Ala Tyr
        195                 200                 205

Asn Trp Leu Val Ile Arg Asn Val Asn Gly His Asp Ala Asp Glu Ile
    210                 215                 220

Arg Thr Ala Ile Glu Thr Ala Arg Lys Ser Asp Arg Pro Thr Leu Ile
225                 230                 235                 240

Cys Cys Lys Thr Ile Ile Gly Phe Gly Ser Pro Asn Lys Gln Gly Lys
                245                 250                 255
```

```
Glu Asp Cys His Gly Ala Pro Leu Gly Asn Asp Glu Ile Ala Leu Ala
                260                 265                 270

Arg Lys Glu Leu Asn Trp Asn His Ala Pro Phe Glu Val Pro Ala Asp
            275                 280                 285

Ile Tyr Ala Glu Trp Asn Ala Lys Glu Ala Gly Ala Lys Ala Glu Ala
        290                 295                 300

Glu Trp Asn Thr Arg Phe Glu Ala Tyr Ala Ala Phe Pro Glu Leu
305                 310                 315                 320

Ala Ser Glu Leu Lys Arg Arg Leu Ser Gly Asp Leu Pro Ala Asp Phe
                325                 330                 335

Ser Glu Lys Ala Ala Ala Tyr Ile Ala Glu Val Ala Ala Lys Gly Glu
            340                 345                 350

Thr Ile Ala Ser Arg Lys Ala Ser Gln Asn Thr Leu Asn Ala Phe Gly
        355                 360                 365

Pro Leu Leu Pro Glu Phe Leu Gly Gly Ser Ala Asp Leu Ala Gly Ser
    370                 375                 380

Asn Leu Thr Leu Trp Lys Gly Cys Lys Gly Val Asp Ala Asn Asp Ala
385                 390                 395                 400

Ser Gly Asn Tyr Val Phe Tyr Gly Val Arg Glu Phe Gly Met Thr Ala
                405                 410                 415

Ile Met Asn Gly Val Ala Leu His Gly Gly Leu Val Pro Tyr Gly Ala
            420                 425                 430

Thr Phe Leu Met Phe Met Glu Tyr Ala Arg Asn Ala Val Arg Met Ser
        435                 440                 445

Ala Leu Met Lys Gln Arg Val Ile His Val Tyr Thr His Asp Ser Ile
    450                 455                 460

Gly Leu Gly Glu Asp Gly Pro Thr His Gln Pro Ile Glu Gln Leu Thr
465                 470                 475                 480

Ser Leu Arg Ser Thr Pro Asn Leu Asp Thr Trp Arg Pro Ala Asp Ala
                485                 490                 495

Val Glu Ser Ala Val Ser Trp Lys His Ala Leu Glu Arg Lys Asp Gly
            500                 505                 510

Pro Ser Ala Leu Ile Phe Ser Arg Gln Asn Leu Gln His Gln Asp Arg
        515                 520                 525

Asp Ala Gln Gln Ile Ala Asp Ile Ala Arg Gly Gly Tyr Val Leu Lys
    530                 535                 540

Asp Cys Ala Gly Glu Pro Glu Leu Ile Leu Ile Ala Thr Gly Ser Glu
545                 550                 555                 560

Val Gly Leu Ala Val Gln Ala Phe Asp Lys Leu Thr Glu Gln Gly Arg
                565                 570                 575

Lys Val Arg Val Val Ser Met Pro Ser Thr Ser Val Phe Asp Ala Gln
            580                 585                 590

Asp Ala Ala Tyr Lys Gln Ser Val Leu Pro Leu Gln Val Gly Ala Arg
        595                 600                 605

Ile Ala Ile Glu Ala Ala His Ala Asp Phe Trp Tyr Lys Tyr Val Gly
    610                 615                 620

Leu Glu Gly Arg Val Ile Gly Met Thr Thr Tyr Gly Glu Ser Ala Pro
625                 630                 635                 640

Ala Ser Ala Leu Phe Glu Glu Phe Gly Phe Thr Leu Glu Asn Ile Leu
                645                 650                 655

Gly Thr Ala Glu Glu Leu Leu Glu Asp
            660                 665

<210> SEQ ID NO 133
```

<211> LENGTH: 1998
<212> TYPE: DNA
<213> ORGANISM: Pseudomonas putida

<400> SEQUENCE: 133

| | | | | | |
|---|---|---|---|---|---|
| atgcccagcc | gtcgtgaacg | tgccaacgcc | attcgtgcac | tcagcatgga | tgccgtgcaa | 60 |
| aaggccaaca | gcggccaccc | aggtgccccc | atgggcatgg | cggatatcgc | cgaagtgctt | 120 |
| tggcgcgact | atctgaagca | caacccgagc | aacccgagct | cgccgaccg | tgaccgcttc | 180 |
| gtgctgtcca | acggccacgg | ctcgatgctg | atctactcgc | tgctgcacct | gaccggctac | 240 |
| gacgtcacca | tcgacgacct | caagtcgttc | cgccagttgc | atagccgtac | cccgggccac | 300 |
| cccgagttcg | gctacacccc | aggtgtggaa | accaccaccg | gcccgctggg | ccaaggtttg | 360 |
| gccaacgccg | tgggctttgc | tttggctgag | aaagtgctgg | gtgcccagtt | caaccgcgaa | 420 |
| ggccacaata | tcgtcgacca | caacacttac | gtgttcctcg | gcgacggctg | catgatggaa | 480 |
| ggtatctccc | acgaagtcgc | ctcgctggcc | ggcaccctgg | gcctgaacaa | gctggttgcc | 540 |
| ttctatgacg | acaacggcat | ctccatcgac | ggtgaagtgg | aaggctggtt | caccgacgac | 600 |
| acgcccaagc | gtttcgaggc | ctacaactgg | ctggtgatcc | gcaacgtcaa | cggccacgac | 660 |
| gccgacgaga | tccgcacggc | catcgagact | gcgcgcaaga | gcgaccgtcc | gaccctgatc | 720 |
| tgctgcaaga | ccatcatcgg | tttcggctcg | cccaacaagc | agggcaagga | agactgccac | 780 |
| ggtgctccac | tgggcaacga | cgaaatcgcc | ctggcccgca | aggagctgaa | ctggaaccac | 840 |
| gctccgttcg | aagttcctgc | cgacatctac | gccgaatgga | atgccaaaga | agcaggcgcc | 900 |
| aaggctgaag | ccgagtggaa | cacgcgtttc | gaggcctatg | ccgccgcctt | cccggaactg | 960 |
| gccagcgagc | tcaagcgccg | tctgagcggt | gacctgccgg | ccgacttctc | ggaaaaagcc | 1020 |
| gctgcctaca | tcgctgaagt | cgctgccaag | ggcgagacca | tcgccagccg | caaggccagc | 1080 |
| cagaacaccc | tgaacgcctt | cggcccactg | ctgccggaat | tccttggcgg | ctcggccgac | 1140 |
| ctggccggct | ccaacctgac | cctgtggaag | ggttgcaagg | gtgtggacgc | caacgacgcc | 1200 |
| agcggcaact | acgtgttcta | cggcgtgcgc | gagttcggca | tgaccgcgat | catgaacggc | 1260 |
| gtcgccctgc | acgcggcct | ggtgccttac | ggcgcgacgt | tcctgatgtt | catggaatac | 1320 |
| gcccgtaacg | ccgtgcgcat | gtccgcccct | atgaagcagc | gcgtcatcca | tgtgtacacc | 1380 |
| cacgactcca | tcggcctggg | cgaagacggc | ccgacccacc | agccgatcga | gcaactgacc | 1440 |
| agcctgcgca | gcacgccgaa | cctggacacc | tggcgcccgg | ccgacgcagt | cgagtcggct | 1500 |
| gtgtcctgga | agcacgccct | ggagcgcaag | acggcccctt | cggcgctgat | cttctcgcgt | 1560 |
| cagaacctgc | agcatcagga | ccgcgacgcc | cagcagatcg | ccgatatcgc | ccgcggcggt | 1620 |
| tacgtgctca | aggactgtgc | cggcgagcct | gagttgatcc | tgatcgccac | cggctcggaa | 1680 |
| gtgggcctgg | ccgttcaggc | gttcgacaag | ctgaccgagc | agggccgcaa | ggtgcgtgtc | 1740 |
| gtgtcgatgc | cgagcaccag | cgtgtttgac | gcccaggatg | cggcctacaa | gcagtccgta | 1800 |
| ctgccgctgc | aagtgggtgc | ccgcatcgcc | atcgaagcgg | ctcatgccga | cttctggtac | 1860 |
| aagtacgtgg | gtctcgaagg | ccgtgtcatc | ggcatgacca | cttacggtga | atcggctccg | 1920 |
| gccagtgcac | tgttcgagga | gttcggcttc | accctggaga | acatcctggg | tactgccgaa | 1980 |
| gagctgctgg | aagactga | | | | | 1998 |

<210> SEQ ID NO 134
<211> LENGTH: 657
<212> TYPE: PRT
<213> ORGANISM: Rhizobium leguminosarum

<400> SEQUENCE: 134

| | | | | | | | | | | | | | | |
|---|---|---|---|---|---|---|---|---|---|---|---|---|---|---|
| Met | Thr | Ser | Pro | Glu | Gln | His | Asp | Arg | Met | Ala | Asn | Ala | Ile | Arg | Phe |
| 1 | | | | 5 | | | | | 10 | | | | | 15 | |

| Leu | Ala | Met | Asp | Ala | Val | Glu | Lys | Ala | Asn | Ser | Gly | His | Pro | Gly | Met |
| | | | 20 | | | | | 25 | | | | | 30 | | |

| Pro | Met | Gly | Met | Ala | Asp | Val | Ala | Thr | Val | Leu | Phe | Thr | Lys | Tyr | Leu |
| | | | 35 | | | | | 40 | | | | | 45 | | |

| Lys | Phe | Asp | Pro | Lys | Lys | Pro | His | Trp | Pro | Asn | Arg | Asp | Arg | Phe | Val |
| | 50 | | | | | 55 | | | | | 60 | | | | |

| Leu | Ser | Ala | Gly | His | Gly | Ser | Met | Leu | Leu | Tyr | Ser | Leu | Leu | Tyr | Leu |
| 65 | | | | | 70 | | | | | 75 | | | | | 80 |

| Thr | Gly | Tyr | Pro | Asp | Met | Thr | Val | Glu | Asp | Leu | Lys | Gln | Phe | Arg | Gln |
| | | | | 85 | | | | | 90 | | | | | 95 | |

| Leu | Gly | Ser | Lys | Thr | Ala | Gly | His | Pro | Glu | Tyr | Gly | His | Ala | Thr | Gly |
| | | | | 100 | | | | | 105 | | | | | 110 | |

| Ile | Glu | Thr | Thr | Thr | Gly | Pro | Leu | Gly | Gln | Gly | Ile | Ala | Asn | Ser | Val |
| | | | | 115 | | | | | 120 | | | | | 125 | |

| Gly | Met | Ala | Ile | Ala | Glu | Arg | Lys | Leu | Arg | Glu | Glu | Phe | Gly | Ala | Asp |
| | 130 | | | | | 135 | | | | | 140 | | | | |

| Leu | Gln | Asp | His | Phe | Thr | Tyr | Ala | Ile | Cys | Gly | Asp | Gly | Cys | Leu | Met |
| 145 | | | | | 150 | | | | | 155 | | | | | 160 |

| Glu | Gly | Ile | Ser | His | Glu | Ala | Ile | Ala | Leu | Ala | Gly | His | Leu | Lys | Leu |
| | | | | 165 | | | | | 170 | | | | | 175 | |

| Asn | Lys | Leu | Val | Leu | Phe | Trp | Asp | Asn | Asn | Ser | Ile | Thr | Ile | Asp | Gly |
| | | | 180 | | | | | 185 | | | | | 190 | | |

| Ala | Val | Ser | Leu | Ser | Asp | Ser | Thr | Asp | Gln | Ile | Ala | Arg | Phe | Lys | Ala |
| | | | 195 | | | | | 200 | | | | | 205 | | |

| Val | His | Trp | Asn | Thr | Ile | Glu | Ile | Asp | Gly | His | Asp | Gln | Ala | Ala | Ile |
| | 210 | | | | | 215 | | | | | 220 | | | | |

| Ala | Ala | Ala | Ile | Asp | Ala | Ala | His | Lys | Ser | Asp | Arg | Pro | Thr | Phe | Ile |
| 225 | | | | | 230 | | | | | 235 | | | | | 240 |

| Ala | Cys | Lys | Thr | Ile | Ile | Gly | Phe | Gly | Ala | Pro | Asn | Lys | Gln | Gly | Thr |
| | | | | 245 | | | | | 250 | | | | | 255 | |

| His | Lys | Val | His | Gly | Asn | Pro | Leu | Gly | Ala | Glu | Glu | Ile | Ala | Ala | Thr |
| | | | | 260 | | | | | 265 | | | | | 270 | |

| Arg | Lys | Ala | Leu | Asn | Trp | Glu | Ser | Glu | Pro | Phe | Val | Ile | Pro | Ser | Asp |
| | | | 275 | | | | | 280 | | | | | 285 | | |

| Val | Leu | Asp | Ser | Trp | Arg | Ala | Ala | Gly | Ala | Arg | Ser | Val | Asp | Leu | Val |
| | 290 | | | | | 295 | | | | | 300 | | | | |

| Asn | Ala | Trp | Glu | Gln | Gly | Leu | Ala | Lys | Ala | Pro | Ala | Lys | Ala | Glu | Phe |
| 305 | | | | | 310 | | | | | 315 | | | | | 320 |

| Thr | Arg | Arg | Met | Ala | Gly | Glu | Leu | Pro | Glu | Gly | Phe | Asp | Ala | Ala | Ile |
| | | | | 325 | | | | | 330 | | | | | 335 | |

| Ser | Ala | Tyr | Lys | Lys | Lys | Leu | Ala | Glu | Thr | Lys | Pro | Thr | Val | Ala | Thr |
| | | | | 340 | | | | | 345 | | | | | 350 | |

| Arg | Lys | Ala | Ser | Glu | Asp | Ala | Leu | Glu | Val | Ile | Asn | Gly | Phe | Leu | Pro |
| | | | 355 | | | | | 360 | | | | | 365 | | |

| Glu | Thr | Leu | Gly | Gly | Ser | Ala | Asp | Leu | Thr | Pro | Ser | Asn | Asn | Thr | Lys |
| | 370 | | | | | 375 | | | | | 380 | | | | |

| Thr | Ser | Gln | Met | His | Ser | Ile | Thr | Pro | Thr | Asp | Phe | Ala | Gly | Arg | Tyr |
| 385 | | | | | 390 | | | | | 395 | | | | | 400 |

| Met | His | Trp | Gly | Ile | Arg | Glu | His | Gly | Met | Ala | Ser | Ala | Met | Asn | Gly |
| | | | | 405 | | | | | 410 | | | | | 415 | |

```
Ile Ala Leu His Gly Gly Leu Ile Pro Tyr Ser Gly Gly Phe Leu Ile
            420                 425                 430

Phe Ser Asp Tyr Cys Arg Pro Pro Ile Arg Leu Ala Ala Leu Met Gly
        435                 440                 445

Ile Arg Val Ile His Val Leu Thr His Asp Ser Ile Gly Val Gly Glu
450                 455                 460

Asp Gly Pro Thr His Gln Pro Val Glu Gln Leu Ala Gly Leu Arg Ala
465                 470                 475                 480

Ile Pro Asn Leu Met Val Phe Arg Pro Ala Asp Ala Thr Glu Thr Ala
                485                 490                 495

Glu Cys Trp Gln Ile Ala Val Lys Thr His Asn Arg Pro Ser Gly Leu
            500                 505                 510

Ala Leu Thr Arg Gln Asn Leu Thr Ala Ser Arg Thr Glu Tyr Ser Glu
        515                 520                 525

Lys Asn Leu Cys Glu Gln Gly Ala Tyr Thr Leu Ala Gly Asn Ala Asp
530                 535                 540

Ala Lys Val Thr Ile Phe Ala Ser Gly Ser Glu Val Glu Ile Ala Val
545                 550                 555                 560

Ala Ala Arg Ala Ala Leu Glu Ala Lys Gly Val Thr Val Arg Val Val
                565                 570                 575

Ser Val Pro Cys Thr Glu Leu Phe Phe Glu Gln Pro Asp Ala Tyr Arg
            580                 585                 590

Lys Glu Ile Leu Gly Asn Ser Pro Val Lys Ile Ala Val Glu Ala Ala
        595                 600                 605

Val Arg Glu Gly Trp Asp Ala Phe Ile Gly Pro Glu Gly Thr Phe Ile
610                 615                 620

Gly Met Lys Gly Phe Gly Ala Ser Gly Pro Val Lys Asp Val Tyr Lys
625                 630                 635                 640

His Phe Gly Ile Thr Ala Asp Ala Val Val Ala Ala Glu Ala Lys
                645                 650                 655

Leu
```

<210> SEQ ID NO 135
<211> LENGTH: 1974
<212> TYPE: DNA
<213> ORGANISM: Rhizobium leguminosarum

<400> SEQUENCE: 135

```
atgacctctc ccgaacaaca tgaccggatg gcgaatgcga tccgtttttct cgccatggac      60
gccgtcgaaa aggcgaactc cggccacccg ggcatgccga tgggcatggc cgatgtggca     120
acggtcctgt tcaccaaata tctgaagttc gatccgaaga agccgcattg gccgaaccgc     180
gatcgcttcg tgctctcggc cggccatggc tcgatgctgc tttattcgct gctgtatttg     240
accggctatc ccgacatgac ggtcgaggat ctaaagcagt tccgccagct cggctcgaag     300
accgccggcc atcctgaata tggtcacgcc accggcatcg aaacgaccac cggcccgctc     360
ggccagggca ttgccaattc cgtcggcatg gcgattgccg aacgcaagct gcgcgaggag     420
ttcggcgccg atcttcagga tcactttacc tatgcgatct gcggcgacgg ctgcctgatg     480
gagggtatca gccacgaagc catagcgctc gccggccacc tgaagctcaa caagctcgtt     540
ctgttctggg ataacaactc gatcaccatc gacggcgcc tatctctgtc ggattccacc     600
gatcagatcg cccgcttcaa ggccgttcac tggaacacga tcgagatcga cggtcacgac     660
caggctgcca tcgccgccgc gatcgacgct gcccacaagt ccgaccggcc gaccttcatt     720
gcctgcaaga cgatcatcgg cttcggcgcc cccaacaagc agggcaccca taaggttcac     780
```

```
ggcaacccgc tcggcgccga agaaatcgcc gccacccgca aggcgctgaa ctgggaatcc      840
gaacccttcg tcatcccgtc ggacgtcctg gacagctggc gtgcagccgg cgcccgctcc      900
gtcgatctcg tcaacgcctg gaacagggt ctggccaagg ctccggccaa ggccgaattc       960
acccgccgta tggcaggcga gttgccggaa ggcttcgatg ccgcgatcag cgcttacaag     1020
aagaagcttg ccgagaccaa gccgacggtt gccacccgca aggcttcgga agacgcgctc    1080
gaggtcatca acggcttcct gccggaaacg ctcggcggct ccgccgacct gacgccgtcg     1140
aacaacacca agaccagcca gatgcattcg atcacgccga cggatttcgc cggccggtac    1200
atgcattggg gcatccgcga gcacggcatg gcttctgcca tgaacggcat tgcgctgcat   1260
ggcggcctca ttccctatag cggcggcttc ctgatcttct cggattattg ccgcccgccg    1320
atccgcctcg ctgcgctgat gggcatccgc gtcattcacg tcctgacgca tgactcgatc    1380
ggcgtcggcg aagatggtcc gacgcaccag ccggtcgaac agctcgccgg tctgcgcgcc   1440
atcccgaacc tgatggtctt ccgtccggcc gacgccacgg aaacggcgga atgctggcag  1500
atcgccgtca agacgcacaa ccgtccttcc ggccttgcgc tgacacgcca gaacctcacc   1560
gcgtcccgca ccgaatacag cgaaaagaac ctctgcgaac agggcgccta acgctggcc    1620 ggcaatgccg acgccaaggt gacgatcttc gcctccggct cggaagtcga aatcgccgtt   1680
gccgcccgcg cagcccttga agccaagggt gtcacggtgc gcgtcgtatc ggttccctgc   1740
acggaactgt tcttcgagca gccggacgcc taccgcaagg aaatccttgg caactcgccg   1800
gtcaagatcg ccgtcgaagc cgccgtccgc gaaggctggg atgctttcat cggaccggaa  1860
ggcactttca tcggcatgaa gggcttcggc gcttccggcc cggtgaagga cgtttacaag   1920
catttcggca tcactgccga cgccgtcgtt gcggccgcgg aagcaaagct ttaa            1974
```

<210> SEQ ID NO 136
<211> LENGTH: 664
<212> TYPE: PRT
<213> ORGANISM: Klebsiella pneumoniae

<400> SEQUENCE: 136

```
Met Ser Ser Arg Lys Glu Leu Ala Asn Ala Ile Arg Ala Leu Ser Met
1               5                   10                  15

Asp Ala Val Gln Lys Ala Lys Ser Gly His Pro Gly Ala Pro Met Gly
            20                  25                  30

Met Ala Asp Ile Ala Glu Val Leu Trp Arg Asp Phe Leu Asn His Asn
        35                  40                  45

Pro Asn Asn Pro Ala Trp Ala Asp Arg Asp Arg Phe Val Leu Ser Asn
    50                  55                  60

Gly His Gly Ser Met Leu Ile Tyr Ser Leu Leu His Leu Thr Gly Tyr
65                  70                  75                  80

Asp Leu Pro Ile Glu Glu Leu Lys Asn Phe Arg Gln Leu His Ser Lys
                85                  90                  95

Thr Pro Gly His Pro Glu Val Gly Tyr Thr Ala Gly Val Glu Thr Thr
            100                 105                 110

Thr Gly Pro Leu Gly Gln Gly Ile Ala Asn Ala Val Gly Met Ala Ile
        115                 120                 125

Ala Glu Lys Thr Leu Ala Ala Gln Phe Asn Arg Pro Gly His Asp Ile
    130                 135                 140

Val Asp His Tyr Thr Tyr Ala Phe Met Gly Asp Gly Cys Met Met Glu
145                 150                 155                 160

Gly Ile Ser His Glu Val Cys Ser Leu Ala Gly Thr Leu Lys Leu Gly
```

```
                        165                 170                 175
Lys Leu Val Ala Phe Tyr Asp Asp Asn Gly Ile Ser Ile Asp Gly His
                180                 185                 190

Val Glu Gly Trp Phe Thr Asp Thr Ala Lys Arg Phe Glu Ala Tyr
                195                 200                 205

Gly Trp His Val Val Arg Gly Val Asp Gly His Asp Ala Asp Ala Ile
                210                 215                 220

Lys Arg Ala Val Glu Ala Arg Ala Val Thr Asp Lys Pro Ser Leu
225                 230                 235                 240

Leu Met Cys Lys Thr Ile Ile Gly Phe Gly Ser Pro Asn Lys Ala Gly
                245                 250                 255

Thr His Asp Ser His Gly Ala Pro Leu Gly Asp Ala Glu Ile Ala Leu
                260                 265                 270

Thr Arg Glu Ala Leu Gly Trp Lys His Ala Pro Phe Asp Ile Pro Ser
                275                 280                 285

Asp Ile Tyr Ala Gln Trp Asp Ala Lys Glu Ala Gly Gln Ala Lys Glu
                290                 295                 300

Ala Ala Trp Asn Glu Lys Phe Ala Ala Tyr Ala Lys Ala Phe Pro Gln
305                 310                 315                 320

Glu Ala Ala Glu Phe Thr Arg Arg Met Lys Gly Met Pro Ser Asp
                325                 330                 335

Phe Asp Ala Lys Ala Asn Glu Phe Ile Ala Lys Leu Gln Ala Asn Pro
                340                 345                 350

Ala Lys Ile Ala Ser Arg Lys Ala Ser Gln Asn Ala Ile Glu Ala Phe
                355                 360                 365

Gly Pro Leu Leu Pro Glu Phe Leu Gly Gly Ser Ala Asp Leu Ala Pro
                370                 375                 380

Ser Asn Leu Thr Leu Trp Ser Gly Ser Lys Pro Ile Asn Glu Asp Ala
385                 390                 395                 400

Ala Gly Asn Tyr Ile His Tyr Gly Val Arg Glu Phe Gly Met Thr Ala
                405                 410                 415

Ile Ala Asn Gly Ile Ala Leu His Gly Gly Phe Leu Pro Tyr Thr Ser
                420                 425                 430

Thr Phe Leu Met Phe Val Glu Tyr Ala Arg Asn Ala Val Arg Met Ala
                435                 440                 445

Ala Leu Met Lys Gln Arg Gln Val Met Val Tyr Thr His Asp Ser Ile
                450                 455                 460

Gly Leu Gly Glu Asp Gly Pro Thr His Gln Pro Val Glu Gln Val Ala
465                 470                 475                 480

Ser Leu Arg Val Thr Pro Asn Met Ser Thr Trp Arg Pro Cys Asp Gln
                485                 490                 495

Val Glu Ser Ala Ile Ala Trp Lys Tyr Gly Val Glu Arg Gln Asp Gly
                500                 505                 510

Pro Thr Ala Leu Ile Leu Ser Arg Gln Asn Leu Ala Gln Gln Glu Arg
                515                 520                 525

Thr Ala Glu Gln Leu Ala Asn Val Ala Arg Gly Gly Tyr Val Leu Lys
                530                 535                 540

Glu Cys Thr Gly Ser Gln Pro Glu Leu Ile Phe Ile Ala Thr Gly Ser
545                 550                 555                 560

Glu Val Glu Leu Ala Val Ala Ala Trp Asp Lys Leu Thr Ala Glu Gly
                565                 570                 575

Val Lys Ala Arg Val Val Ser Met Pro Ser Thr Asp Ala Phe Asp Lys
                580                 585                 590
```

```
      Gln Asp Ala Ala Tyr Arg Glu Ser Val Leu Pro Lys Ala Val Thr Ala
                  595                 600                 605

Arg Val Ala Val Glu Ala Gly Ile Ala Asp Tyr Trp Phe Lys Tyr Val
                  610                 615                 620

Gly Leu Asn Gly Ala Ile Val Gly Met Thr Thr Phe Gly Glu Ser Ala
      625                 630                 635                 640

Pro Ala Glu Gln Leu Phe Glu Glu Phe Gly Phe Thr Val Asp Asn Val
                          645                 650                 655

Val Ala Lys Ala Lys Ala Leu Leu
                  660

<210> SEQ ID NO 137
<211> LENGTH: 1995
<212> TYPE: DNA
<213> ORGANISM: Klebsiella pneumoniae

<400> SEQUENCE: 137
atgtcctcac gtaaagagct tgctaacgct attcgtgcgc tgagcatgga cgctgtacag      60
aaagccaaat ccggccaccc gggggccccg atgggtatgg ctgacattgc gaagtgctg     120 tggcgtgatt tcctgaacca taccccgaac atccggcct gggctgaccg tgaccgtttt     180
gtgttgtcaa atggccatgg ttcgatgctg atttacagcc tgctgcacct cactggctac     240
gatctgccga ttgaagagct gaaaaacttc cgccagctgc actccaaaac cccgggtcac     300
ccggaagtcg gctacaccgc aggcgtggaa accaccaccg tccgctgggg ccagggtatc     360
gctaacgcgg tcgggatggc tatcgccgag aaaaccctgg cggcgcagtt caaccgtccg     420
ggacacgata tcgtcgacca ctacacctac gccttcatgg gcgacggctg catgatggaa     480
ggcatttctc acgaagtgtg ctccctggcc ggtaccctga actgggtaa actggtggcg     540 ttctatgatg acaacggcat ctccatcgac ggccacgttg aaggctggtt caccgacgac     600
accgccaaac gctttgaagc ctacggctgg acgtggtgc gcggcgtgga cggtcacgac     660
gctgacgcca tcaaacgcgc ggtagaagaa gcgcgggcgg tcaccgacaa accgtccctg     720
ctgatgtgta aaaccatcat cggtttcggt tcgccgaaca agccggtac ccacgactcc     780 cacggcgcgc gcctgggcga cgccgaaatc gccctgaccc gcgaagcgct gggctggaaa     840
cacgcgccgt ttgacatccc gtctgacatc tatgcccagt gggatgccaa agaagccggc     900
caggcgaaag aagccgcatg gaacgagaag tttgcggctt acgccaaagc cttcccgcag     960
gaagcagccg aattcacccg ccgtatgaaa ggcgagatgc cgtctgactt cgacgcgaaa    1020
gctaacgagt tcatcgcgaa gctgcaggcc aacccggcga aaatcgccag ccgtaaagcc    1080
tcgcagaacg ccatcgaagc cttcggcccg ctgctgccgg aattcctcgg cggctccgca    1140
gatctcgcgc cgtccaacct gaccctgtgg tccggctcta gccgatcaa cgaagacgct    1200 gccgggaact acatccacta cggcgtgcgc gagttcggta tgaccgctat cgccaacggt    1260
atcgcgctgc acgcggcttt cctgccgtac acctccacct tcctgatgtt cgtggaatac    1320
gcgcgtaacg cggtacgtat ggccgcgctg atgaaacagc gtcaggtgat ggtctacacc    1380
cacgactcga tcggtctggg cgaagacggc ccgactcacc agccggtaga gcaggtggct    1440
tccctgcgcg tgaccccgaa catgtccacc tggcgtccgt gtgaccaggt tgaatccgcg    1500
attgcgtgga aatatggcgt ggagcgtcag gacggcccga ccgcgctgat cctctcccgt    1560
cagaacctgg cgcagcagga gcgtaccgca gagcagctgg cgaacgtggc ccgcggcggt    1620
tatgtgctga aagagtgcac cggctcgcag ccggagctga tcttcatcgc caccggttca    1680
gaagtggagc tggcggttgc cgcatgggac aaactgactg ccgaaggcgt gaaggcgcgc    1740
```

```
gtggtttcca tgccgtccac cgacgcgttc gacaagcagg atgcggctta tcgcgaatcc    1800
gtactgccga aagccgtgac cgcgcgcgtt gccgtggaag cgggtatcgc tgactactgg    1860
ttcaaatacg ttggcctgaa cggcgctatc gttggcatga ccaccttcgg tgagtctgcg    1920
ccggctgagc agctgttcga ggagttcggc ttcaccgttg ataacgtggt cgctaaagcg    1980
aaagcgctgc tgtaa                                                      1995
```

<210> SEQ ID NO 138
<211> LENGTH: 663
<212> TYPE: PRT
<213> ORGANISM: Salmonella typhimurium

<400> SEQUENCE: 138

```
Met Ser Ser Arg Lys Glu Leu Ala Asn Ala Ile Arg Ala Leu Ser Met
1               5                   10                  15

Asp Ala Val Gln Lys Ala Lys Ser Gly His Pro Gly Ala Pro Met Gly
            20                  25                  30

Met Ala Asp Ile Ala Glu Val Leu Trp Arg Asp Phe Leu Asn His Asn
        35                  40                  45

Pro Thr Asn Pro Ser Trp Ala Asp Arg Asp Arg Phe Val Leu Ser Asn
    50                  55                  60

Gly His Gly Ser Met Leu Ile Tyr Ser Leu Leu His Leu Thr Gly Tyr
65                  70                  75                  80

Asp Leu Pro Met Ser Glu Leu Gln Asn Phe Arg Gln Leu His Ser Lys
                85                  90                  95

Thr Pro Gly His Pro Glu Val Gly Tyr Thr Ala Gly Val Glu Thr Thr
            100                 105                 110

Thr Gly Pro Leu Gly Gln Gly Ile Ala Asn Ala Val Gly Met Ala Ile
        115                 120                 125

Ala Glu Lys Thr Leu Ala Ala Gln Phe Asn Arg Pro Gly His Asp Ile
    130                 135                 140

Val Asp His Phe Thr Tyr Val Phe Met Gly Asp Gly Cys Met Met Glu
145                 150                 155                 160

Gly Ile Ser His Glu Val Cys Ser Leu Ala Gly Thr Leu Lys Leu Gly
                165                 170                 175

Lys Leu Ile Ala Phe Tyr Asp Asp Asn Gly Ile Ser Ile Asp Gly His
            180                 185                 190

Val Glu Gly Trp Phe Thr Asp Asp Thr Ala Lys Arg Phe Glu Ala Tyr
        195                 200                 205

Gly Trp His Val Ile Arg Gly Ile Asp Gly His Asp Ala Asp Ala Ile
    210                 215                 220

Lys Arg Ala Thr Glu Glu Ala Arg Ala Val Thr Asp Lys Pro Ser Leu
225                 230                 235                 240

Leu Met Cys Lys Thr Ile Ile Gly Phe Gly Ser Pro Asn Lys Gln Gly
                245                 250                 255

Thr His Asp Ser His Gly Ala Pro Leu Gly Asp Ala Glu Ile Ala Leu
            260                 265                 270

Thr Arg Glu Gln Leu Gly Trp Lys Tyr Ala Pro Phe Glu Ile Pro Ser
        275                 280                 285

Glu Ile Tyr Ala Gln Trp Asp Ala Lys Glu Ala Gly Gln Ala Lys Glu
    290                 295                 300

Ser Ala Trp Asn Glu Lys Phe Ala Ala Tyr Glu Lys Ala Phe Pro Gln
305                 310                 315                 320

Glu Ala Ala Glu Phe Thr Arg Arg Met Lys Gly Asp Met Pro Ala Asp
```

325                 330                 335
Phe Asp Ala Lys Ala Asn Glu Phe Ile Ala Lys Leu Gln Ala Asn Pro
            340                 345                 350
Ser Lys Ile Ala Ser Arg Lys Ala Ser Gln Asn Thr Ile Glu Ala Phe
        355                 360                 365
Gly Pro Leu Pro Glu Phe Leu Gly Gly Ser Ala Asp Leu Ala Pro
    370                 375                 380
Ser Asn Leu Thr Leu Trp Ser Gly Ser Lys Ala Ile Asn Glu Asp Ala
385                 390                 395                 400
Ala Gly Asn Tyr Ile His Tyr Gly Val Arg Glu Phe Gly Met Thr Ala
                405                 410                 415
Ile Ala Asn Gly Ile Ala Leu His Gly Gly Phe Leu Pro Tyr Thr Ser
            420                 425                 430
Thr Phe Leu Met Phe Val Glu Tyr Ala Arg Asn Ala Val Arg Met Ala
        435                 440                 445
Ala Leu Met Lys Gln Arg Gln Val Met Val Tyr Thr His Asp Ser Ile
    450                 455                 460
Gly Leu Gly Glu Asp Gly Pro Thr His Gln Pro Val Glu Gln Val Ala
465                 470                 475                 480
Ser Leu Arg Val Thr Pro Asn Met Ser Thr Trp Arg Pro Cys Asp Gln
                485                 490                 495
Val Glu Ser Ala Val Ala Trp Lys Tyr Gly Val Glu Arg Gln Asp Gly
            500                 505                 510
Pro Thr Ala Leu Ile Leu Ser Arg Gln Asn Leu Ala Gln Gln Glu Arg
        515                 520                 525
Thr Glu Glu Gln Leu Ala Asn Ile Ala Arg Gly Gly Tyr Val Leu Lys
    530                 535                 540
Asp Cys Ala Gly Gln Pro Gln Ile Ile Phe Ile Ala Thr Gly Ser Glu
545                 550                 555                 560
Val Glu Leu Ala Val Ala Ala Tyr Glu Lys Leu Thr Ala Glu Gly Val
                565                 570                 575
Lys Ala Arg Val Val Ser Met Pro Ser Thr Asp Ala Phe Asp Lys Gln
            580                 585                 590
Asp Ala Ala Tyr Arg Glu Ser Val Leu Pro Lys Ala Val Ser Ala Arg
        595                 600                 605
Val Ala Ile Glu Ala Gly Ile Ala Asp Tyr Trp Phe Lys Tyr Val Gly
    610                 615                 620
Leu Asn Gly Ala Ile Val Gly Met Thr Thr Phe Gly Glu Ser Ala Pro
625                 630                 635                 640
Ala Glu Leu Leu Phe Glu Glu Phe Gly Phe Thr Val Asp Asn Val Ile
                645                 650                 655
Ala Lys Ala Lys Ala Leu Leu
            660

<210> SEQ ID NO 139
<211> LENGTH: 1992
<212> TYPE: DNA
<213> ORGANISM: Salmonella typhimurium

<400> SEQUENCE: 139
atgtcctcac gtaaagagct tgccaatgct attcgtgcgc tgagcatgga cgcagtacag      60
aaagccaagt ccggtcaccc gggtgccccg atgggtatgg ctgacattgc cgaagtcctg     120
tggcgtgatt tcctgaacca caacccgacc aaccgtcct gggccgaccg cgaccgcttc      180
gtgctgtcca atgccacgg ctcaatgctg atttacagcc tgctgcacct caccggttat     240

```
gacctgccga tgtccgagct gcagaatttc cgtcagctac attcaaaaac ccctggtcac    300
ccggaagtgg gctacaccgc tggcgttgaa accactactg gcccgctggg tcagggtatt    360
gccaacgccg tcgggatggc gattgccgag aaaactctgg cggcgcagtt taatcgtcct    420
ggccacgata tcgttgacca cttcacctac gtctttatgg gcgacggctg catgatggaa    480
ggcatttctc acgaagtgtg ctctctggct ggtactctga actgggcaa actgatcgcg     540
ttctatgatg acaacggtat ctctatcgat ggtcatgttg aaggctggtt caccgatgac    600
accgcgaaac gttttgaagc ctacggctgg cacgttatcc gtggcattga cggtcacgat    660
gccgacgcca ttaaacgcgc cacggaagaa gctcgcgccg tgactgacaa accgtccctg    720
ctgatgtgca aaaccatcat cggtttcggt tcgccgaaca acagggtac ccacgattcc     780
cacggcgcgc cgctgggcga cgcggaaatc gcgctgaccc gcaacagtt gggctggaaa     840
tacgcgccgt tcgaaatccc gtctgaaatc tacgcccagt gggatgcgaa agaagccggc    900
caggcgaaag agtctgcatg aatgagaaa ttcgcggctt atgagaaagc cttcccgcag     960
gaagctgctg aattcactcg tcgtatgaaa ggcgacatgc cggctgactt cgatgcgaaa   1020
gcgaatgagt tcatcgctaa actgcaggcg aatccatcca aaatcgccag ccgtaaagcg   1080
tcccagaata ccatcgaagc cttcggtccg ctgttgccgg aattcctcgg cggctccgct   1140
gacctggctc cttctaacct gaccctgtgg tccggttcga agcgattaa cgaagatgcc    1200
gcaggtaact acattcatta cggtgtgcgc gaattcggta tgaccgctat cgccaacggt   1260
atcgccctgc acggcggttt cctgccgtac acctccacct tcctgatgtt cgtcgaatat   1320
gcccgtaacg cagtgcgtat ggcagcgttg atgaaacaac gtcaggtgat ggtgtacacc   1380
cacgactcca tcggtctggg cgaagatggc ccgacgcacc agccggtcga gcaggtggca   1440
agcctgcgcg taacgccgaa catgtccaca tggcgtccgt gcgaccaggt ggaatccgcg   1500
gtggcgtgga atatggcgt agagcgtcag gatggcccaa ccgcgctgat cctctcccgt   1560
cagaacctgg cgcagcagga acgtactgaa gagcaactgg cgaatatcgc ccgcggtggt   1620
tacgtactga agattgtgc gggccagccg cagattatct tcattgcgac cggttcagag   1680
gttgagctgg cggttgccgc ttacgaaaaa ctgactgccg aaggcgtgaa ggcgcgcgtg   1740
gtttccatgc cgtccaccga cgcgttcgac aagcaggatg cggcttaccg tgaatccgtg   1800
ctgccgaagg cggtctctgc gcgtgtggcg attgaagcgg gtatcgctga ctactggttc   1860
aaatacgtcg gcctgaacgg cgctattgtc gggatgacca ccttcggtga gtctgctccg   1920
gcagagctgt tgtttgaaga gtttggcttc acggtggaca acgtgatcgc caaagcgaaa   1980
gcactgctgt aa                                                       1992
```

<210> SEQ ID NO 140
<211> LENGTH: 672
<212> TYPE: PRT
<213> ORGANISM: Rhodobacter sphaeroides

<400> SEQUENCE: 140

Met Asp Ile Gln Ser Leu Arg Glu Gln His Pro Asp His Trp Lys Lys
1               5                   10                  15

Ala Cys Ala Ile Arg Ala Leu Thr Leu Asp Ala Val Ala Ala Ala Asn
            20                  25                  30

Ser Gly His Ser Gly Met Pro Met Gly Met Ala Asp Val Ala Thr Val
        35                  40                  45

Leu Tyr Glu Lys His Met Val Phe Asp Ala Gln Ser Pro Asp Trp Pro
    50                  55                  60

```
Asn Arg Asp Arg Phe Val Leu Ser Ala Gly His Gly Ser Met Leu Val
 65                  70                  75                  80

Tyr Ser Leu Leu His Leu Thr Gly Asp Pro Glu Phe Pro Ile Glu Gln
                     85                  90                  95

Ile Arg Asn Phe Arg Gln Trp Gly Ser Arg Thr Ala Gly His Pro Glu
                100                 105                 110

Asn Phe Leu Ala Lys Gly Ile Glu Thr Thr Thr Gly Pro Leu Gly Gln
                115                 120                 125

Gly Leu Ala Met Ala Val Gly Leu Ala Met Ala Glu Glu Ser Leu Arg
130                 135                 140

Ala Arg Trp Gly Ala Lys Ile Ile Asp His Tyr Thr Tyr Cys Ile Ala
145                 150                 155                 160

Gly Asp Gly Cys Leu Met Glu Gly Val Ser Gln Glu Ala Ile Gly Leu
                165                 170                 175

Ala Gly Arg His Glu Leu Ser Arg Leu Ile Val Met Trp Asp Asn Asn
                180                 185                 190

Gly Ile Thr Ile Asp Gly Lys Val Ala Leu Ser Asp Arg Thr Asp Gln
                195                 200                 205

Lys Ala Arg Phe Ala Ala Ala Gly Trp Asp Val Phe Glu Cys Asp Gly
                210                 215                 220

His Asp Pro Ala Asp Ile Asp Arg Ala Leu Thr Glu Ala Lys Ala Ser
225                 230                 235                 240

Lys Gly Pro Ala Phe Ile Ala Cys Thr Thr His Ile Ala Leu Gly Ser
                245                 250                 255

Ser Ala Gln Asp Thr Ser Lys Gly His Gly Ala Leu Thr Asp Ala Lys
                260                 265                 270

Leu Ile Thr Asp Thr Lys Ala Ala Tyr Gly Trp Thr Gly Ala Phe
                275                 280                 285

Glu Ile Pro Ala Asp Ile Lys Thr Ala Trp Glu Thr Ile Gly Ser Arg
                290                 295                 300

Gly Ala Glu Ala Arg Lys Ala Trp Asp Glu Arg Phe Ala Ala Leu Ser
305                 310                 315                 320

Asp Ser Lys Arg Ala Leu Phe Gln Gln Gln Phe Ser Cys Glu Pro Pro
                325                 330                 335

Lys Lys Leu Ala Ala Ala Ile Arg Ala Val Lys Lys Asp Ala Val Glu
                340                 345                 350

Lys Met Pro Lys Val Ala Thr Arg Arg Ala Ser Glu Met Val Leu Glu
                355                 360                 365

Ala Val Asn Pro Ile Met Thr Glu Thr Ile Gly Gly Ser Ala Asp Leu
370                 375                 380

Thr Gly Ser Asn Asn Thr Lys Thr Ala Asp Leu Gly Val Phe Asp Pro
385                 390                 395                 400

Ile Asn Arg Lys Gly Arg Tyr Val Tyr Tyr Gly Ile Arg Glu His
                405                 410                 415

Met Ala Ala Met Asn Gly Met Ala Leu His Gly Gly Leu Arg Pro
                420                 425                 430

Tyr Gly Gly Thr Phe Met Cys Phe Ala Asp Tyr Cys Arg Pro Ala Val
                435                 440                 445

Arg Leu Ser Ala Leu Met His Met Pro Val Val Tyr Val Phe Thr His
                450                 455                 460

Asp Ser Ile Gly Leu Gly Glu Asp Gly Pro Thr His Gln Pro Val Glu
465                 470                 475                 480

His Leu Ala Met Leu Arg Ala Thr Pro Asn Met Leu Val Phe Arg Pro
```

```
                     485                 490                 495
Ala Asp Leu Thr Glu Thr Ala Glu Ala Trp Glu Ile Ala Leu Ser Glu
                500                 505                 510

Lys Ala Thr Pro Ser Val Leu Ala Leu Ser Arg Gln Asn Leu Pro Ala
            515                 520                 525

Val Arg Lys Thr His Thr Asn Lys Asn Leu Val Ala Gln Gly Ala Tyr
        530                 535                 540

Val Leu Glu Glu Ala Thr Ala Lys Arg Gln Val Ile Leu Ile Ala Ser
545                 550                 555                 560

Gly Ser Glu Val Glu Val Ala Leu Lys Ala Arg Glu Ala Leu Glu Ala
                565                 570                 575

Glu Gly Ile Gly Thr Arg Val Val Ser Met Pro Cys Met Glu Leu Phe
            580                 585                 590

Ala Arg Gln Asp Glu Ala Tyr Arg Arg Lys Val Leu Pro Ala Gly Ala
        595                 600                 605

Val Arg Ile Ala Ile Glu Ala Gly Val Arg Met Gly Trp Asp Arg Trp
    610                 615                 620

Leu Leu Gly Glu Arg Gly Arg Glu Gly Lys Asp Gly Phe Ile Gly Met
625                 630                 635                 640

Ser Gly Phe Gly Ala Ser Ala Pro Ala Glu Arg Leu Phe Gln Glu Phe
                645                 650                 655

Gly Ile Thr Pro Glu Ala Thr Val Ala Lys Ala Lys Ala Leu Leu Gly
            660                 665                 670

<210> SEQ ID NO 141
<211> LENGTH: 2019
<212> TYPE: DNA
<213> ORGANISM: Rhodobacter sphaeroides

<400> SEQUENCE: 141
gtggacatac agagcctgcg cgagcagcat cccgatcact ggaagaaagc ctgcgccatc        60
cgcgcgctga cgctcgacgc cgtggcggcg gccaattccg ccattccggc catgccgatg       120
ggcatggcgg acgtcgcgac cgtcctctac gagaagcaca tggtcttcga cgcgcagtcc       180
cccgactggc cgaaccgcga ccggttcgtg ctgtccgcgg gtcacggctc gatgctggtc       240
tattcgctgc ttcacctgac cggcgacccc gagttcccga tcgagcagat caggaacttc       300
cgccagtggg gctcccgaac cgctggccac cccgagaact tcctcgccaa ggggatcgag       360
accacgaccg gcccgctggg ccagggcctg gcgatggccg tgggtctcgc gatggccgaa       420
gagtcgctcc gcgcccgctg ggggcgaag atcatcgacc actacaccta ctgcatcgcc       480
ggcgacggct gcctgatgga gggggtgagc caggaggcca tcggcctcgc cggccggcac       540
gaactgtcgc gcctgatcgt gatgtgggac aacaacggca tcaccatcga cggcaaggtg       600
gcgctgtcgg accgcaccga ccagaaggcg cgcttcgccg ccgcgggctg ggacgtgttc       660
gaatgcgacg ccatgatccc gccgacatc gaccgcgcgc tgaccgaagc caaggcctcg       720
aagggcccgg ccttcatcgc ctgcaccacg catatcgcgc tcggctcttc ggctcaggac       780
acctccaagg gtcacggcgc gctgaccgat gccaagctga tcaccgacac caaggccgcc       840
tatggctgga ccgccggggc cttcgagatc ccggccgaca tcaagacggc ctgggagacc       900
atcggctcgc gcggagccga ggcccgcaag gcatgggacg agcggttcgc cgccctctcg       960
gacagcaagc gcgccctctt ccagcagcag ttctcctgcg agccgccgaa aaagctcgcc      1020
gccgcgatcc gcgccgtgaa gaaggacgcg gtcgagaaga tgccgaaggt cgcgacccgc      1080
cgcgcctcgg agatggtgct ggaagcggtc aatccgatca tgaccgagac catcggcggc      1140
```

-continued

```
tcggccgacc tgaccggctc gaacaacacc aagacggccg acctcggcgt gttcgacccg    1200
atcaaccgca agggccgcta cgtctattac ggcatccgcg agcacggcat ggccgcggcg    1260
atgaacggca tggcgctgca cggcggcctg cgcccctacg gcggcaccct catgtgcttt    1320
gccgactact gccgcccgc cgtgcgcctc tcggcgctga tgcacatgcc ggtggtctat     1380
gtcttcaccc atgactcgat cggtctgggc gaggacgggc cgacccacca gccggtcgag    1440
catctggcca tgctgcgcgc gacgccgaac atgctggtgt tccgcccggc cgacctgacc    1500
gagaccgccg aggcctggga gatcgcgctc tccgaaaagg ccacgccctc ggtgctggcg    1560
ctgtcgcggc agaacctgcc ggcggtgcgc aagacccaca ccaacaagaa cctcgtcgcg    1620
cagggcgcct atgtgctcga agaggctacg gccaagcgtc aggtgatcct gatcgcctcg    1680
ggctccgagg tcgaggtggc gctgaaggcc cgcgaggcgc tcgaggccga gggcatcggc    1740
acccgcgtcg tctcgatgcc ctgcatggag ctgttcgccc ggcaggacga ggcctaccgc    1800
cgcaaggttc tgccggcggg cgccgtccgc atcgccatcg aggcgggtgt ccgcatgggc    1860
tgggaccgct ggcttctggg cgagcgcggc cgcgagggca aggacggctt catcggcatg    1920
tcgggcttcg gcgcctcggc cccggccgag cggctgttcc aggagttcgg catcacgccc    1980
gaggcgaccg tcgccaaggc caaggccctg ctcggctga                           2019
```